US010568947B2

(12) United States Patent
Brogdon et al.

(10) Patent No.: US 10,568,947 B2
(45) Date of Patent: Feb. 25, 2020

(54) TREATMENT OF CANCER USING A CLL-1 CHIMERIC ANTIGEN RECEPTOR

(71) Applicants: Novartis AG, Basel (CH); The Trustees of the University of Pennsylvania, Philadelphia, PA (US)

(72) Inventors: Jennifer Brogdon, Sudbury, MA (US); Hilmar Erhard Ebersbach, Basel (CH); Saar Gill, Philadelphia, PA (US); David Glass, Cambridge, MA (US); Julia Jascur, Basel (CH); Saad Kenderian, Philadelphia, PA (US); Joan Mannick, Cambridge, MA (US); Michael C. Milone, Cherry Hill, NJ (US); Leon Murphy, Cambridge, MA (US); Celeste Richardson, Cambridge, MA (US); Reshma Singh, Cambridge, MA (US); Lai Wei, Shanghai (CN); Qilong Wu, Shanghai (CN); Qiumei Yang, Shanghai (CN); Jiquan Zhang, Shanghai (CN)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 97 days.

(21) Appl. No.: 14/805,075

(22) Filed: Jul. 21, 2015

(65) Prior Publication Data

US 2016/0051651 A1 Feb. 25, 2016

(30) Foreign Application Priority Data

Jul. 21, 2014 (WO) ................ PCT/CN2014/082602
Nov. 6, 2014 (WO) ................ PCT/CN2014/090500

(51) Int. Cl.

| | |
|---|---|
| ***A61K 39/00*** | (2006.01) |
| ***C07K 14/725*** | (2006.01) |
| ***C07K 16/28*** | (2006.01) |
| ***A61K 31/7068*** | (2006.01) |
| ***C07K 14/705*** | (2006.01) |
| ***A61K 45/06*** | (2006.01) |

(52) U.S. Cl.
CPC ...... *A61K 39/0011* (2013.01); *A61K 31/7068* (2013.01); *A61K 45/06* (2013.01); *C07K 14/7051* (2013.01); *C07K 14/70578* (2013.01); *C07K 16/2851* (2013.01); *A61K 2039/5156* (2013.01); *C07K 2317/622* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,792,648 | A | 8/1998 | Hillman et al. |
| 5,874,240 | A | 2/1999 | Ni et al. |
| 5,906,936 | A | 5/1999 | Eshhar et al. |
| 5,912,172 | A | 6/1999 | Eshhar et al. |
| 6,034,219 | A | 3/2000 | Hillman et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,407,213 | B1 | 6/2002 | Carter et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,129,332 | B2 | 10/2006 | Pastan et al. |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,627,643 | B1 | 12/2009 | Ignatoff et al. |
| 7,628,986 | B2 | 12/2009 | Weber et al. |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |

(Continued)

FOREIGN PATENT DOCUMENTS

| | | | |
|---|---|---|---|
| CA | 2863799 | A1 | 8/2013 |
| CN | 102875685 | A | 1/2013 |

(Continued)

OTHER PUBLICATIONS

Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.

(Continued)

*Primary Examiner* — Marianne P Allen
(74) *Attorney, Agent, or Firm* — Lando & Anastasi, LLP

(57) ABSTRACT

The invention provides compositions and methods for treating diseases associated with expression of CLL-1. The invention also relates to chimeric antigen receptor (CAR) specific to CLL-1, vectors encoding the same, and recombinant cells comprising the CLL-1 CAR. The invention also includes methods of administering a genetically modified cell expressing a CAR that comprises a CLL-1 binding domain.

38 Claims, 56 Drawing Sheets

Specification includes a Sequence Listing.

(56) References Cited

U.S. PATENT DOCUMENTS

| | | | |
|---|---|---|---|
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,268,966 | B2 | 9/2012 | van den Oudenrijn et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,852,551 | B2 | 10/2014 | Jordan |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,394,368 | B2 | 7/2016 | Brogdon et al. |
| 9,573,988 | B2 | 2/2017 | Brogdon et al. |
| 9,745,368 | B2 | 8/2017 | Milone et al. |
| 9,777,061 | B2 | 10/2017 | Ebersbach et al. |
| 9,815,901 | B2 | 11/2017 | Brogdon et al. |
| 2003/0060444 | A1 | 3/2003 | Finney et al. |
| 2003/0077249 | A1 | 4/2003 | Bebbington et al. |
| 2003/0148982 | A1 | 8/2003 | Brenner et al. |
| 2003/0171546 | A1 | 9/2003 | Jensen |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2005/0019429 | A1 | 1/2005 | Ivanov et al. |
| 2005/0113564 | A1 | 5/2005 | Campana et al. |
| 2005/0129671 | A1 | 6/2005 | Cooper et al. |
| 2006/0246548 | A1 | 11/2006 | Jensen |
| 2007/0036773 | A1 | 2/2007 | Cooper et al. |
| 2008/0131415 | A1 | 6/2008 | Riddell et al. |
| 2009/0088373 | A1 | 4/2009 | Gallo et al. |
| 2009/0148419 | A1 | 6/2009 | Gonzalez De La Pena et al. |
| 2009/0208488 | A1 | 8/2009 | Clark et al. |
| 2009/0257994 | A1 | 10/2009 | Jensen |
| 2009/0325167 | A1 | 12/2009 | Chappell et al. |
| 2010/0105136 | A1 | 4/2010 | Carter et al. |
| 2010/0196311 | A1 | 8/2010 | Kim et al. |
| 2010/0273797 | A1 | 10/2010 | Boman et al. |
| 2011/0052554 | A1 | 3/2011 | Zakrzewski et al. |
| 2011/0129496 | A1 | 6/2011 | Ahmed et al. |
| 2011/0280894 | A1 | 11/2011 | Krackhardt et al. |
| 2012/0138858 | A1 | 6/2012 | Lee et al. |
| 2012/0148552 | A1 | 6/2012 | Jensen |
| 2012/0244116 | A1 | 9/2012 | Hiwase et al. |
| 2012/0282256 | A1 | 11/2012 | Campana et al. |
| 2012/0321667 | A1 | 12/2012 | Sentman |
| 2013/0040371 | A1 | 2/2013 | Abe et al. |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0287748 | A1 | 10/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0242049 | A1 | 8/2014 | Choi et al. |
| 2014/0271635 | A1 | 9/2014 | Brogdon et al. |
| 2014/0322169 | A1 | 10/2014 | Harper et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0370045 | A1 | 12/2014 | June et al. |
| 2015/0017141 | A1 | 1/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0342994 | A1 | 12/2015 | Riley et al. |
| 2016/0046724 | A1 | 2/2016 | Brogdon et al. |
| 2016/0051651 | A1 | 2/2016 | Brogdon et al. |
| 2016/0068601 | A1 | 3/2016 | Brogdon et al. |
| 2016/0096892 | A1 | 4/2016 | Brogdon et al. |
| 2016/0185861 | A1 | 6/2016 | Bedoya et al. |
| 2016/0311907 | A1 | 10/2016 | Brogdon et al. |
| 2016/0311917 | A1 | 10/2016 | Beatty et al. |
| 2016/0340406 | A1 | 11/2016 | Zhao et al. |
| 2016/0362472 | A1 | 12/2016 | Bitter et al. |
| 2017/0008963 | A1 | 1/2017 | Brogdon et al. |
| 2017/0081411 | A1 | 3/2017 | Engels et al. |
| 2017/0137783 | A1 | 5/2017 | Bedoya et al. |
| 2017/0183415 | A1 | 6/2017 | Brogdon et al. |
| 2017/0209492 | A1 | 7/2017 | June et al. |
| 2017/0211055 | A1 | 7/2017 | Brogdon et al. |
| 2017/0226495 | A1 | 8/2017 | Guimaraes |
| 2017/0239294 | A1 | 8/2017 | Thomas-Tikhonenko et al. |
| 2017/0260268 | A1 | 9/2017 | Beatty et al. |
| 2017/0274014 | A1 | 9/2017 | Brogdon et al. |
| 2017/0306416 | A1 | 10/2017 | Bedoya et al. |
| 2017/0335281 | A1 | 11/2017 | Loew et al. |
| 2018/0022795 | A1 | 1/2018 | Milone et al. |
| 2018/0044423 | A1 | 2/2018 | Ebersbach et al. |
| 2018/0044424 | A1 | 2/2018 | June et al. |
| 2018/0118834 | A1 | 5/2018 | Brogdon et al. |
| 2018/0125892 | A1 | 5/2018 | Brannetti et al. |
| 2018/0133296 | A1 | 5/2018 | Barrett et al. |
| 2018/0140602 | A1 | 5/2018 | Angst et al. |
| 2018/0230193 | A1 | 8/2018 | Loew et al. |
| 2018/0252727 | A1 | 9/2018 | Garfall et al. |
| 2018/0258149 | A1 | 9/2018 | Motz et al. |
| 2018/0298068 | A1 | 10/2018 | Albelda |
| 2018/0312595 | A1 | 11/2018 | Brogdon et al. |
| 2019/0000880 | A1 | 1/2019 | Motz et al. |
| 2019/0000944 | A1 | 1/2019 | Brogdon et al. |
| 2019/0135940 | A1 | 5/2019 | Brogdon et al. |
| 2019/0151365 | A1 | 5/2019 | Anak et al. |
| 2019/0153061 | A1 | 5/2019 | Brogdon et al. |
| 2019/0161542 | A1 | 5/2019 | Gill et al. |

FOREIGN PATENT DOCUMENTS

| | | | |
|---|---|---|---|
| CN | 103113470 | A | 5/2013 |
| CN | 103347897 | A | 10/2013 |
| EP | 0574512 | A1 | 12/1993 |
| EP | 0871495 | A1 | 10/1998 |
| EP | 01226244 | A2 | 7/2002 |
| EP | 2694549 | A1 | 2/2014 |
| WO | 1992015322 | A1 | 9/1992 |
| WO | 09418317 | A1 | 8/1994 |
| WO | 199530014 | A1 | 11/1995 |
| WO | 09623814 | A1 | 8/1996 |
| WO | 09624671 | A1 | 8/1996 |
| WO | 09625953 | A1 | 8/1996 |
| WO | 09640140 | A1 | 12/1996 |
| WO | 1997015669 | A1 | 5/1997 |
| WO | 09723613 | A2 | 7/1997 |
| WO | 09818809 | A1 | 5/1998 |
| WO | 09900494 | A2 | 1/1999 |
| WO | 09957268 | A1 | 11/1999 |
| WO | 0014257 | A1 | 3/2000 |
| WO | 01062931 | A2 | 8/2001 |
| WO | 01/072325 | A1 | 10/2001 |
| WO | 2002033101 | A1 | 4/2002 |
| WO | 02077029 | A2 | 10/2002 |
| WO | 02088334 | A1 | 11/2002 |
| WO | 2003013598 | A2 | 2/2003 |
| WO | 03057171 | A2 | 7/2003 |
| WO | 2004106381 | A1 | 12/2004 |
| WO | 2005000894 | A2 | 1/2005 |
| WO | 2005019429 | A2 | 3/2005 |
| WO | 2005044996 | A2 | 5/2005 |
| WO | 2005090990 | A2 | 9/2005 |
| WO | 2005/118788 | A2 | 12/2005 |
| WO | 2006060878 | A1 | 6/2006 |
| WO | 2006130458 | A2 | 12/2006 |
| WO | 2008045437 | A2 | 4/2008 |

(56) References Cited

FOREIGN PATENT DOCUMENTS

| | | | |
|---|---|---|---|
| WO | 2008110491 | A2 | 9/2008 |
| WO | 2008127735 | A1 | 10/2008 |
| WO | 2009007124 | A1 | 1/2009 |
| WO | 2009051974 | A1 | 4/2009 |
| WO | 2010025177 | A1 | 3/2010 |
| WO | 2010056754 | A2 | 5/2010 |
| WO | 2010085660 | A2 | 7/2010 |
| WO | 2010121141 | A1 | 10/2010 |
| WO | 2011041093 | A1 | 4/2011 |
| WO | 2011059836 | A2 | 5/2011 |
| WO | 2011097477 | A1 | 8/2011 |
| WO | 201207414 | A2 | 1/2012 |
| WO | 2012025530 | A1 | 3/2012 |
| WO | 2012033885 | A1 | 3/2012 |
| WO | 2012058460 | A2 | 5/2012 |
| WO | 2012066058 | A1 | 5/2012 |
| WO | 2012072505 | A1 | 6/2012 |
| WO | 2012079000 | A1 | 6/2012 |
| WO | 2012082841 | A2 | 6/2012 |
| WO | 2012/099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138475 | A1 | 10/2012 |
| WO | 2012138858 | A1 | 10/2012 |
| WO | 2012163805 | A1 | 12/2012 |
| WO | 2013009690 | A2 | 1/2013 |
| WO | 2013019615 | A2 | 2/2013 |
| WO | 2013026833 | A1 | 2/2013 |
| WO | 2013026837 | A1 | 2/2013 |
| WO | 2013026839 | A1 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013063419 | A2 | 5/2013 |
| WO | 2013074916 | A1 | 5/2013 |
| WO | 2013092001 | A1 | 6/2013 |
| WO | 2013/126712 | A1 | 8/2013 |
| WO | 2013123061 | A1 | 8/2013 |
| WO | 2013126726 | A1 | 8/2013 |
| WO | 2013126729 | A1 | 8/2013 |
| WO | 2013126733 | A1 | 8/2013 |
| WO | 2013139906 | A1 | 9/2013 |
| WO | 2013142034 | A1 | 9/2013 |
| WO | 2013153270 | A1 | 10/2013 |
| WO | 2013154760 | A1 | 10/2013 |
| WO | 2013169625 | A1 | 11/2013 |
| WO | 2013173820 | A2 | 11/2013 |
| WO | 2013185552 | A1 | 12/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014051433 | A1 | 4/2014 |
| WO | 2014055657 | A1 | 4/2014 |
| WO | 2014068079 | A1 | 5/2014 |
| WO | 2014100385 | A1 | 6/2014 |
| WO | 2014124143 | A1 | 8/2014 |
| WO | 2014130635 | A1 | 8/2014 |
| WO | 2014130657 | A1 | 8/2014 |
| WO | 2014/145252 | A2 | 9/2014 |
| WO | 2014144622 | A2 | 9/2014 |
| WO | 2014153270 | A1 | 9/2014 |
| WO | 2014/172584 | A1 | 10/2014 |
| WO | 2014186469 | A2 | 11/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |

OTHER PUBLICATIONS

Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.

Uckun et al., "Detailed studies on expression and function of CD19 surface determinant by using B43 monoclonal antibody and the clinical potential of anti-CD19 immunotoxins" Blood (1988) vol. 71 pp. 13-29.

Vinay & Kwon, "Role of 4-1BB in immune responses" Immunology (1998) vol. 10 pp. 481-489.

Willemsen et al., "Genetic Engineering of T Cell Specificity for Immunotherapy of Cancer" Human Immunology (2003) vol. 64 pp. 56-68.

Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.

Zufferey et al., "Multiply attenuated lentiviral vector achieves efficient gene delivery in vivo" Nature Biotechnology (1997) vol. 15 pp. 871-876.

Bakker et al. "C-typelectin-like molecule-1: a novel myeloid cell surface marker associated with acute myeloid leukemia", Cancer Research (2004) vol. 64, No. 22,pp. 8443-8450.

Barrett, et al., "Pre-clinical model of eradication of B cell leukemia with lentiviral transduced anti-CD19 chimeric immunoreceptor-modified T cells" Cancer Research:AACR 101st Annual Meeting, Abstract 2933 (Apr. 17-21, 2010).

Barrett, et al., "Treatment of Advanced Leukemia in Mice with mRNA Engineered T Cells" Human Gene Therapy, 22(12):1575-1586 (2011).

Beers, et al., "Immunotoxins with Increased Activity against Epidermal Growth Factor Receptor vIII-expressing Cells Produced by Antibody Phage Display" Clinical Cancer Research, 6:2835-2843 (2000).

Bendig, M.M. Humanization of rodent monoclonal antibodies by CDR grafting. Methods: A Companion to Methods in Enzymology, 1995; vol. 8, p. 83-93.

Birkholz et al. "Transfer of mRNA encoding recombinant immunoreceptors reprograms CD4+ and CD8+ T cells for use in the adoptive immunotherapy of cancer," Gene Therapy 16:596-604 (2009).

Brentjens et al. "Genetically Targeted T Cells Eradicate Systemic Acute Lymphoblastic Leukemia Xenografts", Clinical Cancer Research(2007) vol. 13, No. 18, pp. 5426-5435.

Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).

Brown J R et al: "Novel Treatments for Chronic Lymphocytic Leukemia and Moving Forward",American Society of Clinical Oncology Educational Book,vol. 34, 2014, pp. e317-e325,XP05520 1368,ISSN: 1548-8748, DOI:10.14694/EdBook_AM.2014..34. e317 the whole document.

Bullain, et al., "Genetically engineered T cells to target EGFRvIII expressing glioblastoma" J Neurooncol, 94:373-382 (2009).

Carpenter, Robert O. et al. "B-cell Maturation Antigen is a Promising Target for Adoptive T-cell Therapy of Multiple Myeloma", Clinical Cancer Research, Apr. 15, 2013, vol. 19 No. 8, pp. 2048-2060.

(56) References Cited

OTHER PUBLICATIONS

Casset F, et al. A peptide mimetic of an anti-CD4 monoclonal antibody by rational design. Biochemical and Biophysical Research Communications, 2003, vol. 307, p. 198-205.
Casucci et al. "CD44v6-targeted T cells mediate potent antitumor effects against acute myeloid leukemia and multiple myeloma", Blood (2013) vol. 122 No. 20 pp. 3461-3472.
Chinnasamy et al. "Local Delivery of Interleukin-12 Using T Cells Targeting VEGF Receptor-2 Eradicates Multiple Vascularized Tumors in Mice", Clinical Cancer Research, vol. 18, No. 6, Jan. 30, 2012, pp. 1672-1683.
Chmielewski et al. "IL-12 Release by Engineered T Cells Expressing Chimeric Antigen Receptors Can Effectively Muster an Antigen Receptors Can Effectively Muster an Antigen-Independent Macrophage Response on Tumor Cells That Have Shut Down Tumor Antigen Expression", Cancer Research, vol. 71, No. 17, Jul. 8, 2011, pp. 5697-7506.
Chmielewski et al. "Of CARs and TRUCKs: chimeric antigen receptor (CAR) T cells engineered with an inducible cytokine to modulate the tumor stroma", Immunological Reviews, vol. 257, No. 1, Jan. 13, 2014, pp. 83-90.
Dotti et al. "Design and development of therapies using chimeric antigen receptor-expressing T cells", Immunological Reviews, vol. 257, No. 1, Dec. 13, 2013, pp. 107-126.
Du et al., "New Immunotoxins Targeting CD123, a Stem Cell Antigen on Acute Myeloid Leukemia Cells" J. Immunother. vol. 30, No. 6 pp. 607-613 (2007).
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
European Search Report for EP Application No. 12820516.8, dated Mar. 30, 2015.
Extended European Search Report for EP Application No. 12832609.7, dated Mar. 25, 2015.
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Friedmann-Morvinski et al., "Redirected primary T cells harboring a chimeric receptor require costimulation for their antigen-specific activation," Blood 105: 3087-3093 (2005).
Garfall, et al. "Imunotherapy with chimeric antigen receptors for multiple myeloma." Discovery Medicine. 17 (91) (pp. 37-46), Jan. 2014.
Gaviolo et al., "Protein kinase C mediates human neutrophil cytotoxicity" Biochemical and Biophysical Research Communications 148(3): 1290-1294 (1987).
Geiger et al., "Integrated src kinase and constimulatory activity enhances signal transduction through single-chain chimeric receptors in T lymphocytes," Blood 98(8): 2364-2371 (2001).
Gonzalez et al. "Genetic engineering of cytolytic T lymphocytes for adoptive T-cell therapy of neuroblastoma," The Journal of Gene Medicine 6(6): 704-711 (2004).
Gross et al., "Endowing T cells with antibody specificity using chimeric T cell receptors," The FASEB Journal 6: 3370-3378 (1992).
Gross et al., "Expression of immunoglobulin-T-cell receptor chimeric molecules as functional receptors with antibody-type specificity," PNAS 86: 10024-10028 (1989) (discuss "gene pair approach:" VH spliced to the C-region gene segment of alpha or beta TcR chain, or gamma or zeta TcR chain, VL is attached to the other chain).
Grupp et al., "Chimeric antigen receptor-modified T cells for acute lymphoid leukemia," New England Journal of Medicine 368: 1509-1518 (2013).
Gupta, et al., "Development of an EGFRvIII specific recombinant antibody" BMC Biotechnology, 10(72):1-13 (2010).
Holtkamp, et al., "Modification of antigen-encoding RNA increases stability, translational efficacy, and T-cell stimulatory capacity of dendritic cells" Blood, 108(13):4009-4071 (2006).
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Hoyos et al. "Engineering CD19-specific T lymphocytes with interleukin-15 and a suicide gene to enhance their anti-lymphoma/leukemia effects and safety", Leukemia, vol. 24, No. 6, Apr. 29, 2010, pp. 1160-1170.
Hunder et al., "Treatment of Metastic Melanoma with Autologous CD4+ T Cells against NY-ESO-'1." The New England Journal of Medicine 358(25): 2698-2703 (2008).
Huye E L et al: 'Combining mTor Inhibitors With Rapamycin-resistant T Cells: A Two-pronged Approach to Tumor Elimination',Molecular Therapy,vol. 19, No. 12, Aug. 30, 2011 (Aug. 30, 2011), pp. 2239-2248, XP055191016, GB, ISSN: 1525-0016, DOI: 10.1038/mt.2011.179 the whole document.
Imai et al., "Chimeric receptors with 4-1BB signaling capacity provoke potent cytotoxicity against acute lymphoblastic leukemia," Leukemia 18: 676-684 (2004).
International Search Report and Written Opinion for International Application No. PCT/CN2014/090501, dated Jun. 5, 2015.
International Search Report and Written Opinion for International application No. PCT/CN2014/090503, dated Apr. 22, 2015.
International Search Report and Written Opinion for International Application No. PCT/CN2014/094383, dated Mar. 20, 2015.
International Search Report and Written Opinion for International application No. PCT/CN2014/094393, dated Mar. 30, 2015.
International Search Report and Written Opinion for International Application No. PCT/US2014/065408, dated May 6, 2015.
International Search Report and Written Opinion for International application No. PCT/US2015/024671, dated Jul. 31, 2015.
International Search Report and Written Opinion for PCT/CN2014/090508 dated May 22, 2015.
International Search Report and Written Opinion for PCT/US2015/020606 dated Sep. 14, 2015.
International Search Report and Written Opinion for PCT/US2015/041337 dated Oct. 19, 2015.
International Search Report and Written Opinion of the International Search Authority for International Application No. PCT/CN2014/082586 dated Apr. 24, 2015.
International Search Report and Written Opinon for PCT/US2013/057991, dated Jan. 3, 2014.
International Search Report for International Application No. PCT/US13/032029, dated Jun. 20, 2013.
International Search Report for International Application No. PCT/US13/63083, dated Jan. 17, 2014.
International Search Report for International Application No. PCT/US2013/027347, dated Apr. 30, 2013.
International Search Report for International Application No. PCT/US2013/050267, dated Nov. 29, 2013.
International Search Report for International Application No. PCT/US2013/050272, dated Nov. 12, 2013.
International Search Report for International Application No. PCT/US2013/050275, dated Dec. 17, 2013.
International Search Report for International Application No. PCT/US2013/050287, dated Dec. 2, 2013.
International Search Report for International Application No. PCT/US2013/050293, dated Dec. 9, 2013.
International Search Report for International Application No. PCT/US2014/017364, dated Jul. 8, 2014.
International Search Report including Written Opinon for PCT/US2014/017328 dated Jun. 26, 2014.
Invitation to Pay Additional Fees and, Where Applicable, Protest Fee for International Application No. PCT/US2014/065408, dated Feb. 4, 2015.
Irving et al., "The cytoplasmic domain of the T cell receptor zeta chain is sufficient to couple to receptor-associated signal transduction pathways," Cell 64: 891-901 (1991).

(56) References Cited

OTHER PUBLICATIONS

Jena et al. "Chimeric Antigen Receptor (CAR)-Specific Monoclonal Antibody to Detect CD19-Specific T Cells in Clinical Trials," PLOS 8(3): e57838 (2013).
Jena, Bipulendu et al. "Redirecting T-cell specificity by introducing a tumor-specific chimeric antigen receptor, Blood, May 3, 2010", vol. 116, No. 7, pp. 1035-1044.
John et al, "Anti-PD-1 antibody therapy potently enhances the eradication of established tumors by gene-modified T cells", Clinical Cancer Research, The American Association for Cancer Research, US (2013) vol. 19, No. 20, pp. 5636-5646.
Kalos et al. "Adoptive T Cell Transfer for Cancer Immunotherapy in the Era of Synthetic Biology", Immunity, Cell Press, US, vol. 39, No. 1, Jul. 25, 2013. pp. 49-60.
Kalos et al., "T cells with chimeric antigen receptors have potent antitumor effects and can establish memory in patients with advanced leukemia," Science Translational Medicine 3: 95ra73 (2011).
Kerkar. "'Model T' Cells: A Time-Tested Vehicle for Gene Therapy." Frontiers in Immunology 4 (2013): 304. PMC. Web. Aug. 18, 2015.
Kershaw et al. "Gene-engineered T cells for cancer therapy", Nature Reviews Cancer, vol. 13, No. 8, Jul. 24, 2013, pp. 525-541.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Krebs et al. "Genetically Modified T Cells to Target Glioblastoma", Frontiers in Oncology, vol. 3, Jan. 1, 2013.
Kuhn, et al., "Determinants of intracellular RNA pharmacokinetics: Implication for RNA-based immunotherapeutics" RNA Biology, 8(1):35-43 (2011).
Kuwana et al., "Expression of Chimeric Receptor Composed of Immunoglobulin-derived V Resions and T-cell Receptor-derived C Regions" Biochem. Biophys. Res. Commun. 149: 964-968 (1987).
Kwon et al., "cDNA sequences of two inducible T-cell genes". Proc. Natl. Acad. Sci. U.S.A. 86(6): 1963-1967 (1989).
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanitis et al., "Redirected Antitumor Activity of Primary Human Lymphocytes Transduced With a Fully Human Anti-mesothelin Chimeric Receptor" Molecular Therapy, 20(3):633-643 (2012).
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Liu et al, "Metformin and the mTOR Inhibitor Everolimus (RAD001) Sensitize Breast Cancer Cells to the Cytotoxic Effect of Chemotherapeutic Drugs In Vitro", Anticancer Research, 32: 1627-1638 (2012).
Lorimer, et al., "Recombinant immunotoxins specific for a mutant epidermal growth factor receptor: Targeting with a single chain antibody variable domain isolated by phage display" Proc. Natl. Acad. Sci. USA, 93:14815-14820 (1996).
MacCallum R.M. et al, Antibody-antigen interactions: Contact analysis and binding site topography. J. Mol. Bioi., 1998, vol. 262, p. 732-745.
Maher et al., "Human T lymphocyte cytotoxicity and proliferation directed by a single chimeric TCRzeta/CD28 receptor," Nat. Biotechnol. 20: 70-75 (2002).
Majeti et al. "Monoclonal antibody therapy directed against human acute myeloid leukemia stem cells", Oncogene (2011) vol. 30 No. 9 pp. 1009-1019.
Mardiros et al., "CD123-Specific Chimeric Antigen Receptor Redirected T Cells Exhibit Potent Cytolytic Activity and Multiple Effector Functions Against Acute Myeloid Leukemia without Altering Normal Hematopoietic Colony Formation in Vitro" Blood 120(21): abstract 950 (2011).
Marshall et al. "Identification and characterization of a novel human myeloid inhibitory C-type lectin-like receptor (MICL) that is predominantly expressed on granulocytes and monocytes", The Journal of Biological Chemistry (2001) vol. 279 No. 15, pp. 14792-14802.
Maus et al., "T cells expressing chimeric antigen receptors can cause anaphylaxis in humans" Cancel Immunol Res, 1:26-31 (2013).
Maus, Marcela V. et al. "Zoom zoom: racing CARs for multiple myeloma", Clinical Cancer Research, Apr. 15, 2013, vol. 19 No. 8, pp. 1917-1919.
McCormack et al., "Bi-specific TCR-anti CD3 redirected T-cell targeting of NY-ESO-1-and LAGE-1-positive tumors," Cancer Immunol. Immunother. 62:773-785 (2012).
McGuinness et al., "Anti-tumor activity of human T cells expressing the CC49-zeta chimeric immune receptor," Hum. Gene Ther. 10: 165-173 (1999).
Melero et al., "Amplification of Tumor Immunity by Gene Transfer of the Co-Stimulatory 4-1BB Ligand: Synergy with the CD28 Co-Stimulatory Pathway," Eur. J. Immunol. 28(3): 1116-1121 abstract (1998).
Moon, et al., "A PDI-CD28 'Switch Receptor' Is Able to Augment Mesothelin-Directed Chimeric Antigen Receptor T Cell Therapy in a Resistant In Vivo Model of Human Tumor" 17th Annual Meeting of the American Society of Gene and Cell Therapy, Abstract 520 (May 21-24, 2014).
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Morgan, et al., "Recognition of Glioma Stem Cells by Genetically Modified T Cells Targeting EGFRvIII and Development of Adoptive Cell Therapy for Glioma" Human Gene Therapy, 23:1043-1053 (2012).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Nakayashiki, et al., "Production of a Single-chain Variable Fragment Antibody Recognizing Type III Mutant Epidermal Growth Factor Receptor" Jpn. J. Cancer Res., 91:1035-1043 (2000).
NCBI accession NM_001207010.1 accessed Oct. 5, 2015 from <http://www.ncbi.nlm.nih.gov/nuccore/NM_001207010.1>.
NCBI accession NM_138337.5 accessed Oct. 5, 2015 from <http://www.ncbi.nlm.nih.gov/nuccore/NM_138337.5>.
NCBI accession NM_201623.3 accessed Oct. 5, 2015 from http://www.ncbi.nlm.nih.gov/nuccore/NM_201623.3.
NCBI accession NM_201625.1 accessed Oct. 5, 2015 <http://www.ncbi.nlm.nih.gov/nuccore/NM_201625.1>.
Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.

(56) References Cited

OTHER PUBLICATIONS

Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Geiger & Jyothi, "Development and Application of Receptor-Modified T Lymphocytes for Adoptive Immunotherapy" Transfusion Medicine Reviews (2001) vol. 15 No. 1 pp. 21-34.
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Imai et al., "Genetic modification of primary natural killer cells overcomes inhibitory signals and induces specific killing of leukemic cells" Blood (2005) vol. 106 No. 1 pp. 376-383.
International Search Report from PCT/US2011/064191 dated Jan. 5, 2012.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kim et al., "Human 4-1BB regulates CD28 co-stimulation to promote Th1 cell responses" Eur. J. Immunol. (1998) vol. 28 pp. 881-890.
Kohn et al., "CARs on Track in the Clinic—Workshop of the Blood and Marrow Transplant Clinical Trials Network Subcommittee on Cell and Gene Therapy" Meeting Report—Molecular Therapy (2011) vol. 19 No. 3.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Levine et al., "Gene transfer in humans using a conditionally replicating lentiviral vector" PNAS (2006) vol. 103 No. 46 pp. 17372-17377.
MacAllan et al., "Measurement and modeling of human T cell kinetics" European Journal of Immunology (2003) vol. 33 pp. 2316-2326.
Molina, "A Decade of Rituximab: Improving Survival Outcomes in Non-Hodgkin's Lymphoma" Annu. Rev. Med. (2008) vol. 59 pp. 237-250.
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Patel et al., "Impact of chimeric immune receptor extracellular protein domains on T cell function" Gene Therapy (1999) vol. 6 pp. 412-419.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Sabbagh et al., "TNF family ligands define niches for T cell memory" Trends in Immunology (2007) vol. 28 No. 8 pp. 333-339.
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.

(56) References Cited

OTHER PUBLICATIONS

Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Notification of Transmittal of the International Search Report and Written Opinion of the International Search Authority for International Application No. PCT/US2014/065408 dated May 6, 2015.
Notification of Transmittal of the International Search Report and Written Opinion of the International Search Authority for International Application No. PCT/US2015/012284 dated May 8, 2015.
Ohno, et al., "Expression of miR-17-92 enhances anti-tumor activity of T-cells transduced with the anti-EGFRvIII chimeric antigen receptor in mice bearing human GBM xenografts" Journal of ImmunoTherapy of Cancer, 1:21 (2013).
Ohno, et al., "Retrovirally engineered T-cell-based immunotherapy targeting type III variant epidermal growth factor receptor, a glioma-associated antigen" Cancer Science, 101(12):2518-2524 (2010).
Okamoto, et al., "Monoclonal antibody against the fusion junction of a deletion-mutant epidermal growth factor receptor" British Journal of Cancer, 73:1366-1372 (1996).
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Paul, W.E. Fundamental Immunology, 3rd Edition, 1993, pp. 292-295.
Pizzitola et al, "Chimeric antigen receptors against CD33/CD123 antigens efficiently target primary acute myeloid leukemia cells in vivo", Leukemia (2014) vol. 28 No. 8 pp. 1596-1605.
Porter et al., "Chimeric antigen receptor-modified T cells in chronic lymphoid leukemia," New England Journal of Medicine 365: 725-733 (2011).
Prinz et al., "High DGK-a and Disabled MAPK Pathways cause Dysfunction of Human Tumor-Infiltrating CD8+ T Cells That Is Reversable by Pharmacologic Intervention," The Journal of Immunology 188: 5990-6000, 2012.
Prosser, et al., "Tumor PD-L1 co-stimulates primary human CD8+ cytotoxic T cells modified to express a PD1: CD28 chimeric receptor" Molecular Immunology, 51:263-272 (2012).
Radhika et al., "Targeting Leukemias by CD123 Specific Chimerica Antigen Receptor" Blood(ASH Annual Meeting Abstracts) 118(21): abstract 1908 (2011).
Rambaldi et al, "Cell-based strategies to manage leukemia relapse: efficacy and feasibility of immunotherapy approaches",Leukemia (2014).,vol. 29, No. 1, pp. 1-10.
Riese et al "Enhanced Effector Responses in Activated CD8+ T Cells Deficient in Diacylglycerol Kinases", Cancer Research (2013) vol. 73 No. 12 pp. 3566-3577.
Riet et al. "Nonviral RNA transfection to transiently modify T cells with chimeric antigen receptors for adoptive therapy", Methods in Molecular Biology, Humana Press, Inc, US, vol. 969, Jan. 1, 2013, pp. 187-201.
Romeo et al., "Cellular immunity to HIV activated by CD4 fused to T cell or Fc receptor polypeptides," Cell 64:1037-1046 (1991).
Rouas et al. "Lentiviral-mediated gene delivery in human monocyte-derived dendritic cells: Optimized design and procedures for highly efficient transduction compatible with clinical constraints". Cancer Gene Therapy (2002) vol. 9 pp. 715-724.
Sadelain et al., "Targeting Tumours with Genetically Enhanced T Lymphocytes," Nature Reviews: Cancer 3: 35-45 (2003).
Sagiv-Barfi, et al., "Ibrutinib enhances the antitumor immune response induced by intratumoral injection of a TLR9 ligand in mouse lymphoma" Blood, 125(13):2079-2086 (2015).
Sagiv-Barfi, et al., "Therapeutic antitumor immunity by checkpoint blockade is enhanced by ibrutinib, an inhibitor of both BTK and ITK" PNAS, 112(9):E966-E972 (2015).

Sampson, et al., "EGFRvIII mCAR-Modified T-Cell Therapy Cures Mice with Established Intracerebral Glioma and Generates Host Immunity against Tumor-Antigen Loss" Clinical Cancer Research, 20(4):972-984 (2013).
Shirasu et al., "Functional Design of Chimeric T-Cell Antigen Receptors for Adoptive Immunotherapy of Cancer: Architecture and Outcomes," AntiCancer Res. 32: 2377-2384 (2012).
Singh, et al., "Third Generation Chimeric Antigen Receptors Containing CD137 or CD134 Signaling Endodomains Augment CD19-Specific T-Cell Effector Function" Blood: Ash Annual Meeting Abstracts; 114:22 (2009).
Stromnes et al. "Abrogation of Src Homology Region 2 Domain-Containing Phosphatase 1 in Tumor-Specific T Cells Improves Efficacy of Adoptive Immunotherapy by Enhancing the Effector Function and Accumulation of Short-Lived Effector T Cells In Vivo",The Journal of Immunology, (2012) vol. 189, No. 4, pp. 1812-1825.
Tettamanti et al., "Targeting of the acute myeloid leukemia stem cells through immunotherapy: development of novel chimeric receptors specific for the CD123 antigen," OMICS group conference 2nd world congress on biotechology (2011) retrieved from internet www.omicsonline.org/biotechnology2011.
Uniprot identifier Q02223-2 accessed Sep. 28, 2015 from <http://www.uniprot.org/uniprot/Q02223>.
Uniprot identifier Q5QGZ9 accessed Oct. 5, 2015 from http://www.uniprot.org/uniprot/Q5QGZ9.
Urbanska et al., "A Universal Strategy for Adoptive Immunotherapy of Cancer Through Use of a Novel T-Cell Antigen Receptor," Cancer Res. 72(7): 1844-1852 (2012).
Van Duyne et al. "Atomic Structure of the Rapamycin Human Immunophilin FKBP-12 Complex" American Chemical Society (1991) vol. 113, pp. 7433-7434.
Van Rhenen et al. "The novel AML stem cell associated antigen CLL-1 aids in discrimination between normal and leukemic stem cells", Blood (2007) vol. 110 No. 7 pp. 2659-2666.
Wang et al. "Overcoming intrinsic inhibitory pathways to augment the antineoplastic activity of adoptively transferred T cells: Re-tuning your CAR before hitting a rocky road", Oncoimmunology (2013) vol. 2, No. 11, p. e264921-3.
Weijyens, "Immuno-gene therapy for renal cancer chimeric receptor-mediated lysis of tumorcells," Thesis: 1-128 (2001).
Written Opinion for PCT/US13/63083. dated Jan. 17, 2014.
Written Opinion of the International Searching Authority for International Application No. PCT/US13/032029, dated Oct. 11, 2014.
Xu V et al: "Closely related T-memory stem cells correlate with in vivo expansion of CAR.CD19-T cells and are preserved by IL-7 and IL-15", Blood, vol. 123, No. 24, Apr. 29, 2014 (Apr. 29, 2014), pp. 3750-3759, XP055201372, ISSN: 0006-4971, DOI:10.1182/blood-2014-01-552174.
Zhao et al. "Targeting C-type lectin-like molecule-1 for antibody-mediated immunotherapy in acute myeloid leukemia", Haematologica (2010) vol. 95 No. 1 pp. 71-78.
Zhong et al., "Enhanced T cell response due to diacylglycerol kinase deficiency" Nature Immunology 4(9): 882-890 (2003).
Singapore Search Report and Written Opinion for Singapore Application No. 11201700418V dated Nov. 2, 2017.
Kanazawa et al. "Dendritic cell immunoreceptors: C-type lectin receptors for pattern-recognition and signaling on antigen-presenting cells" Journal of Dermatological Science (2007) vol. 45, pp. 77-86.
"Illustrated Dictionary of Immunology," Julius M. Cruse, Robert E. Lewis.—2nd ed., CRC Press (2003) pp. 270 & 514.
Singapore Written Opinion for Singapore Application No. 11201700418V dated Sep. 2, 2019.
Yarilin "Osnovy immunologii" Immunology basics: a textbook—M., Medicine (1999) pp. 354-360.
Zhong et al., "Chimeric Antigen Receptors Combining 4-1BB and CD28 Signaling Domains Augment Pl3kinase/AKT/Bcl-XL Activation and CD8+ T cell-mediated Tumor Eradication" Mol Ther (2010) vol. 18, No. 2, pp. 413-420.

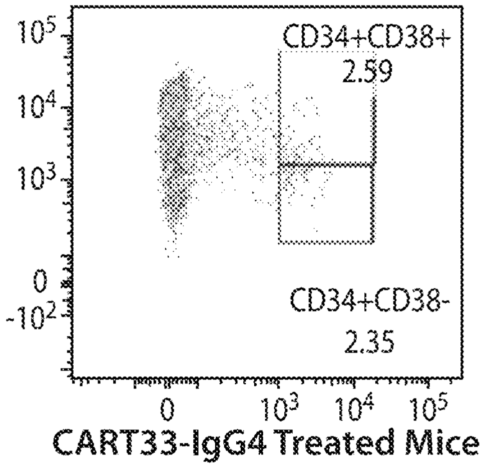
FIG. 19A
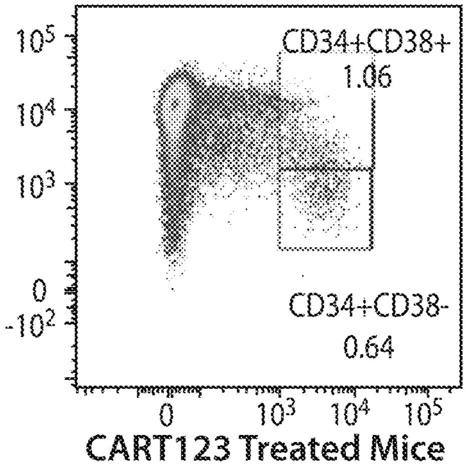
FIG. 19B
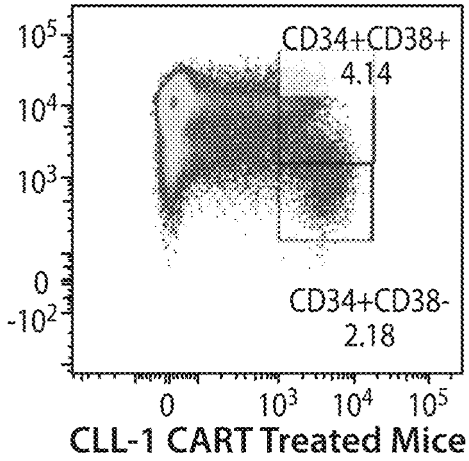
FIG. 19C
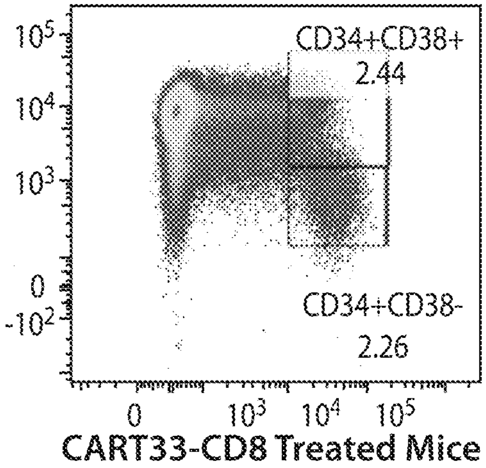
FIG. 19D
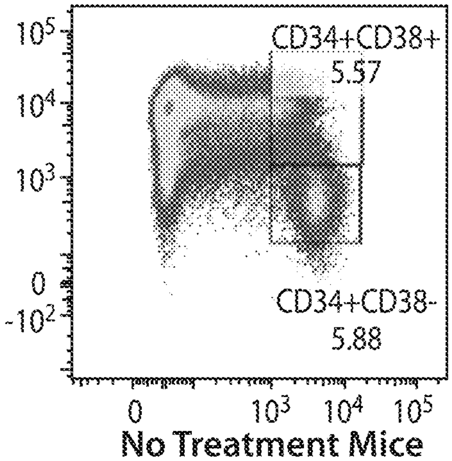
FIG. 19E
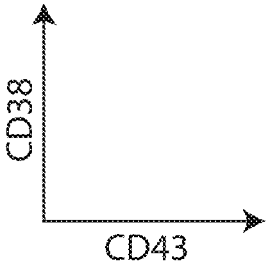

CART33-IgG4 Treated Mice

CART123 Treated Mice

CLL-1 CART Treated Mice

CART33-CD8 Treated Mice

No Treatment Mice

Vector constructs

SEQUENCE LISTING

```
<160> NUMBER OF SEQ ID NOS: 495

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Met Ala Leu Pro Val Thr Ala Leu Leu Leu Pro Leu Ala Leu Leu Leu
1               5                   10                  15

His Ala Ala Arg Pro
            20


<210> SEQ ID NO 2
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 3
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Ser Lys Tyr Gly Pro Pro Cys Pro Pro Cys Pro Ala Pro Glu Phe
1               5                   10                  15
```

```
Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230


<210> SEQ ID NO 4
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
```

```
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly Ser Gly Gly Gly Gly Ser
1               5                   10


<210> SEQ ID NO 6
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 7
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30
```

```
Pro Glu Glu Glu Glu Gly Gly Cys Glu Leu
        35                  40


<210> SEQ ID NO 8
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 9
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
```

-continued

```
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 11
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

cgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184


<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

atggccctgc ctgtgacagc cctgctgctg cctctggctc tgctgctgca tgccgctaga     60

ccc                                                                   63


<210> SEQ ID NO 13
<211> LENGTH: 135
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 14
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
gagagcaagt acggccctcc ctgccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 15
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgcccca 480 cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 19
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 20
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 21
<211> LENGTH: 336
<212> TYPE: DNA
<213> ORGANISM: Homo sapiens

<400> SEQUENCE: 21
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 22
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

Pro Gly Trp Phe Leu Asp Ser Pro Asp Arg Pro Trp Asn Pro Pro Thr
1 5 10 15

Phe Ser Pro Ala Leu Leu Val Val Thr Glu Gly Asp Asn Ala Thr Phe
20 25 30

Thr Cys Ser Phe Ser Asn Thr Ser Glu Ser Phe Val Leu Asn Trp Tyr
35 40 45

Arg Met Ser Pro Ser Asn Gln Thr Asp Lys Leu Ala Ala Phe Pro Glu
50 55 60

Asp Arg Ser Gln Pro Gly Gln Asp Cys Arg Phe Arg Val Thr Gln Leu
65 70 75 80

Pro Asn Gly Arg Asp Phe His Met Ser Val Val Arg Ala Arg Arg Asn
85 90 95

Asp Ser Gly Thr Tyr Leu Cys Gly Ala Ile Ser Leu Ala Pro Lys Ala
100 105 110

Gln Ile Lys Glu Ser Leu Arg Ala Glu Leu Arg Val Thr Glu Arg Arg

```
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370


<210> SEQ ID NO 23
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

atggccctcc ctgtcactgc cctgcttctc cccctcgcac tcctgctcca cgccgctaga      60

ccacccggat ggtttctgga ctctccggat cgcccgtgga atcccccaac cttctcaccg     120

gcactcttgg ttgtgactga gggcgataat gcgaccttca cgtgctcgtt ctccaacacc     180

tccgaatcat tcgtgctgaa ctggtaccgc atgagcccgt caaaccagac cgacaagctc     240

gccgcgtttc cggaagatcg gtcgcaaccg ggacaggatt gtcggttccg cgtgactcaa     300

ctgccgaatg gcagagactt ccacatgagc gtggtccgcg ctaggcgaaa cgactccggg     360

acctacctgt gcggagccat ctcgctggcg cctaaggccc aaatcaaaga gagcttgagg     420

gccgaactga gagtgaccga gcgcagagct gaggtgccaa ctgcacatcc atccccatcg     480

cctcggcctg cggggcagtt tcagaccctg gtcacgacca ctccggcgcc gcgcccaccg     540
```

```
actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182
```

```
<210> SEQ ID NO 24
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240
```

```
Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Gly Gly Ser
1               5


<210> SEQ ID NO 26
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(30)
<223> OTHER INFORMATION: /note="This sequence may encompass 1-6 'Gly Gly
      Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 27
<211> LENGTH: 20
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 27

Gly Gly Gly Gly Ser Gly Gly Gly Gly Ser Gly Gly Gly Gly Ser Gly
1               5                   10                  15

Gly Gly Gly Ser
            20

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Ser
1

<210> SEQ ID NO 30
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5,000
      nucleotides, wherein some positions may be absent"
<220> FEATURE:
<221> NAME/KEY: source
<223> OTHER INFORMATION: /note="See specification as filed for detailed
      description of substitutions and preferred embodiments"

<400> SEQUENCE: 30
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480

-continued aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820

-continued aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 31
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
tttttttttt tttttttttt tttttttttt tttttttttt tttttttttt tttttttttt     60
tttttttttt tttttttttt tttttttttt tttttttttt                          100

<210> SEQ ID NO 32
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5,000
      nucleotides, wherein some positions may be absent"

<400> SEQUENCE: 32
tttttttttt tttttttttt tttttttttt tttttttttt tttttttttt tttttttttt     60
tttttttttt tttttttttt tttttttttt tttttttttt tttttttttt tttttttttt    120
tttttttttt tttttttttt tttttttttt tttttttttt tttttttttt tttttttttt    180
tttttttttt tttttttttt tttttttttt tttttttttt tttttttttt tttttttttt    240
tttttttttt tttttttttt tttttttttt tttttttttt tttttttttt tttttttttt    300
tttttttttt tttttttttt tttttttttt tttttttttt tttttttttt tttttttttt    360
tttttttttt tttttttttt tttttttttt tttttttttt tttttttttt tttttttttt    420
tttttttttt tttttttttt tttttttttt tttttttttt tttttttttt tttttttttt    480
tttttttttt tttttttttt tttttttttt tttttttttt tttttttttt tttttttttt    540
tttttttttt tttttttttt tttttttttt tttttttttt tttttttttt tttttttttt    600
tttttttttt tttttttttt tttttttttt tttttttttt tttttttttt tttttttttt    660
tttttttttt tttttttttt tttttttttt tttttttttt tttttttttt tttttttttt    720
tttttttttt tttttttttt tttttttttt tttttttttt tttttttttt tttttttttt    780
tttttttttt tttttttttt tttttttttt tttttttttt tttttttttt tttttttttt    840
tttttttttt tttttttttt tttttttttt tttttttttt tttttttttt tttttttttt    900
tttttttttt tttttttttt tttttttttt tttttttttt tttttttttt tttttttttt    960
tttttttttt tttttttttt tttttttttt tttttttttt tttttttttt tttttttttt   1020
tttttttttt tttttttttt tttttttttt tttttttttt tttttttttt tttttttttt   1080
tttttttttt tttttttttt tttttttttt tttttttttt tttttttttt tttttttttt   1140
tttttttttt tttttttttt tttttttttt tttttttttt tttttttttt tttttttttt   1200
tttttttttt tttttttttt tttttttttt tttttttttt tttttttttt tttttttttt   1260
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560

-continued

```
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
tttttttttt tttttttttt tttttttttt tttttttttt tttttttttt tttttttttt   3720
tttttttttt tttttttttt tttttttttt tttttttttt tttttttttt tttttttttt   3780
tttttttttt tttttttttt tttttttttt tttttttttt tttttttttt tttttttttt   3840
tttttttttt tttttttttt tttttttttt tttttttttt tttttttttt tttttttttt   3900
```

tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 33
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 100-5,000 nucleotides, wherein some positions may be absent"

<400> SEQUENCE: 33
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720

-continued aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 34
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(400)
<223> OTHER INFORMATION: /note="This sequence may encompass 100-400 nucleotides, wherein some positions may be absent"

<220> FEATURE:
<221> NAME/KEY: source
<223> OTHER INFORMATION: /note="See specification as filed for detailed
description of substitutions and preferred embodiments"

<400> SEQUENCE: 34

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

<210> SEQ ID NO 35
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: misc_feature
<222> LOCATION: (1)..(2000)
<223> OTHER INFORMATION: /note="This sequence may encompass 50-2,000
nucleotides, wherein some positions may be absent"

<400> SEQUENCE: 35

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260
```

```
aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000


<210> SEQ ID NO 36
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
```

```
    210                 215                 220

Leu Ser Leu Gly Lys Met
225                 230


<210> SEQ ID NO 37
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

gagagcaagt acggccctcc ctgcccccct tgccctgccc ccgagttcct gggcggaccc     60

agcgtgttcc tgttcccccc caagcccaag gacaccctga tgatcagccg gacccccgag    120

gtgacctgtg tggtggtgga cgtgtcccag gaggaccccg aggtccagtt caactggtac    180

gtggacggcg tggaggtgca caacgccaag accaagcccc gggaggagca gttcaatagc    240

acctaccggg tggtgtccgt gctgaccgtg ctgcaccagg actggctgaa cggcaaggaa    300

tacaagtgta aggtgtccaa caagggcctg cccagcagca tcgagaaaac catcagcaag    360

gccaagggcc agcctcggga gccccaggtg tacaccctgc cccctagcca agaggagatg    420

accaagaacc aggtgtccct gacctgcctg gtgaagggct tctaccccag cgacatcgcc    480

gtggagtggg agagcaacgg ccagcccgag aacaactaca agaccacccc ccctgtgctg    540

gacagcgacg gcagcttctt cctgtacagc cggctgaccg tggacaagag ccggtggcag    600

gagggcaacg tctttagctg ctccgtgatg cacgaggccc tgcacaacca ctacacccag    660

aagagcctga gcctgtccct gggcaagatg                                      690


<210> SEQ ID NO 38
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(40)
<223> OTHER INFORMATION: /note="This sequence may encompass 1-10 'Gly
      Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 38

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 39
<211> LENGTH: 247
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 39

Glu Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Glu Met Ala Thr Ile Met Gly Gly Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gln Ser Ala Leu Thr Gln Pro Ala Ser
130 135 140

Val Ser Gly Ser Pro Gly Gln Ser Ile Thr Ile Ser Cys Thr Gly Thr
145 150 155 160

Ser Ser Asp Val Gly Gly Tyr Asn Tyr Val Ser Trp Tyr Gln Gln His
165 170 175

Pro Gly Lys Ala Pro Lys Leu Met Ile Tyr Asp Val Ser Asn Arg Pro
180 185 190

Ser Gly Val Ser Asn Arg Phe Ser Gly Ser Lys Ser Gly Asn Thr Ala
195 200 205

Ser Leu Thr Ile Ser Gly Leu Gln Ala Glu Asp Glu Ala Asp Tyr Tyr
210 215 220

Cys Ser Ser Tyr Thr Ser Ser Ser Thr Leu Asp Val Val Phe Gly Gly
225 230 235 240

Gly Thr Lys Leu Thr Val Leu
245

<210> SEQ ID NO 40
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Leu Ile Ser Gly Asp Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Val Glu Asp Thr Ala Val Tyr Tyr Cys
                85                  90                  95

Ala Arg Val Phe Asp Ser Tyr Tyr Met Asp Val Trp Gly Lys Gly Thr
            100                 105                 110

Thr Val Thr Val Ser Ser Gly Gly Gly Gly Ser Gly Gly Gly Gly Ser
        115                 120                 125

Gly Ser Gly Gly Ser Glu Ile Val Leu Thr Gln Ser Pro Leu Ser Leu
    130                 135                 140

Pro Val Thr Pro Gly Gln Pro Ala Ser Ile Ser Cys Arg Ser Ser Gln
145                 150                 155                 160

Ser Leu Val Tyr Thr Asp Gly Asn Thr Tyr Leu Asn Trp Phe Gln Gln
                165                 170                 175

Arg Pro Gly Gln Ser Pro Arg Arg Leu Ile Tyr Lys Val Ser Asn Arg
            180                 185                 190

Asp Ser Gly Val Pro Asp Arg Phe Ser Gly Ser Gly Ser Asp Thr Asp
        195                 200                 205

Phe Thr Leu Lys Ile Ser Arg Val Glu Ala Glu Asp Val Gly Ile Tyr
    210                 215                 220

Tyr Cys Met Gln Gly Thr His Trp Ser Phe Thr Phe Gly Gln Gly Thr
225                 230                 235                 240

Arg Leu Glu Ile Lys
                245


<210> SEQ ID NO 41
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Lys Tyr Val Thr Ala Ala Asp Thr Ala Val Tyr Tyr
                85                  90                  95

Cys Ala Thr Pro Gly Thr Tyr Tyr Asp Phe Leu Ser Gly Tyr Tyr Pro
            100                 105                 110

Phe Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Asp Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Ser Ser Tyr Leu Ala Trp Tyr
                165                 170                 175
```

```
Gln Gln Lys Pro Gly Lys Ala Pro Lys Leu Leu Ile Tyr Ala Ala Ser
            180                 185                 190

Thr Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Leu Asn Ser Tyr Pro Tyr Thr Phe Gly Gln
225                 230                 235                 240

Gly Thr Lys Leu Glu Ile Lys
                245


<210> SEQ ID NO 42
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Ala Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Leu Arg Ser Gly Arg Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Ile Val Leu Thr Gln Ser Pro Gly Thr Leu Ser Leu
    130                 135                 140

Ser Pro Gly Gly Arg Ala Thr Leu Ser Cys Arg Ala Ser Gln Ser Ile
145                 150                 155                 160

Ser Gly Ser Phe Leu Ala Trp Tyr Gln Gln Lys Pro Gly Gln Ala Pro
                165                 170                 175

Arg Leu Leu Ile Tyr Gly Ala Ser Ser Arg Ala Thr Gly Ile Pro Asp
            180                 185                 190

Arg Phe Ser Gly Ser Gly Ser Gly Thr Asp Phe Thr Leu Thr Ile Ser
        195                 200                 205

Arg Leu Glu Pro Glu Asp Phe Ala Val Tyr Tyr Cys Gln Gln Tyr Gly
    210                 215                 220

Ser Ser Pro Pro Thr Phe Gly Leu Gly Thr Lys Leu Glu Ile Lys
225                 230                 235


<210> SEQ ID NO 43
<211> LENGTH: 245
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 43

```
Glu Val Gln Leu Gln Gln Ser Gly Pro Gly Leu Val Arg Pro Ser Glu
1               5                   10                  15

Thr Leu Ser Leu Thr Cys Thr Val Ser Gly Gly Pro Val Arg Ser Gly
            20                  25                  30

Ser His Tyr Trp Asn Trp Ile Arg Gln Pro Pro Gly Arg Gly Leu Glu
        35                  40                  45

Trp Ile Gly Tyr Ile Tyr Tyr Ser Gly Ser Thr Asn Tyr Asn Pro Ser
    50                  55                  60

Leu Glu Asn Arg Val Thr Ile Ser Ile Asp Thr Ser Asn Asn His Phe
65                  70                  75                  80

Ser Leu Lys Leu Ser Ser Val Thr Ala Ala Asp Thr Ala Leu Tyr Phe
                85                  90                  95

Cys Ala Arg Gly Thr Ala Thr Phe Asp Trp Asn Phe Pro Phe Asp Ser
            100                 105                 110

Trp Gly Gln Gly Thr Leu Val Thr Val Ser Ser Gly Gly Gly Gly Ser
        115                 120                 125

Gly Gly Gly Gly Ser Gly Ser Gly Gly Ser Asp Ile Gln Met Thr Gln
    130                 135                 140

Ser Pro Ser Ser Leu Ser Ala Ser Ile Gly Asp Arg Val Thr Ile Thr
145                 150                 155                 160

Cys Arg Ala Ser Gln Ser Ile Ser Ser Tyr Leu Asn Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Ser Thr Pro Trp Thr Phe Gly Gln Gly Thr
225                 230                 235                 240

Lys Leu Glu Ile Lys
                245
```

<210> SEQ ID NO 44
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Val
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Gly Ser Gly Leu Val Val Tyr Ala Ile Arg Val Gly Ser Gly Trp
            100                 105                 110

Phe Asp Tyr Trp Gly Gln Gly Thr Leu Val Thr Val Ser Ser Gly Gly
        115                 120                 125

Gly Gly Ser Gly Gly Gly Asp Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Met Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Pro Trp Thr Phe
225                 230                 235                 240

Gly Gln Gly Thr Lys Val Asp Ile Lys
                245


<210> SEQ ID NO 45
<211> LENGTH: 255
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Ser Ser Gly Ser Tyr Tyr Met Glu Asp Ser Tyr
            100                 105                 110

Tyr Tyr Gly Met Asp Val Trp Gly Gln Gly Thr Thr Val Thr Val Ser
        115                 120                 125

Ser Gly Gly Gly Gly Ser Gly Gly Gly Gly Ser Gly Gly Gly Gly Ser
    130                 135                 140

Asn Phe Met Leu Thr Gln Pro His Ser Val Ser Glu Ser Pro Gly Lys
145                 150                 155                 160

Thr Val Thr Ile Ser Cys Thr Gly Ser Ser Gly Ser Ile Ala Ser Asn
                165                 170                 175
```

```
Tyr Val Gln Trp Tyr Gln Gln Arg Pro Gly Ser Ala Pro Thr Thr Val
            180                 185                 190

Ile Tyr Glu Asp Asn Gln Arg Pro Ser Gly Val Pro Asp Arg Phe Ser
        195                 200                 205

Gly Ser Ile Asp Ser Ser Ser Asn Ser Ala Ser Leu Thr Ile Ser Gly
    210                 215                 220

Leu Lys Thr Glu Asp Glu Ala Asp Tyr Tyr Cys Gln Ser Tyr Asp Ser
225                 230                 235                 240

Ser Asn Gln Val Val Phe Gly Gly Gly Thr Lys Leu Thr Val Leu
                245                 250                 255


<210> SEQ ID NO 46
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Gly Ser Ser Trp Glu Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro Leu Thr Phe Gly Gly Gly Thr Lys Leu Glu Ile Lys
225                 230                 235


<210> SEQ ID NO 47
<211> LENGTH: 246
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 47

Gln Val Gln Leu Val Gln Ser Gly Ala Glu Val Lys Glu Pro Gly Ala
1 5 10 15

Ser Val Lys Val Ser Cys Lys Ala Pro Ala Asn Thr Phe Ser Asp His
20 25 30

Val Met His Trp Val Arg Gln Ala Pro Gly Gln Arg Phe Glu Trp Met
35 40 45

Gly Tyr Ile His Ala Ala Asn Gly Gly Thr His Tyr Ser Gln Lys Phe
50 55 60

Gln Asp Arg Val Thr Ile Thr Arg Asp Thr Ser Ala Asn Thr Val Tyr
65 70 75 80

Met Asp Leu Ser Ser Leu Arg Ser Glu Asp Thr Ala Val Tyr Tyr Cys
85 90 95

Ala Arg Gly Gly Tyr Asn Ser Asp Ala Phe Asp Ile Trp Gly Gln Gly
100 105 110

Thr Met Val Thr Val Ser Ser Gly Gly Gly Gly Ser Gly Gly Gly Gly
115 120 125

Ser Gly Gly Gly Gly Ser Gly Gly Gly Gly Ser Asp Ile Val Met Thr
130 135 140

Gln Ser Pro Ser Ser Val Ser Ala Ser Val Gly Asp Arg Val Thr Ile
145 150 155 160

Thr Cys Arg Ala Ser Gln Asp Ile Ser Ser Trp Leu Ala Trp Tyr Gln
165 170 175

Gln Lys Pro Gly Lys Ala Pro Lys Leu Leu Ile Tyr Ala Ala Ser Ser
180 185 190

Leu Gln Ser Gly Val Pro Ser Arg Phe Asn Gly Ser Gly Ser Gly Thr
195 200 205

Asp Phe Thr Leu Thr Ile Ser Ser Leu Gln Pro Glu Asp Phe Ala Thr
210 215 220

Tyr Tyr Cys Gln Gln Ser Tyr Ser Thr Pro Leu Thr Phe Gly Gly Gly
225 230 235 240

Thr Lys Val Glu Ile Lys
245

<210> SEQ ID NO 48
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 48

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

```
Leu Gln Met Asn Ser Leu Arg Ala Glu Asp Thr Ala Val Tyr Tyr Cys
                85                  90                  95

Ala Arg Asp Leu Ser Val Arg Ala Ile Asp Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Val
    130                 135                 140

Leu Thr Gln Ser Pro Ser Ser Leu Ser Ala Ser Val Gly Asp Arg Val
145                 150                 155                 160

Thr Ile Thr Cys Gln Ala Ser Gln Asp Ile Ser Asn Tyr Leu Asn Trp
                165                 170                 175

Tyr Gln Gln Lys Pro Gly Lys Ala Pro Lys Leu Leu Ile Tyr Asp Ala
            180                 185                 190

Ser Asn Leu Glu Thr Gly Val Pro Ser Arg Phe Ser Gly Ser Gly Ser
        195                 200                 205

Gly Thr Asp Phe Thr Phe Thr Ile Ser Ser Leu Gln Pro Glu Asp Phe
    210                 215                 220

Ala Thr Tyr Tyr Cys Gln Gln Ala Tyr Ser Thr Pro Phe Thr Phe Gly
225                 230                 235                 240

Pro Gly Thr Lys Val Glu Ile Lys
                245
```

<210> SEQ ID NO 49
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Glu Val Gln Leu Val Gln Ser Gly Gly Gly Val Val Arg Ser Gly Arg
1               5                   10                  15

Ser Leu Arg Leu Ser Cys Ala Ala Ser Gly Phe Thr Phe Asn Ser Tyr
            20                  25                  30

Gly Leu His Trp Val Arg Gln Ala Pro Gly Lys Gly Leu Glu Trp Val
        35                  40                  45

Ala Leu Ile Glu Tyr Asp Gly Ser Asn Lys Tyr Tyr Gly Asp Ser Val
    50                  55                  60

Lys Gly Arg Phe Thr Ile Ser Arg Asp Lys Ser Lys Ser Thr Leu Tyr
65                  70                  75                  80

Leu Gln Met Asp Asn Leu Arg Ala Glu Asp Thr Ala Val Tyr Tyr Cys
                85                  90                  95

Ala Arg Glu Gly Asn Glu Asp Leu Ala Phe Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ser Ser Leu Ser Ala Ser Val Gly Asp Arg Val Thr Ile
145                 150                 155                 160

Thr Cys Gln Ala Ser Gln Phe Ile Lys Lys Asn Leu Asn Trp Tyr Gln
                165                 170                 175
```

-continued

```
His Lys Pro Gly Lys Ala Pro Lys Leu Leu Ile Tyr Asp Ala Ser Ser
            180                 185                 190

Leu Gln Thr Gly Val Pro Ser Arg Phe Ser Gly Asn Arg Ser Gly Thr
        195                 200                 205

Thr Phe Ser Phe Thr Ile Ser Ser Leu Gln Pro Glu Asp Val Ala Thr
    210                 215                 220

Tyr Tyr Cys Gln Gln His Asp Asn Leu Pro Leu Thr Phe Gly Gly Gly
225                 230                 235                 240

Thr Lys Val Glu Ile Lys
                245
```

<210> SEQ ID NO 50
<211> LENGTH: 255
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Ser Ser Asn
            20                  25                  30

Tyr Met Thr Trp Val Arg Gln Ala Pro Gly Lys Gly Leu Glu Trp Val
        35                  40                  45

Ser Val Ile Tyr Ser Gly Gly Ala Thr Tyr Tyr Gly Asp Ser Val Lys
    50                  55                  60

Gly Arg Phe Thr Val Ser Arg Asp Asn Ser Lys Asn Thr Val Tyr Leu
65                  70                  75                  80

Gln Met Asn Arg Leu Thr Ala Glu Asp Thr Ala Val Tyr Tyr Cys Ala
                85                  90                  95

Arg Asp Arg Leu Tyr Cys Gly Asn Asn Cys Tyr Leu Tyr Tyr Tyr Tyr
            100                 105                 110

Gly Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Val Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Ala Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
    210                 215                 220

Leu Gln Pro Glu Asp Phe Ala Thr Tyr Tyr Cys Gln Gln Ser Tyr Ser
225                 230                 235                 240

Thr Pro Pro Leu Thr Phe Gly Gln Gly Thr Lys Val Glu Ile Lys
                245                 250                 255
```

<210> SEQ ID NO 51
<211> LENGTH: 247
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Gln Val Gln Leu Val Gln Ser Gly Ala Glu Val Lys Lys Ser Gly Ala
1               5                   10                  15

Ser Val Lys Val Ser Cys Lys Ala Ser Gly Tyr Pro Phe Thr Gly Tyr
            20                  25                  30

Tyr Ile Gln Trp Val Arg Gln Ala Pro Gly Gln Gly Leu Glu Trp Met
        35                  40                  45

Gly Trp Ile Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Ser Tyr Gly Tyr Tyr Tyr Gly Met Asp Val Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Phe Thr Cys Arg Ala Ser Gln Gly Ile Ser Ser Ala Leu Ala Trp Tyr
                165                 170                 175

Gln Gln Lys Pro Gly Lys Pro Pro Lys Leu Leu Ile Tyr Asp Ala Ser
            180                 185                 190

Ser Leu Glu Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Phe Asn Asn Tyr Pro Leu Thr Phe Gly Gly
225                 230                 235                 240

Gly Thr Lys Val Glu Ile Lys
                245
```

<210> SEQ ID NO 52
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

```
gaagtgcaac tccaacagtc aggcgcagaa gtcaagaagc ccggatcgtc agtgaaagtg      60

tcctgcaaag cctccggcgg aaccttcagc tcctacgcaa tcagctgggt gcggcaggcg     120

cccggacagg gactggagtg gatgggcggt atcattccga tctttggcac cgccaattac     180

gcccagaagt tccagggacg cgtcacaatc accgccgacg aatcgacttc caccgcctac     240

atggagctgt cgtccttgag gagcgaagat accgccgtgt actactgcgc tcgggatctg     300

gagatggcca ctatcatggg ggttactgg ggccagggga ccctggtcac tgtgtcctcg     360
```

ggaggagggg gatcaggcgg cggcggttcc gggggaggag gaagccagtc cgcgctgact 420
cagccagctt ccgtgtctgg ttcgccggga cagtccatca ctattagctg taccggcacc 480
agcagcgacg tgggcggcta caactatgtg tcatggtacc agcagcaccc ggggaaggcg 540
cctaagctga tgatctacga cgtgtccaac cgccctagcg gagtgtccaa cagattctcc 600
ggttcgaagt cagggaacac tgcctccctc acgattagcg ggctgcaagc cgaggatgaa 660
gccgactact actgctcctc ctatacctcc tcctcgaccc tggacgtggt gttcggagga 720
ggcaccaagc tcaccgtcct t 741

<210> SEQ ID NO 53
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53
gaagtgcaat tggtggaaag cggaggagga gtggtgcaac ctggaggaag cctgagactg 60
tcatgtgccg cctcgggatt cactttcgat gactacgcaa tgcactgggt ccgccaggcc 120
cccggaaagg gtctggaatg ggtgtccctc atctccggcg atgggggttc cacttactat 180
gcggattctg tgaagggccg cttcacaatc tcccgggaca attccaagaa cactctgtac 240
cttcaaatga actccctgag ggtggaggac accgctgtgt actactgcgc gagagtgttt 300
gactcgtact atatggacgt ctggggaaag ggcaccaccg tgaccgtgtc cagcggtggc 360
ggtggatcgg ggggcggcgg ctccgggagc ggaggttccg agattgtgct gactcagtcg 420
ccgttgtcac tgcctgtcac ccccgggcag ccggcctcca tttcatgccg gtccagccag 480
tccctggtct acaccgatgg gaacacttac ctcaactggt tccagcagcg cccaggacag 540
tccccgcgga ggctgatcta caaagtgtca aaccgggact ccggcgtccc cgatcggttc 600
tcgggaagcg gcagcgacac cgacttcacg ctgaagattt cccgcgtgga agccgaggac 660
gtgggcatct actactgtat gcagggcacc cactggtcgt ttaccttcgg acaaggaact 720
aggctcgaga tcaag 735

<210> SEQ ID NO 54
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54
caagtgcagc ttcaagaaag cggtccagga ctcgtcaagc catcagaaac tctttccctc 60
acttgtaccg tgtcgggagg cagcatctcc tcgagctcct actactgggg ttggattaga 120
cagcccccgg gaaaggggtt ggagtggatc ggttccatct actactccgg gtcgacctac 180
tacaaccctt ccctgaaatc tcgggtgtcc atctccgtcg acacctccaa gaaccagttc 240
agcctgaagc tgaaatatgt gaccgcggcc gatactgccg tgtactattg cgccaccccg 300
ggaacctact acgacttcct ctcggggtac tacccgtttt actggggaca ggggactctc 360
gtgaccgtgt cctcgggcgg cggaggttca ggcggtggcg gatcgggggg aggaggctca 420

```
gacattgtga tgacccagag cccgtccagc ctgagcgcct ccgtgggcga tagggtcacg    480

attacttgcc gggcgtccca gggaatctca agctacctgg cctggtacca acagaagccc    540

ggaaaggcac ccaagttgct gatctatgcc gctagcactc tgcagtccgg ggtgccttcc    600

cgcttctccg gctccggctc gggcaccgac ttcaccctga ccatttcctc actgcaaccc    660

gaggacttcg ccacttacta ctgccagcag ctgaactcct acccttacac attcggacag    720

ggaaccaagc tggaaatcaa g                                              741


<210> SEQ ID NO 55
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

caagtgcaac tcgtggaatc tggtggagga ctcgtgcaac ccggaggatc attgcgactc     60

tcgtgtgcgg catccggctt taccttttca tcctactgga tgtcctgggt cagacaggcc    120

cccgggaagg gactggaatg ggtcgcgaac atcaacgagg acggctcggc caagttctac    180

gtggactccg tgaagggccg cttcacgatc tcacgggata acgccaagaa ttccctgtat    240

ctgcaaatga acagcctgag ggccgaggac actgcggtgt acttctgcgc acgcgacctg    300

aggtccggga gatactgggg acagggcacc ctcgtgaccg tgtcgagcgg aggagggggg    360

tcgggcggcg gcggttccgg tggcggcggt agcgaaattg tgttgaccca gtcccctgga    420

accctgagcc tgtcacctgg aggacgcgcc accctgtcct gccgggccag ccagagcatc    480

tcagggtcct tcctggcttg gtaccagcag aagccgggac aggctccgag acttctgatc    540

tacggcgcct cctcgcgggc gaccggaatc ccggatcggt tctccggctc gggaagcgga    600

actgacttca ctcttaccat ttcccgcctg gagccggaag atttcgccgt gtactactgc    660

cagcagtacg ggtcatcccc tccaaccttc ggcctgggaa ctaagctgga aatcaaa       717


<210> SEQ ID NO 56
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56

gaagtgcaac tccaacaatc cggtccagga ctcgtcagac cctccgaaac tctctcgctt     60

acatgcactg tgtccggcgg ccctgtgcgg tccggctctc attactggaa ctggattcgc    120

cagcccccgg gacgcggact ggagtggatc ggctacatct attactcggg gtcgactaac    180

tacaacccga gcctggaaaa tagagtgacc atctcaatcg acacgtccaa caaccacttc    240

tcgctgaagt tgtcctccgt gactgccgcc gatactgccc tgtacttctg tgctcgcgga    300

accgccacct tcgactggaa cttccctttt gactcatggg gccaggggac ccttgtgacc    360

gtgtccagcg gaggaggagg ctccggtggt ggcgggagcg gtagcggcgg aagcgacatc    420

cagatgaccc agtcaccgtc ctcgctgtcc gcatccattg gggatcgggt cactattact    480

tgccgggcgt cccagtccat ctcgtcctac ctgaactggt atcagcagaa gccagggaaa    540

gcccccaagc tgctgatcta cgcggccagc agcctgcagt caggagtgcc ttcaaggttt    600
```

agcggcagcg gatcgggaac cgacttcacc ctgaccattt cctccctcca acccgaggat 660
ttcgccacct actactgcca gcagtcctac tccaccccgt ggaccttcgg acagggaacc 720
aagctggaga tcaag 735

<210> SEQ ID NO 57
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57
caagtgcaac ttcaagaatc aggcgcagga cttctcaagc catccgaaac actctccctc 60
acttgcgcgg tgtacggggg aagcttctcg ggatactact ggtcctggat taggcagcct 120
cccggcaaag gcctggaatg ggtcggggag atcaaccact ccggttcaac caactacaac 180
ccgtcgctga agtcccgcgt gaccatttcc gtggacacct ctaagaatca gttcagcctg 240
aagctctcgt ccgtgaccgc ggcggacacc gccgtctact actgcgctcg gggatcagga 300
ctggtggtgt acgccatccg cgtgggctcg ggctggttcg attactgggg ccagggaacc 360
ctggtcactg tgtcgtccgg cggaggaggt tcgggggggcg gagacagcgg tggagggggt 420
agcgacatcc agatgaccca gtccccgtcc tcgctgtccg cctccgtggg agatagagtg 480
accatcacct gtcgggcatc ccagagcatt tccagctacc tgaactggta tcagcagaag 540
cccggaaagg cccctaagct gttgatgtac gccgccagca gcttgcagtc gggcgtgccg 600
agccggtttt ccggttccgg ctccgggact gacttcaccc tgactatctc atccctgcaa 660
cccgaggact tcgccactta ttactgccag cagtcctact caacccctcc ctggacgttc 720
ggacagggca ccaaggtcga tatcaag 747

<210> SEQ ID NO 58
<211> LENGTH: 765
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58
gaagtgcaat tggtggaatc tggaggagga cttgtgaaac ctggtggaag cctgagactt 60
tcctgtgcgg cctcgggatt cactttctcc tcctactcca tgaactgggt cagacaggcc 120
cctgggaagg gactggaatg ggtgtcatcc atctcctcct catcgtcgta catctactac 180
gccgatagcg tgaaggggcg gttcaccatt tcccgggaca acgctaagaa cagcctctat 240
ctgcaaatga attccctccg cgccgaggac actgccgtgt actactgcgc gagggacccc 300
tcatcaagcg gcagctacta catggaggac tcgtattact acggaatgga cgtctggggc 360
cagggaacca ctgtgacggt gtcctccggt ggagggggct ccgggggcgg gggatctggc 420
ggaggaggct ccaacttcat gctgacccag ccgcactccg tgtccgaaag ccccggaaag 480
accgtgacaa tttcctgcac cgggtcctcc ggctcgatcg catcaaacta cgtgcagtgg 540
taccagcagc gcccgggcag cgcccccacc actgtcatct acgaggataa ccagcggccg 600
tcgggtgtcc cagaccggtt ttccggttcg atcgatagca gcagcaacag cgcctccctg 660
accatttccg gcctcaagac cgaggatgag gctgactact actgccagtc gtatgactcc 720
tcgaaccaag tggtgttcgg tggcggcacc aagctgactg tgctg 765

<210> SEQ ID NO 59
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59
caagtgaacc tgagagaaag cggcggagga cttgtgcaac ctggaggaag cctgagactg 60
tcatgtgccg cgtccggctt caccttctcg tcctacgaga tgaactgggt ccgccaggca 120
ccgggcaaag gactggaatg ggtgtcctac atttcctcgt ccgggtccac catctattac 180
gccgactccg tgaagggacg gttcaccatc tcccgggaca acgccaagaa ctccctctac 240
ctccaaatga actcactgag ggcagaggac actgcggtct actactgcgc ccgcgaagct 300
ttgggtagct cctgggagtg gggccaggga accactgtga ccgtgtcctc gggtggaggg 360
ggctccggtg gcgggggttc agggggtggc ggaagcgata tccagatgac tcagtcacca 420
agctccctga gcgcctcagt gggagatcgg gtcacaatca cgtgccaggc gtcccaggac 480
atttctaact acctcaattg gtaccagcag aagccgggga aggcccccaa gcttctgatc 540
tacgatgcct ccaacctgga aaccggcgtg ccctcccgct tctcgggatc gggcagcggc 600
actgacttca cctttaccat ctcgtccctg caacctgagg acatcgccac ctattactgc 660
cagcagtacg ataacctccc gctgactttc ggaggcggaa ctaagctgga gattaag 717

<210> SEQ ID NO 60
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60
caagtgcaac tcgtccagtc cggtgcagaa gtcaaggaac ccggagcctc cgtgaaagtg 60
tcctgcaaag ctcctgccaa cactttctcg gaccacgtga tgcactgggt gcgccaggcg 120
ccgggccagc gcttcgaatg gatgggatac attcatgccg ccaatggcgg tacccactac 180
tcccaaaagt tccaggatag agtcaccatc acccgggaca ccagcgccaa caccgtgtat 240
atggatctgt ccagcctgag gtccgaggat accgccgtgt actactgcgc ccggggcgga 300
tacaactcag acgcgttcga catttgggga cagggtacta tggtcaccgt gtcatccggg 360
ggcggtggca gcgggggcgg aggctctggc ggaggcggat caggggggagg agggtccgac 420 atcgtgatga cccagtcccc gtcatcggtg tccgcgtccg tgggagacag agtgaccatc 480
acgtgtcgcg ccagccagga catctcctcg tggttggcat ggtaccagca gaagcctgga 540
aaggccccga agctgctcat ctacgccgcc tcctcccttc aatcgggagt gccctcgcgg 600
ttcaacggaa gcggaagcgg gacagatttt accctgacta ttagctcgct gcagcccgag 660
gacttcgcta cttactactg ccaacagagc tactccaccc cactgacttt cggcgggggt 720
accaaggtcg agatcaag 738

<210> SEQ ID NO 61
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61
caagtgcaac ttgttcaatc cggtggaggt cttgtgcagc ccggaggatc actcagactg 60
tcgtgcgccg cctctgggtt cactttctcc tcatactcga tgaactgggt gcgccaggcg 120
ccgggaaagg gcctggaatg ggtgtcatac atctcctcct catcctccac catctactac 180
gccgattccg tgaagggccg cttcactatt tcccgggaca acgcgaaaaa ctcgctctat 240
ctgcaaatga actccctgcg cgccgaggac accgccgtgt actactgcgc ccgggacctg 300
agcgtgcggg ctattgatgc gttcgacatc tggggacagg gcaccatggt cacagtgtcc 360
agcggaggcg gcggcagcgg tggaggagga tcagggggag gaggttcggg gggcggtggc 420
tccgatatcg tgctgaccca gagcccgtcg agcctctccg cctccgtcgg cgacagagtg 480
accatcacgt gtcaggcatc ccaggacatt agcaactacc tgaattggta ccagcagaag 540
cctggaaagg cacccaagtt gctgatctac gacgcctcca acctggaaac cggagtgcca 600
tccaggttct cgggcagcgg ctcgggaacc gacttcactt ttactatctc ctccctgcaa 660
cccgaggatt tcgcgaccta ctactgccag caggcctaca gcaccccttt caccttcggg 720
ccgggaacta aggtcgaaat caag 744

<210> SEQ ID NO 62
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62
gaagtgcaat tggtgcaatc aggaggagga gtggtcagat ctggaagaag cctgagactg 60
tcatgcgcgg cttcgggctt taccttcaac tcctacggcc tccactgggt gcgccaggcc 120
cccggaaaag gcctcgaatg ggtcgcactg attgagtacg acgggtccaa caagtactac 180
ggagatagcg tgaagggccg cttcaccatc tcacgggaca agtccaagtc caccctgtat 240
ctgcaaatgg acaacctgag ggccgaggat actgccgtgt actactgcgc ccgcgaagga 300
aacgaagatc tggccttcga tatttggggc cagggtactc ttgtgaccgt gtcgagcgga 360
ggcggaggct ccggtggagg aggatcgggg ggtggtggtt ccggcggcgg ggggagcgaa 420
atcgtgctga cccagtcgcc ttcctccctc tccgcttccg tgggggaccg ggtcactatt 480
acgtgtcagg cgtcccaatt catcaagaag aatctgaact ggtaccagca caagccggga 540
aaggccccca aactgctcat ctacgacgcc agctcgctgc agactggcgt gccttcccgg 600
ttttccggga accggtcggg aaccaccttc tcattcacca tcagcagcct ccagccggag 660
gacgtggcga cctactactg ccagcagcat gacaaccttc cactgacttt cggcgggggc 720
accaaggtcg agattaag 738

<210> SEQ ID NO 63
<211> LENGTH: 765
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63
caagtgcaac tcgtggaatc aggcggagga ctcgtgcaac ccggaggttc ccttagactg 60
tcatgtgccg cttccgggtt caatgtgtcc agcaactaca tgacctgggt cagacaggcg 120
ccgggaaagg gacttgaatg ggtgtccgtg atctactccg gtggagcaac atactacgga 180
gactccgtga aaggccgctt taccgtgtcc cgcgataact cgaagaacac cgtgtacttg 240
cagatgaaca ggctgactgc cgaggacacc gccgtgtatt attgcgcccg ggacaggctg 300
tactgtggaa acaactgcta cctgtactac tactacggga tggacgtgtg gggacagggc 360
actctcgtca ctgtgtcatc cggggggggc ggtagcggtg gcggagggtc cggcggagga 420
ggctcagggg gaggcggaag cgatatccag gtcacccagt ctccctcctc gctgtccgcc 480
tccgtgggcg accgcgtcac cattacttgc cgggcgtcgc agtcgatcag ctcctacctg 540
aactggtacc agcagaagcc tggaaaggcc ccgaagctgc tgatctacgc ggcctcgtcc 600
ctgcaaagcg gcgtcccgtc gcggttcagc ggttccggtt cgggaaccga cttcaccctg 660
actatttcct ccctgcaacc cgaggatttc gccacttact actgccagca gtcctactcc 720
accccacctc tgaccttcgg ccaaggaacc aaggtcgaaa tcaag 765

<210> SEQ ID NO 64
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64
caagtgcaac tcgtccagtc cggtgcagaa gtgaaaaaga gcggagcctc agtgaaagtg 60
tcctgcaagg cctccggtta ccccttcact ggatactaca ttcagtgggt ccgccaagcc 120
ccgggacagg gtctggagtg gatggggtgg attgacccta actcgggaaa tacgggatac 180
gcgcagaagt tccagggccg cgtgaccatg accaggaaca cctcgatcag caccgcctac 240
atggaactgt cctccctgcg gtcggaggat actgccgtgt actactgcgc ctccgattcc 300
tatgggtact actacggaat ggacgtctgg ggacagggca ccctcgtgac cgtgtcctcg 360
ggaggcggag ggagcggcgg gggtggatcg ggaggaggcg gctccggcgg cggcggtagc 420
gacatccaga tgacccagtc accatcaagc cttagcgcct ccgtgggcga cagagtgaca 480
ttcacttgtc gggcgtccca gggaatctcc tccgctctgg cttggtatca gcagaagcct 540
gggaagcctc cgaagctgtt gatctacgac gcgagcagcc tggaatcagg ggtgccctcc 600
cggttttccg ggtccggttc tggcaccgat ttcaccctga ccatttcgtc cctccaaccc 660
gaggacttcg ccacttacta ctgccagcag ttcaacaact acccgctgac cttcggagga 720
ggcactaagg tcgagatcaa g 741

<210> SEQ ID NO 65
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 65

Glu Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Glu Met Ala Thr Ile Met Gly Gly Tyr Trp Gly Gln
100 105 110

Gly Thr Leu Val Thr Val Ser Ser
115 120

<210> SEQ ID NO 66
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 66

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Leu Ile Ser Gly Asp Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Ala Arg Val Phe Asp Ser Tyr Tyr Met Asp Val Trp Gly Lys Gly Thr
100 105 110

Thr Val Thr Val Ser Ser
115

<210> SEQ ID NO 67
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 67

Gln Val Gln Leu Gln Glu Ser Gly Pro Gly Leu Val Lys Pro Ser Glu
1 5 10 15

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Lys Tyr Val Thr Ala Ala Asp Thr Ala Val Tyr Tyr
                85                  90                  95

Cys Ala Thr Pro Gly Thr Tyr Tyr Asp Phe Leu Ser Gly Tyr Tyr Pro
            100                 105                 110

Phe Tyr Trp Gly Gln Gly Thr Leu Val Thr Val Ser Ser
        115                 120                 125


<210> SEQ ID NO 68
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Ala Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Leu Arg Ser Gly Arg Tyr Trp Gly Gln Gly Thr Leu Val
            100                 105                 110

Thr Val Ser Ser
        115


<210> SEQ ID NO 69
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Gln Gln Ser Gly Pro Gly Leu Val Arg Pro Ser Glu
1               5                   10                  15

Thr Leu Ser Leu Thr Cys Thr Val Ser Gly Gly Pro Val Arg Ser Gly
            20                  25                  30

Ser His Tyr Trp Asn Trp Ile Arg Gln Pro Pro Gly Arg Gly Leu Glu
        35                  40                  45
```

```
Trp Ile Gly Tyr Ile Tyr Tyr Ser Gly Ser Thr Asn Tyr Asn Pro Ser
    50                  55                  60

Leu Glu Asn Arg Val Thr Ile Ser Ile Asp Thr Ser Asn Asn His Phe
65                  70                  75                  80

Ser Leu Lys Leu Ser Ser Val Thr Ala Ala Asp Thr Ala Leu Tyr Phe
                85                  90                  95

Cys Ala Arg Gly Thr Ala Thr Phe Asp Trp Asn Phe Pro Phe Asp Ser
            100                 105                 110

Trp Gly Gln Gly Thr Leu Val Thr Val Ser Ser
        115                 120


<210> SEQ ID NO 70
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Val
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Leu Val Val Tyr Ala Ile Arg Val Gly Ser Gly Trp
            100                 105                 110

Phe Asp Tyr Trp Gly Gln Gly Thr Leu Val Thr Val Ser Ser
        115                 120                 125


<210> SEQ ID NO 71
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95

Ala Arg Asp Pro Ser Ser Ser Gly Ser Tyr Tyr Met Glu Asp Ser Tyr
            100                 105                 110

Tyr Tyr Gly Met Asp Val Trp Gly Gln Gly Thr Thr Val Thr Val Ser
        115                 120                 125

Ser
```

<210> SEQ ID NO 72
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Gly Ser Ser Trp Glu Trp Gly Gln Gly Thr Thr
            100                 105                 110

Val Thr Val Ser Ser
        115
```

<210> SEQ ID NO 73
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Gln Val Gln Leu Val Gln Ser Gly Ala Glu Val Lys Glu Pro Gly Ala
1               5                   10                  15

Ser Val Lys Val Ser Cys Lys Ala Pro Ala Asn Thr Phe Ser Asp His
            20                  25                  30

Val Met His Trp Val Arg Gln Ala Pro Gly Gln Arg Phe Glu Trp Met
        35                  40                  45

Gly Tyr Ile His Ala Ala Asn Gly Gly Thr His Tyr Ser Gln Lys Phe
    50                  55                  60

Gln Asp Arg Val Thr Ile Thr Arg Asp Thr Ser Ala Asn Thr Val Tyr
65                  70                  75                  80

Met Asp Leu Ser Ser Leu Arg Ser Glu Asp Thr Ala Val Tyr Tyr Cys
                85                  90                  95

Ala Arg Gly Gly Tyr Asn Ser Asp Ala Phe Asp Ile Trp Gly Gln Gly
            100                 105                 110
```

Thr Met Val Thr Val Ser Ser
115

<210> SEQ ID NO 74
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Leu Ser Val Arg Ala Ile Asp Ala Phe Asp Ile Trp Gly
100 105 110

Gln Gly Thr Met Val Thr Val Ser Ser
115 120

<210> SEQ ID NO 75
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Glu Val Gln Leu Val Gln Ser Gly Gly Gly Val Val Arg Ser Gly Arg
1 5 10 15

Ser Leu Arg Leu Ser Cys Ala Ala Ser Gly Phe Thr Phe Asn Ser Tyr
20 25 30

Gly Leu His Trp Val Arg Gln Ala Pro Gly Lys Gly Leu Glu Trp Val
35 40 45

Ala Leu Ile Glu Tyr Asp Gly Ser Asn Lys Tyr Tyr Gly Asp Ser Val
50 55 60

Lys Gly Arg Phe Thr Ile Ser Arg Asp Lys Ser Lys Ser Thr Leu Tyr
65 70 75 80

Leu Gln Met Asp Asn Leu Arg Ala Glu Asp Thr Ala Val Tyr Tyr Cys
85 90 95

Ala Arg Glu Gly Asn Glu Asp Leu Ala Phe Asp Ile Trp Gly Gln Gly
100 105 110

Thr Leu Val Thr Val Ser Ser
115

<210> SEQ ID NO 76
<211> LENGTH: 127
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Ser Ser Asn
            20                  25                  30

Tyr Met Thr Trp Val Arg Gln Ala Pro Gly Lys Gly Leu Glu Trp Val
        35                  40                  45

Ser Val Ile Tyr Ser Gly Gly Ala Thr Tyr Tyr Gly Asp Ser Val Lys
    50                  55                  60

Gly Arg Phe Thr Val Ser Arg Asp Asn Ser Lys Asn Thr Val Tyr Leu
65                  70                  75                  80

Gln Met Asn Arg Leu Thr Ala Glu Asp Thr Ala Val Tyr Tyr Cys Ala
                85                  90                  95

Arg Asp Arg Leu Tyr Cys Gly Asn Asn Cys Tyr Leu Tyr Tyr Tyr Tyr
            100                 105                 110

Gly Met Asp Val Trp Gly Gln Gly Thr Leu Val Thr Val Ser Ser
        115                 120                 125
```

<210> SEQ ID NO 77
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Gln Val Gln Leu Val Gln Ser Gly Ala Glu Val Lys Lys Ser Gly Ala
1               5                   10                  15

Ser Val Lys Val Ser Cys Lys Ala Ser Gly Tyr Pro Phe Thr Gly Tyr
            20                  25                  30

Tyr Ile Gln Trp Val Arg Gln Ala Pro Gly Gln Gly Leu Glu Trp Met
        35                  40                  45

Gly Trp Ile Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Ser Tyr Gly Tyr Tyr Tyr Gly Met Asp Val Trp Gly Gln
            100                 105                 110

Gly Thr Leu Val Thr Val Ser Ser
        115                 120
```

<210> SEQ ID NO 78
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Val Val Phe Gly Gly Gly Thr Lys Leu Thr Val Leu
            100                 105                 110


<210> SEQ ID NO 79
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Ile Val Leu Thr Gln Ser Pro Leu Ser Leu Pro Val Thr Pro Gly
1               5                   10                  15

Gln Pro Ala Ser Ile Ser Cys Arg Ser Ser Gln Ser Leu Val Tyr Thr
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Ser Phe Thr Phe Gly Gln Gly Thr Arg Leu Glu Ile Lys
            100                 105                 110


<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys
            100                 105


<210> SEQ ID NO 81
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Glu Ile Val Leu Thr Gln Ser Pro Gly Thr Leu Ser Leu Ser Pro Gly
1               5                   10                  15

Gly Arg Ala Thr Leu Ser Cys Arg Ala Ser Gln Ser Ile Ser Gly Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Phe Gly Leu Gly Thr Lys Leu Glu Ile Lys
            100                 105


<210> SEQ ID NO 82
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105


<210> SEQ ID NO 83
<211> LENGTH: 108
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Met
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Asp Ile Lys
            100                 105
```

<210> SEQ ID NO 84
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Val Val Phe Gly Gly Gly Thr Lys Leu Thr Val Leu
            100                 105                 110
```

<210> SEQ ID NO 85
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30
```

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Leu
85 90 95

Thr Phe Gly Gly Gly Thr Lys Leu Glu Ile Lys
100 105

<210> SEQ ID NO 86
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 86

Asp Ile Val Met Thr Gln Ser Pro Ser Ser Val Ser Ala Ser Val Gly
1 5 10 15

Asp Arg Val Thr Ile Thr Cys Arg Ala Ser Gln Asp Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Asn Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Val Glu Ile Lys
100 105

<210> SEQ ID NO 87
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

Asp Ile Val Leu Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Phe Ala Thr Tyr Tyr Cys Gln Gln Ala Tyr Ser Thr Pro Phe
85 90 95

```
Thr Phe Gly Pro Gly Thr Lys Val Glu Ile Lys
            100                 105


<210> SEQ ID NO 88
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Phe Ile Lys Lys Asn
            20                  25                  30

Leu Asn Trp Tyr Gln His Lys Pro Gly Lys Ala Pro Lys Leu Leu Ile
        35                  40                  45

Tyr Asp Ala Ser Ser Leu Gln Thr Gly Val Pro Ser Arg Phe Ser Gly
    50                  55                  60

Asn Arg Ser Gly Thr Thr Phe Ser Phe Thr Ile Ser Ser Leu Gln Pro
65                  70                  75                  80

Glu Asp Val Ala Thr Tyr Tyr Cys Gln Gln His Asp Asn Leu Pro Leu
                85                  90                  95

Thr Phe Gly Gly Gly Thr Lys Val Glu Ile Lys
            100                 105


<210> SEQ ID NO 89
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Leu Thr Phe Gly Gln Gly Thr Lys Val Glu Ile Lys
            100                 105


<210> SEQ ID NO 90
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 90

Asp Ile Gln Met Thr Gln Ser Pro Ser Ser Leu Ser Ala Ser Val Gly
1               5                   10                  15

Asp Arg Val Thr Phe Thr Cys Arg Ala Ser Gln Gly Ile Ser Ser Ala
            20                  25                  30

Leu Ala Trp Tyr Gln Gln Lys Pro Gly Lys Pro Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Leu
                85                  90                  95

Thr Phe Gly Gly Gly Thr Lys Val Glu Ile Lys
            100                 105

<210> SEQ ID NO 91
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Asp Leu Glu Met Ala Thr Ile Met Gly
        115                 120                 125

Gly Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gln Ser Ala Leu
145                 150                 155                 160

Thr Gln Pro Ala Ser Val Ser Gly Ser Pro Gly Gln Ser Ile Thr Ile
                165                 170                 175

Ser Cys Thr Gly Thr Ser Ser Asp Val Gly Gly Tyr Asn Tyr Val Ser
            180                 185                 190

Trp Tyr Gln Gln His Pro Gly Lys Ala Pro Lys Leu Met Ile Tyr Asp
        195                 200                 205

Val Ser Asn Arg Pro Ser Gly Val Ser Asn Arg Phe Ser Gly Ser Lys
    210                 215                 220

Ser Gly Asn Thr Ala Ser Leu Thr Ile Ser Gly Leu Gln Ala Glu Asp
225                 230                 235                 240

```
Glu Ala Asp Tyr Tyr Cys Ser Ser Tyr Thr Ser Ser Ser Thr Leu Asp
                245                 250                 255

Val Val Phe Gly Gly Gly Thr Lys Leu Thr Val Leu Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 92
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Val
            20                  25                  30

Val Gln Pro Gly Gly Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Leu Ile Ser Gly Asp Gly Gly Ser Thr Tyr
65                  70                  75                  80

Tyr Ala Asp Ser Val Lys Gly Arg Phe Thr Ile Ser Arg Asp Asn Ser
                85                  90                  95
```

```
Lys Asn Thr Leu Tyr Leu Gln Met Asn Ser Leu Arg Val Glu Asp Thr
            100                 105                 110

Ala Val Tyr Tyr Cys Ala Arg Val Phe Asp Ser Tyr Tyr Met Asp Val
        115                 120                 125

Trp Gly Lys Gly Thr Thr Val Thr Val Ser Ser Gly Gly Gly Gly Ser
    130                 135                 140

Gly Gly Gly Gly Ser Gly Ser Gly Gly Ser Glu Ile Val Leu Thr Gln
145                 150                 155                 160

Ser Pro Leu Ser Leu Pro Val Thr Pro Gly Gln Pro Ala Ser Ile Ser
                165                 170                 175

Cys Arg Ser Ser Gln Ser Leu Val Tyr Thr Asp Gly Asn Thr Tyr Leu
            180                 185                 190

Asn Trp Phe Gln Gln Arg Pro Gly Gln Ser Pro Arg Arg Leu Ile Tyr
        195                 200                 205

Lys Val Ser Asn Arg Asp Ser Gly Val Pro Asp Arg Phe Ser Gly Ser
    210                 215                 220

Gly Ser Asp Thr Asp Phe Thr Leu Lys Ile Ser Arg Val Glu Ala Glu
225                 230                 235                 240

Asp Val Gly Ile Tyr Tyr Cys Met Gln Gly Thr His Trp Ser Phe Thr
                245                 250                 255

Phe Gly Gln Gly Thr Arg Leu Glu Ile Lys Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 93
<211> LENGTH: 491
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 93

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Ser Ser Tyr Tyr Trp Gly Trp Ile Arg Gln Pro Pro
    50                  55                  60

Gly Lys Gly Leu Glu Trp Ile Gly Ser Ile Tyr Tyr Ser Gly Ser Thr
65                  70                  75                  80

Tyr Tyr Asn Pro Ser Leu Lys Ser Arg Val Ser Ile Ser Val Asp Thr
                85                  90                  95

Ser Lys Asn Gln Phe Ser Leu Lys Leu Lys Tyr Val Thr Ala Ala Asp
            100                 105                 110

Thr Ala Val Tyr Tyr Cys Ala Thr Pro Gly Thr Tyr Tyr Asp Phe Leu
        115                 120                 125

Ser Gly Tyr Tyr Pro Phe Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ser Pro Ser Ser Leu Ser Ala Ser Val
                165                 170                 175

Gly Asp Arg Val Thr Ile Thr Cys Arg Ala Ser Gln Gly Ile Ser Ser
            180                 185                 190

Tyr Leu Ala Trp Tyr Gln Gln Lys Pro Gly Lys Ala Pro Lys Leu Leu
        195                 200                 205

Ile Tyr Ala Ala Ser Thr Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Leu Asn Ser Tyr Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380
```

```
Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 94
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Trp Met Ser Trp Val Arg Gln Ala Pro Gly Lys
    50                  55                  60

Gly Leu Glu Trp Val Ala Asn Ile Asn Glu Asp Gly Ser Ala Lys Phe
65                  70                  75                  80

Tyr Val Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Phe Cys Ala Arg Asp Leu Arg Ser Gly Arg Tyr Trp Gly
        115                 120                 125

Gln Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Gly Thr Leu Ser Leu Ser Pro Gly Gly Arg Ala Thr Leu Ser Cys Arg
                165                 170                 175

Ala Ser Gln Ser Ile Ser Gly Ser Phe Leu Ala Trp Tyr Gln Gln Lys
            180                 185                 190

Pro Gly Gln Ala Pro Arg Leu Leu Ile Tyr Gly Ala Ser Ser Arg Ala
        195                 200                 205

Thr Gly Ile Pro Asp Arg Phe Ser Gly Ser Gly Ser Gly Thr Asp Phe
    210                 215                 220

Thr Leu Thr Ile Ser Arg Leu Glu Pro Glu Asp Phe Ala Val Tyr Tyr
225                 230                 235                 240
```

```
Cys Gln Gln Tyr Gly Ser Ser Pro Pro Thr Phe Gly Leu Gly Thr Lys
                245                 250                 255

Leu Glu Ile Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg


<210> SEQ ID NO 95
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Gly Leu
            20                  25                  30

Val Arg Pro Ser Glu Thr Leu Ser Leu Thr Cys Thr Val Ser Gly Gly
        35                  40                  45

Pro Val Arg Ser Gly Ser His Tyr Trp Asn Trp Ile Arg Gln Pro Pro
    50                  55                  60

Gly Arg Gly Leu Glu Trp Ile Gly Tyr Ile Tyr Tyr Ser Gly Ser Thr
65                  70                  75                  80

Asn Tyr Asn Pro Ser Leu Glu Asn Arg Val Thr Ile Ser Ile Asp Thr
                85                  90                  95

Ser Asn Asn His Phe Ser Leu Lys Leu Ser Ser Val Thr Ala Ala Asp
            100                 105                 110
```

```
Thr Ala Leu Tyr Phe Cys Ala Arg Gly Thr Ala Thr Phe Asp Trp Asn
        115                 120                 125

Phe Pro Phe Asp Ser Trp Gly Gln Gly Thr Leu Val Thr Val Ser Ser
    130                 135                 140

Gly Gly Gly Gly Ser Gly Gly Gly Gly Ser Gly Ser Gly Gly Ser Asp
145                 150                 155                 160

Ile Gln Met Thr Gln Ser Pro Ser Ser Leu Ser Ala Ser Ile Gly Asp
                165                 170                 175

Arg Val Thr Ile Thr Cys Arg Ala Ser Gln Ser Ile Ser Ser Tyr Leu
            180                 185                 190

Asn Trp Tyr Gln Gln Lys Pro Gly Lys Ala Pro Lys Leu Leu Ile Tyr
        195                 200                 205

Ala Ala Ser Ser Leu Gln Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Ser Thr Pro Trp Thr
                245                 250                 255

Phe Gly Gln Gly Thr Lys Leu Glu Ile Lys Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 96
<211> LENGTH: 493
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 96

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Ala Gly Leu
            20                  25                  30

Leu Lys Pro Ser Glu Thr Leu Ser Leu Thr Cys Ala Val Tyr Gly Gly
        35                  40                  45

Ser Phe Ser Gly Tyr Tyr Trp Ser Trp Ile Arg Gln Pro Pro Gly Lys
    50                  55                  60

Gly Leu Glu Trp Val Gly Glu Ile Asn His Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Gly Ser Gly Leu Val Val Tyr Ala Ile Arg
        115                 120                 125

Val Gly Ser Gly Trp Phe Asp Tyr Trp Gly Gln Gly Thr Leu Val Thr
    130                 135                 140

Val Ser Ser Gly Gly Gly Gly Ser Gly Gly Gly Asp Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
        195                 200                 205

Leu Met Tyr Ala Ala Ser Ser Leu Gln Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
                245                 250                 255

Pro Pro Trp Thr Phe Gly Gln Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
```

```
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 97
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Ser Ile Ser Ser Ser Ser Ser Tyr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp Pro Ser Ser Ser Gly Ser Tyr Tyr
        115                 120                 125

Met Glu Asp Ser Tyr Tyr Tyr Gly Met Asp Val Trp Gly Gln Gly Thr
    130                 135                 140

Thr Val Thr Val Ser Ser Gly Gly Gly Gly Ser Gly Gly Gly Gly Ser
145                 150                 155                 160

Gly Gly Gly Gly Ser Asn Phe Met Leu Thr Gln Pro His Ser Val Ser
                165                 170                 175

Glu Ser Pro Gly Lys Thr Val Thr Ile Ser Cys Thr Gly Ser Ser Gly
            180                 185                 190

Ser Ile Ala Ser Asn Tyr Val Gln Trp Tyr Gln Gln Arg Pro Gly Ser
        195                 200                 205

Ala Pro Thr Thr Val Ile Tyr Glu Asp Asn Gln Arg Pro Ser Gly Val
    210                 215                 220

Pro Asp Arg Phe Ser Gly Ser Ile Asp Ser Ser Ser Asn Ser Ala Ser
225                 230                 235                 240

Leu Thr Ile Ser Gly Leu Lys Thr Glu Asp Glu Ala Asp Tyr Tyr Cys
                245                 250                 255
```

```
Gln Ser Tyr Asp Ser Ser Asn Gln Val Val Phe Gly Gly Gly Thr Lys
            260                 265                 270

Leu Thr Val Leu Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg


<210> SEQ ID NO 98
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Met Ala Leu Pro Val Thr Ala Leu Leu Leu Pro Leu Ala Leu Leu Leu
1               5                   10                  15

His Ala Ala Arg Pro Gln Val Asn Leu Arg Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Glu Met Asn Trp Val Arg Gln Ala Pro Gly Lys
    50                  55                  60

Gly Leu Glu Trp Val Ser Tyr Ile Ser Ser Ser Gly Ser Thr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
```

-continued

```
            100                 105                 110

Ala Val Tyr Tyr Cys Ala Arg Glu Ala Leu Gly Ser Ser Trp Glu Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Gln Ala Ser Gln Asp Ile Ser Asn Tyr Leu Asn Trp Tyr Gln Gln Lys
            180                 185                 190

Pro Gly Lys Ala Pro Lys Leu Leu Ile Tyr Asp Ala Ser Asn Leu Glu
        195                 200                 205

Thr Gly Val Pro Ser Arg Phe Ser Gly Ser Gly Ser Gly Thr Asp Phe
    210                 215                 220

Thr Phe Thr Ile Ser Ser Leu Gln Pro Glu Asp Ile Ala Thr Tyr Tyr
225                 230                 235                 240

Cys Gln Gln Tyr Asp Asn Leu Pro Leu Thr Phe Gly Gly Gly Thr Lys
                245                 250                 255

Leu Glu Ile Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg
```

<210> SEQ ID NO 99
<211> LENGTH: 490
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic polypeptide"

<400> SEQUENCE: 99

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Glu Pro Gly Ala Ser Val Lys Val Ser Cys Lys Ala Pro Ala Asn
35 40 45

Thr Phe Ser Asp His Val Met His Trp Val Arg Gln Ala Pro Gly Gln
50 55 60

Arg Phe Glu Trp Met Gly Tyr Ile His Ala Ala Asn Gly Gly Thr His
65 70 75 80

Tyr Ser Gln Lys Phe Gln Asp Arg Val Thr Ile Thr Arg Asp Thr Ser
85 90 95

Ala Asn Thr Val Tyr Met Asp Leu Ser Ser Leu Arg Ser Glu Asp Thr
100 105 110

Ala Val Tyr Tyr Cys Ala Arg Gly Gly Tyr Asn Ser Asp Ala Phe Asp
115 120 125

Ile Trp Gly Gln Gly Thr Met Val Thr Val Ser Ser Gly Gly Gly Gly
130 135 140

Ser Gly Gly Gly Gly Ser Gly Gly Gly Gly Ser Gly Gly Gly Gly Ser
145 150 155 160

Asp Ile Val Met Thr Gln Ser Pro Ser Ser Val Ser Ala Ser Val Gly
165 170 175

Asp Arg Val Thr Ile Thr Cys Arg Ala Ser Gln Asp Ile Ser Ser Trp
180 185 190

Leu Ala Trp Tyr Gln Gln Lys Pro Gly Lys Ala Pro Lys Leu Leu Ile
195 200 205

Tyr Ala Ala Ser Ser Leu Gln Ser Gly Val Pro Ser Arg Phe Asn Gly
210 215 220

Ser Gly Ser Gly Thr Asp Phe Thr Leu Thr Ile Ser Ser Leu Gln Pro
225 230 235 240

Glu Asp Phe Ala Thr Tyr Tyr Cys Gln Gln Ser Tyr Ser Thr Pro Leu
245 250 255

Thr Phe Gly Gly Gly Thr Lys Val Glu Ile Lys Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn 385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 100
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Ser Met Asn Trp Val Arg Gln Ala Pro Gly Lys
50 55 60

Gly Leu Glu Trp Val Ser Tyr Ile Ser Ser Ser Ser Ser Thr Ile Tyr
65 70 75 80

Tyr Ala Asp Ser Val Lys Gly Arg Phe Thr Ile Ser Arg Asp Asn Ala
85 90 95

Lys Asn Ser Leu Tyr Leu Gln Met Asn Ser Leu Arg Ala Glu Asp Thr
100 105 110

Ala Val Tyr Tyr Cys Ala Arg Asp Leu Ser Val Arg Ala Ile Asp Ala
115 120 125

Phe Asp Ile Trp Gly Gln Gly Thr Met Val Thr Val Ser Ser Gly Gly
130 135 140

Gly Gly Ser Gly Gly Gly Gly Ser Gly Gly Gly Gly Ser Gly Gly Gly
145 150 155 160

Gly Ser Asp Ile Val Leu Thr Gln Ser Pro Ser Ser Leu Ser Ala Ser
165 170 175

Val Gly Asp Arg Val Thr Ile Thr Cys Gln Ala Ser Gln Asp Ile Ser
180 185 190

Asn Tyr Leu Asn Trp Tyr Gln Gln Lys Pro Gly Lys Ala Pro Lys Leu
195 200 205

Leu Ile Tyr Asp Ala Ser Asn Leu Glu Thr Gly Val Pro Ser Arg Phe
210 215 220

Ser Gly Ser Gly Ser Gly Thr Asp Phe Thr Phe Thr Ile Ser Ser Leu
225 230 235 240

Gln Pro Glu Asp Phe Ala Thr Tyr Tyr Cys Gln Gln Ala Tyr Ser Thr
245 250 255

```
Pro Phe Thr Phe Gly Pro Gly Thr Lys Val Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 101
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Gly Gly Val
            20                  25                  30

Val Arg Ser Gly Arg Ser Leu Arg Leu Ser Cys Ala Ala Ser Gly Phe
        35                  40                  45

Thr Phe Asn Ser Tyr Gly Leu His Trp Val Arg Gln Ala Pro Gly Lys
    50                  55                  60

Gly Leu Glu Trp Val Ala Leu Ile Glu Tyr Asp Gly Ser Asn Lys Tyr
65                  70                  75                  80

Tyr Gly Asp Ser Val Lys Gly Arg Phe Thr Ile Ser Arg Asp Lys Ser
                85                  90                  95

Lys Ser Thr Leu Tyr Leu Gln Met Asp Asn Leu Arg Ala Glu Asp Thr
            100                 105                 110
```

-continued

```
Ala Val Tyr Tyr Cys Ala Arg Glu Gly Asn Glu Asp Leu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Ser Ser Leu Ser Ala Ser Val Gly
                165                 170                 175

Asp Arg Val Thr Ile Thr Cys Gln Ala Ser Gln Phe Ile Lys Lys Asn
            180                 185                 190

Leu Asn Trp Tyr Gln His Lys Pro Gly Lys Ala Pro Lys Leu Leu Ile
        195                 200                 205

Tyr Asp Ala Ser Ser Leu Gln Thr Gly Val Pro Ser Arg Phe Ser Gly
    210                 215                 220

Asn Arg Ser Gly Thr Thr Phe Ser Phe Thr Ile Ser Ser Leu Gln Pro
225                 230                 235                 240

Glu Asp Val Ala Thr Tyr Tyr Cys Gln Gln His Asp Asn Leu Pro Leu
                245                 250                 255

Thr Phe Gly Gly Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 102
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 102

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Asn Val Ser Ser Asn Tyr Met Thr Trp Val Arg Gln Ala Pro Gly Lys
    50                  55                  60

Gly Leu Glu Trp Val Ser Val Ile Tyr Ser Gly Gly Ala Thr Tyr Tyr
65                  70                  75                  80

Gly Asp Ser Val Lys Gly Arg Phe Thr Val Ser Arg Asp Asn Ser Lys
                85                  90                  95

Asn Thr Val Tyr Leu Gln Met Asn Arg Leu Thr Ala Glu Asp Thr Ala
            100                 105                 110

Val Tyr Tyr Cys Ala Arg Asp Arg Leu Tyr Cys Gly Asn Asn Cys Tyr
        115                 120                 125

Leu Tyr Tyr Tyr Tyr Gly Met Asp Val Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Gly Gly Gly Gly Ser Asp Ile Gln Val Thr Gln Ser Pro
                165                 170                 175

Ser Ser Leu Ser Ala Ser Val Gly Asp Arg Val Thr Ile Thr Cys Arg
            180                 185                 190

Ala Ser Gln Ser Ile Ser Ser Tyr Leu Asn Trp Tyr Gln Gln Lys Pro
        195                 200                 205

Gly Lys Ala Pro Lys Leu Leu Ile Tyr Ala Ala Ser Ser Leu Gln Ser
    210                 215                 220

Gly Val Pro Ser Arg Phe Ser Gly Ser Gly Ser Gly Thr Asp Phe Thr
225                 230                 235                 240

Leu Thr Ile Ser Ser Leu Gln Pro Glu Asp Phe Ala Thr Tyr Tyr Cys
                245                 250                 255

Gln Gln Ser Tyr Ser Thr Pro Pro Leu Thr Phe Gly Gln Gly Thr Lys
            260                 265                 270

Val Glu Ile Lys Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400
```

Lys Gln Gly Gln Asn Gln Leu Tyr Asn Glu Leu Asn Leu Gly Arg Arg
405 410 415

Glu Glu Tyr Asp Val Leu Asp Lys Arg Arg Gly Arg Asp Pro Glu Met
420 425 430

Gly Gly Lys Pro Arg Arg Lys Asn Pro Gln Glu Gly Leu Tyr Asn Glu
435 440 445

Leu Gln Lys Asp Lys Met Ala Glu Ala Tyr Ser Glu Ile Gly Met Lys
450 455 460

Gly Glu Arg Arg Arg Gly Lys Gly His Asp Gly Leu Tyr Gln Gly Leu
465 470 475 480

Ser Thr Ala Thr Lys Asp Thr Tyr Asp Ala Leu His Met Gln Ala Leu
485 490 495

Pro Pro Arg

<210> SEQ ID NO 103
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 103

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Ser Gly Ala Ser Val Lys Val Ser Cys Lys Ala Ser Gly Tyr
35 40 45

Pro Phe Thr Gly Tyr Tyr Ile Gln Trp Val Arg Gln Ala Pro Gly Gln
50 55 60

Gly Leu Glu Trp Met Gly Trp Ile Asp Pro Asn Ser Gly Asn Thr Gly
65 70 75 80

Tyr Ala Gln Lys Phe Gln Gly Arg Val Thr Met Thr Arg Asn Thr Ser
85 90 95

Ile Ser Thr Ala Tyr Met Glu Leu Ser Ser Leu Arg Ser Glu Asp Thr
100 105 110

Ala Val Tyr Tyr Cys Ala Ser Asp Ser Tyr Gly Tyr Tyr Tyr Gly Met
115 120 125

Asp Val Trp Gly Gln Gly Thr Leu Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Asp Ile Gln Met Thr Gln Ser Pro Ser Ser Leu Ser Ala Ser Val
165 170 175

Gly Asp Arg Val Thr Phe Thr Cys Arg Ala Ser Gln Gly Ile Ser Ser
180 185 190

Ala Leu Ala Trp Tyr Gln Gln Lys Pro Gly Lys Pro Pro Lys Leu Leu
195 200 205

Ile Tyr Asp Ala Ser Ser Leu Glu Ser Gly Val Pro Ser Arg Phe Ser
210 215 220

Gly Ser Gly Ser Gly Thr Asp Phe Thr Leu Thr Ile Ser Ser Leu Gln
225 230 235 240

Pro Glu Asp Phe Ala Thr Tyr Tyr Cys Gln Gln Phe Asn Asn Tyr Pro

```
                245                 250                 255

Leu Thr Phe Gly Gly Gly Thr Lys Val Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 104
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104

```
atggccctcc ctgtcaccgc cctgctgctt ccgctggctc ttctgctcca cgccgctcgg     60

cccgaagtgc aactccaaca gtcaggcgca gaagtcaaga agcccggatc gtcagtgaaa    120

gtgtcctgca aagcctccgg cggaaccttc agctcctacg caatcagctg ggtgcggcag    180

gcgcccggac agggactgga gtggatgggc ggtatcattc cgatctttgg caccgccaat    240

tacgcccaga agttccaggg acgcgtcaca atcaccgccg acgaatcgac ttccaccgcc    300

tacatggagc tgtcgtcctt gaggagcgaa gataccgccg tgtactactg cgctcgggat    360

ctggagatgg ccactatcat ggggggttac tggggccagg ggaccctggt cactgtgtcc    420

tcgggaggag ggggatcagg cggcggcggt tccgggggag gaggaagcca gtccgcgctg    480

actcagccag cttccgtgtc tggttcgccg ggacagtcca tcactattag ctgtaccggc    540

accagcagcg acgtgggcgg ctacaactat gtgtcatggt accagcagca cccggggaag    600
```

-continued

```
gcgcctaagc tgatgatcta cgacgtgtcc aaccgcccta gcggagtgtc caacagattc     660

tccggttcga agtcagggaa cactgcctcc ctcacgatta gcgggctgca agccgaggat     720

gaagccgact actactgctc ctcctatacc tcctcctcga ccctggacgt ggtgttcgga     780

ggaggcacca agctcaccgt ccttaccact accccagcac cgaggccacc cacccccggct    840

cctaccatcg cctcccagcc tctgtccctg cgtccggagg catgtagacc cgcagctggt     900

ggggccgtgc atacccgggg tcttgacttc gcctgcgata tctacatttg ggcccctctg     960

gctggtactt gcggggtcct gctgctttca ctcgtgatca ctctttactg taagcgcggt    1020

cggaagaagc tgctgtacat ctttaagcaa cccttcatga ggcctgtgca gactactcaa    1080

gaggaggacg gctgttcatg ccggttccca gaggaggagg aaggcggctg cgaactgcgc    1140

gtgaaattca gccgcagcgc agatgctcca gcctacaagc aggggcagaa ccagctctac    1200

aacgaactca atcttggtcg gagagaggag tacgacgtgc tggacaagcg gagaggacgg    1260

gacccagaaa tgggcgggaa gccgcgcaga aagaatcccc aagagggcct gtacaacgag    1320

ctccaaaagg ataagatggc agaagcctat agcgagattg gtatgaaagg ggaacgcaga    1380

agaggcaaag gccacgacgg actgtaccag ggactcagca ccgccaccaa ggacacctat    1440

gacgctcttc acatgcaggc cctgccgcct cgg                                 1473
```

<210> SEQ ID NO 105
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

```
atggccctcc ctgtcaccgc cctgctgctt ccgctggctc ttctgctcca cgccgctcgg      60

cccgaagtgc aattggtgga aagcggagga ggagtggtgc aacctggagg aagcctgaga     120

ctgtcatgtg ccgcctcggg attcactttc gatgactacg caatgcactg ggtccgccag     180

gcccccggaa agggtctgga atgggtgtcc ctcatctccg gcgatggggg ttccacttac     240

tatgcggatt ctgtgaaggg ccgcttcaca atctcccggg acaattccaa gaacactctg     300

taccttcaaa tgaactccct gagggtggag gacaccgctg tgtactactg cgcgagagtg     360

tttgactcgt actatatgga cgtctgggga aagggcacca ccgtgaccgt gtccagcggt     420

ggcggtggat cgggggggcgg cggctccggg agcggaggtt ccgagattgt gctgactcag    480

tcgccgttgt cactgcctgt cacccccggg cagccggcct ccatttcatg ccggtccagc     540

cagtccctgg tctacaccga tggaacact tacctcaact ggttccagca gcgcccagga      600

cagtccccgc ggaggctgat ctacaaagtg tcaaaccggg actccggcgt ccccgatcgg     660

ttctcgggaa gcggcagcga caccgacttc acgctgaaga tttcccgcgt ggaagccgag     720

gacgtgggca tctactactg tatgcagggc acccactggt cgtttacctt cggacaagga     780

actaggctcg agatcaagac cactacccca gcaccgaggc cacccacccc ggctcctacc     840

atcgcctccc agcctctgtc cctgcgtccg gaggcatgta gacccgcagc tggtggggcc     900

gtgcataccc ggggtcttga cttcgcctgc gatatctaca tttgggcccc tctggctggt     960

acttgcgggg tcctgctgct ttcactcgtg atcactcttt actgtaagcg cggtcggaag    1020

aagctgctgt acatctttaa gcaacccttc atgaggcctg tgcagactac tcaagaggag    1080

gacggctgtt catgccggtt cccagaggag gaggaaggcg gctgcgaact gcgcgtgaaa    1140
```

```
ttcagccgca gcgcagatgc tccagcctac aagcaggggc agaaccagct ctacaacgaa   1200

ctcaatcttg gtcggagaga ggagtacgac gtgctggaca agcggagagg acgggaccca   1260

gaaatgggcg ggaagccgcg cagaaagaat ccccaagagg gcctgtacaa cgagctccaa   1320

aaggataaga tggcagaagc ctatagcgag attggtatga aaggggaacg cagaagaggc   1380

aaaggccacg acggactgta ccagggactc agcaccgcca ccaaggacac ctatgacgct   1440

cttcacatgc aggccctgcc gcctcgg                                       1467
```

<210> SEQ ID NO 106
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
atggccctcc ctgtcaccgc cctgctgctt ccgctggctc ttctgctcca cgccgctcgg     60

ccccaagtgc agcttcaaga aagcggtcca ggactcgtca agccatcaga aactctttcc    120

ctcacttgta ccgtgtcggg aggcagcatc tcctcgagct cctactactg ggttggatt     180

agacagcccc cgggaaaggg gttggagtgg atcggttcca tctactactc cgggtcgacc    240

tactacaacc cttccctgaa atctcgggtg tccatctccg tcgacacctc caagaaccag    300

ttcagcctga agctgaaata tgtgaccgcg gccgatactg ccgtgtacta ttgcgccacc    360

ccgggaacct actacgactt cctctcgggg tactacccgt tttactgggg acaggggact    420

ctcgtgaccg tgtcctcggg cggcggaggt tcaggcggtg gcggatcggg gggaggaggc    480

tcagacattg tgatgaccca gagcccgtcc agcctgagcg cctccgtggg cgatagggtc    540

acgattactt gccgggcgtc ccagggaatc tcaagctacc tggcctggta ccaacagaag    600

cccggaaagg cacccaagtt gctgatctat gccgctagca ctctgcagtc cggggtgcct    660

tcccgcttct ccggctccgg ctcgggcacc gacttcaccc tgaccatttc ctcactgcaa    720

cccgaggact tcgccactta ctactgccag cagctgaact cctaccctta cacattcgga    780

cagggaacca agctggaaat caagaccact accccagcac cgaggccacc caccccggct    840

cctaccatcg cctcccagcc tctgtccctg cgtccggagg catgtagacc cgcagctggt    900

ggggccgtgc atacccgggg tcttgacttc gcctgcgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgcgc   1140

gtgaaattca gccgcagcgc agatgctcca gcctacaagc aggggcagaa ccagctctac   1200

aacgaactca atcttggtcg gagagaggag tacgacgtgc tggacaagcg gagaggacgg   1260

gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                1473
```

<210> SEQ ID NO 107
<211> LENGTH: 1449
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 107
atggccctcc ctgtcaccgc cctgctgctt ccgctggctc ttctgctcca cgccgctcgg 60
ccccaagtgc aactcgtgga atctggtgga ggactcgtgc aacccggagg atcattgcga 120
ctctcgtgtg cggcatccgg ctttaccttt tcatcctact ggatgtcctg ggtcagacag 180
gcccccggga agggactgga atgggtcgcg aacatcaacg aggacggctc ggccaagttc 240
tacgtggact ccgtgaaggg ccgcttcacg atctcacggg ataacgccaa gaattccctg 300
tatctgcaaa tgaacagcct gagggccgag gacactgcgg tgtacttctg cgcacgcgac 360
ctgaggtccg ggagatactg gggacagggc accctcgtga ccgtgtcgag cggaggaggg 420
gggtcgggcg gcggcggttc cggtggcggc ggtagcgaaa ttgtgttgac ccagtcccct 480
ggaaccctga gcctgtcacc tggaggacgc gccaccctgt cctgccgggc cagccagagc 540
atctcagggt ccttcctggc ttggtaccag cagaagccgg gacaggctcc gagacttctg 600
atctacggcg cctcctcgcg ggcgaccgga atcccggatc ggttctccgg ctcgggaagc 660
ggaactgact tcactcttac catttcccgc ctggagccgg aagatttcgc cgtgtactac 720
tgccagcagt acgggtcatc ccctccaacc ttcggcctgg gaactaagct ggaaatcaaa 780
accactaccc cagcaccgag gccacccacc ccggctccta ccatcgcctc ccagcctctg 840
tccctgcgtc cggaggcatg tagacccgca gctggtgggg ccgtgcatac ccggggtctt 900
gacttcgcct gcgatatcta catttgggcc cctctggctg gtacttgcgg ggtcctgctg 960
ctttcactcg tgatcactct ttactgtaag cgcggtcgga agaagctgct gtacatcttt 1020
aagcaaccct tcatgaggcc tgtgcagact actcaagagg aggacggctg ttcatgccgg 1080
ttcccagagg aggaggaagg cggctgcgaa ctgcgcgtga aattcagccg cagcgcagat 1140
gctccagcct acaagcaggg gcagaaccag ctctacaacg aactcaatct tggtcggaga 1200
gaggagtacg acgtgctgga caagcggaga ggacgggacc cagaaatggg cgggaagccg 1260
cgcagaaaga atccccaaga gggcctgtac aacgagctcc aaaaggataa gatggcagaa 1320
gcctatagcg agattggtat gaaaggggaa cgcagaagag gcaaaggcca cgacggactg 1380
taccagggac tcagcaccgc caccaaggac acctatgacg ctcttcacat gcaggccctg 1440
ccgcctcgg 1449

<210> SEQ ID NO 108
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 108
atggccctcc ctgtcaccgc cctgctgctt ccgctggctc ttctgctcca cgccgctcgg 60
cccgaagtgc aactccaaca atccggtcca ggactcgtca gaccctccga aactctctcg 120
cttacatgca ctgtgtccgg cggccctgtg cggtccggct ctcattactg gaactggatt 180
cgccagcccc cgggacgcgg actggagtgg atcggctaca tctattactc ggggtcgact 240
aactacaacc cgagcctgga aaatagagtg accatctcaa tcgacacgtc caacaaccac 300
ttctcgctga agttgtcctc cgtgactgcc gccgatactg ccctgtactt ctgtgctcgc 360
ggaaccgcca ccttcgactg gaacttccct tttgactcat ggggccaggg gacccttgtg 420
accgtgtcca gcggaggagg aggctccggt ggtggcggga gcggtagcgg cggaagcgac 480
atccagatga cccagtcacc gtcctcgctg tccgcatcca ttggggatcg ggtcactatt 540
acttgccggg cgtcccagtc catctcgtcc tacctgaact ggtatcagca gaagccaggg 600
aaagccccca agctgctgat ctacgcggcc agcagcctgc agtcaggagt gccttcaagg 660
tttagcggca gcggatcggg aaccgacttc accctgacca tttcctccct ccaacccgag 720
gatttcgcca cctactactg ccagcagtcc tactccaccc cgtggacctt cggacaggga 780
accaagctgg agatcaagac cactacccca gcaccgaggc cacccacccc ggctcctacc 840
atcgcctccc agcctctgtc cctgcgtccg gaggcatgta gacccgcagc tggtggggcc 900
gtgcataccc ggggtcttga cttcgcctgc gatatctaca tttgggcccc tctggctggt 960
acttgcgggg tcctgctgct ttcactcgtg atcactcttt actgtaagcg cggtcggaag 1020
aagctgctgt acatctttaa gcaacccttc atgaggcctg tgcagactac tcaagaggag 1080
gacggctgtt catgccggtt cccagaggag gaggaaggcg gctgcgaact gcgcgtgaaa 1140
ttcagccgca gcgcagatgc tccagcctac aagcaggggc agaaccagct ctacaacgaa 1200
ctcaatcttg gtcggagaga ggagtacgac gtgctggaca agcggagagg acgggaccca 1260
gaaatgggcg ggaagccgcg cagaaagaat ccccaagagg gcctgtacaa cgagctccaa 1320
aaggataaga tggcagaagc ctatagcgag attggtatga aaggggaacg cagaagaggc 1380
aaaggccacg acggactgta ccagggactc agcaccgcca ccaaggacac ctatgacgct 1440
cttcacatgc aggccctgcc gcctcgg 1467

<210> SEQ ID NO 109
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 109
atggccctcc ctgtcaccgc cctgctgctt ccgctggctc ttctgctcca cgccgctcgg 60
ccccaagtgc aacttcaaga atcaggcgca ggacttctca agccatccga aacactctcc 120
ctcacttgcg cggtgtacgg gggaagcttc tcgggatact actggtcctg gattaggcag 180
cctcccggca aaggcctgga atgggtcggg gagatcaacc actccggttc aaccaactac 240
aacccgtcgc tgaagtcccg cgtgaccatt tccgtggaca cctctaagaa tcagttcagc 300
ctgaagctct cgtccgtgac cgcggcggac accgccgtct actactgcgc tcggggatca 360
ggactggtgg tgtacgccat ccgcgtgggc tcgggctggt tcgattactg gggccaggga 420
accctggtca ctgtgtcgtc cggcggagga ggttcggggg gcggagacag cggtggaggg 480
ggtagcgaca tccagatgac ccagtccccg tcctcgctgt ccgcctccgt gggagataga 540
gtgaccatca cctgtcgggc atcccagagc atttccagct acctgaactg gtatcagcag 600
aagcccggaa aggcccctaa gctgttgatg tacgccgcca gcagcttgca gtcgggcgtg 660
ccgagccggt tttccggttc cggctccggg actgacttca ccctgactat ctcatccctg 720
caacccgagg acttcgccac ttattactgc cagcagtcct actcaacccc tccctggacg 780
ttcggacagg gcaccaaggt cgatatcaag accactaccc cagcaccgag gccacccacc 840
ccggctccta ccatcgcctc ccagcctctg tccctgcgtc cggaggcatg tagacccgca 900
gctggtgggg ccgtgcatac ccggggtctt gacttcgcct gcgatatcta catttgggcc 960
cctctggctg gtacttgcgg ggtcctgctg ctttcactcg tgatcactct ttactgtaag 1020
cgcggtcgga agaagctgct gtacatcttt aagcaaccct tcatgaggcc tgtgcagact 1080
actcaagagg aggacggctg ttcatgccgg ttcccagagg aggaggaagg cggctgcgaa 1140
ctgcgcgtga aattcagccg cagcgcagat gctccagcct acaagcaggg gcagaaccag 1200
ctctacaacg aactcaatct tggtcggaga gaggagtacg acgtgctgga caagcggaga 1260
ggacgggacc cagaaatggg cgggaagccg cgcagaaaga atccccaaga gggcctgtac 1320
aacgagctcc aaaaggataa gatggcagaa gcctatagcg agattggtat gaaaggggaa 1380
cgcagaagag gcaaaggcca cgacggactg taccagggac tcagcaccgc caccaaggac 1440
acctatgacg ctcttcacat gcaggccctg ccgcctcgg 1479

<210> SEQ ID NO 110
<211> LENGTH: 1497
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110
atggccctcc ctgtcaccgc cctgctgctt ccgctggctc ttctgctcca cgccgctcgg 60
cccgaagtgc aattggtgga atctggagga ggacttgtga aacctggtgg aagcctgaga 120
ctttcctgtg cggcctcggg attcactttc tcctcctact ccatgaactg ggtcagacag 180
gcccctggga agggactgga atgggtgtca tccatctcct cctcatcgtc gtacatctac 240
tacgccgata gcgtgaaggg gcggttcacc atttcccggg acaacgctaa gaacagcctc 300
tatctgcaaa tgaattccct ccgcgccgag gacactgccg tgtactactg cgcgagggac 360
ccctcatcaa gcggcagcta ctacatggag gactcgtatt actacggaat ggacgtctgg 420
ggccagggaa ccactgtgac ggtgtcctcc ggtggagggg gctccggggg cgggggatct 480
ggcggaggag gctccaactt catgctgacc cagccgcact ccgtgtccga aagccccgga 540
aagaccgtga caatttcctg caccgggtcc tccggctcga tcgcatcaaa ctacgtgcag 600
tggtaccagc agcgcccggg cagcgccccc accactgtca tctacgagga taaccagcgg 660
ccgtcgggtg tcccagaccg gttttccggt tcgatcgata gcagcagcaa cagcgcctcc 720
ctgaccattt ccggcctcaa gaccgaggat gaggctgact actactgcca gtcgtatgac 780
tcctcgaacc aagtggtgtt cggtggcggc accaagctga ctgtgctgac cactacccca 840
gcaccgaggc cacccacccc ggctcctacc atcgcctccc agcctctgtc cctgcgtccg 900
gaggcatgta gacccgcagc tggtggggcc gtgcataccc ggggtcttga cttcgcctgc 960
gatatctaca tttgggcccc tctggctggt acttgcgggg tcctgctgct ttcactcgtg 1020
atcactcttt actgtaagcg cggtcggaag aagctgctgt acatctttaa gcaacccttc 1080
atgaggcctg tgcagactac tcaagaggag gacggctgtt catgccggtt cccagaggag 1140
gaggaaggcg gctgcgaact gcgcgtgaaa ttcagccgca gcgcagatgc tccagcctac 1200
aagcaggggc agaaccagct ctacaacgaa ctcaatcttg gtcggagaga ggagtacgac 1260
gtgctggaca agcggagagg acgggaccca gaaatgggcg ggaagccgcg cagaaagaat 1320
ccccaagagg gcctgtacaa cgagctccaa aaggataaga tggcagaagc ctatagcgag 1380
attggtatga aaggggaacg cagaagaggc aaaggccacg acggactgta ccagggactc 1440
agcaccgcca ccaaggacac ctatgacgct cttcacatgc aggccctgcc gcctcgg 1497

<210> SEQ ID NO 111
<211> LENGTH: 1449
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
atggccctcc ctgtcaccgc cctgctgctt ccgctggctc ttctgctcca cgccgctcgg 60
ccccaagtga acctgagaga aagcggcgga ggacttgtgc aacctggagg aagcctgaga 120
ctgtcatgtg ccgcgtccgg cttcaccttc tcgtcctacg agatgaactg ggtccgccag 180
gcaccgggca aaggactgga atgggtgtcc tacatttcct cgtccgggtc caccatctat 240
tacgccgact ccgtgaaggg acggttcacc atctcccggg acaacgccaa gaactccctc 300
tacctccaaa tgaactcact gagggcagag gacactgcgg tctactactg cgcccgcgaa 360
gctttgggta gctcctggga gtggggccag ggaaccactg tgaccgtgtc ctcgggtgga 420
gggggctccg gtggcggggg ttcagggggt ggcggaagcg atatccagat gactcagtca 480
ccaagctccc tgagcgcctc agtgggagat cgggtcacaa tcacgtgcca ggcgtcccag 540
gacatttcta actacctcaa ttggtaccag cagaagccgg ggaaggcccc caagcttctg 600
atctacgatg cctccaacct ggaaaccggc gtgccctccc gcttctcggg atcgggcagc 660
ggcactgact tcacctttac catctcgtcc ctgcaacctg aggacatcgc cacctattac 720
tgccagcagt acgataacct cccgctgact ttcggaggcg gaactaagct ggagattaag 780
accactaccc cagcaccgag gccacccacc ccggctccta ccatcgcctc ccagcctctg 840
tccctgcgtc cggaggcatg tagacccgca gctggtgggg ccgtgcatac ccggggtctt 900
gacttcgcct gcgatatcta catttgggcc cctctggctg gtacttgcgg ggtcctgctg 960
ctttcactcg tgatcactct ttactgtaag cgcggtcgga agaagctgct gtacatcttt 1020
aagcaaccct tcatgaggcc tgtgcagact actcaagagg aggacggctg ttcatgccgg 1080
ttcccagagg aggaggaagg cggctgcgaa ctgcgcgtga aattcagccg cagcgcagat 1140
gctccagcct acaagcaggg gcagaaccag ctctacaacg aactcaatct tggtcggaga 1200
gaggagtacg acgtgctgga caagcggaga ggacgggacc cagaaatggg cgggaagccg 1260
cgcagaaaga atccccaaga gggcctgtac aacgagctcc aaaaggataa gatggcagaa 1320
gcctatagcg agattggtat gaaaggggaa cgcagaagag gcaaaggcca cgacggactg 1380
taccagggac tcagcaccgc caccaaggac acctatgacg ctcttcacat gcaggccctg 1440
ccgcctcgg 1449

<210> SEQ ID NO 112
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112
atggccctcc ctgtcaccgc cctgctgctt ccgctggctc ttctgctcca cgccgctcgg 60
ccccaagtgc aactcgtcca gtccggtgca gaagtcaagg aacccggagc ctccgtgaaa 120
gtgtcctgca aagctcctgc caacactttc tcggaccacg tgatgcactg ggtgcgccag 180
gcgccgggcc agcgcttcga atggatggga tacattcatg ccgccaatgg cggtacccac 240
tactcccaaa agttccagga tagagtcacc atcacccggg acaccagcgc caacaccgtg 300
tatatggatc tgtccagcct gaggtccgag gataccgccg tgtactactg cgcccggggc 360
ggatacaact cagacgcgtt cgacatttgg ggacagggta ctatggtcac cgtgtcatcc 420
gggggcggtg gcagcggggg cggaggctct ggcggaggcg gatcaggggg aggagggtcc 480
gacatcgtga tgacccagtc cccgtcatcg gtgtccgcgt ccgtgggaga cagagtgacc 540
atcacgtgtc gcgccagcca ggacatctcc tcgtggttgg catggtacca gcagaagcct 600
ggaaaggccc cgaagctgct catctacgcc gcctcctccc ttcaatcggg agtgccctcg 660
cggttcaacg gaagcggaag cgggacagat tttaccctga ctattagctc gctgcagccc 720
gaggacttcg ctacttacta ctgccaacag agctactcca ccccactgac tttcggcggg 780
ggtaccaagg tcgagatcaa gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960
ggtacttgcg gggtcctgct gctttcactc gtgatcactc tttactgtaa gcgcggtcgg 1020
aagaagctgc tgtacatctt taagcaaccc ttcatgaggc ctgtgcagac tactcaagag 1080
gaggacggct gttcatgccg gttcccagag gaggaggaag gcggctgcga actgcgcgtg 1140
aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320
caaaaggata agatggcaga agcctatagc gagattggta tgaaagggga acgcagaaga 1380
ggcaaaggcc acgacggact gtaccaggga ctcagcaccg ccaccaagga cacctatgac 1440
gctcttcaca tgcaggccct gccgcctcgg 1470

<210> SEQ ID NO 113
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113
atggccctcc ctgtcaccgc cctgctgctt ccgctggctc ttctgctcca cgccgctcgg 60
ccccaagtgc aacttgttca atccggtgga ggtcttgtgc agcccggagg atcactcaga 120
ctgtcgtgcg ccgcctctgg gttcactttc tcctcatact cgatgaactg ggtgcgccag 180
gcgccgggaa agggcctgga atgggtgtca tacatctcct cctcatcctc caccatctac 240
tacgccgatt ccgtgaaggg ccgcttcact atttcccggg acaacgcgaa aaactcgctc 300
tatctgcaaa tgaactccct gcgcgccgag gacaccgccg tgtactactg cgcccgggac 360
ctgagcgtgc gggctattga tgcgttcgac atctggggac agggcaccat ggtcacagtg 420
tccagcggag gcggcggcag cggtggagga ggatcagggg gaggaggttc ggggggcggt 480
ggctccgata tcgtgctgac ccagagcccg tcgagcctct ccgcctccgt cggcgacaga 540
gtgaccatca cgtgtcaggc atcccaggac attagcaact acctgaattg gtaccagcag 600
aagcctggaa aggcacccaa gttgctgatc tacgacgcct ccaacctgga aaccggagtg 660
ccatccaggt tctcgggcag cggctcggga accgacttca cttttactat ctcctccctg 720
caacccgagg atttcgcgac ctactactgc cagcaggcct acagcacccc tttcaccttc 780
gggccgggaa ctaaggtcga aatcaagacc actaccccag caccgaggcc acccaccccg 840
gctcctacca tcgcctccca gcctctgtcc ctgcgtccgg aggcatgtag acccgcagct 900
ggtggggccg tgcatacccg ggtcttgac ttcgcctgcg atatctacat ttgggcccct 960
ctggctggta cttgcggggt cctgctgctt tcactcgtga tcactcttta ctgtaagcgc 1020
ggtcggaaga agctgctgta catctttaag caacccttca tgaggcctgt gcagactact 1080
caagaggagg acggctgttc atgccggttc ccagaggagg aggaaggcgg ctgcgaactg 1140
cgcgtgaaat tcagccgcag cgcagatgct ccagcctaca agcaggggca gaaccagctc 1200
tacaacgaac tcaatcttgg tcggagagag gagtacgacg tgctggacaa gcggagagga 1260
cgggacccag aaatgggcgg gaagccgcgc agaaagaatc cccaagaggg cctgtacaac 1320
gagctccaaa aggataagat ggcagaagcc tatagcgaga ttggtatgaa aggggaacgc 1380
agaagaggca aaggccacga cggactgtac cagggactca gcaccgccac caaggacacc 1440
tatgacgctc ttcacatgca ggccctgccg cctcgg 1476

<210> SEQ ID NO 114
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114
atggccctcc ctgtcaccgc cctgctgctt ccgctggctc ttctgctcca cgccgctcgg 60
cccgaagtgc aattggtgca atcaggagga ggagtggtca gatctggaag aagcctgaga 120
ctgtcatgcg cggcttcggg ctttaccttc aactcctacg gcctccactg ggtgcgccag 180
gcccccggaa aaggcctcga atgggtcgca ctgattgagt acgacgggtc caacaagtac 240
tacggagata gcgtgaaggg ccgcttcacc atctcacggg acaagtccaa gtccaccctg 300
tatctgcaaa tggacaacct gagggccgag gatactgccg tgtactactg cgcccgcgaa 360
ggaaacgaag atctggcctt cgatatttgg ggccagggta ctcttgtgac cgtgtcgagc 420
ggaggcggag gctccggtgg aggaggatcg gggggtggtg gttccggcgg cggggggagc 480
gaaatcgtgc tgacccagtc gccttcctcc ctctccgctt ccgtggggga ccgggtcact 540
attacgtgtc aggcgtccca attcatcaag aagaatctga actggtacca gcacaagccg 600
ggaaaggccc ccaaactgct catctacgac gccagctcgc tgcagactgg cgtgccttcc 660
cggttttccg ggaaccggtc gggaaccacc ttctcattca ccatcagcag cctccagccg 720
gaggacgtgg cgacctacta ctgccagcag catgacaacc ttccactgac tttcggcggg 780
ggcaccaagg tcgagattaa gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960

```
ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                     1470
```

```
<210> SEQ ID NO 115
<211> LENGTH: 1497
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115

atggccctcc ctgtcaccgc cctgctgctt ccgctggctc ttctgctcca cgccgctcgg     60

ccccaagtgc aactcgtgga atcaggcgga ggactcgtgc aacccggagg ttcccttaga    120

ctgtcatgtg ccgcttccgg gttcaatgtg tccagcaact acatgacctg ggtcagacag    180

gcgccgggaa agggacttga atgggtgtcc gtgatctact ccggtggagc aacatactac    240

ggagactccg tgaaaggccg ctttaccgtg tcccgcgata actcgaagaa caccgtgtac    300

ttgcagatga acaggctgac tgccgaggac accgccgtgt attattgcgc ccgggacagg    360

ctgtactgtg gaaacaactg ctacctgtac tactactacg ggatggacgt gtggggacag    420

ggcactctcg tcactgtgtc atccgggggg ggcggtagcg gtggcggagg gtccggcgga    480

ggaggctcag gggaggcgg aagcgatatc caggtcaccc agtctccctc ctcgctgtcc    540

gcctccgtgg gcgaccgcgt caccattact tgccgggcgt cgcagtcgat cagctcctac    600

ctgaactggt accagcagaa gcctggaaag gccccgaagc tgctgatcta cgcggcctcg    660

tccctgcaaa gcggcgtccc gtcgcggttc agcggttccg gttcgggaac cgacttcacc    720

ctgactattt cctccctgca acccgaggat ttcgccactt actactgcca gcagtcctac    780

tccaccccac ctctgacctt cggccaagga accaaggtcg aaatcaagac cactacccca    840

gcaccgaggc cacccacccc ggctcctacc atcgcctccc agcctctgtc cctgcgtccg    900

gaggcatgta gacccgcagc tggtggggcc gtgcataccc ggggtcttga cttcgcctgc    960

gatatctaca tttgggcccc tctggctggt acttgcgggg tcctgctgct ttcactcgtg   1020

atcactcttt actgtaagcg cggtcggaag aagctgctgt acatctttaa gcaacccttc   1080

atgaggcctg tgcagactac tcaagaggag gacggctgtt catgccggtt cccagaggag   1140

gaggaaggcg gctgcgaact gcgcgtgaaa ttcagccgca gcgcagatgc tccagcctac   1200

aagcaggggc agaaccagct ctacaacgaa ctcaatcttg gtcggagaga ggagtacgac   1260

gtgctggaca agcggagagg acgggaccca gaaatgggcg ggaagccgcg cagaaagaat   1320

ccccaagagg gcctgtacaa cgagctccaa aaggataaga tggcagaagc ctatagcgag   1380

attggtatga aggggaacg cagaagaggc aaaggccacg acggactgta ccagggactc   1440

agcaccgcca ccaaggacac ctatgacgct cttcacatgc aggccctgcc gcctcgg      1497
```

<210> SEQ ID NO 116
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116

```
atggccctcc ctgtcaccgc cctgctgctt ccgctggctc ttctgctcca cgccgctcgg     60

ccccaagtgc aactcgtcca gtccggtgca gaagtgaaaa agagcggagc ctcagtgaaa    120

gtgtcctgca aggcctccgg ttacccccttc actggatact acattcagtg ggtccgccaa    180

gccccgggac agggtctgga gtggatgggg tggattgacc ctaactcggg aaatacggga    240

tacgcgcaga agttccaggg ccgcgtgacc atgaccagga acacctcgat cagcaccgcc    300

tacatggaac tgtcctccct gcggtcggag gatactgccg tgtactactg cgcctccgat    360

tcctatgggt actactacgg aatggacgtc tggggacagg gcaccctcgt gaccgtgtcc    420

tcgggaggcg gagggagcgg cgggggtgga tcgggaggag gcggctccgg cggcggcggt    480

agcgacatcc agatgaccca gtcaccatca agccttagcg cctccgtggg cgacagagtg    540

acattcactt gtcgggcgtc ccagggaatc tcctccgctc tggcttggta tcagcagaag    600

cctgggaagc ctccgaagct gttgatctac gacgcgagca gcctggaatc aggggtgccc    660

tcccggtttt ccgggtccgg ttctggcacc gatttcaccc tgaccatttc gtccctccaa    720

cccgaggact tcgccactta ctactgccag cagttcaaca actacccgct gaccttcgga    780

ggaggcacta aggtcgagat caagaccact accccagcac cgaggccacc caccccggct    840

cctaccatcg cctcccagcc tctgtccctg cgtccggagg catgtagacc cgcagctggt    900

ggggccgtgc atacccgggg tcttgacttc gcctgcgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgcgc   1140

gtgaaattca gccgcagcgc agatgctcca gcctacaagc aggggcagaa ccagctctac   1200

aacgaactca atcttggtcg gagagaggag tacgacgtgc tggacaagcg gagaggacgg   1260

gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                  1473
```

<210> SEQ ID NO 117
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 117

```
Gly Gly Thr Phe Ser Ser Tyr Ala Ile Ser
1               5                   10
```

<210> SEQ ID NO 118
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 118

Gly Phe Thr Phe Asp Asp Tyr Ala Met His
1 5 10

<210> SEQ ID NO 119
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 119

Gly Gly Ser Ile Ser Ser Ser Ser Tyr Tyr Trp Gly
1 5 10

<210> SEQ ID NO 120
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 120

Gly Phe Thr Phe Ser Ser Tyr Trp Met Ser
1 5 10

<210> SEQ ID NO 121
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 121

Gly Gly Pro Val Arg Ser Gly Ser His Tyr Trp Asn
1 5 10

<210> SEQ ID NO 122
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 122

Gly Gly Ser Phe Ser Gly Tyr Tyr Trp Ser
1 5 10

<210> SEQ ID NO 123
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 123

Gly Phe Thr Phe Ser Ser Tyr Ser Met Asn
1 5 10

<210> SEQ ID NO 124
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 124

Gly Phe Thr Phe Ser Ser Tyr Glu Met Asn
1 5 10

<210> SEQ ID NO 125
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 125

Ala Asn Thr Phe Ser Asp His Val Met His
1 5 10

<210> SEQ ID NO 126
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 126

Gly Phe Thr Phe Ser Ser Tyr Ser Met Asn
1 5 10

<210> SEQ ID NO 127
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 127

Gly Phe Thr Phe Asn Ser Tyr Gly Leu His
1 5 10

<210> SEQ ID NO 128
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

```
<400> SEQUENCE: 128

Gly Phe Asn Val Ser Ser Asn Tyr Met Thr
1               5                   10


<210> SEQ ID NO 129
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Tyr Pro Phe Thr Gly Tyr Tyr Ile Gln
1               5                   10


<210> SEQ ID NO 130
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Gly Ile Ile Pro Ile Phe Gly Thr Ala Asn Tyr Ala Gln Lys Phe Gln
1               5                   10                  15


<210> SEQ ID NO 131
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Leu Ile Ser Gly Asp Gly Gly Ser Thr Tyr Tyr Ala Asp Ser Val Lys
1               5                   10                  15

Gly


<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ser Ile Tyr Tyr Ser Gly Ser Thr Tyr Tyr Asn Pro Ser Leu Lys Ser
1               5                   10                  15


<210> SEQ ID NO 133
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133
```

```
Asn Ile Asn Glu Asp Gly Ser Ala Lys Phe Tyr Val Asp Ser Val Lys
1               5                   10                  15

Gly


<210> SEQ ID NO 134
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Tyr Ile Tyr Tyr Ser Gly Ser Thr Asn Tyr Asn Pro Ser Leu Glu Asn
1               5                   10                  15


<210> SEQ ID NO 135
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Glu Ile Asn His Ser Gly Ser Thr Asn Tyr Asn Pro Ser Leu Lys Ser
1               5                   10                  15


<210> SEQ ID NO 136
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ser Ile Ser Ser Ser Ser Ser Tyr Ile Tyr Tyr Ala Asp Ser Val Lys
1               5                   10                  15

Gly


<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Tyr Ile Ser Ser Ser Gly Ser Thr Ile Tyr Tyr Ala Asp Ser Val Lys
1               5                   10                  15

Gly


<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 138

Tyr Ile His Ala Ala Asn Gly Gly Thr His Tyr Ser Gln Lys Phe Gln
1 5 10 15

Asp

<210> SEQ ID NO 139
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Tyr Ile Ser Ser Ser Ser Ser Thr Ile Tyr Tyr Ala Asp Ser Val Lys
1 5 10 15

Gly

<210> SEQ ID NO 140
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Leu Ile Glu Tyr Asp Gly Ser Asn Lys Tyr Tyr Gly Asp Ser Val Lys
1 5 10 15

Gly

<210> SEQ ID NO 141
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Val Ile Tyr Ser Gly Gly Ala Thr Tyr Tyr Gly Asp Ser Val Lys Gly
1 5 10 15

<210> SEQ ID NO 142
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Trp Ile Asp Pro Asn Ser Gly Asn Thr Gly Tyr Ala Gln Lys Phe Gln
1 5 10 15

Gly

<210> SEQ ID NO 143
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 143

Asp Leu Glu Met Ala Thr Ile Met Gly Gly Tyr
1 5 10

<210> SEQ ID NO 144
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Val Phe Asp Ser Tyr Tyr Met Asp Val
1 5

<210> SEQ ID NO 145
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

Pro Gly Thr Tyr Tyr Asp Phe Leu Ser Gly Tyr Tyr Pro Phe Tyr
1 5 10 15

<210> SEQ ID NO 146
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

Asp Leu Arg Ser Gly Arg Tyr
1 5

<210> SEQ ID NO 147
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Gly Thr Ala Thr Phe Asp Trp Asn Phe Pro Phe Asp Ser
1 5 10

<210> SEQ ID NO 148
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Gly Ser Gly Leu Val Val Tyr Ala Ile Arg Val Gly Ser Gly Trp Phe
1 5 10 15

Asp Tyr

<210> SEQ ID NO 149
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Asp Pro Ser Ser Ser Gly Ser Tyr Tyr Met Glu Asp Ser Tyr Tyr Tyr
1 5 10 15

Gly Met Asp Val
20

<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

Glu Ala Leu Gly Ser Ser Trp Glu
1 5

<210> SEQ ID NO 151
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 151

Gly Gly Tyr Asn Ser Asp Ala Phe Asp Ile
1 5 10

<210> SEQ ID NO 152
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 152

Asp Leu Ser Val Arg Ala Ile Asp Ala Phe Asp Ile
1 5 10

<210> SEQ ID NO 153
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 153

Glu Gly Asn Glu Asp Leu Ala Phe Asp Ile
1               5                   10

<210> SEQ ID NO 154
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Asp Arg Leu Tyr Cys Gly Asn Asn Cys Tyr Leu Tyr Tyr Tyr Tyr Gly
1               5                   10                  15

Met Asp Val

<210> SEQ ID NO 155
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Asp Ser Tyr Gly Tyr Tyr Tyr Gly Met Asp Val
1               5                   10

<210> SEQ ID NO 156
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Thr Gly Thr Ser Ser Asp Val Gly Gly Tyr Asn Tyr Val Ser
1               5                   10

<210> SEQ ID NO 157
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Arg Ser Ser Gln Ser Leu Val Tyr Thr Asp Gly Asn Thr Tyr Leu Asn
1               5                   10                  15

<210> SEQ ID NO 158
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Arg Ala Ser Gln Gly Ile Ser Ser Tyr Leu Ala
1 5 10

<210> SEQ ID NO 159
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 159

Arg Ala Ser Gln Ser Ile Ser Gly Ser Phe Leu Ala
1 5 10

<210> SEQ ID NO 160
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 160

Arg Ala Ser Gln Ser Ile Ser Ser Tyr Leu Asn
1 5 10

<210> SEQ ID NO 161
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Arg Ala Ser Gln Ser Ile Ser Ser Tyr Leu Asn
1 5 10

<210> SEQ ID NO 162
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 162

Thr Gly Ser Ser Gly Ser Ile Ala Ser Asn Tyr Val Gln
1 5 10

<210> SEQ ID NO 163
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 163

Gln Ala Ser Gln Asp Ile Ser Asn Tyr Leu Asn
1 5 10

<210> SEQ ID NO 164
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 164

Arg Ala Ser Gln Asp Ile Ser Ser Trp Leu Ala
1 5 10

<210> SEQ ID NO 165
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 165

Gln Ala Ser Gln Asp Ile Ser Asn Tyr Leu Asn
1 5 10

<210> SEQ ID NO 166
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 166

Gln Ala Ser Gln Phe Ile Lys Lys Asn Leu Asn
1 5 10

<210> SEQ ID NO 167
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 167

Arg Ala Ser Gln Ser Ile Ser Ser Tyr Leu Asn
1 5 10

<210> SEQ ID NO 168
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 168

Arg Ala Ser Gln Gly Ile Ser Ser Ala Leu Ala
1 5 10

<210> SEQ ID NO 169
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Asp Val Ser Asn Arg Pro Ser
1               5


<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Lys Val Ser Asn Arg Asp Ser
1               5


<210> SEQ ID NO 171
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Ala Ala Ser Thr Leu Gln Ser
1               5


<210> SEQ ID NO 172
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gly Ala Ser Ser Arg Ala Thr
1               5


<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Ala Ala Ser Ser Leu Gln Ser
1               5


<210> SEQ ID NO 174
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 174

Ala Ala Ser Ser Leu Gln Ser
1               5


<210> SEQ ID NO 175
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Glu Asp Asn Gln Arg Pro Ser
1               5


<210> SEQ ID NO 176
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Asp Ala Ser Asn Leu Glu Thr
1               5


<210> SEQ ID NO 177
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ala Ala Ser Ser Leu Gln Ser
1               5


<210> SEQ ID NO 178
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Asp Ala Ser Asn Leu Glu Thr
1               5


<210> SEQ ID NO 179
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179
```

Asp Ala Ser Ser Leu Gln Thr
1 5

<210> SEQ ID NO 180
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 180

Ala Ala Ser Ser Leu Gln Ser
1 5

<210> SEQ ID NO 181
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 181

Asp Ala Ser Ser Leu Glu Ser
1 5

<210> SEQ ID NO 182
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 182

Ser Ser Tyr Thr Ser Ser Ser Thr Leu Asp Val Val
1 5 10

<210> SEQ ID NO 183
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 183

Met Gln Gly Thr His Trp Ser Phe Thr
1 5

<210> SEQ ID NO 184
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 184

Gln Gln Leu Asn Ser Tyr Pro Tyr Thr
1 5

```
<210> SEQ ID NO 185
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Gln Gln Tyr Gly Ser Ser Pro Pro Thr
1               5


<210> SEQ ID NO 186
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gln Gln Ser Tyr Ser Thr Pro Trp Thr
1               5


<210> SEQ ID NO 187
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gln Gln Ser Tyr Ser Thr Pro Pro Trp Thr
1               5                   10


<210> SEQ ID NO 188
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gln Ser Tyr Asp Ser Ser Asn Gln Val Val
1               5                   10


<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Gln Gln Tyr Asp Asn Leu Pro Leu Thr
1               5


<210> SEQ ID NO 190
<211> LENGTH: 9
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 190

Gln Gln Ser Tyr Ser Thr Pro Leu Thr
1 5

<210> SEQ ID NO 191
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 191

Gln Gln Ala Tyr Ser Thr Pro Phe Thr
1 5

<210> SEQ ID NO 192
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 192

Gln Gln His Asp Asn Leu Pro Leu Thr
1 5

<210> SEQ ID NO 193
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 193

Gln Gln Ser Tyr Ser Thr Pro Pro Leu Thr
1 5 10

<210> SEQ ID NO 194
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 194

Gln Gln Phe Asn Asn Tyr Pro Leu Thr
1 5

<210> SEQ ID NO 195
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 195

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Glu Met Asn Trp Val Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Pro Tyr Ser Ser Ser Trp His Asp Ala Phe Asp Ile Trp
100 105 110

Gly Gln Gly Thr Met Val Thr Val Ser Ser
115 120

<210> SEQ ID NO 196
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 196

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Leu Thr Phe Gly Gly Gly Thr Lys Val Asp Ile Lys
100 105

<210> SEQ ID NO 197
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 197

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

-continued

```
Val Gln Pro Gly Gly Ser Leu Arg Leu Ser Cys Ala Ala Ser Gly Phe
        35                  40                  45

Thr Phe Ser Ser Tyr Glu Met Asn Trp Val Arg Gln Ala Pro Gly Lys
    50                  55                  60

Gly Leu Glu Trp Val Ser Tyr Ile Ser Ser Ser Gly Ser Thr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp Pro Tyr Ser Ser Ser Trp His Asp
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Val Ser Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Ser Arg Ala Thr Gly Ile Pro Asp Arg Phe Ser Gly Ser
    210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr Gly Ser Ser Pro Leu Thr
                245                 250                 255

Phe Gly Gly Gly Thr Lys Val Asp Ile Lys Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
```

```
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 198
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 198

```
atggccctcc ctgtcaccgc cctgctgctt ccgctggctc ttctgctcca cgccgctcgg     60

cccgaagtgc aactcgtgga aagcggtgga ggtcttgtgc aacctggagg ttccttgcgc    120

ctgtcatgtg cagcttccgg cttcactttc tcctcgtacg agatgaattg ggtgcggcag    180

gcgcctggaa aggggctgga atgggtgtcc tacatctcaa gctccggctc gaccatctac    240

tacgcggaca gcgtgaaggg gcggttcacg atttcgaggg acaacgccaa gaactcgctc    300

tatctgcaaa tgaactccct gagagccgag gacaccgctg tgtattactg cgcccgggac    360

ccctactcct cctcatggca cgacgccttt gatatctggg gccagggaac catggtcacc    420

gtcagcagcg gggcggaggg ttccgggggga gggggctccg gcggaggagg ctccgagatt    480

gtgttgactc agagcccggg taccctgtcg ctgagccccg gagagcgggc caccctttca    540

tgccgcgcca gccagtccgt gtcctcatcc tacctcgcgt ggtaccagca gaaacctggc    600

caggccccgc ggctgctgat ctacggcgcc tcctcgcgcg caaccggaat ccccgaccgg    660

ttctccgggt ctggcagcgg aaccgacttc actctcacca tttcgaggct ggagccggaa    720

gatttcgccg tgtactactg ccagcagtac ggctcctcgc cactgacttt cggcggagga    780

accaaggtcg atatcaagac cactacccca gcaccgaggc cacccacccc ggctcctacc    840

atcgcctccc agcctctgtc cctgcgtccg gaggcatgta gacccgcagc tggtggggcc    900

gtgcataccc ggggtcttga cttcgcctgc gatatctaca tttgggcccc tctggctggt    960

acttgcgggg tcctgctgct ttcactcgtg atcactcttt actgtaagcg cggtcggaag   1020

aagctgctgt acatctttaa gcaacccttc atgaggcctg tgcagactac tcaagaggag   1080

gacggctgtt catgccggtt cccagaggag gaggaaggcg gctgcgaact gcgcgtgaaa   1140

ttcagccgca gcgcagatgc tccagcctac aagcaggggc agaaccagct ctacaacgaa   1200

ctcaatcttg gtcggagaga ggagtacgac gtgctggaca agcggagagg acgggaccca   1260

gaaatgggcg ggaagccgcg cagaaagaat ccccaagagg gcctgtacaa cgagctccaa   1320

aaggataaga tggcagaagc ctatagcgag attggtatga aaggggaacg cagaagaggc   1380

aaaggccacg acggactgta ccagggactc agcaccgcca ccaaggacac ctatgacgct   1440

cttcacatgc aggccctgcc gcctcgg                                       1467
```

<210> SEQ ID NO 199
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 199

Gly Phe Thr Phe Ser Ser Tyr Glu Met Asn
1               5                   10

<210> SEQ ID NO 200
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Tyr Ile Ser Ser Ser Gly Ser Thr Ile Tyr Tyr Ala Asp Ser Val Lys
1               5                   10                  15

Gly

<210> SEQ ID NO 201
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Asp Pro Tyr Ser Ser Ser Trp His Asp Ala Phe Asp Ile
1               5                   10

<210> SEQ ID NO 202
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Arg Ala Ser Gln Ser Val Ser Ser Ser Tyr Leu Ala
1               5                   10

<210> SEQ ID NO 203
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gly Ala Ser Ser Arg Ala Thr
1               5

<210> SEQ ID NO 204
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Gln Gln Tyr Gly Ser Ser Pro Leu Thr
1               5

<210> SEQ ID NO 205
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 206
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105

<210> SEQ ID NO 207
<211> LENGTH: 93

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 207

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90
```

<210> SEQ ID NO 208
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 208

```
Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95
```

<210> SEQ ID NO 209
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 209

```
Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
```

50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys Thr Ser
85 90 95

<210> SEQ ID NO 210
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 210

Ile Leu Trp His Glu Met Trp His Glu Gly Leu Glu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 211
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 211

Ile Leu Trp His Glu Met Trp His Glu Gly Leu Xaa Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Xaa Gln Ala
65 70 75 80

Trp Asp Leu Tyr Tyr His Val Phe Arg Arg Ile Ser Lys Thr Ser
85 90 95

<210> SEQ ID NO 212
<211> LENGTH: 95

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 212

Ile Leu Trp His Glu Met Trp His Glu Gly Leu Ile Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 213
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 213

Ile Leu Trp His Glu Met Trp His Glu Gly Leu Leu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 214
<211> LENGTH: 1132
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 214

Met Pro Arg Ala Pro Arg Cys Arg Ala Val Arg Ser Leu Leu Arg Ser
1 5 10 15

His Tyr Arg Glu Val Leu Pro Leu Ala Thr Phe Val Arg Arg Leu Gly
20 25 30

Pro Gln Gly Trp Arg Leu Val Gln Arg Gly Asp Pro Ala Ala Phe Arg
35 40 45

Ala Leu Val Ala Gln Cys Leu Val Cys Val Pro Trp Asp Ala Arg Pro

-continued

```
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480
```

```
Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895
```

```
Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Val  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Val  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130


<210> SEQ ID NO 215
<211> LENGTH: 4027
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215

caggcagcgt ggtcctgctg cgcacgtggg aagccctggc cccggccacc cccgcgatgc     60

cgcgcgctcc ccgctgccga gccgtgcgct ccctgctgcg cagccactac cgcgaggtgc    120

tgccgctggc cacgttcgtg cggcgcctgg ggccccaggg ctggcggctg gtgcagcgcg    180

gggacccggc ggctttccgc gcgctggtgg cccagtgcct ggtgtgcgtg ccctgggacg    240

cacggccgcc ccccgccgcc ccctccttcc gccaggtgtc ctgcctgaag gagctggtgg    300

cccgagtgct gcagaggctg tgcgagcgcg gcgcgaagaa cgtgctggcc ttcggcttcg    360

cgctgctgga cggggcccgc gggggccccc ccgaggcctt caccaccagc gtgcgcagct    420

acctgcccaa cacggtgacc gacgcactgc gggggagcgg ggcgtggggg ctgctgttgc    480

gccgcgtggg cgacgacgtg ctggttcacc tgctggcacg ctgcgcgctc tttgtgctgg    540

tggctcccag ctgcgcctac caggtgtgcg ggccgccgct gtaccagctc ggcgctgcca    600
```

-continued

```
ctcaggcccg gcccccgcca cacgctagtg gaccccgaag gcgtctggga tgcgaacggg    660
cctggaacca tagcgtcagg gaggccgggg tccccctggg cctgccagcc ccgggtgcga    720
ggaggcgcgg gggcagtgcc agccgaagtc tgccgttgcc caagaggccc aggcgtggcg    780
ctgcccctga gccggagcgg acgcccgttg ggcaggggtc ctgggcccac ccgggcagga    840
cgcgtggacc gagtgaccgt ggtttctgtg tggtgtcacc tgccagaccc gccgaagaag    900
ccacctcttt ggagggtgcg ctctctggca cgcgccactc ccacccatcc gtgggccgcc    960
agcaccacgc gggcccccca tccacatcgc ggccaccacg tccctgggac acgccttgtc   1020
ccccggtgta cgccgagacc aagcacttcc tctactcctc aggcgacaag gagcagctgc   1080
ggccctcctt cctactcagc tctctgaggc ccagcctgac tggcgctcgg aggctcgtgg   1140
agaccatctt tctgggttcc aggccctgga tgccagggac tccccgcagg ttgccccgcc   1200
tgccccagcg ctactggcaa atgcggcccc tgtttctgga gctgcttggg aaccacgcgc   1260
agtgccccta cggggtgctc ctcaagacgc actgcccgct gcgagctgcg gtcaccccag   1320
cagccggtgt ctgtgcccgg gagaagcccc agggctctgt ggcggccccc gaggaggagg   1380
acacagaccc ccgtcgcctg gtgcagctgc tccgccagca cagcagcccc tggcaggtgt   1440
acggcttcgt gcgggcctgc ctgcgccggc tggtgccccc aggcctctgg ggctccaggc   1500
acaacgaacg ccgcttcctc aggaacacca agaagttcat ctccctgggg aagcatgcca   1560
agctctcgct gcaggagctg acgtggaaga tgagcgtgcg gggctgcgct tggctgcgca   1620
ggagcccagg ggttggctgt gttccggccg cagagcaccg tctgcgtgag gagatcctgg   1680
ccaagttcct gcactggctg atgagtgtgt acgtcgtcga gctgctcagg tctttctttt   1740
atgtcacgga gaccacgttt caaaagaaca ggctcttttt ctaccggaag agtgtctgga   1800
gcaagttgca aagcattgga atcagacagc acttgaagag ggtgcagctg cgggagctgt   1860
cggaagcaga ggtcaggcag catcgggaag ccaggcccgc cctgctgacg tccagactcc   1920
gcttcatccc caagcctgac gggctgcggc cgattgtgaa catggactac gtcgtgggag   1980
ccagaacgtt ccgcagagaa aagagggccg agcgtctcac ctcgagggtg aaggcactgt   2040
tcagcgtgct caactacgag cgggcgcggc gccccggcct cctgggcgcc tctgtgctgg   2100
gcctggacga tatccacagg gcctggcgca ccttcgtgct gcgtgtgcgg gcccaggacc   2160
cgccgcctga gctgtacttt gtcaaggtgg atgtgacggg cgcgtacgac accatccccc   2220
aggacaggct cacggaggtc atcgccagca tcatcaaacc ccagaacacg tactgcgtgc   2280
gtcggtatgc cgtggtccag aaggccgccc atgggcacgt ccgcaaggcc ttcaagagcc   2340
acgtctctac cttgacagac ctccagccgt acatgcgaca gttcgtggct cacctgcagg   2400
agaccagccc gctgagggat gccgtcgtca tcgagcagag ctcctccctg aatgaggcca   2460
gcagtggcct cttcgacgtc ttcctacgct tcatgtgcca ccacgccgtg cgcatcaggg   2520
gcaagtccta cgtccagtgc caggggatcc cgcagggctc catcctctcc acgctgctct   2580
gcagcctgtg ctacggcgac atggagaaca agctgtttgc ggggattcgg cgggacgggc   2640
tgctcctgcg tttggtggat gatttcttgt tggtgacacc tcacctcacc cacgcgaaaa   2700
ccttcctcag gaccctggtc cgaggtgtcc ctgagtatgg ctgcgtggtg aacttgcgga   2760
agacagtggt gaacttccct gtagaagacg aggccctggg tggcacggct tttgttcaga   2820
tgccggccca cggcctattc ccctggtgcg gcctgctgct ggatacccgg accctggagg   2880
tgcagagcga ctactccagc tatgcccgga cctccatcag agccagtctc accttcaacc   2940
```

gcggcttcaa ggctgggagg aacatgcgtc gcaaactctt tggggtcttg cggctgaagt 3000
gtcacagcct gtttctggat ttgcaggtga acagcctcca gacggtgtgc accaacatct 3060
acaagatcct cctgctgcag gcgtacaggt ttcacgcatg tgtgctgcag ctcccatttc 3120
atcagcaagt ttggaagaac ccccacattt tcctgcgcgt catctctgac acggcctccc 3180
tctgctactc catcctgaaa gccaagaacg cagggatgtc gctgggggcc aagggcgccg 3240
ccggccctct gccctccgag gccgtgcagt ggctgtgcca ccaagcattc ctgctcaagc 3300
tgactcgaca ccgtgtcacc tacgtgccac tcctggggtc actcaggaca gcccagacgc 3360
agctgagtcg gaagctcccg gggacgacgc tgactgccct ggaggccgca gccaacccgg 3420
cactgccctc agacttcaag accatcctgg actgatggcc acccgcccac agccaggccg 3480
agagcagaca ccagcagccc tgtcacgccg ggctctacgt cccagggagg gaggggcggc 3540
ccacacccag gcccgcaccg ctgggagtct gaggcctgag tgagtgtttg gccgaggcct 3600
gcatgtccgg ctgaaggctg agtgtccggc tgaggcctga gcgagtgtcc agccaagggc 3660
tgagtgtcca gcacacctgc cgtcttcact tccccacagg ctggcgctcg gctccacccc 3720
agggccagct tttcctcacc aggagcccgg cttccactcc ccacatagga atagtccatc 3780
cccagattcg ccattgttca cccctcgccc tgccctcctt tgccttccac ccccaccatc 3840
caggtggaga ccctgagaag gaccctggga gctctgggaa tttggagtga ccaaaggtgt 3900
gccctgtaca caggcgagga ccctgcacct ggatgggggt ccctgtgggt caaattgggg 3960
ggaggtgctg tgggagtaaa atactgaata tatgagtttt tcagttttga aaaaaaaaaa 4020
aaaaaaa 4027

<210> SEQ ID NO 216
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
ggaggtccct caccttcta 19

<210> SEQ ID NO 217
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 217
cggaggatct tatgctgaa 19

<210> SEQ ID NO 218
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
cccgcttcca gatcataca 19

<210> SEQ ID NO 219
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 219
ggagacctca acaagatat 19

<210> SEQ ID NO 220
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 220
aaggcatggt cattggtat 19

<210> SEQ ID NO 221
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
gcatggtcat tggtatcat 19

<210> SEQ ID NO 222
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
ggtcattggt atcatgagt 19

<210> SEQ ID NO 223
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
cctagtgggt atccctgta 19

<210> SEQ ID NO 224
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 224
gaggatggac attgttctt 19

<210> SEQ ID NO 225
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
gcatgcaggc tacagttca 19

<210> SEQ ID NO 226
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
ccagcacatg cactgttga 19

<210> SEQ ID NO 227
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
cacatgcact gttgagtga 19

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
ctggaggtcc ctcaccttct a 21

<210> SEQ ID NO 229
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 229
gtcggaggat cttatgctga a 21

<210> SEQ ID NO 230
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
tgcccgcttc cagatcatac a 21

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
ctggagacct caacaagata t 21

<210> SEQ ID NO 232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
tcaaggcatg gtcattggta t 21

<210> SEQ ID NO 233
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
aggcatggtc attggtatca t 21

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
atggtcattg gtatcatgag t 21

<210> SEQ ID NO 235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
gccctagtgg gtatccctgt a 21

<210> SEQ ID NO 236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
atgaggatgg acattgttct t 21

<210> SEQ ID NO 237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 237
gagcatgcag gctacagttc a 21

<210> SEQ ID NO 238
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 238
ttccagcaca tgcactgttg a 21

<210> SEQ ID NO 239
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 239
agcacatgca ctgttgagtg a 21

<210> SEQ ID NO 240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 240
tagaaggtga gggacctcca g 21

<210> SEQ ID NO 241
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 241

ttcagcataa gatcctccga c                                          21


<210> SEQ ID NO 242
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242

tgtatgatct ggaagcgggc a                                          21


<210> SEQ ID NO 243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243

atatcttgtt gaggtctcca g                                          21


<210> SEQ ID NO 244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244

ataccaatga ccatgccttg a                                          21


<210> SEQ ID NO 245
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245

atgataccaa tgaccatgcc t                                          21


<210> SEQ ID NO 246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246

atggtcattg gtatcatgag t                                          21


<210> SEQ ID NO 247
```

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 247
gccctagtgg gtatccctgt a 21

<210> SEQ ID NO 248
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
atgaggatgg acattgttct t 21

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
gagcatgcag gctacagttc a 21

<210> SEQ ID NO 250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
ttccagcaca tgcactgttg a 21

<210> SEQ ID NO 251
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
agcacatgca ctgttgagtg a 21

<210> SEQ ID NO 252
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
tagaaggtga gggacctcc 19

<210> SEQ ID NO 253
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
ttcagcataa gatcctccg 19

<210> SEQ ID NO 254
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
tgtatgatct ggaagcggg 19

<210> SEQ ID NO 255
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
atatcttgtt gaggtctcc 19

<210> SEQ ID NO 256
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
ataccaatga ccatgcctt 19

<210> SEQ ID NO 257
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
atgataccaa tgaccatgc 19

<210> SEQ ID NO 258
<211> LENGTH: 19
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 258
atggtcattg gtatcatga 19

<210> SEQ ID NO 259
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 259
gccctagtgg gtatccctg 19

<210> SEQ ID NO 260
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:\
Synthetic oligonucleotide"

<400> SEQUENCE: 260
atgaggatgg acattgttc 19

<210> SEQ ID NO 261
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 261
gagcatgcag gctacagtt 19

<210> SEQ ID NO 262
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 262
ttccagcaca tgcactgtt 19

<210> SEQ ID NO 263
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 263
agcacatgca ctgttgagt 19

<210> SEQ ID NO 264
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 264
ggccaggatg gttcttaga 19

<210> SEQ ID NO 265
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 265
gcttcgtgct aaactggta 19

<210> SEQ ID NO 266
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
gggcgtgact tccacatga 19

<210> SEQ ID NO 267
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
caggcctaga gaagtttca 19

<210> SEQ ID NO 268
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
cttggaaccc attcctgaa 19

<210> SEQ ID NO 269
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
ggaacccatt cctgaaatt 19

<210> SEQ ID NO 270
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 270
gaacccattc ctgaaatta 19

<210> SEQ ID NO 271
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 271
aacccattcc tgaaattat 19

<210> SEQ ID NO 272
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 272
acccattcct gaaattatt 19

<210> SEQ ID NO 273
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 273
cccattcctg aaattattt 19

<210> SEQ ID NO 274
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 274
ctgtggttct attatatta 19

<210> SEQ ID NO 275
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 275
aaatatgaga gcatgctaa 19

<210> SEQ ID NO 276
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 276
tctaagaacc atcctggcc 19

<210> SEQ ID NO 277
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 277
taccagttta gcacgaagc 19

<210> SEQ ID NO 278
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 278
tcatgtggaa gtcacgccc 19

<210> SEQ ID NO 279
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 279
tgaaacttct ctaggcctg 19

<210> SEQ ID NO 280
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 280
ttcaggaatg ggttccaag 19

<210> SEQ ID NO 281
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
aatttcagga atgggttcc 19

<210> SEQ ID NO 282
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 282
taatttcagg aatgggttc 19

<210> SEQ ID NO 283
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 283
ataatttcag gaatgggtt 19

<210> SEQ ID NO 284
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 284
aataatttca ggaatgggt 19

<210> SEQ ID NO 285
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 285
aaataatttc aggaatggg 19

<210> SEQ ID NO 286
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 286
taatataata gaaccacag 19

<210> SEQ ID NO 287
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
ttagcatgct ctcatattt 19

<210> SEQ ID NO 288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
gcggccagga tggttcttag a 21

<210> SEQ ID NO 289
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
gagcttcgtg ctaaactggt a 21

<210> SEQ ID NO 290
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
acgggcgtga cttccacatg a 21

<210> SEQ ID NO 291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
tgcaggccta gagaagtttc a 21

<210> SEQ ID NO 292
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
tccttggaac ccattcctga a 21

<210> SEQ ID NO 293
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 293
ttggaaccca ttcctgaaat t 21

<210> SEQ ID NO 294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 294
tggaacccat tcctgaaatt a 21

<210> SEQ ID NO 295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 295
ggaacccatt cctgaaatta t 21

<210> SEQ ID NO 296
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 296
gaacccattc ctgaaattat t 21

<210> SEQ ID NO 297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 297
aacccattcc tgaaattatt t 21

<210> SEQ ID NO 298
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
ccctgtggtt ctattatatt a 21

<210> SEQ ID NO 299
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
ttaaatatga gagcatgcta a 21

<210> SEQ ID NO 300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
tctaagaacc atcctggccg c 21

<210> SEQ ID NO 301
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
taccagttta gcacgaagct c 21

<210> SEQ ID NO 302
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
tcatgtggaa gtcacgcccg t 21

<210> SEQ ID NO 303
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 303
tgaaacttct ctaggcctgc a 21

<210> SEQ ID NO 304
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 304
ttcaggaatg ggttccaagg a 21

<210> SEQ ID NO 305
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 305
aatttcagga atgggttcca a 21

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 306
taatttcagg aatgggttcc a 21

<210> SEQ ID NO 307
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 307
ataatttcag gaatgggttc c 21

<210> SEQ ID NO 308
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 308
aataatttca ggaatgggtt c 21

<210> SEQ ID NO 309
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
aaataatttc aggaatgggt t 21

<210> SEQ ID NO 310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
taatataata gaaccacagg g 21

<210> SEQ ID NO 311
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
ttagcatgct ctcatattta a 21

<210> SEQ ID NO 312
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 312
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa 150

<210> SEQ ID NO 313
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Arg Gly Asp Ser
1

<210> SEQ ID NO 314
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 314

Ser Tyr Ala Ile Ser
1 5

<210> SEQ ID NO 315
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 315

Asp Tyr Ala Met His
1 5

<210> SEQ ID NO 316
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 316

Ser Ser Ser Tyr Tyr Trp Gly
1 5

<210> SEQ ID NO 317
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 317

Ser Tyr Trp Met Ser
1 5

<210> SEQ ID NO 318
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 318

Ser Gly Ser His Tyr Trp Asn
1 5

<210> SEQ ID NO 319
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 319

Gly Tyr Tyr Trp Ser
1 5

<210> SEQ ID NO 320
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 320

Ser Tyr Ser Met Asn
1 5

<210> SEQ ID NO 321
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 321

Ser Tyr Glu Met Asn
1 5

<210> SEQ ID NO 322
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 322

Asp His Val Met His
1 5

<210> SEQ ID NO 323
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 323

Ser Tyr Ser Met Asn
1 5

<210> SEQ ID NO 324
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 324

Ser Tyr Gly Leu His
1 5

<210> SEQ ID NO 325
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 325

Ser Asn Tyr Met Thr
1 5

<210> SEQ ID NO 326
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 326

Gly Tyr Tyr Ile Gln
1 5

<210> SEQ ID NO 327
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 327

Ser Tyr Glu Met Asn
1 5

<210> SEQ ID NO 328
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 328

Gly Ile Ile Pro Ile Phe Gly Thr Ala Asn Tyr Ala Gln Lys Phe Gln
1 5 10 15

Gly

<210> SEQ ID NO 329
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 329

Leu Ile Ser Gly Asp Gly Gly Ser Thr Tyr Tyr Ala Asp Ser Val Lys
1 5 10 15

Gly

<210> SEQ ID NO 330
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 330

Ser Ile Tyr Tyr Ser Gly Ser Thr Tyr Tyr Asn Pro Ser Leu Lys Ser
1 5 10 15

<210> SEQ ID NO 331
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 331

Asn Ile Asn Glu Asp Gly Ser Ala Lys Phe Tyr Val Asp Ser Val Lys
1 5 10 15

Gly

<210> SEQ ID NO 332
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 332

Tyr Ile Tyr Tyr Ser Gly Ser Thr Asn Tyr Asn Pro Ser Leu Glu Asn
1 5 10 15

<210> SEQ ID NO 333
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 333

Glu Ile Asn His Ser Gly Ser Thr Asn Tyr Asn Pro Ser Leu Lys Ser
1 5 10 15

<210> SEQ ID NO 334
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 334

Ser Ile Ser Ser Ser Ser Ser Tyr Ile Tyr Tyr Ala Asp Ser Val Lys
1 5 10 15

Gly

<210> SEQ ID NO 335
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 335

Tyr Ile Ser Ser Ser Gly Ser Thr Ile Tyr Tyr Ala Asp Ser Val Lys
1 5 10 15

Gly

<210> SEQ ID NO 336
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 336

Tyr Ile His Ala Ala Asn Gly Gly Thr His Tyr Ser Gln Lys Phe Gln
1 5 10 15

Asp

<210> SEQ ID NO 337
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 337

Tyr Ile Ser Ser Ser Ser Ser Thr Ile Tyr Tyr Ala Asp Ser Val Lys
1 5 10 15

Gly

<210> SEQ ID NO 338
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 338

Leu Ile Glu Tyr Asp Gly Ser Asn Lys Tyr Tyr Gly Asp Ser Val Lys
1 5 10 15

Gly

<210> SEQ ID NO 339
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 339

```
Val Ile Tyr Ser Gly Gly Ala Thr Tyr Tyr Gly Asp Ser Val Lys Gly
1               5                   10                  15


<210> SEQ ID NO 340
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Trp Ile Asp Pro Asn Ser Gly Asn Thr Gly Tyr Ala Gln Lys Phe Gln
1               5                   10                  15

Gly


<210> SEQ ID NO 341
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Tyr Ile Ser Ser Ser Gly Ser Thr Ile Tyr Tyr Ala Asp Ser Val Lys
1               5                   10                  15

Gly


<210> SEQ ID NO 342
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Asp Leu Glu Met Ala Thr Ile Met Gly Gly Tyr
1               5                   10


<210> SEQ ID NO 343
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Val Phe Asp Ser Tyr Tyr Met Asp Val
1               5


<210> SEQ ID NO 344
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344
```

```
Pro Gly Thr Tyr Tyr Asp Phe Leu Ser Gly Tyr Tyr Pro Phe Tyr
1               5                   10                  15


<210> SEQ ID NO 345
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Asp Leu Arg Ser Gly Arg Tyr
1               5


<210> SEQ ID NO 346
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Gly Thr Ala Thr Phe Asp Trp Asn Phe Pro Phe Asp Ser
1               5                   10


<210> SEQ ID NO 347
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Gly Ser Gly Leu Val Val Tyr Ala Ile Arg Val Gly Ser Gly Trp Phe
1               5                   10                  15

Asp Tyr


<210> SEQ ID NO 348
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Asp Pro Ser Ser Ser Gly Ser Tyr Tyr Met Glu Asp Ser Tyr Tyr Tyr
1               5                   10                  15

Gly Met Asp Val
            20


<210> SEQ ID NO 349
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 349

Glu Ala Leu Gly Ser Ser Trp Glu
1 5

<210> SEQ ID NO 350
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 350

Gly Gly Tyr Asn Ser Asp Ala Phe Asp Ile
1 5 10

<210> SEQ ID NO 351
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 351

Asp Leu Ser Val Arg Ala Ile Asp Ala Phe Asp Ile
1 5 10

<210> SEQ ID NO 352
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 352

Glu Gly Asn Glu Asp Leu Ala Phe Asp Ile
1 5 10

<210> SEQ ID NO 353
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 353

Asp Arg Leu Tyr Cys Gly Asn Asn Cys Tyr Leu Tyr Tyr Tyr Tyr Gly
1 5 10 15

Met Asp Val

<210> SEQ ID NO 354
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 354

```
Asp Ser Tyr Gly Tyr Tyr Tyr Gly Met Asp Val
1               5                   10


<210> SEQ ID NO 355
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Asp Pro Tyr Ser Ser Ser Trp His Asp Ala Phe Asp Ile
1               5                   10


<210> SEQ ID NO 356
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Thr Gly Thr Ser Ser Asp Val Gly Gly Tyr Asn Tyr Val Ser
1               5                   10


<210> SEQ ID NO 357
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Arg Ser Ser Gln Ser Leu Val Tyr Thr Asp Gly Asn Thr Tyr Leu Asn
1               5                   10                  15


<210> SEQ ID NO 358
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Arg Ala Ser Gln Gly Ile Ser Ser Tyr Leu Ala
1               5                   10


<210> SEQ ID NO 359
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Arg Ala Ser Gln Ser Ile Ser Gly Ser Phe Leu Ala
1               5                   10
```

<210> SEQ ID NO 360
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 360

Arg Ala Ser Gln Ser Ile Ser Ser Tyr Leu Asn
1 5 10

<210> SEQ ID NO 361
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 361

Arg Ala Ser Gln Ser Ile Ser Ser Tyr Leu Asn
1 5 10

<210> SEQ ID NO 362
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 362

Thr Gly Ser Ser Gly Ser Ile Ala Ser Asn Tyr Val Gln
1 5 10

<210> SEQ ID NO 363
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 363

Gln Ala Ser Gln Asp Ile Ser Asn Tyr Leu Asn
1 5 10

<210> SEQ ID NO 364
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 364

Arg Ala Ser Gln Asp Ile Ser Ser Trp Leu Ala
1 5 10

<210> SEQ ID NO 365
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 365

Gln Ala Ser Gln Asp Ile Ser Asn Tyr Leu Asn
1 5 10

<210> SEQ ID NO 366
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 366

Gln Ala Ser Gln Phe Ile Lys Lys Asn Leu Asn
1 5 10

<210> SEQ ID NO 367
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 367

Arg Ala Ser Gln Ser Ile Ser Ser Tyr Leu Asn
1 5 10

<210> SEQ ID NO 368
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 368

Arg Ala Ser Gln Gly Ile Ser Ser Ala Leu Ala
1 5 10

<210> SEQ ID NO 369
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 369

Arg Ala Ser Gln Ser Val Ser Ser Ser Tyr Leu Ala
1 5 10

<210> SEQ ID NO 370
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 370

Asp Val Ser Asn Arg Pro Ser
1 5

<210> SEQ ID NO 371
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 371

Lys Val Ser Asn Arg Asp Ser
1 5

<210> SEQ ID NO 372
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 372

Ala Ala Ser Thr Leu Gln Ser
1 5

<210> SEQ ID NO 373
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 373

Gly Ala Ser Ser Arg Ala Thr
1 5

<210> SEQ ID NO 374
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 374

Ala Ala Ser Ser Leu Gln Ser
1 5

<210> SEQ ID NO 375
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 375

Ala Ala Ser Ser Leu Gln Ser 1 5

<210> SEQ ID NO 376
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 376

Glu Asp Asn Gln Arg Pro Ser
1 5

<210> SEQ ID NO 377
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 377

Asp Ala Ser Asn Leu Glu Thr
1 5

<210> SEQ ID NO 378
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 378

Ala Ala Ser Ser Leu Gln Ser
1 5

<210> SEQ ID NO 379
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 379

Asp Ala Ser Asn Leu Glu Thr
1 5

<210> SEQ ID NO 380
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 380

Asp Ala Ser Ser Leu Gln Thr
1 5

<210> SEQ ID NO 381

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 381

Ala Ala Ser Ser Leu Gln Ser
1 5

<210> SEQ ID NO 382
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 382

Asp Ala Ser Ser Leu Glu Ser
1 5

<210> SEQ ID NO 383
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 383

Gly Ala Ser Ser Arg Ala Thr
1 5

<210> SEQ ID NO 384
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 384

Ser Ser Tyr Thr Ser Ser Ser Thr Leu Asp Val Val
1 5 10

<210> SEQ ID NO 385
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 385

Met Gln Gly Thr His Trp Ser Phe Thr
1 5

<210> SEQ ID NO 386
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 386

Gln Gln Leu Asn Ser Tyr Pro Tyr Thr
1 5

<210> SEQ ID NO 387
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 387

Gln Gln Tyr Gly Ser Ser Pro Pro Thr
1 5

<210> SEQ ID NO 388
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 388

Gln Gln Ser Tyr Ser Thr Pro Trp Thr
1 5

<210> SEQ ID NO 389
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 389

Gln Gln Ser Tyr Ser Thr Pro Pro Trp Thr
1 5 10

<210> SEQ ID NO 390
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 390

Gln Ser Tyr Asp Ser Ser Asn Gln Val Val
1 5 10

<210> SEQ ID NO 391
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 391

Gln Gln Tyr Asp Asn Leu Pro Leu Thr
1               5

<210> SEQ ID NO 392
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 392

Gln Gln Ser Tyr Ser Thr Pro Leu Thr
1               5

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 393

Gln Gln Ala Tyr Ser Thr Pro Phe Thr
1               5

<210> SEQ ID NO 394
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 394

Gln Gln His Asp Asn Leu Pro Leu Thr
1               5

<210> SEQ ID NO 395
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 395

Gln Gln Ser Tyr Ser Thr Pro Pro Leu Thr
1               5                   10

<210> SEQ ID NO 396
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 396

Gln Gln Phe Asn Asn Tyr Pro Leu Thr
1               5

<210> SEQ ID NO 397
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 397

Gln Gln Tyr Gly Ser Ser Pro Leu Thr
1 5

<210> SEQ ID NO 398
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 398

Gly Gly Thr Phe Ser Ser Tyr
1 5

<210> SEQ ID NO 399
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 399

Gly Phe Thr Phe Asp Asp Tyr
1 5

<210> SEQ ID NO 400
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 400

Gly Gly Ser Ile Ser Ser Ser Ser Tyr
1 5

<210> SEQ ID NO 401
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 401

Gly Phe Thr Phe Ser Ser Tyr
1 5

<210> SEQ ID NO 402
<211> LENGTH: 9

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 402

Gly Gly Pro Val Arg Ser Gly Ser His
1 5

<210> SEQ ID NO 403
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 403

Gly Gly Ser Phe Ser Gly Tyr
1 5

<210> SEQ ID NO 404
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 404

Gly Phe Thr Phe Ser Ser Tyr
1 5

<210> SEQ ID NO 405
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 405

Gly Phe Thr Phe Ser Ser Tyr
1 5

<210> SEQ ID NO 406
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 406

Ala Asn Thr Phe Ser Asp His
1 5

<210> SEQ ID NO 407
<211> LENGTH: 7
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 407

Gly Phe Thr Phe Ser Ser Tyr
1               5


<210> SEQ ID NO 408
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Gly Phe Thr Phe Asn Ser Tyr
1               5


<210> SEQ ID NO 409
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Gly Phe Asn Val Ser Ser Asn
1               5


<210> SEQ ID NO 410
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Gly Tyr Pro Phe Thr Gly Tyr
1               5


<210> SEQ ID NO 411
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Gly Phe Thr Phe Ser Ser Tyr
1               5


<210> SEQ ID NO 412
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412
```

Ile Pro Ile Phe Gly Thr
1 5

<210> SEQ ID NO 413
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 413

Ser Gly Asp Gly Gly Ser
1 5

<210> SEQ ID NO 414
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 414

Tyr Tyr Ser Gly Ser
1 5

<210> SEQ ID NO 415
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 415

Asn Glu Asp Gly Ser Ala
1 5

<210> SEQ ID NO 416
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 416

Tyr Tyr Ser Gly Ser
1 5

<210> SEQ ID NO 417
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 417

Asn His Ser Gly Ser
1 5

<210> SEQ ID NO 418
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 418

Ser Ser Ser Ser Ser Tyr
1 5

<210> SEQ ID NO 419
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 419

Ser Ser Ser Gly Ser Thr
1 5

<210> SEQ ID NO 420
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 420

His Ala Ala Asn Gly Gly
1 5

<210> SEQ ID NO 421
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 421

Ser Ser Ser Ser Ser Thr
1 5

<210> SEQ ID NO 422
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 422

Glu Tyr Asp Gly Ser Asn
1 5

<210> SEQ ID NO 423
<211> LENGTH: 5
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 423

Tyr Ser Gly Gly Ala
1 5

<210> SEQ ID NO 424
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 424

Asp Pro Asn Ser Gly Asn
1 5

<210> SEQ ID NO 425
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 425

Ser Ser Ser Gly Ser Thr
1 5

<210> SEQ ID NO 426
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 426

Asp Leu Glu Met Ala Thr Ile Met Gly Gly Tyr
1 5 10

<210> SEQ ID NO 427
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 427

Val Phe Asp Ser Tyr Tyr Met Asp Val
1 5

<210> SEQ ID NO 428
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 428

Pro Gly Thr Tyr Tyr Asp Phe Leu Ser Gly Tyr Tyr Pro Phe Tyr
1 5 10 15

<210> SEQ ID NO 429
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 429

Asp Leu Arg Ser Gly Arg Tyr
1 5

<210> SEQ ID NO 430
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 430

Gly Thr Ala Thr Phe Asp Trp Asn Phe Pro Phe Asp Ser
1 5 10

<210> SEQ ID NO 431
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 431

Gly Ser Gly Leu Val Val Tyr Ala Ile Arg Val Gly Ser Gly Trp Phe
1 5 10 15

Asp Tyr

<210> SEQ ID NO 432
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 432

Asp Pro Ser Ser Ser Gly Ser Tyr Tyr Met Glu Asp Ser Tyr Tyr Tyr
1 5 10 15

Gly Met Asp Val
20

<210> SEQ ID NO 433
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 433

Glu Ala Leu Gly Ser Ser Trp Glu
1 5

<210> SEQ ID NO 434
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 434

Gly Gly Tyr Asn Ser Asp Ala Phe Asp Ile
1 5 10

<210> SEQ ID NO 435
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 435

Asp Leu Ser Val Arg Ala Ile Asp Ala Phe Asp Ile
1 5 10

<210> SEQ ID NO 436
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 436

Glu Gly Asn Glu Asp Leu Ala Phe Asp Ile
1 5 10

<210> SEQ ID NO 437
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 437

Asp Arg Leu Tyr Cys Gly Asn Asn Cys Tyr Leu Tyr Tyr Tyr Tyr Gly
1 5 10 15

Met Asp Val

<210> SEQ ID NO 438
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 438

Asp Ser Tyr Gly Tyr Tyr Tyr Gly Met Asp Val
1 5 10

<210> SEQ ID NO 439
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 439

Asp Pro Tyr Ser Ser Ser Trp His Asp Ala Phe Asp Ile
1 5 10

<210> SEQ ID NO 440
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 440

Thr Ser Ser Asp Val Gly Gly Tyr Asn Tyr
1 5 10

<210> SEQ ID NO 441
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 441

Ser Gln Ser Leu Val Tyr Thr Asp Gly Asn Thr Tyr
1 5 10

<210> SEQ ID NO 442
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 442

Ser Gln Gly Ile Ser Ser Tyr
1 5

<210> SEQ ID NO 443
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 443

Ser Gln Ser Ile Ser Gly Ser Phe 1 5

<210> SEQ ID NO 444
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 444

Ser Gln Ser Ile Ser Ser Tyr
1 5

<210> SEQ ID NO 445
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 445

Ser Gln Ser Ile Ser Ser Tyr
1 5

<210> SEQ ID NO 446
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 446

Ser Ser Gly Ser Ile Ala Ser Asn Tyr
1 5

<210> SEQ ID NO 447
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 447

Ser Gln Asp Ile Ser Asn Tyr
1 5

<210> SEQ ID NO 448
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 448

Ser Gln Asp Ile Ser Ser Trp
1 5

<210> SEQ ID NO 449

-continued

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 449

Ser Gln Asp Ile Ser Asn Tyr
1 5

<210> SEQ ID NO 450
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 450

Ser Gln Phe Ile Lys Lys Asn
1 5

<210> SEQ ID NO 451
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 451

Ser Gln Ser Ile Ser Ser Tyr
1 5

<210> SEQ ID NO 452
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 452

Ser Gln Gly Ile Ser Ser Ala
1 5

<210> SEQ ID NO 453
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 453

Ser Gln Ser Val Ser Ser Ser Tyr
1 5

<210> SEQ ID NO 454
<211> LENGTH: 3
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 454

Asp Val Ser
1

<210> SEQ ID NO 455
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

Lys Val Ser
1

<210> SEQ ID NO 456
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Ala Ala Ser
1

<210> SEQ ID NO 457
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

Gly Ala Ser
1

<210> SEQ ID NO 458
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Ala Ala Ser
1

<210> SEQ ID NO 459
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459

Ala Ala Ser
1

<210> SEQ ID NO 460
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 460

Glu Asp Asn
1

<210> SEQ ID NO 461
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 461

Asp Ala Ser
1

<210> SEQ ID NO 462
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 462

Ala Ala Ser
1

<210> SEQ ID NO 463
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 463

Asp Ala Ser
1

<210> SEQ ID NO 464
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 464

Asp Ala Ser
1

<210> SEQ ID NO 465
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 465

Ala Ala Ser
1

<210> SEQ ID NO 466
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 466

Asp Ala Ser
1

<210> SEQ ID NO 467
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 467

Gly Ala Ser
1

<210> SEQ ID NO 468
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 468

Tyr Thr Ser Ser Ser Thr Leu Asp Val
1 5

<210> SEQ ID NO 469
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 469

Gly Thr His Trp Ser Phe
1 5

<210> SEQ ID NO 470
<211> LENGTH: 6

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Leu Asn Ser Tyr Pro Tyr
1               5


<210> SEQ ID NO 471
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Tyr Gly Ser Ser Pro Pro
1               5


<210> SEQ ID NO 472
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Ser Tyr Ser Thr Pro Trp
1               5


<210> SEQ ID NO 473
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Ser Tyr Ser Thr Pro Pro Trp
1               5


<210> SEQ ID NO 474
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Tyr Asp Ser Ser Asn Gln Val
1               5


<210> SEQ ID NO 475
<211> LENGTH: 6
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 475

Tyr Asp Asn Leu Pro Leu
1               5

<210> SEQ ID NO 476
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Ser Tyr Ser Thr Pro Leu
1               5

<210> SEQ ID NO 477
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Ala Tyr Ser Thr Pro Phe
1               5

<210> SEQ ID NO 478
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

His Asp Asn Leu Pro Leu
1               5

<210> SEQ ID NO 479
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Ser Tyr Ser Thr Pro Pro Leu
1               5

<210> SEQ ID NO 480
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 480

-continued

```
Phe Asn Asn Tyr Pro Leu
1               5


<210> SEQ ID NO 481
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 481

Tyr Gly Ser Ser Pro Leu
1               5


<210> SEQ ID NO 482
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 482

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 483
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 483

aggagtaaga ggagcaggct cctgcacagt gactacatga acatgactcc ccgccgcccc      60

gggcccaccc gcaagcatta ccagccctat gccccaccac gcgacttcgc agcctatcgc     120

tcc                                                                   123


<210> SEQ ID NO 484
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 484

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35
```

<210> SEQ ID NO 485
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 485
acaaaaaaga agtattcatc cagtgtgcac gaccctaacg gtgaatacat gttcatgaga 60
gcagtgaaca cagccaaaaa atccagactc acagatgtga cccta 105

<210> SEQ ID NO 486
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 486

Gly Ser Thr Ser Gly Ser Gly Lys Pro Gly Ser Gly Glu Gly Ser Thr
1 5 10 15

Lys Gly

<210> SEQ ID NO 487
<211> LENGTH: 521
<212> TYPE: DNA
<213> ORGANISM: Unknown
<220> FEATURE:
<221> NAME/KEY: source
<223> OTHER INFORMATION: /note="Description of Unknown: Wild-type PGK promoter polynucleotide"

<400> SEQUENCE: 487
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 488
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 488
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 489
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 489

```
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc    180
gataaccggt gtcgggtagc gccagccgcg cgacggtaac g                        221
```

<210> SEQ ID NO 490
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 490

```
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga   240
cgctcccatg atcactctgc acgccgaagg caaatagtgc aggccgtgcg gcgcttggcg    300
ttccttggaa gggctgaatc cccg                                           324
```

<210> SEQ ID NO 491
<211> LENGTH: 422
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 491

```
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga   240
cgctcccatg atcactctgc acgccgaagg caaatagtgc aggccgtgcg gcgcttggcg    300
ttccttggaa gggctgaatc cccgcctcgt ccttcgcagc ggccccccgg gtgttcccat   360
cgccgcttct aggcccactg cgacgcttgc ctgcacttct tacacgctct gggtcccagc    420
cg                                                                   422
```

<210> SEQ ID NO 492
<211> LENGTH: 21
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(3)
<223> OTHER INFORMATION: /note="Variant residues given in the sequence
      have no preference with respect to those in the annotations
      for variant positions"

<400> SEQUENCE: 492

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 493
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(3)
<223> OTHER INFORMATION: /note="Variant residues given in the sequence
      have no preference with respect to those in the annotations
      for variant positions"

<400> SEQUENCE: 493

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 494
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(3)
<223> OTHER INFORMATION: /note="Variant residues given in the sequence
      have no preference with respect to those in the annotations
      for variant positions"

<400> SEQUENCE: 494

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 495
```

-continued

```
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(3)
<223> OTHER INFORMATION: /note="Variant residues given in the sequence
      have no preference with respect to those in the annotations
      for variant positions"

<400> SEQUENCE: 495

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

TREATMENT OF CANCER USING A CLL-1 CHIMERIC ANTIGEN RECEPTOR

RELATED APPLICATIONS

This application claims priority to PCT Application No. PCT/CN2014/082602, filed Jul. 21, 2014, and PCT Application No. PCT/CN2014/090500, filed Nov. 6, 2014. The entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on Oct. 7, 2015, is named N2067-7044WO3_SL.txt and is 347,719 bytes in size.

FIELD OF THE INVENTION

The present invention relates generally to the use of immune effector cells (e.g., T cells, NK cells) engineered to express a Chimeric Antigen Receptor (CAR) to treat a disease associated with expression of C-type lectin-like-1 (CLL-1).

BACKGROUND OF THE INVENTION

C-type lectin-like-1 (CLL-1) is also known as MICL, CLEC12A, CLEC-1, Dendritic Cell-Associated Lectin 1, and DCAL-2. CLL-1 is a glycoprotein receptor and member of the large family of C-type lectin-like receptors involved in immune regulation. CLL-1 is expressed in hematopoietic cells, primarily on innate immune cells including monocytes, DCs, pDCs, and granulocytes (Cancer Res. 2004; J Immunol 2009) and myeloid progenitor cells (Blood, 2007). CLL-1 is also found on acute myeloid leukemia (AML) blasts and leukemic stem cells (e.g., $CD34^+/CD38^-$) (Zhao et al., Haematologica. 2010, 95(1):71-78.). CLL-1 expression may also be relevant for other myeloid leukemias, such as acute myelomonocytic leukemia, acute monocytic leukemia, acute promyelocytic leukemia, chronic myeloid leukemia (CML), and myelodysplastic syndrome (MDS).

SUMMARY OF THE INVENTION

In a first aspect, the invention features an isolated nucleic acid molecule encoding a chimeric antigen receptor (CAR), wherein the CAR comprises an antibody or antibody fragment which includes a human anti-CLL-1 binding domain, a transmembrane domain, and an intracellular signaling domain (e.g., an intracellular signaling domain comprising a costimulatory domain and/or a primary signaling domain). In one embodiment, the CAR comprises an antibody or antibody fragment which includes a human anti-CLL-1 binding domain described herein, a transmembrane domain described herein, and an intracellular signaling domain described herein (e.g., an intracellular signaling domain comprising a costimulatory domain and/or a primary signaling domain).

In embodiments, the CAR comprises a human anti-CLL-1 binding domain, a transmembrane domain, and an intracellular signaling domain, and wherein said anti-CLL-1binding domain comprises a heavy chain complementary determining region 1 (HC CDR1), a heavy chain complementary determining region 2 (HC CDR2), and a heavy chain complementary determining region 3 (HC CDR3) of any CLL-1 heavy chain binding domain amino acid sequences listed in Table 8. In embodiments, the human CLL-1binding domain further comprises a light chain complementary determining region 1 (LC CDR1), a light chain complementary determining region 2 (LC CDR2), and a light chain complementary determining region 3 (LC CDR3). In embodiments, the human CLL-1 binding domain comprises a light chain complementary determining region 1 (LC CDR1), a light chain complementary determining region 2 (LC CDR2), and a light chain complementary determining region 3 (LC CDR3) of any CLL-1 light chain binding domain amino acid sequences listed in Table 8.

In some embodiments, the CAR comprises an antibody or antibody fragment which includes a human CLL-1binding domain, a transmembrane domain, and an intracellular signaling domain comprising a costimulatory domain and/or a primary signaling domain, and wherein said CLL-1binding domain comprises one or more of light chain complementary determining region 1 (LC CDR1), light chain complementary determining region 2 (LC CDR2), and light chain complementary determining region 3 (LC CDR3) of any CLL-1light chain binding domain amino acid sequences listed in Table 8, and one or more of heavy chain complementary determining region 1 (HC CDR1), heavy chain complementary determining region 2 (HC CDR2), and heavy chain complementary determining region 3 (HC CDR3) of any CLL-1heavy chain binding domain amino acid sequences listed in Table 8.

In one embodiment, the encoded human anti-CLL-1 binding domain comprises one or more (e.g., all three) light chain complementary determining region 1 (LC CDR1), light chain complementary determining region 2 (LC CDR2), and light chain complementary determining region 3 (LC CDR3) of a human anti-CLL-1 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a human anti-CLL-1 binding domain described herein, e.g., a human anti-CLL-1 binding domain comprising one or more, e.g., all three, LC CDRs and one or more, e.g., all three, HC CDRs.

In one embodiment, the encoded human anti-CLL-1 binding domain comprises a light chain variable region described herein (e.g., in Table 8) and/or a heavy chain variable region described herein (e.g., in Table 8). In one embodiment, the encoded human anti-CLL-1 binding domain is a scFv comprising a light chain and a heavy chain of an amino acid sequence of Table 8. In an embodiment, the human anti-CLL-1 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 8, or a sequence with 95-99% identity with an amino acid sequence of Table 8; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 8, or a sequence with 95-99% identity to an amino acid sequence of Table 8.

In other embodiments, the encoded CLL-1 binding domain comprises a HC CDR1, a HC CDR2, and a HC CDR3 of any CLL-1 heavy chain binding domain amino acid sequences listed in Table 8. In embodiments, the CLL-1 binding domain further comprises a LC CDR1, a LC CDR2, and a LC CDR3. In embodiments, the CLL-1 binding domain comprises a LC CDR1, a LC CDR2, and a LC CDR3 of any CLL-1 light chain binding domain amino acid sequences listed in Table 8.

In some embodiments, the encoded CLL-1 binding domain comprises one, two or all of LC CDR1, LC CDR2, and LC CDR3 of any CLL-1 light chain binding domain amino acid sequences listed in Table 8, and one, two or all of HC CDR1, HC CDR2, and HC CDR3 of any CLL-1 heavy chain binding domain amino acid sequences listed in Table 8.

In one embodiment, the encoded human anti-CLL-1 binding domain comprises an amino acid sequence selected from a group consisting of SEQ ID NO:39-51, 65-77, 195, 78-90, or 196. In an embodiment, the encoded CLL-1 binding domain (e.g., an scFv) comprises an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of SEQ ID NO: 39-51, 65-77, 195, 78-90, or 196, or a sequence with 95-99% identity with an amino acid sequence of SEQ ID NO: 39-51, 65-77, 195, 78-90, or 196. In another embodiment, the encoded CLL-1 binding domain comprises a heavy chain variable region comprising an amino acid sequence selected from the group consisting of SEQ ID NO: 65-77, or 195, or a sequence with 95-99% identity thereof. In another embodiment, the encoded CLL-1 binding domain comprises a light chain variable region comprising an amino acid sequence selected from the group consisting of SEQ ID NO: 66-74, or 196, or a sequence with 95-99% identity thereof. In one embodiment, the nucleic acid molecule comprises a nucleotide sequence selected from the group consisting of SEQ ID NO: 52-64, or a sequence with 95-99% identity thereof.

In one embodiment, the encoded humanized anti-CLL-1 binding domain includes a (Gly4-Ser)n linker, wherein n is 1, 2, 3, 4, 5, or 6, preferably 3 or 4 (SEQ ID NO:26). The light chain variable region and heavy chain variable region of a scFv can be, e.g., in any of the following orientations: light chain variable region-linker-heavy chain variable region or heavy chain variable region-linker-light chain variable region.

In one embodiment, the encoded CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises the sequence of SEQ ID NO: 6. In one embodiment, the encoded transmembrane domain comprises an amino acid sequence comprising at least one, two or three modifications but not more than 20, 10 or 5 modifications of the amino acid sequence of SEQ ID NO:6, or a sequence with 95-99% identity to an amino acid sequence of SEQ ID NO:6. In one embodiment, the nucleic acid sequence encoding the transmembrane domain comprises the sequence of SEQ ID NO: 17, or a sequence with 95-99% identity thereof.

In one embodiment, the encoded anti-CLL-1 binding domain is connected to the transmembrane domain by a hinge region, e.g., a hinge region described herein. In one embodiment, the encoded hinge region comprises SEQ ID NO:2, or a sequence with 95-99% identity thereof. In one embodiment, the nucleic acid sequence encoding the hinge region comprises the sequence of SEQ ID NO: 13, or a sequence with 95-99% identity thereof.

In one embodiment, the isolated nucleic acid molecule further comprises a sequence encoding a costimulatory domain, e.g., a costimulatory domain described herein. In embodiments, the intracellular signaling domain comprises a costimulatory domain. In embodiments, the intracellular signaling domain comprises a primary signaling domain. In embodiments, the intracellular signaling domain comprises a costimulatory domain and a primary signaling domain.

In one embodiment, the encoded costimulatory domain is a functional signaling domain obtained from a protein selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In embodiments, the encoded costimulatory domain comprises 4-1BB, CD27, CD28, or ICOS.

In one embodiment, the encoded costimulatory domain of 4-1BB comprises the amino acid sequence of SEQ ID NO:7. In one embodiment, the encoded costimulatory domain comprises an amino acid sequence having at least one, two or three modifications but not more than 20, 10 or 5 modifications of the amino acid sequence of SEQ ID NO:7, or a sequence with 95-99% identity to the amino acid sequence of SEQ ID NO:7. In one embodiment, the nucleic acid sequence encoding the costimulatory domain comprises the nucleotide sequence of SEQ ID NO:18, or a sequence with 95-99% identity thereof. In another embodiment, the encoded costimulatory domain of CD28 comprises the amino acid sequence of SEQ ID NO:482. In one embodiment, the encoded costimulatory domain comprises an amino acid sequence having at least one, two or three modifications but not more than 20, 10 or 5 modifications of an amino acid sequence of SEQ ID NO:482, or a sequence with 95-99% identity to an amino acid sequence of SEQ ID NO:482. In one embodiment, the nucleic acid sequence encoding the costimulatory domain of CD28 comprises the nucleotide sequence of SEQ ID NO:483, or a sequence with 95-99% identity thereof. In another embodiment, the encoded costimulatory domain of CD27 comprises the amino acid sequence of SEQ ID NO:8. In one embodiment, the encoded costimulatory domain comprises an amino acid sequence having at least one, two or three modifications but not more than 20, 10 or 5 modifications of an amino acid sequence of SEQ ID NO:8, or a sequence with 95-99% identity to an amino acid sequence of SEQ ID NO:8. In one embodiment, the nucleic acid sequence encoding the costimulatory domain of CD27 comprises the nucleotide sequence of SEQ ID NO:19, or a sequence with 95-99% identity thereof.

In another embodiment, the encoded costimulatory domain of ICOS comprises the amino acid sequence of SEQ ID NO:484. In one embodiment, the encoded costimulatory domain comprises an amino acid sequence having at least one, two or three modifications but not more than 20, 10 or 5 modifications of an amino acid sequence of SEQ ID NO:484, or a sequence with 95-99% identity to an amino acid sequence of SEQ ID NO:484. In one embodiment, the nucleic acid sequence encoding the costimulatory domain of ICOS comprises the nucleotide sequence of SEQ ID NO:485, or a sequence with 95-99% identity thereof.

In embodiments, the encoded primary signaling domain comprises a functional signaling domain of CD3 zeta. In embodiments, the functional signaling domain of CD3 zeta comprises the sequence of SEQ ID NO: 9 (mutant CD3 zeta) or SEQ ID NO: 10 (wild-type human CD3 zeta), or a sequence with 95-99% identity thereof.

In one embodiment, the encoded intracellular signaling domain comprises a functional signaling domain of 4-1BB and/or a functional signaling domain of CD3 zeta. In one embodiment, the encoded intracellular signaling domain of 4-1BB comprises the amino acid sequence of SEQ ID NO: 7 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:7 and/or an amino acid sequence of SEQ ID NO:9 or SEQ ID NO:10, or a sequence with 95-99% identity to an amino acid sequence of SEQ ID NO:7 and/or an amino acid sequence of SEQ ID NO:9 or SEQ ID NO:10. In one embodiment, the encoded intracellular signaling domain comprises the sequence of SEQ ID NO:7 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of 4-1BB comprises the nucleotide sequence of SEQ ID NO:18, or a sequence with 95-99% identity thereof, and/or a sequence of SEQ ID NO:20 or SEQ ID NO:21, or the CD3 zeta nucleotide sequence with 95-99% identity thereof.

In one embodiment, the encoded intracellular signaling domain comprises a functional signaling domain of CD27 and/or a functional signaling domain of CD3 zeta. In one embodiment, the encoded intracellular signaling domain of CD27 comprises the amino acid sequence of SEQ ID NO: 8 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:8 and/or an amino acid sequence of SEQ ID NO:9 or SEQ ID NO:10, or a sequence with 95-99% identity to an amino acid sequence of SEQ ID NO:8 and/or an amino acid sequence of SEQ ID NO:9 or SEQ ID NO:10. In one embodiment, the encoded intracellular signaling domain comprises the sequence of SEQ ID NO:8 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD27 comprises the nucleotide sequence of SEQ ID NO:19, or a sequence with 95-99% identity thereof, and/or the CD3 zeta nucleotide sequence of SEQ ID NO:20 or SEQ ID NO:21, or a sequence with 95-99% identity thereof.

In one embodiment, the encoded intracellular signaling domain comprises a functional signaling domain of CD28 and/or a functional signaling domain of CD3 zeta. In one embodiment, the encoded intracellular signaling domain of CD28 comprises the amino acid sequence of SEQ ID NO: 482 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:482 and/or an amino acid sequence of SEQ ID NO:9 or SEQ ID NO:10, or a sequence with 95-99% identity to an amino acid sequence of SEQ ID NO:482 and/or an amino acid sequence of SEQ ID NO:9 or SEQ ID NO:10. In one embodiment, the encoded intracellular signaling domain comprises the sequence of SEQ ID NO:482 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD28 comprises the nucleotide sequence of SEQ ID NO:483, or a sequence with 95-99% identity thereof, and/or the CD3 zeta nucleotide sequence of SEQ ID NO:20 or SEQ ID NO:21, or a sequence with 95-99% identity thereof.

In one embodiment, the encoded intracellular signaling domain comprises a functional signaling domain of ICOS and/or a functional signaling domain of CD3 zeta. In one embodiment, the encoded intracellular signaling domain of ICOS comprises the amino acid sequence of SEQ ID NO: 484 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:484 and/or an amino acid sequence of SEQ ID NO:9 or SEQ ID NO:10, or a sequence with 95-99% identity to an amino acid sequence of SEQ ID NO:484 and/or an amino acid sequence of SEQ ID NO:9 or SEQ ID NO:10. In one embodiment, the encoded intracellular signaling domain comprises the sequence of SEQ ID NO:484 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of ICOS comprises the nucleotide sequence of SEQ ID NO:485, or a sequence with 95-99% identity thereof, and/or the CD3 zeta nucleotide sequence of SEQ ID NO:20 or SEQ ID NO:21, or a sequence with 95-99% identity thereof.

In one embodiment, the isolated CAR molecule further comprises a leader sequence, e.g., a leader sequence described herein. In one embodiment, the leader sequence comprises an amino acid sequence of SEQ ID NO: 1, or a sequence with 95-99% identity to an amino acid sequence of SEQ ID NO:1.

In another aspect, the invention pertains to an isolated nucleic acid molecule encoding a CAR construct comprising a leader sequence, e.g., a leader sequence described herein, e.g., the amino acid sequence of SEQ ID NO: 1, an anti-CLL-1 binding domain described herein, e.g., human anti-CLL-1 binding domain comprising a LC CDR1, a LC CDR2, a LC CDR3, a HC CDR1, a HC CDR2 and a HC CDR3 described herein, e.g., a human anti-CLL-1 binding domain described in Table 8, or a sequence with 95-99% identify thereof, a hinge region described herein, e.g., the amino acid sequence of SEQ ID NO:2, a transmembrane domain described herein, e.g., having a sequence of SEQ ID NO: 6, and an intracellular signaling domain, e.g., an intracellular signaling domain described herein. In one embodiment, the encoded intracellular signaling domain comprises a costimulatory domain, e.g., a costimulatory domain described herein (e.g., a 4-1BB costimulatory domain having the amino acid sequence of SEQ ID NO:7, a CD28 costimulatory domain having the amino acid sequence of SEQ ID NO: 482, or an ICOS costimulatory domain having the amino acid sequence of SEQ ID NO: 484, or a CD27 costimulatory domain having the amino acid sequence of SEQ ID NO:8), and/or a primary signaling domain, e.g., a primary signaling domain described herein, (e.g., a CD3 zeta stimulatory domain having a sequence of SEQ ID NO:9 or SEQ ID NO:10).

In one embodiment, the isolated nucleic acid molecule encoding the CAR construct includes a human anti-CLL-1 binding domain sequence encoded by the nucleic acid sequence of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, or a sequence with 95-99% identity thereto.

In one embodiment, the isolated nucleic acid molecule comprises (e.g., consists of) a nucleic acid encoding a CAR amino acid sequence of SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO:103, or SEQ ID NO: 197; or an amino acid sequence having one, two or three modifications (e.g., substitutions, e.g., conservative substitutions) but not more than 30, 20, or 10 modifications of an amino acid sequence of SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO:103, or SEQ ID NO: 197; or an amino acid sequence having 85%, 90%, 95%, 96%, 97%, 98% or 99% identity to an amino acid sequence of SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO:103 or SEQ ID NO:197.

In one embodiment, the isolated nucleic acid molecule comprises (e.g., consists of) a nucleic acid sequence of SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, or SEQ ID NO:198; or a nucleic acid sequence having 85%, 90%, 95%, 96%, 97%, 98% or 99% identity to a nucleic acid sequence of SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, or SEQ ID NO:198.

In one aspect, the invention pertains to an isolated nucleic acid molecule encoding an anti-CLL-1 binding domain, wherein the anti-CLL-1 binding domain comprises one or more (e.g., all three) light chain complementary determining region 1 (LC CDR1), light chain complementary determining region 2 (LC CDR2), and light chain complementary determining region 3 (LC CDR3) of an anti-CLL-1 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of an anti-CLL-1 binding domain described herein, e.g., a human anti-CLL-1 binding domain comprising one or more, e.g., all three, LC CDRs and one or more, e.g., all three, HC CDRs.

In other embodiments, the CLL-1 binding domain comprises a HC CDR1, a HC CDR2, and a HC CDR3 of any CLL-1 heavy chain binding domain amino acid sequences listed in Table 8. In embodiments, the CLL-1 binding domain further comprises a LC CDR1, a LC CDR2, and a LC CDR3. In embodiments, the CLL-1 binding domain comprises a LC CDR1, a LC CDR2, and a LC CDR3)\ of any CLL-1 light chain binding domain amino acid sequences listed in Table 8.

In some embodiments, the CLL-1 binding domain comprises one, two or all of LC CDR1, LC CDR2, and LC CDR3 of any CLL-1 light chain binding domain amino acid sequences listed in Table 8, and one, two or all of HC CDR1, HC CDR2, and HC CDR3 of any CLL-1 heavy chain binding domain amino acid sequences listed in Table 8.

In one embodiment, the encoded anti-CLL-1 binding domain comprises a light chain variable region described herein (e.g., in SEQ ID NO:78, 79, 80, 81, 82, 83, 84, 85, 86, 87, 88, 89, 90, or 196) and/or a heavy chain variable region described herein (e.g., in SEQ ID NO:65, 66, 67, 68, 69, 70, 71, 72, 73, 74, 75, 76, 77, or 195). In one embodiment, the encoded anti-CLL-1 binding domain is a scFv comprising a light chain and a heavy chain of an amino acid sequence of in SEQ ID NO:39, 40, 41, 42, 43, 44, 45, 46, 47, 48, 49, 50, or 51. In an embodiment, the anti-CLL-1 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in SEQ ID NO: 78, 79, 80, 81, 82, 83, 84, 85, 86, 87, 88, 89, 90, or 196, or a sequence with 95-99% identity with an amino acid sequence of SEQ ID NO: 78, 79, 80, 81, 82, 83, 84, 85, 86, 87, 88, 89, 90, or 196; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in SEQ ID NO: 65, 66, 67, 68, 69, 70, 71, 72, 73, 74, 75, 76, 77, or 195, or a sequence with 95-99% identity to an amino acid sequence in SEQ ID NO: 65, 66, 67, 68, 69, 70, 71, 72, 73, 74, 75, 76, 77, or 195. In one embodiment, the anti-CLL-1 binding domain comprises a sequence selected from a group consisting of SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, or a sequence with 95-99% identify thereof. In one embodiment, the encoded anti-CLL-1 binding domain is a scFv, and a light chain variable region comprising an amino acid sequence described herein, e.g., in Table 8, is attached to a heavy chain variable region comprising an amino acid sequence described herein, e.g., in Table 8, via a linker, e.g., a linker described herein. In one embodiment, the encoded anti-CLL-1 binding domain includes a $(Gly_4\text{-}Ser)n$ linker, wherein n is 1, 2, 3, 4, 5, or 6, preferably 4 (SEQ ID NO: 26). The light chain variable region and heavy chain variable region of a scFv can be, e.g., in any of the following orientations: light chain variable region-linker-heavy chain variable region or heavy chain variable region-linker-light chain variable region. In one embodiment, the isolated nucleic acid sequence encoding the human anti-CLL-1 binding domain comprises a sequence selected from a group consisting of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, or a sequence with 95-99% identity thereof.

In another aspect, the invention pertains to an isolated CAR (e.g., a polypeptide) molecule encoded by the nucleic acid molecule. In one embodiment, the isolated CAR molecule comprises a sequence selected from the group consisting of SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:197 or a sequence with 95-99% identify thereof.

In another aspect, the invention pertains to an isolated chimeric antigen receptor (CAR) molecule (e.g., polypeptide) comprising an anti-CLL-1 binding domain (e.g., a human antibody or antibody fragment that specifically binds to CLL-1), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-CLL-1 binding domain described herein (e.g., a human antibody or antibody fragment that specifically binds to CLL-1 as described herein), a transmembrane domain described herein, and an intracellular signaling domain described herein (e.g., an intracellular signaling domain comprising a costimulatory domain and/or a primary signaling domain described herein).

In one embodiment, the anti-CLL-1 binding domain comprises one or more (e.g., all three) light chain complementary determining region 1 (LC CDR1), light chain complementary determining region 2 (LC CDR2), and light chain complementary determining region 3 (LC CDR3) of an anti-CLL-1 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of an anti-CLL-1 binding domain described herein, e.g., a human anti-CLL-1 binding domain comprising one or more, e.g., all three, LC CDRs and one or more, e.g., all three, HC CDRs. In one embodiment, the anti-CLL-1 binding domain comprises a light chain variable region described herein (e.g., in Table 8) and/or a heavy chain variable region described herein (e.g., in Table 8). In one embodiment, the anti-CLL-1 binding domain is a scFv comprising a light chain and a heavy chain of an amino acid sequence listed in Table 8. In an embodiment, the anti-CLL-1 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 8, or a sequence with 95-99% identity with an amino acid sequence provided in Table 8; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 8, or a sequence with 95-99% identity to an amino acid sequence provided in Table 8.

In other embodiments, the encoded CLL-1 binding domain comprises a HC CDR1, a HC CDR2, and a HC CDR3 of any CLL-1 heavy chain binding domain amino acid sequences listed in Table 8. In embodiments, the CLL-1 binding domain further comprises a LC CDR1, a LC CDR2, and a LC CDR3. In embodiments, the CLL-1 binding domain comprises a LC CDR1, a LC CDR2, and a LC CDR3 of any CLL-1 light chain binding domain amino acid sequences listed in Table 8.

In some embodiments, the encoded CLL-1 binding domain comprises one, two or all of LC CDR1, LC CDR2, and LC CDR3 of any CLL-1 light chain binding domain amino acid sequences listed in Table 8, and one, two or all of HC CDR1, HC CDR2, and HC CDR3 of any CLL-1 heavy chain binding domain amino acid sequences listed in Table 8.

In one embodiment, the anti-CLL-1 binding domain comprises a sequence selected from a group consisting of SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO: 65-90, or SEQ ID NO: 195-196, or an amino acid sequence having at least one, two or three modifications (e.g., substitutions, e.g., conservative substitutions) but not more than 30, 20 or 10 modifications (e.g., substitutions, e.g., conservative substitutions) to any of the aforesaid sequences; or a sequence with 95-99% identify thereof. In one embodiment, the anti-CLL-1 binding domain is a scFv, and a light chain variable region comprising an amino acid sequence described herein, e.g., in Table 8, is attached to a heavy chain variable region comprising an amino acid sequence described herein, e.g., in Table 8, via a linker, e.g., a linker described herein. In one embodiment, the anti-CLL-1 binding domain includes a $(Gly_4\text{-}Ser)n$ linker, wherein n is 1, 2, 3, 4, 5, or 6, preferably 4 (SEQ ID NO: 26). The light chain variable region and heavy chain variable region of a scFv can be, e.g., in any of the following orientations: light chain variable region-linker-heavy chain variable region or heavy chain variable region-linker-light chain variable region.

In one embodiment, the isolated CAR molecule comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6. In one embodiment, the transmembrane domain comprises an amino acid sequence having at least one, two or three modifications (e.g., substitutions, e.g., conservative substitutions) but not more than 20, 10 or 5 modifications (e.g., substitutions, e.g., conservative substitutions) of an amino acid sequence of SEQ ID NO: 6, or a sequence with 95-99% identity to an amino acid sequence of SEQ ID NO: 6.

In one embodiment, the anti-CLL-1 binding domain is connected to the transmembrane domain by a hinge region, e.g., a hinge region described herein. In one embodiment, the encoded hinge region comprises SEQ ID NO:2, or a sequence with 95-99% identity thereof.

In embodiments, the intracellular signaling domain of the isolated CAR molecule comprises a costimulatory domain. In embodiments, the intracellular signaling domain of the isolated CAR molecule comprises a primary signaling domain. In embodiments, the intracellular signaling domain of the isolated CAR molecule comprises a costimulatory domain and a primary signaling domain. In one embodiment, the isolated CAR molecule further comprises a sequence encoding a costimulatory domain, e.g., a costimulatory domain described herein. In one embodiment, the costimulatory domain comprises a functional signaling domain of a protein selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In one embodiment, the costimulatory domain of 4-1BB comprises the amino acid sequence of SEQ ID NO:7. In one embodiment, the costimulatory domain comprises an amino acid sequence having at least one, two or three modifications (e.g., substitutions, e.g., conservative substitutions) but not more than 20, 10 or 5 modifications (e.g., substitutions, e.g., conservative substitutions) of an amino acid sequence of SEQ ID NO:7, or a sequence with 95-99% identity to an amino acid sequence of SEQ ID NO:7. In another embodiment, the costimulatory domain of CD28 comprises the amino acid sequence of SEQ ID NO:482. In one embodiment, the costimulatory domain comprises an amino acid sequence having at least one, two or three modifications but not more than 20, 10 or 5 modifications of an amino acid sequence of SEQ ID NO:482, or a sequence with 95-99% identity to an amino acid sequence of SEQ ID NO:482. In another embodiment, the costimulatory domain of CD27 comprises the amino acid sequence of SEQ ID NO:8. In one embodiment, the costimulatory domain comprises an amino acid sequence having at least one, two or three modifications but not more than 20, 10 or 5 modifications of an amino acid sequence of SEQ ID NO:8, or a sequence with 95-99% identity to an amino acid sequence of SEQ ID NO:8. In another embodiment, the costimulatory domain of ICOS comprises the amino acid sequence of SEQ ID NO:484. In one embodiment, the costimulatory domain comprises an amino acid sequence having at least one, two or three modifications but not more than 20, 10 or 5 modifications of an amino acid sequence of SEQ ID NO:484, or a sequence with 95-99% identity to an amino acid sequence of SEQ ID NO:484.

In embodiments, the primary signaling domain comprises a functional signaling domain of CD3 zeta. In embodiments, the functional signaling domain of CD3 zeta comprises the amino acid sequence of SEQ ID NO: 9 (mutant CD3 zeta) or SEQ ID NO: 10 (wild type human CD3 zeta), or a sequence with 95-99% identity thereof.

In one embodiment, the intracellular signaling domain comprises a functional signaling domain of 4-1BB and/or a functional signaling domain of CD3 zeta. In one embodiment, the intracellular signaling domain comprises the sequence of SEQ ID NO: 7 and/or the sequence of SEQ ID NO:9 or SEQ ID NO:10. In one embodiment, the intracellular signaling domain comprises an amino acid sequence having at least one, two or three modifications (e.g., substitutions, e.g., conservative substitutions) but not more than 20, 10 or 5 modifications (e.g., substitutions, eg., conservative substitutions) of an amino acid sequence of SEQ ID NO: 7 and/or the sequence of SEQ ID NO:9 or SEQ ID NO:10, or a sequence with 95-99% identity to an amino acid sequence of SEQ ID NO: 7 and/or the sequence of SEQ ID NO:9 or SEQ ID NO:10. In one embodiment, the intracellular signaling domain comprises the sequence of SEQ ID NO: 7 and/or the sequence of SEQ ID NO:9 or SEQ ID NO:10, wherein the sequences comprising the intracellular signaling domain are expressed in the same frame and as a single polypeptide chain.

In one embodiment, the intracellular signaling domain comprises a functional signaling domain of CD27 and/or a functional signaling domain of CD3 zeta. In one embodiment, the intracellular signaling domain of CD27 comprises the amino acid sequence of SEQ ID NO: 8 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:8 and/or an amino acid sequence of SEQ ID NO:9 or SEQ ID NO:10, or a sequence with 95-99% identity to an amino acid sequence of SEQ ID NO:8 and/or an amino acid sequence of SEQ ID NO:9 or SEQ ID NO:10. In one embodiment, the intracellular signaling domain comprises the sequence of SEQ ID NO:8 and the sequence of SEQ ID NO:9 or SEQ ID NO:10, wherein the sequences comprising the intracellular signaling domain are expressed in the same frame and as a single polypeptide chain.

In one embodiment, the intracellular signaling domain comprises a functional signaling domain of CD28 and/or a functional signaling domain of CD3 zeta. In one embodiment, the encoded intracellular signaling domain of CD28 comprises the amino acid sequence of SEQ ID NO: 482 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO: 482 and/or an amino acid sequence of SEQ ID NO:9 or SEQ ID NO:10, or a sequence with 95-99% identity to an amino acid sequence of SEQ ID NO: 482 and/or an amino acid sequence of SEQ ID NO:9 or SEQ ID NO:10. In one embodiment, the intracellular signaling domain comprises the sequence of SEQ ID NO: 482 and the sequence of SEQ ID NO:9 or SEQ ID NO:10, wherein the sequences comprising the intracellular signaling domain are expressed in the same frame and as a single polypeptide chain.

In one embodiment, the intracellular signaling domain comprises a functional signaling domain of ICOS and/or a functional signaling domain of CD3 zeta. In one embodiment, the encoded intracellular signaling domain of ICOS comprises the amino acid sequence of SEQ ID NO: 484 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO: 484 and/or an amino acid sequence of SEQ ID NO:9 or SEQ ID NO:10, or a sequence with 95-99% identity to an amino acid sequence of SEQ ID NO: 482 and/or an amino acid sequence of SEQ ID NO:9 or SEQ ID NO:10. In one embodiment, the intracellular signaling domain comprises the sequence of SEQ ID NO: 484 and the sequence of SEQ ID NO:9 or SEQ ID NO:10, wherein the sequences comprising the intracellular signaling domain are expressed in the same frame and as a single polypeptide chain.

In one embodiment, the isolated CAR molecule further comprises a leader sequence, e.g., a leader sequence described herein. In one embodiment, the leader sequence comprises an amino acid sequence of SEQ ID NO: 1, or a sequence with 95-99% identity to an amino acid sequence of SEQ ID NO:1.

In another aspect, the invention pertains to an isolated CAR molecule comprising a leader sequence, e.g., a leader sequence described herein, e.g., a leader sequence of SEQ ID NO: 1, or having 95-99% identity thereof, an anti-CLL-1 binding domain described herein, e.g., an anti-CLL-1 binding domain comprising a LC CDR1, a LC CDR2, a LC CDR3, a HC CDR1, a HC CDR2 and a HC CDR3 described herein, e.g., an anti-CLL-1 binding domain described in Table 8, or a sequence with 95-99% identify thereof, a hinge region, e.g., a hinge region described herein, e.g., a hinge region of SEQ ID NO:2, or having 95-99% identity thereof, a transmembrane domain, e.g., a transmembrane domain described herein, e.g., a transmembrane domain having a sequence of SEQ ID NO: 6 or a sequence having 95-99% identity thereof, an intracellular signaling domain, e.g., an intracellular signaling domain described herein (e.g., an intracellular signaling domain comprising a costimulatory domain and/or a primary signaling domain). In one embodiment, the intracellular signaling domain comprises a costimulatory domain, e.g., a costimulatory domain described herein, e.g., a 4-1BB costimulatory domain having a sequence of SEQ ID NO:7, or having 95-99% identity thereof, and/or a primary signaling domain, e.g., a primary signaling domain described herein, e.g., a CD3 zeta stimulatory domain having a sequence of SEQ ID NO:9 or SEQ ID NO:10, or having 95-99% identity thereof. In one embodiment, the intracellular signaling domain comprises a costimulatory domain, e.g., a costimulatory domain described herein, e.g., a 4-1BB costimulatory domain having a sequence of SEQ ID NO:7, and/or a primary signaling domain, e.g., a primary signaling domain described herein, e.g., a CD3 zeta stimulatory domain having a sequence of SEQ ID NO:9 or SEQ ID NO:10.

In one embodiment, the isolated CAR molecule comprises (e.g., consists of) an amino acid sequence of SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, or SEQ ID NO:197, or an amino acid sequence having at least one, two, three, four, five, 10, 15, 20 or 30 modifications (e.g., substitutions, e.g., conservative substitutions) but not more than 60, 50 or 40 modifications (e.g., substitutions, e.g., conservative substitutions) of an amino acid sequence of SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, or SEQ ID NO:197, or an amino acid sequence having 85%, 90%, 95%, 96%, 97%, 98% or 99% identity to an amino acid sequence of SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:197.

In one aspect, the invention pertains to an anti-CLL-1 binding domain comprising one or more (e.g., all three) light chain complementary determining region 1 (LC CDR1), light chain complementary determining region 2 (LC CDR2), and light chain complementary determining region 3 (LC CDR3) of an anti-CLL-1 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of an anti-CLL-1 binding domain described herein, e.g., a human anti-CLL-1 binding domain comprising one or more, e.g., all three, LC CDRs and one or more, e.g., all three, HC CDRs.

In other embodiments, the encoded CLL-1 binding domain comprises a HC CDR1, a HC CDR2, and a HC CDR3 of any CLL-1 heavy chain binding domain amino acid sequences listed in Table 8. In embodiments, the CLL-1 binding domain further comprises a LC CDR1, a LC CDR2, and a LC CDR3. In embodiments, the CLL-1 binding domain comprises a LC CDR1, a LC CDR2, and a LC CDR3 of any CLL-1 light chain binding domain amino acid sequences listed in Table 8.

In some embodiments, the encoded CLL-1 binding domain comprises one, two or all of LC CDR1, LC CDR2, and LC CDR3 of any CLL-1 light chain binding domain amino acid sequences listed in Table 8, and one, two or all of HC CDR1, HC CDR2, and HC CDR3 of any CLL-1 heavy chain binding domain amino acid sequences listed in Table 8.

In one embodiment, the anti-CLL-1 binding domain comprises a light chain variable region described herein (e.g., in SEQ ID NO: 78, 79, 80, 81, 82, 83, 84, 85, 86, 87, 88, 89, 90, or 196) and/or a heavy chain variable region described herein (e.g. in SEQ ID NO: 65, 66, 67, 68, 69, 70, 71, 72, 73, 74, 75, 76, 77, or 195). In one embodiment, the anti-CLL-1 binding domain is a scFv comprising a light chain and a heavy chain of an amino acid sequence of SEQ ID NO:39, 40, 41, 42, 43, 44, 45, 46, 47, 48, 49, 50, or 51. In an embodiment, the anti-CLL-1 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided, in SEQ ID NO: 78, 79, 80, 81, 82, 83, 84, 85, 86, 87, 88, 89, 90, or 196 or a sequence with 95-99% identity with an amino acid sequence in SEQ ID NO: 78, 79, 80, 81, 82, 83, 84, 85, 86, 87, 88, 89, 90, or 196; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in SEQ ID NO: 65, 66, 67, 68, 69, 70, 71, 72, 73, 74, 75, 76, 77, or 195, or a sequence with 95-99% identity to an amino acid sequence in SEQ ID NO: 65, 66, 67, 68, 69, 70, 71, 72, 73, 74, 75, 76, 77, or 195. In one embodiment, the anti-CLL-1 binding domain comprises a sequence selected from a group consisting of SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, or SEQ ID NO:51 or a sequence with 95-99% identify thereof. In one embodiment, the anti-CLL-1 binding domain is a scFv, and a light chain variable region comprising an amino acid sequence described herein, e.g., in Table 2, is attached to a heavy chain variable region comprising an amino acid sequence described herein, e.g., in Table 8, via a linker, e.g., a linker described herein. In one embodiment, the anti-CLL-1 binding domain includes a $(Gly_4\text{-}Ser)n$ linker, wherein n is 1, 2, 3, 4, 5, or 6, preferably 4 (SEQ ID NO: 26). The light chain variable region and heavy chain variable region of a scFv can be, e.g., in any of the following orientations: light chain variable region-linker-heavy chain variable region or heavy chain variable region-linker-light chain variable region.

In another aspect, the invention pertains to a vector comprising a nucleic acid molecule described herein, e.g., a nucleic acid molecule encoding a CAR described herein. In one embodiment, the vector is selected from the group consisting of a DNA, a RNA, a plasmid, a lentivirus vector, adenoviral vector, or a retrovirus vector.

In one embodiment, the vector is a lentivirus vector. In one embodiment, the vector further comprises a promoter. In one embodiment, the promoter is an EF-1 promoter. In one embodiment, the EF-1 promoter comprises a sequence of SEQ ID NO: 11. In another embodiment, the promoter is a PGK promoter, e.g., a truncated PGK promoter as described herein.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases (SEQ ID NO:312). In one embodiment, the nucleic acid sequence in the vector further comprises a 3'UTR, e.g., a 3' UTR described herein, e.g., comprising at least one repeat of a 3'UTR derived from human beta-globulin. In one embodiment, the nucleic acid sequence in the vector further comprises promoter, e.g., a T2A promoter.

In another aspect, the invention pertains to a cell comprising a vector described herein. In one embodiment, the cell is a cell described herein, e.g., an immune effector cell, e.g., a human T cell, e.g., a human T cell described herein; or a human NK cell, e.g., a human NK cell described herein. In one embodiment, the human T cell is a CD8+ T cell.

In another embodiment, the CAR-expressing cell described herein can further express another agent, e.g., an agent which enhances the activity of a CAR-expressing cell. For example, in one embodiment, the agent can be an agent which inhibits an inhibitory molecule. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In another aspect, the invention pertains to a method of making a cell comprising transducing a cell described herein, e.g., an immune effector cell described herein, e.g., a T cell or a NK cell described herein, with a vector of comprising a nucleic acid encoding a CAR, e.g., a CAR described herein.

The present invention also provides a method of generating a population of RNA-engineered cells, e.g., cells described herein, e.g., immune effector cells, e.g., T cells or NK cells, transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a mammal comprising administering to the mammal an effective amount of a cell expressing a CAR molecule, e.g., a cell expressing a CAR molecule described herein. In one embodiment, the cell is an autologous immune effector cell, e.g., T cell. In one embodiment, the cell is an allogeneic immune effector cell, e.g., T cell. In one embodiment, the mammal is a human, e.g., a patient with a hematologic cancer. In another aspect, the invention pertains to a method of treating a mammal having a disease associated with expression of CLL-1 (e.g., a proliferative disease, a precancerous condition, and a non-cancer related indication associated with the expression of CLL-1) comprising administering to the mammal an effective amount of the cells expressing a CAR molecule, e.g., a CAR molecule described herein. In one embodiment, the mammal is a human, e.g., a patient with a hematologic cancer.

In one embodiment, the disease is a disease described herein. In one embodiment, the disease associated with CLL-1 expression is selected from a hematologic cancer such as acute leukemias including but not limited to acute myeloid leukemia (AML); myelodysplastic syndrome; myeloproliferative neoplasms; chronic myeloid leukemia (CML); Blastic plasmacytoid dendritic cell neoplasm; and to disease associated with CLL-1 expression including, but not limited to atypical and/or non-classical cancers, malignancies, precancerous conditions or proliferative diseases expressing CLL-1; and combinations thereof. In one embodiment, the disease associated with CLL-1 expression is a hematologic cancer selected from the group consisting of one or more acute leukemias including but not limited to acute myelogenous leukemia (or acute myeloid leukemia, AML); chronic myelogenous leukemia (or chronic myeloid leukemia, CML): acute lymphoid leukemia (or acute lymphoblastic leukemia, ALL); chronic lymphoid leukemia (or chronic lymphocytic leukemia, CLL) and myelodysplastic syndrome, B-cell acute lymphoid leukemia (“BALL”, or acute lymphoblastic B-cell leukemia), T-cell acute lymphoid leukemia ("TALL", or acute lymphoblastic T-cell leukemia), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, lymphomas including but not limited to multiple myeloma; non-Hodgkin's lymphoma; Burkitt's lymphoma; small cell-follicular lymphoma; and large cell-follicular lymphoma Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, Hodgkin's lymphoma, plasmablastic lymphoma, plasmacytoid dendritic cell neoplasm, plasma cell myeloma, Waldenstrom macroglobulinemia, and "preleukemia" which are a diverse collection of hematological conditions united by ineffective production (or dysplasia) of myeloid blood cells, and to disease associated with CLL-1 expression including, but not limited to atypical and/or non-classical cancers, malignancies, precancerous conditions or proliferative diseases expressing CLL-1; and combinations thereof.

In another aspect, the invention pertains to a method of conditioning a subject prior to cell transplantation comprising administering to the subject an effective amount of the cell of comprising a CAR molecule disclosed herein. In one embodiment, the cell transplantation is a stem cell transplantation. The stem cell transplantation is a hematopoietic stem cell transplantation or a bone marrow transplantation. In one embodiment, the cell transplantation is allogeneic or autologous.

In one embodiment, the conditioning a subject prior to cell transplantation comprises reducing the number of CLL-1-expressing cells in a subject. The CLL-1-expressing cells in the subject are CLL-1-expressing normal cells or CLL-1-expressing cancer cells, and in some cases, the condition in the subject will reduce both CLL-1-expressing normal and cancer cells prior to a cell transplantation.

In one embodiment, the cells expressing a CAR molecule, e.g., a CAR molecule described herein, are administered in combination with an agent that increases the efficacy of a cell expressing a CAR molecule, e.g., an agent described herein.

In one embodiment, the cells expressing a CAR molecule, e.g., a CAR molecule described herein, are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment this approach can be used to optimize the performance of CAR cells described herein in the subject. While not wishing to be bound by theory, it is believed that, in an embodiment, the performance of endogenous, non-modified immune effector cells, e.g., T cells, is improved. While not wishing to be bound by theory, it is believed that, in an embodiment, the performance of a CLL-1 CAR expressing cell is improved. In other embodiments, cells, e.g., T cells, which have, or will be that expresses a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells. In an embodiment, the CAR cells are administered after a sufficient time, or sufficient dosing, of an mTOR inhibitor, such that the level of PD1 negative immune effector cells, e.g., T cells, or the ratio of PD1 negative immune effector cells, e.g., T cells/PD1 positive immune effector cells, e.g., T cells, has been, at least transiently, increased.

In an embodiment, the invention provides an mTOR inhibitor for use in the treatment of a subject, wherein said mTOR inhibitor enhances an immune response of said subject, and wherein said subject has received, is receiving or is about to receive an immune effector cell that expresses a CLL-1 CAR as described herein.

In an embodiment, the cell, e.g., T cell, to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the cells expressing a CAR molecule, e.g., a CAR molecule described herein, are administered in combination with an agent that ameliorates one or more side effect associated with administration of a cell expressing a CAR molecule, e.g., an agent described herein.

In one embodiment, the cells expressing a CAR molecule, e.g., a CAR molecule described herein, are administered in combination with an agent that treats the disease associated with CLL-1, e.g., an agent described herein. In another embodiment, the cells expressing a CAR molecule, e.g., a CAR molecule described herein, are administered in combination with a chemotherapeutic agent, e.g., a chemotherapeutic agent described herein. In an embodiment, the chemotherapeutic agent is administered prior to administration of the cell expressing a CAR molecule, e.g., a CAR molecule described herein. For example, in chemotherapeutic regimens where more than one administration of the chemotherapeutic agent is desired, the chemotherapeutic regimen is initiated or completed prior to administration of a cell expressing a CAR molecule, e.g., a CAR molecule described herein. In embodiments, the chemotherapeutic agent is administered at least 5 days, 10 days, 15 days, 30 days prior to administration of the cell expressing the CAR molecule. In embodiments, the chemotherapeutic agent is a chemotherapeutic agent that increases CLL-1 expression on the cancer cells, e.g., the tumor cells, e.g., as compared to CLL-1 expression on normal or non-cancer cells. For example, the chemotherapeutic agent is cytarabine (Ara-C). In embodiments, the combination of chemotherapy and a cell expressing a CAR molecule described herein is useful for treating a hematological cancer, e.g., a leukemia, e.g., AML, or a minimal residual disease (MRD) of a hematological cancer described herein.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament, e.g., as described herein. In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing CLL-1, e.g., a disease expressing CLL-1 as described herein.

Additional features and embodiments of the aforesaid compositions and methods include one or more of the following:

In certain embodiments, the CLL-1 CAR molecule (e.g., a CLL-1 CAR nucleic acid or a CLL-1 CAR polypeptide as described herein), or the CLL-1 binding domain as described herein, includes one, two or three CDRs from the heavy chain variable region (e.g., HC CDR1, HC CDR2 and/or HC CDR3), provided in Table 1; and/or one, two or three CDRs from the light chain variable region (e.g., LC CDR1, LC CDR2 and/or LC CDR3) of CLL-1 CAR-1, CLL-1 CAR-2, CLL-1 CAR-3, CLL-1 CAR-4, CLL-1 CAR-5, CLL-1 CAR-6, CLL-1 CAR-7, CLL-1 CAR-8, CLL-1 CAR-9, CLL-1 CAR-10, CLL-1 CAR-11, CLL-1 CAR-12, CLL-1 CAR-13, or 181268 provided in Table 2; or a sequence substantially identical (e.g., 95-99% identical, or up to 5, 4, 3, 2, or 1 amino acid changes, e.g., substitutions (e.g., e.g., conservative substitutions)) to any of the aforesaid sequences.

In certain embodiments, the CLL-1 CAR molecule (e.g., a CLL-1 CAR nucleic acid or a CLL-1 CAR polypeptide as described herein), or the CLL-1 binding domain as described herein, includes one, two or three CDRs from the heavy chain variable region (e.g., HC CDR1, HC CDR2 and/or HC CDR3), provided in Table 3; and/or one, two or three CDRs from the light chain variable region (e.g., LC CDR1, LC CDR2 and/or LC CDR3) of CLL-1 CAR-1, CLL-1 CAR-2, CLL-1 CAR-3, CLL-1 CAR-4, CLL-1 CAR-5, CLL-1 CAR-6, CLL-1 CAR-7, CLL-1 CAR-8, CLL-1 CAR-9, CLL-1 CAR-10, CLL-1 CAR-11, CLL-1 CAR-12, CLL-1 CAR-13, or 181268 provided in Table 4; or a sequence substantially identical (e.g., 95-99% identical, or up to 5, 4, 3, 2, or 1 amino acid changes, e.g., substitutions (e.g., e.g., conservative substitutions)) to any of the aforesaid sequences.

In certain embodiments, the CLL-1 CAR molecule (e.g., a CLL-1 CAR nucleic acid or a CLL-1 CAR polypeptide as described herein), or the CLL-1 binding domain as described herein, includes one, two or three CDRs from the heavy chain variable region (e.g., HC CDR1, HC CDR2 and/or HC CDR3), provided in Table 5; and/or one, two or three CDRs from the light chain variable region (e.g., LC CDR1, LC CDR2 and/or LC CDR3) of CLL-1 CAR-1, CLL-1 CAR-2, CLL-1 CAR-3, CLL-1 CAR-4, CLL-1 CAR-5, CLL-1 CAR-6, CLL-1 CAR-7, CLL-1 CAR-8, CLL-1 CAR-9, CLL-1 CAR-10, CLL-1 CAR-11, CLL-1 CAR-12, CLL-1 CAR-13, or 181268 provided in Table 6; or a sequence substantially identical (e.g., 95-99% identical, or up to 5, 4, 3, 2, or 1 amino acid changes, e.g., substitutions (e.g., e.g., conservative substitutions)) to any of the aforesaid sequences.

In certain embodiments, the CAR molecule described herein (e.g., the CAR nucleic acid or the CAR polypeptide) includes:

(1) one, two, or three light chain (LC) CDRs chosen from one of the following:

(i) a LC CDR1 of SEQ ID NO: 156, LC CDR2 of SEQ ID NO: 169 and LC CDR3 of SEQ ID NO: 182 of CLL-1 CAR-1;

(ii) a LC CDR1 of SEQ ID NO: 157, LC CDR2 of SEQ ID NO: 170 and LC CDR3 of SEQ ID NO: 183 of CLL-1 CAR-2;

(iii) a LC CDR1 of SEQ ID NO: 158, LC CDR2 of SEQ ID NO: 171 and LC CDR3 of SEQ ID NO: 184 of CLL-1 CAR-3;

(iv) a LC CDR1 of SEQ ID NO: 159, LC CDR2 of SEQ ID NO: 172 and LC CDR3 of SEQ ID NO: 185 of CLL-1 CAR-4;

(v) a LC CDR1 of SEQ ID NO: 160, LC CDR2 of SEQ ID NO: 173 and LC CDR3 of SEQ ID NO: 186 of CLL-1 CAR-5;

(vi) a LC CDR1 of SEQ ID NO: 161, LC CDR2 of SEQ ID NO: 174 and LC CDR3 of SEQ ID NO: 187 of CLL-1 CAR-6;

(vii) a LC CDR1 of SEQ ID NO: 162, LC CDR2 of SEQ ID NO: 175 and LC CDR3 of SEQ ID NO: 188 of CLL-1 CAR-7;

(viii) a LC CDR1 of SEQ ID NO: 163, LC CDR2 of SEQ ID NO: 176 and LC CDR3 of SEQ ID NO: 189 of CLL-1 CAR-8; or (ix) a LC CDR1 of SEQ ID NO: 164, LC CDR2 of SEQ ID NO: 177 and LC CDR3 of SEQ ID NO: 190 of CLL-1 CAR-9;

(x) a LC CDR1 of SEQ ID NO: 165, LC CDR2 of SEQ ID NO: 178 and LC CDR3 of SEQ ID NO: 191 of CLL-1 CAR-10;

(xi) a LC CDR1 of SEQ ID NO: 166, LC CDR2 of SEQ ID NO: 179 and LC CDR3 of SEQ ID NO: 192 of CLL-1 CAR-11;

(xii) a LC CDR1 of SEQ ID NO: 167, LC CDR2 of SEQ ID NO: 180 and LC CDR3 of SEQ ID NO: 193 of CLL-1 CAR-12;

(xiii) a LC CDR1 of SEQ ID NO: 168, LC CDR2 of SEQ ID NO: 181 and LC CDR3 of SEQ ID NO: 194 of CLL-1 CAR-13;

(xiv) a LC CDR1 of SEQ ID NO: 202, LC CDR2 of SEQ ID NO: 203 and LC CDR3 of SEQ ID NO: 204 of 181286; and/or (2) one, two, or three heavy chain (HC) CDRs from one of the following:

(i) a HC CDR1 of SEQ ID NO: 117, HC CDR2 of SEQ ID NO: 130 and HC CDR3 of SEQ ID NO: 143 of CLL-1 CAR-1;

(ii) a HC CDR1 of SEQ ID NO: 118, HC CDR2 of SEQ ID NO: 131 and HC CDR3 of SEQ ID NO: 144 of CLL-1 CAR-2;

(iii) a HC CDR1 of SEQ ID NO: 119, HC CDR2 of SEQ ID NO: 132 and HC CDR3 of SEQ ID NO: 145 of CLL-1 CAR-3;

(iv) a HC CDR1 of SEQ ID NO: 120, HC CDR2 of SEQ ID NO: 133 and HC CDR3 of SEQ ID NO: 146 of CLL-1 CAR-4;

(v) a HC CDR1 of SEQ ID NO: 121, HC CDR2 of SEQ ID NO: 134 and HC CDR3 of SEQ ID NO: 147 of CLL-1 CAR-5;

(vi) a HC CDR1 of SEQ ID NO: 122, HC CDR2 of SEQ ID NO: 135 and HC CDR3 of SEQ ID NO: 148 of CLL-1 CAR-6;

(vii) a HC CDR1 of SEQ ID NO: 123, HC CDR2 of SEQ ID NO: 136 and HC CDR3 of SEQ ID NO: 149 of CLL-1 CAR-7;

(viii) a HC CDR1 of SEQ ID NO: 124, HC CDR2 of SEQ ID NO: 137 and HC CDR3 of SEQ ID NO: 150 of CLL-1 CAR-8; or (ix) a HC CDR1 of SEQ ID NO: 125, HC CDR2 of SEQ ID NO: 138 and HC CDR3 of SEQ ID NO: 151 of CLL-1 CAR-9;

(x) a HC CDR1 of SEQ ID NO: 126, HC CDR2 of SEQ ID NO: 139 and HC CDR3 of SEQ ID NO: 152 of CLL-1 CAR-10;

(xi) a HC CDR1 of SEQ ID NO: 127, HC CDR2 of SEQ ID NO: 140 and HC CDR3 of SEQ ID NO: 153 of CLL-1 CAR-11;

(xii) a HC CDR1 of SEQ ID NO: 128, HC CDR2 of SEQ ID NO: 141 and HC CDR3 of SEQ ID NO: 154 of CLL-1 CAR-12;

(xiii) a HC CDR1 of SEQ ID NO: 129, HC CDR2 of SEQ ID NO: 142 and HC CDR3 of SEQ ID NO: 155 of CLL-1 CAR-13;

(xiv) a HC CDR1 of SEQ ID NO: 199, HC CDR2 of SEQ ID NO: 200 and HC CDR3 of SEQ ID NO: 201 of 181286.

In certain embodiments, the CAR molecule described herein (e.g., the CAR nucleic acid or the CAR polypeptide) or a CLL-1 binding domain includes:

(1) one, two, or three light chain (LC) CDRs chosen from one of the following:

(i) a LC CDR1 of SEQ ID NO: 356, LC CDR2 of SEQ ID NO: 370 and LC CDR3 of SEQ ID NO: 384 of CLL-1 CAR-1;

(ii) a LC CDR1 of SEQ ID NO: 357, LC CDR2 of SEQ ID NO: 371 and LC CDR3 of SEQ ID NO: 385 of CLL-1 CAR-2;

(iii) a LC CDR1 of SEQ ID NO: 358, LC CDR2 of SEQ ID NO: 372 and LC CDR3 of SEQ ID NO: 386 of CLL-1 CAR-3;

(iv) a LC CDR1 of SEQ ID NO: 359, LC CDR2 of SEQ ID NO: 373 and LC CDR3 of SEQ ID NO: 387 of CLL-1 CAR-4;

(v) a LC CDR1 of SEQ ID NO: 360, LC CDR2 of SEQ ID NO: 374 and LC CDR3 of SEQ ID NO: 388 of CLL-1 CAR-5;

(vi) a LC CDR1 of SEQ ID NO: 361, LC CDR2 of SEQ ID NO: 375 and LC CDR3 of SEQ ID NO: 389 of CLL-1 CAR-6;

(vii) a LC CDR1 of SEQ ID NO: 362, LC CDR2 of SEQ ID NO: 376 and LC CDR3 of SEQ ID NO: 390 of CLL-1 CAR-7;

(viii) a LC CDR1 of SEQ ID NO: 363, LC CDR2 of SEQ ID NO: 377 and LC CDR3 of SEQ ID NO: 391 of CLL-1 CAR-8; or (ix) a LC CDR1 of SEQ ID NO: 364, LC CDR2 of SEQ ID NO: 378 and LC CDR3 of SEQ ID NO: 392 of CLL-1 CAR-9;

(x) a LC CDR1 of SEQ ID NO: 365, LC CDR2 of SEQ ID NO: 379 and LC CDR3 of SEQ ID NO: 393 of CLL-1 CAR-10;

(xi) a LC CDR1 of SEQ ID NO: 366, LC CDR2 of SEQ ID NO: 380 and LC CDR3 of SEQ ID NO: 394 of CLL-1 CAR-11;

(xii) a LC CDR1 of SEQ ID NO: 367, LC CDR2 of SEQ ID NO: 381 and LC CDR3 of SEQ ID NO: 395 of CLL-1 CAR-12;

(xiii) a LC CDR1 of SEQ ID NO: 368, LC CDR2 of SEQ ID NO: 382 and LC CDR3 of SEQ ID NO: 396 of CLL-1 CAR-13;

(xiv) a LC CDR1 of SEQ ID NO: 369, LC CDR2 of SEQ ID NO: 383 and LC CDR3 of SEQ ID NO: 397 of 181286; and/or (2) one, two, or three heavy chain (HC) CDRs from one of the following:

(i) a HC CDR1 of SEQ ID NO: 314, HC CDR2 of SEQ ID NO: 328 and HC CDR3 of SEQ ID NO: 342 of CLL-1 CAR-1;

(ii) a HC CDR1 of SEQ ID NO: 315, HC CDR2 of SEQ ID NO: 329 and HC CDR3 of SEQ ID NO: 343 of CLL-1 CAR-2;

(iii) a HC CDR1 of SEQ ID NO: 316, HC CDR2 of SEQ ID NO: 330 and HC CDR3 of SEQ ID NO: 344 of CLL-1 CAR-3;

(iv) a HC CDR1 of SEQ ID NO: 317, HC CDR2 of SEQ ID NO: 331 and HC CDR3 of SEQ ID NO: 345 of CLL-1 CAR-4;

(v) a HC CDR1 of SEQ ID NO: 318, HC CDR2 of SEQ ID NO: 332 and HC CDR3 of SEQ ID NO: 346 of CLL-1 CAR-5;

(vi) a HC CDR1 of SEQ ID NO: 319, HC CDR2 of SEQ ID NO: 333 and HC CDR3 of SEQ ID NO: 347 of CLL-1 CAR-6;

(vii) a HC CDR1 of SEQ ID NO: 320, HC CDR2 of SEQ ID NO: 334 and HC CDR3 of SEQ ID NO: 348 of CLL-1 CAR-7;

(viii) a HC CDR1 of SEQ ID NO: 321, HC CDR2 of SEQ ID NO: 335 and HC CDR3 of SEQ ID NO: 349 of CLL-1 CAR-8; or (ix) a HC CDR1 of SEQ ID NO: 322, HC CDR2 of SEQ ID NO: 336 and HC CDR3 of SEQ ID NO: 350 of CLL-1 CAR-9;

(x) a HC CDR1 of SEQ ID NO: 323, HC CDR2 of SEQ ID NO: 337 and HC CDR3 of SEQ ID NO: 351 of CLL-1 CAR-10;

(xi) a HC CDR1 of SEQ ID NO: 324, HC CDR2 of SEQ ID NO: 338 and HC CDR3 of SEQ ID NO: 352 of CLL-1 CAR-11;

(xii) a HC CDR1 of SEQ ID NO: 325, HC CDR2 of SEQ ID NO: 339 and HC CDR3 of SEQ ID NO: 353 of CLL-1 CAR-12;

(xiii) a HC CDR1 of SEQ ID NO: 326, HC CDR2 of SEQ ID NO: 340 and HC CDR3 of SEQ ID NO: 354 of CLL-1 CAR-13;

(xiv) a HC CDR1 of SEQ ID NO: 327, HC CDR2 of SEQ ID NO: 341 and HC CDR3 of SEQ ID NO: 355 of 181286.

In certain embodiments, the CAR molecule described herein (e.g., the CAR nucleic acid or the CAR polypeptide) includes:

(1) one, two, or three light chain (LC) CDRs chosen from one of the following:

(i) a LC CDR1 of SEQ ID NO: 440, LC CDR2 of SEQ ID NO: 454 and LC CDR3 of SEQ ID NO: 468 of CLL-1 CAR-1;

(ii) a LC CDR1 of SEQ ID NO: 441, LC CDR2 of SEQ ID NO: 455 and LC CDR3 of SEQ ID NO: 469 of CLL-1 CAR-2;

(iii) a LC CDR1 of SEQ ID NO: 442, LC CDR2 of SEQ ID NO: 456 and LC CDR3 of SEQ ID NO: 470 of CLL-1 CAR-3;

(iv) a LC CDR1 of SEQ ID NO: 443, LC CDR2 of SEQ ID NO: 457 and LC CDR3 of SEQ ID NO: 471 of CLL-1 CAR-4;

(v) a LC CDR1 of SEQ ID NO: 444, LC CDR2 of SEQ ID NO: 458 and LC CDR3 of SEQ ID NO: 472 of CLL-1 CAR-5;

(vi) a LC CDR1 of SEQ ID NO: 445, LC CDR2 of SEQ ID NO: 459 and LC CDR3 of SEQ ID NO: 473 of CLL-1 CAR-6;

(vii) a LC CDR1 of SEQ ID NO: 446, LC CDR2 of SEQ ID NO: 460 and LC CDR3 of SEQ ID NO: 474 of CLL-1 CAR-7;

(viii) a LC CDR1 of SEQ ID NO: 447, LC CDR2 of SEQ ID NO: 461 and LC CDR3 of SEQ ID NO: 475 of CLL-1 CAR-8; or (ix) a LC CDR1 of SEQ ID NO: 448, LC CDR2 of SEQ ID NO: 462 and LC CDR3 of SEQ ID NO: 476 of CLL-1 CAR-9;

(x) a LC CDR1 of SEQ ID NO: 449, LC CDR2 of SEQ ID NO: 463 and LC CDR3 of SEQ ID NO: 477 of CLL-1 CAR-10;

(xi) a LC CDR1 of SEQ ID NO: 450, LC CDR2 of SEQ ID NO: 464 and LC CDR3 of SEQ ID NO: 478 of CLL-1 CAR-11;

(xii) a LC CDR1 of SEQ ID NO: 451, LC CDR2 of SEQ ID NO: 465 and LC CDR3 of SEQ ID NO: 479 of CLL-1 CAR-12;

(xiii) a LC CDR1 of SEQ ID NO: 452, LC CDR2 of SEQ ID NO: 466 and LC CDR3 of SEQ ID NO: 480 of CLL-1 CAR-13;

(xiv) a LC CDR1 of SEQ ID NO: 453, LC CDR2 of SEQ ID NO: 467 and LC CDR3 of SEQ ID NO: 481 of 181286; and/or (2) one, two, or three heavy chain (HC) CDRs from one of the following:

(i) a HC CDR1 of SEQ ID NO: 398, HC CDR2 of SEQ ID NO: 412 and HC CDR3 of SEQ ID NO: 426 of CLL-1 CAR-1;

(ii) a HC CDR1 of SEQ ID NO: 399, HC CDR2 of SEQ ID NO: 413 and HC CDR3 of SEQ ID NO: 427 of CLL-1 CAR-2;

(iii) a HC CDR1 of SEQ ID NO: 400, HC CDR2 of SEQ ID NO: 414 and HC CDR3 of SEQ ID NO: 428 of CLL-1 CAR-3;

(iv) a HC CDR1 of SEQ ID NO: 401, HC CDR2 of SEQ ID NO: 415 and HC CDR3 of SEQ ID NO: 429 of CLL-1 CAR-4;

(v) a HC CDR1 of SEQ ID NO: 402, HC CDR2 of SEQ ID NO: 416 and HC CDR3 of SEQ ID NO: 430 of CLL-1 CAR-5;

(vi) a HC CDR1 of SEQ ID NO: 403, HC CDR2 of SEQ ID NO: 417 and HC CDR3 of SEQ ID NO: 431 of CLL-1 CAR-6;

(vii) a HC CDR1 of SEQ ID NO: 404, HC CDR2 of SEQ ID NO: 418 and HC CDR3 of SEQ ID NO: 432 of CLL-1 CAR-7;

(viii) a HC CDR1 of SEQ ID NO: 405, HC CDR2 of SEQ ID NO: 419 and HC CDR3 of SEQ ID NO: 433 of CLL-1 CAR-8; or (ix) a HC CDR1 of SEQ ID NO: 406, HC CDR2 of SEQ ID NO: 420 and HC CDR3 of SEQ ID NO: 434 of CLL-1 CAR-9;

(x) a HC CDR1 of SEQ ID NO: 407, HC CDR2 of SEQ ID NO: 421 and HC CDR3 of SEQ ID NO: 435 of CLL-1 CAR-10;

(xi) a HC CDR1 of SEQ ID NO: 408, HC CDR2 of SEQ ID NO: 422 and HC CDR3 of SEQ ID NO: 436 of CLL-1 CAR-11;

(xii) a HC CDR1 of SEQ ID NO: 409, HC CDR2 of SEQ ID NO: 423 and HC CDR3 of SEQ ID NO: 437 of CLL-1 CAR-12;

(xiii) a HC CDR1 of SEQ ID NO: 410, HC CDR2 of SEQ ID NO: 424 and HC CDR3 of SEQ ID NO: 438 of CLL-1 CAR-13;

(xiv) a HC CDR1 of SEQ ID NO: 411, HC CDR2 of SEQ ID NO: 425 and HC CDR3 of SEQ ID NO: 439 of 181286.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising

FIG. 2, comprising

FIG. 3, comprising FIG. 3A shows detection of CART expression in primary T cells using Protein L. FIG. 3B shows detection of CART expression in primary T cells using recombinant CLL-1 protein.

FIG. 4, comprising

FIG. 5, comprising

FIG. 7, comprising

FIG. 8, comprising

FIG. 9, comprising

FIG. 10, comprising

FIG. 11, comprising

FIG. 12, comprising

FIG. 14, comprising

FIG. 15, comprising

FIG. 16, comprising

FIG. 18, comprising

FIG. 19, comprising FIGS. 19A, 19B, 19C, 19D, and 19E, is a series of images demonstrating bone marrow analysis 4 weeks post T cells.

FIG. 21, comprising

FIG. 22, comprising FIG. 22A shows detection of CART expression in primary T cells using Protein L. FIG. 22B shows detection of CART expression in primary T cells using recombinant CLL-1 protein.

FIG. 23, comprising

FIG. 25, comprising

FIG. 26, comprising

FIG. 27, comprising

FIG. 28, comprising FIG. 28A is a schematic illustrating the experimental schema for the combined therapy of chemotherapy and CLL-1-CART cells in primary AML xenografts. FIG. 28B is a bar graph showing the mean fluorescence intensity (MFI) of CLL1 in leukemic cells (live huCD45dim compartment). FIG. 28C is a graph showing the quantification of peripheral blood leukemic blast count per 1 ul of peripheral blood (mean+/−SD) at different time points post AML injection as indicated. The arrows denote administration Ara-C (grey arrows) and administration of T cells (untransduced or CLL-1 CAR-expressing T cells, black arrows). FIG. 28D is a graph showing the survival of the AML xenografts.

FIG. 29, comprising In FIG. 29E, the shRNA (and corresponding U6 promoter) is on a first vector, and the CAR (and corresponding EF1 alpha promoter) is on a second vector.

FIG. 33, comprising FIG. 33A shows day 0 PK following the first dose of RAD001. FIG. 33B shows Day 14 PK following the final RAD001 dose. Diamonds denote the 10 mg/kg dose of RAD001; squares denote the 1 mg/kg dose of RAD001; triangles denote the 3 mg/kg dose of RAD001; and x's denote the 10 mg/kg dose of RAD001.

FIG. 34, comprising FIG. 34A shows $CD4^+$ CAR T cells; FIG. 34B shows $CD8^+$ CAR T cells. Circles denote PBS; squares denote huCTL019; triangles denote huCTL019 with 3 mg/kg RAD001; inverted triangles denote huCTL019 with 0.3 mg/kg RAD001; diamonds denote huCTL019 with 0.03 mg/kg RAD001; and circles denote huCTL019 with 0.003 mg/kg RAD001.

DETAILED DESCRIPTION

Definitions

Figure 1A:
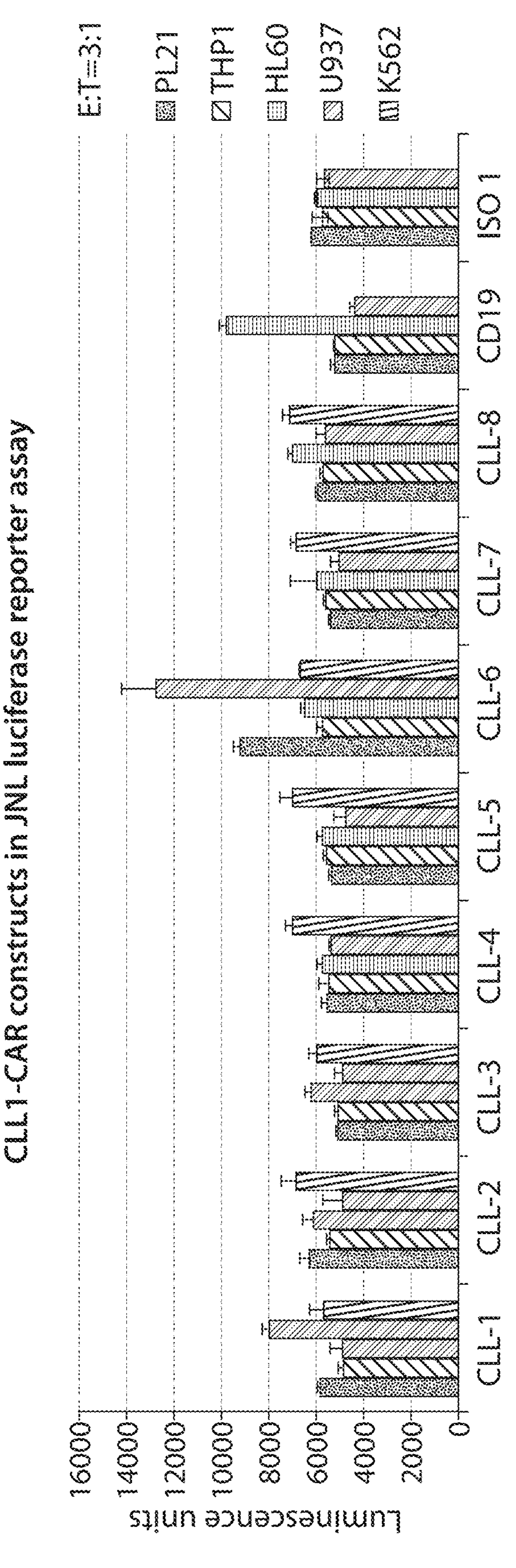
FIGS. 1A 1B, and 1C, is a series of images demonstrating luciferase levels in target-positive (PL21, THP1, HL60, U937) or target-negative (K562) cell lines mixed with a JNL cell line transduced with anti-CLL-1 CAR.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein In one aspect, the stimulatory molecule of the CAR is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., aa scFv) during cellular processing and localization of the CAR to the cellular membrane.

A CAR that comprises an antigen binding domain (e.g., a scFv, a single domain antibody, or TCR (e.g., a TCR alpha binding domain or TCR beta binding domain)) that specifically binds a specific tumor marker X, wherein X can be a tumor marker as described herein, is also referred to as XCAR. For example, a CAR that comprises an antigen binding domain that specifically binds CLL-1 is referred to as CLL-1 CAR. The CAR can be expressed in any cell, e.g., an immune effector cell as described herein (e.g., a T cell or an NK cell).

The term "signaling domain" refers to the functional portion of a protein which acts by transmitting information within the cell to regulate cellular activity via defined signaling pathways by generating second messengers or functioning as effectors by responding to such messengers.

As used herein, the term "CLL-1" refers to C-type lectin-like molecule-1, which is an antigenic determinant detectable on leukemia precursor cells and on normal immune cells. C-type lectin-like-1 (CLL-1) is also known as MICL, CLEC12A, CLEC-1, Dendritic Cell-Associated Lectin 1, and DCAL-2. The human and murine amino acid and nucleic acid sequences can be found in a public database, such as GenBank, UniProt and Swiss-Prot. For example, the amino acid sequence of human CLL-1 can be found as UniProt/Swiss-Prot Accession No. Q5QGZ9 and the nucleotide sequence encoding of the human CLL-1 can be found at Accession Nos. NM 001207010.1, NM 138337.5, NM 201623.3, and NM 201625.1. In one embodiment, the antigen-binding portion of the CAR recognizes and binds an epitope within the extracellular domain of the CLL-1 protein or a fragment thereof. In one embodiment, the CLL-1 protein is expressed on a cancer cell.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide bridge at the hinge region, or two or more, e.g., two, isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR composition of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), e.g., a human antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

As used herein, the term "binding domain" or "antibody molecule" (also referred to herein as "anti-target (e.g., CLL-1) binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (K) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of CLL-1" includes, but is not limited to, a disease associated with a cell which expresses CLL-1 or condition associated with a cell which expresses CLL-1 including, e.g., proliferative diseases such as a cancer or malignancy or a precancerous condition such as a myelodysplasia, a myelodysplastic syndrome or a preleukemia; or a noncancer related indication associated with a cell which expresses CLL-1 (e.g., wild-type or mutant CLL-1). For the avoidance of doubt, a disease associated with expression of CLL-1 may include a condition associated with a cell which do not presently express CLL-1, e.g., because CLL-1 expression has been downregulated, e.g., due to treatment with a molecule targeting CLL-1, e.g., a CLL-1 inhibitor described herein, but which at one time expressed CLL-1. In one aspect, a cancer associated with expression of CLL-1 is a hematological cancer. In one aspect, a hematological cancer includes but is not limited to leukemia (such as acute myelogenous leukemia, chronic myelogenous leukemia, acute lymphoid leukemia, chronic lymphoid leukemia and myelodysplastic syndrome) and malignant lymphoproliferative conditions, including lymphoma (such as multiple myeloma, non-Hodgkin's lymphoma, Burkitt's lymphoma, and small cell- and large cell-follicular lymphoma). Further diseases associated with expression of CLL-1 expression include, but not limited to, e.g., atypical and/or non-classical cancers, malignancies, precancerous conditions or proliferative diseases associated with expression of CLL-1. Non-cancer related indications associated with expression of CLL-1 may also be included. In some embodiments, the tumor antigen-expressing cell expresses, or at any time expressed, mRNA encoding the tumor antigen. In an embodiment, the tumor antigen-expressing cell produces the tumor antigen protein (e.g., wild-type or mutant), and the tumor antigen protein may be present at normal levels or reduced levels. In an embodiment, the tumor antigen-expressing cell produced detectable levels of a tumor antigen protein at one point, and subsequently produced substantially no detectable tumor antigen protein.

The terms "conservative sequence modifications" or "conservative substitutions" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI, CD66d, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:9, or the equivalent residues from a non-human species, e.g., mouse, rodent, monkey, ape and the like. In a specific CAR of the invention, the primary signaling sequence of CD3-zeta is the sequence as provided in SEQ ID NO:10, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as “ICOS”), FcεRI, CD66d, DAP10, and DAP12.

The term “zeta” or alternatively “zeta chain”, “CD3-zeta” or “TCR-zeta” is defined as the protein provided as GenBan Acc. No. BAG36664.1, or the equivalent residues from a non-human species, e.g., mouse, rodent, monkey, ape and the like, and a “zeta stimulatory domain” or alternatively a “CD3-zeta stimulatory domain” or a “TCR-zeta stimulatory domain” is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the “zeta stimulatory domain” or a “CD3-zeta stimulatory domain” is the sequence provided as SEQ ID NO:9. In one aspect, the “zeta stimulatory domain” or a “CD3-zeta stimulatory domain” is the sequence provided as SEQ ID NO:10.

The term “costimulatory molecule” refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term “4-1BB” refers to a member of the TNFR superfamily with an amino acid sequence provided as GenBank Acc. No. AAA62478.2, or the equivalent residues from a non-human species, e.g., mouse, rodent, monkey, ape and the like; and a “4-1BB costimulatory domain” is defined as amino acid residues 214-255 of GenBank Acc. No. AAA62478.2, or the equivalent residues from a non-human species, e.g., mouse, rodent, monkey, ape and the like. In one aspect, the “4-1BB costimulatory domain” is the sequence provided as SEQ ID NO:7 or the equivalent residues from a non-human species, e.g., mouse, rodent, monkey, ape and the like.

“Immune effector cell,” as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

“Immune effector function or immune effector response,” as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term “effector function” refers to a specialized function of a cell. Effector function of a T cell, for example, may be cytolytic activity or helper activity including the secretion of cytokines.

The term “encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a “nucleotide sequence encoding an amino acid sequence” includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term “effective amount” or “therapeutically effective amount” are used interchangeably herein, and refer to an amount of a compound, formulation, material, or composition, as described herein effective to achieve a particular biological result.

The term “endogenous” refers to any material from or produced inside an organism, cell, tissue or system.

The term “exogenous” refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms “peptide,” “polypeptide,” and “protein” are used interchangeably, and refer to a compound comprised of amino acid residues covalently linked by peptide bonds. A protein or peptide must contain at least two amino acids, and no limitation is placed on the maximum number of amino acids that can comprise a protein’s or peptide’s sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. “Polypeptides” include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term “promoter” refers to a DNA sequence recognized by the synthetic machinery of the cell, or introduced synthetic machinery, required to initiate the specific transcription of a polynucleotide sequence.

The term “promoter/regulatory sequence” refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term “constitutive” promoter refers to a nucleotide sequence which, when operably linked with a polynucleotide which encodes or specifies a gene product, causes the gene product to be produced in a cell under most or all physiological conditions of the cell.

The term “inducible” promoter refers to a nucleotide sequence which, when operably linked with a polynucleotide which encodes or specifies a gene product, causes the gene product to be produced in a cell substantially only when an inducer which corresponds to the promoter is present in the cell.

The term “tissue-specific” promoter refers to a nucleotide sequence which, when operably linked with a polynucleotide encodes or specified by a gene, causes the gene product to be produced in a cell substantially only if the cell is a cell of the tissue type corresponding to the promoter.

The term “flexible polypeptide linker” or “linker” as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n (SEQ ID NO: 38), where n is a positive integer equal to or greater than 1. For example, n=1, n=2, n=3. n=4, n=5 and n=6, n=7, n=8, n=9 and n=10 In one embodiment, the flexible polypeptide linkers include, but are not limited to, $(Gly_4\ Ser)_4$ (SEQ ID NO:27) or $(Gly_4\ Ser)_3$ (SEQ ID NO:28). In another embodiment, the linkers include multiple repeats of $(Gly_2Ser)$, (GlySer) or $(Gly_3Ser)$ (SEQ ID NO:29). Also included within the scope of the invention are linkers described in WO2012/138475, incorporated herein by reference.

As used herein, a 5' cap (also termed an RNA cap, an RNA 7-methylguanosine cap or an RNA $m^7G$ cap) is a modified guanine nucleotide that has been added to the “front” or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, “in vitro transcribed RNA” refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a “poly(A)” is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, “polyadenylation” refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, “transient” refers to expression of a non-integrated transgene for a period of hours, days or weeks, wherein the period of time of expression is less than the period of time for expression of the gene if integrated into the genome or contained within a stable plasmid replicon in the host cell.

As used herein, the terms “treat”, “treatment” and “treating” refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms “treat”, “treatment” and “treating” refer to the amelioration of at least one measurable physical parameter of a proliferative disorder, such as growth of a tumor, not necessarily discernible by the patient. In other embodiments the terms “treat”, “treatment” and “treating”-refer to the inhibition of the progression of a proliferative disorder, either physically by, e.g., stabilization of a discernible symptom, physiologically by, e.g., stabilization of a physical parameter, or both. In other embodiments the terms “treat”, “treatment” and “treating” refer to the reduction or stabilization of tumor size or cancerous cell count.

The term “signal transduction pathway” refers to the biochemical relationship between a variety of signal transduction molecules that play a role in the transmission of a signal from one portion of a cell to another portion of a cell. The phrase “cell surface receptor” includes molecules and complexes of molecules capable of receiving a signal and transmitting signal across the membrane of a cell.

The term “subject” is intended to include living organisms in which an immune response can be elicited (e.g., mammals, human).

The term, a “substantially purified” cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term “therapeutic” as used herein means a treatment. A therapeutic effect is obtained by reduction, suppression, remission, or eradication of a disease state.

The term “prophylaxis” as used herein means the prevention of or protective treatment for a disease or disease state.

In the context of the present invention, “tumor antigen” or “hyperproliferative disorder antigen” or “antigen associated with a hyperproliferative disorder” refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin’s lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term “transfected” or “transformed” or “transduced” refers to a process by which exogenous nucleic acid is transferred or introduced into the host cell. A “transfected” or “transformed” or “transduced” cell is one which has been transfected, transformed or transduced with exogenous nucleic acid. The cell includes the primary subject cell and its progeny.

The term “specifically binds,” refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

“Regulatable chimeric antigen receptor (RCAR),” as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as “an intracellular signaling domain”) comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as “RCARX cell”). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

“Membrane anchor” or “membrane tethering domain”, as that term is used herein, refers to a polypeptide or moiety, e.g., a myristoyl group, sufficient to anchor an extracellular or intracellular domain to the plasma membrane.

“Switch domain,” as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^{+}$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or a "relapse" as used herein refers to the reappearance of a disease (e.g., cancer) or the signs and symptoms of a disease such as cancer after a period of improvement or responsiveness, e.g., after prior treatment of a therapy, e.g., cancer therapy. For example, the period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

DESCRIPTION

Provided herein are compositions of matter and methods of use for the treatment of a disease such as cancer using CLL-1 chimeric antigen receptors (CAR).

In one aspect, the invention provides a number of chimeric antigen receptors (CAR) comprising an antibody or antibody fragment engineered for specific binding to a CLL-1 protein or a fragment thereof. In one aspect, the invention provides a cell (e.g., an immune effector cell, e.g., a T cell or a NK cell) engineered to express a CAR, wherein the CAR T cell ("CART") exhibits an antitumor property. In one aspect a cell is transformed with the CAR and at least part of the CAR construct is expressed on the cell surface. In some embodiments, the cell (e.g., an immune effector cell, e.g., a T cell or a NK cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., an immune effector cell, e.g., a T cell or a NK cell) is transfected with a nucleic acid, e.g., mRNA, cDNA, DNA, encoding a CAR. In some such embodiments, the cell may transiently express the CAR.

In one aspect, the human anti-CLL-1 protein binding portion of the CAR is a scFv antibody fragment. In one aspect such antibody fragments are functional in that they retain the equivalent binding affinity, e.g., they bind the same antigen with comparable efficacy, as the IgG antibody having the same heavy and light chain variable regions. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In some aspects, the antibodies of the invention are incorporated into a chimeric antigen receptor (CAR). In one aspect, the CAR comprises the polypeptide sequence provided herein as SEQ ID NO: 91-103.

In one aspect, the anti-CLL-1 binding domain, e.g., human scFv, portion of a CAR of the invention is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the human CLL-1 binding domain comprises the scFv portion provided in SEQ ID NOs:39-51. In one embodiment, the human anti-CLL-1 binding domain comprises the scFv portion provided in SEQ ID NO:39. In one embodiment, the human anti-CLL-1 binding domain comprises the scFv portion provided in SEQ ID NO:40. In one embodiment, the human anti-CLL-1 binding domain comprises the scFv portion provided in SEQ ID NO:41. In one embodiment, the human anti-CLL-1 binding domain comprises the scFv portion provided in SEQ ID NO:42. In one embodiment, the human anti-CLL-1 binding domain comprises the scFv portion provided in SEQ ID NO:43. In one embodiment, the human anti-CLL-1 binding domain comprises the scFv portion provided in SEQ ID NO:44. In one embodiment, the human anti-CLL-1 binding domain comprises the scFv portion provided in SEQ ID NO:45. In one embodiment, the human anti-CLL-1 binding domain comprises the scFv portion provided in SEQ ID NO:46. In one embodiment, the human anti-CLL-1 binding domain comprises the scFv portion provided in SEQ ID NO:47. In one embodiment, the human anti-CLL-1 binding domain comprises the scFv portion provided in SEQ ID NO:48. In one embodiment, the human anti-CLL-1 binding domain comprises the scFv portion provided in SEQ ID NO:49. In one embodiment, the human anti-CLL-1 binding domain comprises the scFv portion provided in SEQ ID NO:50. In one embodiment, the human anti-CLL-1 binding domain comprises the scFv portion provided in SEQ ID NO:51. In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to CLL-1. In one aspect, the CLL-1 CAR comprises a CAR selected from the sequence provided in one or more of SEQ ID NOs: 91-103 or 197. In one aspect, the CLL-1 CAR comprises the sequence provided in SEQ ID NO:91. In one aspect, the CLL-1 CAR comprises the sequence provided in SEQ ID NO:92. In one aspect, the CLL-1 CAR comprises the sequence provided in SEQ ID NO:93. In one aspect, the CLL-1 CAR comprises the sequence provided in SEQ ID NO:94. In one aspect, the CLL-1 CAR comprises the sequence provided in SEQ ID NO:95. In one aspect, the CLL-1 CAR comprises the sequence provided in SEQ ID NO:96. In one aspect, the CLL-1 CAR comprises the sequence provided in SEQ ID NO:97. In one aspect, the CLL-1 CAR comprises the sequence provided in SEQ ID NO:98. In one aspect, the CLL-1 CAR comprises the sequence provided in SEQ ID NO:99. In one aspect, the CLL-1 CAR comprises the sequence provided in SEQ ID NO:100. In one aspect, the CLL-1 CAR comprises the sequence provided in SEQ ID NO:101. In one aspect, the CLL-1 CAR comprises the sequence provided in SEQ ID NO:102. In one aspect, the CLL-1 CAR comprises the sequence provided in SEQ ID NO:103. In one aspect, the CLL-1 CAR comprises the sequence provided in SEQ ID NO:197. Furthermore, the present invention provides CLL-1 CAR compositions and their use in medicaments or methods for treating, among other diseases, cancer or any malignancy or autoimmune diseases involving cells or tissues which express CLL-1.

In one aspect, the CAR of the invention can be used to eradicate CLL-1-expressing normal cells, thereby applicable for use as a cellular conditioning therapy prior to cell transplantation. In one aspect, the CLL-1-expressing normal cell is a CLL-1-expressing normal stem cell and the cell transplantation is a stem cell transplantation.

In one aspect, the invention provides a cell (e.g., an immune effector cell, e.g., a T cell or a NK cell) engineered to express a chimeric antigen receptor (CAR) of the present invention, wherein the cell (e.g., CAR-expressing immune effector cell, e.g., CAR T cell, e.g., "CART") exhibits an antitumor property. A preferred antigen is CLL-1. In one aspect, the antigen binding domain of the CAR comprises a human anti-CLL-1 antibody fragment. In one aspect, the antigen binding domain of the CAR comprises human anti-CLL-1 antibody fragment comprising an scFv. In one embodiment, the antigen binding domain of the CAR comprises a human anti-CLL-1 scFv. Accordingly, the invention provides a CLL-1-CAR that comprises an anti-CLL-1 binding domain and is engineered into an immune effector cell, e.g., a T cell or a NK cell and methods of their use for adoptive therapy. In one aspect, the CLL-1-CAR comprises a human anti-CLL-1 binding domain.

In one aspect, the CLL-1-CAR comprises at least one intracellular domain selected from the group of a CD137 (4-1BB) signaling domain, a CD28 signaling domain, a CD3zeta signal domain, and any combination thereof. In one aspect, the CLL-1-CAR comprises at least one intracellular signaling domain is from one or more co-stimulatory molecule(s) other than a CD137 (4-1BB) or CD28.

Chimeric Antigen Receptor (CAR)

The present invention provides a CAR (e.g., a CAR polypeptide) that comprises an anti-CLL-1 binding domain (e.g., human or humanized CLL-1 binding domain as described herein), a transmembrane domain, and an intracellular signaling domain, and wherein said anti-CLL-1 binding domain comprises a heavy chain complementary determining region 1 (HC CDR1), a heavy chain complementary determining region 2 (HC CDR2), and a heavy chain complementary determining region 3 (HC CDR3) of any anti-CLL-1 heavy chain binding domain amino acid sequences listed in Table 8. The anti-CLL-1 binding domain of the CAR can further comprise a light chain complementary determining region 1 (LC CDR1), a light chain complementary determining region 2 (LC CDR2), and a light chain complementary determining region 3 (LC CDR3) of any anti-CLL-1 light chain binding domain amino acid sequences listed in Table 8.

The present invention also provides nucleic acid molecules encoding the CAR as described herein, e.g., encoding a CAR that comprises an anti-CLL-1 binding domain (e.g., human or humanized CLL-1 binding domain as described herein), a transmembrane domain, and an intracellular signaling domain, and wherein said anti-CLL-1 binding domain comprises a heavy chain complementary determining region 1 (HC CDR1), a heavy chain complementary determining region 2 (HC CDR2), and a heavy chain complementary determining region 3 (HC CDR3) of any anti-CLL-1 heavy chain binding domain amino acid sequences listed in Table 8.

In one embodiment, the encoded anti-CLL-1 binding domain of the CAR can further comprise a light chain complementary determining region 1 (LC CDR1), a light chain complementary determining region 2 (LC CDR2), and a light chain complementary determining region 3 (LC CDR3) of any anti-CLL-1 light chain binding domain amino acid sequences listed in Table 8.

In specific aspects, a CAR construct of the invention comprises a scFv domain selected from the group consisting of SEQ ID NOs:39-51, wherein the scFv may be preceded by an optional leader sequence such as provided in SEQ ID NO: 1, and followed by an optional hinge sequence such as provided in SEQ ID NO:2 or SEQ ID NO:3 or SEQ ID NO:4 or SEQ ID NO:5, a transmembrane region such as provided in SEQ ID NO:6, an intracellular signalling domain that includes SEQ ID NO:7 or SEQ ID NO:8 and a CD3 zeta sequence that includes SEQ ID NO:9 or SEQ ID NO:10, e.g., wherein the domains are contiguous with and in the same reading frame to form a single fusion protein. Also included in the invention is a nucleotide sequence that encodes the polypeptide of each of the scFv fragments selected from the group consisting of SEQ ID NO: 39-51. Also included in the invention is a nucleotide sequence that encodes the polypeptide of each of the scFv fragments selected from the group consisting of SEQ ID NO: 39-51, and each of the domains of SEQ ID NOs: 1, 2, and 6-9. In one aspect an exemplary CLL-1 CAR constructs comprise an optional leader sequence, an extracellular antigen binding domain, a hinge, a transmembrane domain, and an intracellular stimulatory domain. In one aspect an exemplary CLL-1 CAR construct comprises an optional leader sequence, an extracellular antigen binding domain, a hinge, a transmembrane domain, an intracellular costimulatory domain and an intracellular stimulatory domain.

In some embodiments, full-length CAR sequences are also provided herein as SEQ ID NOs: 91-103, as shown in Table 8.

An exemplary leader sequence is provided as SEQ ID NO: 1. An exemplary hinge/spacer sequence is provided as SEQ ID NO:2 or SEQ ID NO:3 or SEQ ID NO:4 or SEQ ID NO:5. An exemplary transmembrane domain sequence is provided as SEQ ID NO:6. An exemplary sequence of the intracellular signaling domain of the 4-1BB protein is provided as SEQ ID NO: 7. An exemplary sequence of the intracellular signaling domain of CD27 is provided as SEQ ID NO:8. An exemplary CD3zeta domain sequence is provided as SEQ ID NO: 9 or SEQ ID NO:10.

In one aspect, the present invention encompasses a recombinant nucleic acid construct comprising a nucleic acid molecule encoding a CAR, wherein the nucleic acid molecule comprises the nucleic acid sequence encoding a CLL-1 binding domain, e.g., described herein, e.g., that is contiguous with and in the same reading frame as a nucleic acid sequence encoding an intracellular signaling domain. In one aspect, the CLL-1 binding domain is selected from one or more of SEQ ID NOs:39-51. In one embodiment, the CLL-1 binding domain comprises SEQ ID NO:39. In one embodiment, the CLL-1 binding domain comprises SEQ ID NO:40. In one embodiment, the CLL-1 binding domain comprises SEQ ID NO:41. In one embodiment, the CLL-1 binding domain comprises SEQ ID NO:42. In one embodiment, the CLL-1 binding domain comprises SEQ ID NO:43. In one embodiment, the CLL-1 binding domain comprises SEQ ID NO:44. In one embodiment, the CLL-1 binding domain comprises SEQ ID NO:45. In one embodiment, the CLL-1 binding domain comprises SEQ ID NO:46. In one embodiment, the CLL-1 binding domain comprises SEQ ID NO:47. In one embodiment, the CLL-1 binding domain comprises SEQ ID NO:48. In one embodiment, the CLL-1 binding domain comprises SEQ ID NO:49. In one embodiment, the CLL-1 binding domain comprises SEQ ID NO:50. In one embodiment, the CLL-1 binding domain comprises SEQ ID NO:51.

In one aspect, the present invention encompasses a recombinant nucleic acid construct comprising a transgene encoding a CAR, wherein the nucleic acid molecule comprises a nucleic acid sequence encoding an anti-CLL-1 binding domain selected from one or more of SEQ ID NOs:39-51, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of CD3-zeta, CD28, 4-1BB, and the like. In one aspect the nucleic acid sequence of a CAR construct of the invention is selected from one or more of SEQ ID NOs: 104-116, or 198. In one aspect the nucleic acid sequence of a CAR construct is SEQ ID NO:104. In one aspect the nucleic acid sequence of a CAR construct is SEQ ID NO:105. In one aspect the nucleic acid sequence of a CAR construct is SEQ ID NO:106. In one aspect the nucleic acid sequence of a CAR construct is SEQ ID NO:107. In one aspect the nucleic acid sequence of a CAR construct is SEQ ID NO:108. In one aspect the nucleic acid sequence of a CAR construct is SEQ ID NO:109. In one aspect the nucleic acid sequence of a CAR construct is SEQ ID NO:110. In one aspect the nucleic acid sequence of a CAR construct is SEQ ID NO:111. In one aspect the nucleic acid sequence of a CAR construct is SEQ ID NO:112. In one aspect the nucleic acid sequence of a CAR construct is SEQ ID NO:113. In one aspect the nucleic acid sequence of a CAR construct is SEQ ID NO:114. In one aspect the nucleic acid sequence of a CAR construct is SEQ ID NO:115. In one aspect the nucleic acid sequence of a CAR construct is SEQ ID NO:116. In one aspect the nucleic acid sequence of a CAR construct is SEQ ID NO:198. The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one embodiment, the template includes sequences for the CAR. In an embodiment, an RNA CAR vector is transduced into a T cell by electroporation.

Antigen Binding Domain

The CARs of the present invention comprise a target-specific binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the CAR of the present invention comprises a binding domain that specifically binds CLL-1. In one aspect, the antigen binding domain specifically binds human CLL-1.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a human antibody or an antibody fragment.

Thus, in one aspect, the antigen binding domain comprises a human antibody or an antibody fragment. In one embodiment, the human anti-CLL-1 binding domain comprises one or more (e.g., all three) light chain complementary determining region 1 (LC CDR1), light chain complementary determining region 2 (LC CDR2), and light chain complementary determining region 3 (LC CDR3) of a human anti-CLL-1binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a human anti-CLL-1 binding domain described herein, e.g., a human anti-CLL-1 binding domain comprising one or more, e.g., all three, LC CDRs and one or more, e.g., all three, HC CDRs. In one embodiment, the human anti-CLL-1 binding domain comprises one or more (e.g., all three) heavy chain complementary determining region 1 (HC CDR1), heavy chain complementary determining region 2 (HC CDR2), and heavy chain complementary determining region 3 (HC CDR3) of a human anti-CLL-1 binding domain described herein, e.g., the human anti-CLL-1 binding domain has two variable heavy chain regions, each comprising a HC CDR1, a HC CDR2 and a HC CDR3 described herein. In one embodiment, the human anti-CLL-1 binding domain comprises a human light chain variable region described herein (e.g., in Table 2) and/or a human heavy chain variable region described herein (e.g., in Table 1). In one embodiment, the human anti-CLL-1 binding domain comprises a human heavy chain variable region described herein (e.g., in Table 1), e.g., at least two human heavy chain variable regions described herein (e.g., in Table 1). In one embodiment, the anti-CLL-1 binding domain is a scFv comprising a light chain and a heavy chain of an amino acid sequence of Table 2. In an embodiment, the anti-CLL-1 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 2, or a sequence with 95-99% identity with an amino acid sequence of Table 2; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 1, or a sequence with 95-99% identity to an amino acid sequence of Table 1. In one embodiment, the human anti-CLL-1binding domain comprises a sequence selected from a group consisting of SEQ ID NO:39-51, or a sequence with 95-99% identity thereof. In one embodiment, the nucleic acid sequence encoding the human anti-CLL-1 binding domain comprises a sequence selected from a group consisting of SEQ ID NO:52-64, or a sequence with 95-99% identity thereof. In one embodiment, the human anti-CLL-1 binding domain is a scFv, and a light chain variable region comprising an amino acid sequence described herein, e.g., in Table 8, is attached to a heavy chain variable region comprising an amino acid sequence described herein, e.g., in Table 8, via a linker, e.g., a linker described herein. In one embodiment, the human anti-CLL-1 binding domain includes a $(Gly_4\text{-}Ser)n$ linker, wherein n is 1, 2, 3, 4, 5, or 6, preferably 3 or 4 (SEQ ID NO:26). The light chain variable region and heavy chain variable region of a scFv can be, e.g., in any of the following orientations: light chain variable region-linker-heavy chain variable region or heavy chain variable region-linker-light chain variable region.

In one aspect, the antigen binding domain portion comprises one or more sequence selected from SEQ ID NOs: 39-41. In one aspect the CAR is selected from one or more sequence selected from SEQ ID NOs: 91-103, or 197.

In one aspect, the anti-CLL-1 binding domain is characterized by particular functional features or properties of an antibody or antibody fragment. For example, in one aspect, the portion of a CAR composition of the invention that comprises an antigen binding domain specifically binds human CLL-1.

In one aspect, the invention relates to an antigen binding domain comprising an antibody or antibody fragment, wherein the antibody binding domain specifically binds to a CLL-1 protein or fragment thereof, wherein the antibody or antibody fragment comprises a variable light chain and/or a variable heavy chain that includes an amino acid sequence of SEQ ID NO: 39-51. In one aspect, the antigen binding domain comprises an amino acid sequence of an scFv selected from SEQ ID NOs: 39-51. In certain aspects, the scFv is contiguous with and in the same reading frame as a leader sequence. In one aspect the leader sequence is the polypeptide sequence provided as SEQ ID NO:1.

In one aspect, the human anti-CLL-1 binding domain is a fragment, e.g., a single chain variable fragment (scFv). In one aspect, the human anti-CLL-1 binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a CLL-1 protein or a fragment thereof with wild-type or enhanced affinity.

In some instances a human scFv be derived from a display library. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a Fab. In one exemplary embodiment, a display library can be used to identify a human CLL-1 binding domain. In a selection, the polypeptide component of each member of the library is probed with CLL-1, or a fragment there, and if the polypeptide component binds to CLL-1, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component, i.e., the CLL-1 binding domain, and purification of the polypeptide component for detailed characterization.

A variety of formats can be used for display libraries. Examples include the phage display. In phage display, the protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (2005 Nov. 22; PMID: 16337958).

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO:25). In one embodiment, the linker can be $(Gly_4Ser)_4$ (SEQ ID NO:27) or $(Gly_4Ser)_3$ (SEQ ID NO:28). Variation in the linker length may retain or enhance activity, giving rise to superior efficacy in activity studies.

Exemplary Human CLL-1 CAR Constructs and Antigen Binding Domains

Exemplary CLL-1 CAR constructs disclose herein comprise an scFv (e.g., a human scFv as disclosed in Tables 8 herein, optionally preceded with an optional leader sequence (e.g., SEQ ID NO:1 and SEQ ID NO:12 for exemplary leader amino acid and nucleotide sequences, respectively). The sequences of the human scFv fragments (amino acid sequences of SEQ ID NOs:39-51, and nucleotide sequences of SEQ ID NOs:52-64) are provided herein in Table 8. The CLL-1 CAR construct can further include an optional hinge domain, e.g., a CD8 hinge domain (e.g., including the amino acid sequence of SEQ ID NO: 2 or encoded by a nucleic acid sequence of SEQ ID NO:13); a transmembrane domain, e.g., a CD8 transmembrane domain (e.g., including the amino acid sequence of SEQ ID NO: 6 or encoded by the nucleotide sequence of SEQ ID NO: 17); an intracellular domain, e.g., a 4-1BB intracellular domain (e.g., including the amino acid sequence of SEQ ID NO: 7 or encoded by the nucleotide sequence of SEQ ID NO: 18; and a functional signaling domain, e.g., a CD3 zeta domain (e.g., including amino acid sequence of SEQ ID NO: 9 or 10, or encoded by the nucleotide sequence of SEQ ID NO: 20 or 21). In certain embodiments, the domains are contiguous with and in the same reading frame to form a single fusion protein. In other embodiments, the domain are in separate polypeptides, e.g., as in an RCAR molecule as described herein.

In certain embodiments, the full length CLL-1 CAR molecule includes the amino acid sequence of, or is encoded by the nucleotide sequence of, CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268 provided in Table 8, or a sequence substantially (e.g., 95-99%) identical thereto.

In certain embodiments, the CLL-1 CAR molecule, or the anti-CLL-1 antigen binding domain, includes the scFv amino acid sequence of CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, provided in Table 8; or includes the scFv amino acid sequence of, or is encoded by the nucleotide sequence of, CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, or a sequence substantially identical (e.g., 95-99% identical, or up to 20, 15, 10, 8, 6, 5, 4, 3, 2, or 1 amino acid changes, e.g., substitutions (e.g., conservative substitutions)) to any of the aforesaid sequences.

In certain embodiments, the CLL-1 CAR molecule, or the anti-CLL-1 antigen binding domain, includes the heavy chain variable region and/or the light chain variable region of CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, provided in Table 8, or a sequence substantially identical (e.g., 95-99% identical, or up to 20, 15, 10, 8, 6, 5, 4, 3, 2, or 1 amino acid changes, e.g., substitutions (e.g., conservative substitutions)) to any of the aforesaid sequences.

In certain embodiments, the CLL-1 CAR molecule, or the anti-CLL-1 antigen binding domain, includes one, two or three CDRs from the heavy chain variable region (e.g., HCDR1, HCDR2 and/or HCDR3), provided in Table 1; and/or one, two or three CDRs from the light chain variable region (e.g., LCDR1, LCDR2 and/or LCDR3) of CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, provided in Table 2; or a sequence substantially identical (e.g., 95-99% identical, or up to 5, 4, 3, 2, or 1 amino acid changes, e.g., substitutions (e.g., conservative substitutions)) to any of the aforesaid sequences.

In certain embodiments, the CLL-1 CAR molecule, or the anti-CLL-1 antigen binding domain, includes one, two or three CDRs from the heavy chain variable region (e.g., HCDR1, HCDR2 and/or HCDR3), provided in Table 3; and/or one, two or three CDRs from the light chain variable region (e.g., LCDR1, LCDR2 and/or LCDR3) of CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, provided in Table 4; or a sequence substantially identical (e.g., 95-99% identical, or up to 5, 4, 3, 2, or 1 amino acid changes, e.g., substitutions (e.g., conservative substitutions)) to any of the aforesaid sequences.

In certain embodiments, the CLL-1 CAR molecule, or the anti-CLL-1 antigen binding domain, includes one, two or three CDRs from the heavy chain variable region (e.g., HCDR1, HCDR2 and/or HCDR3), provided in Table 5; and/or one, two or three CDRs from the light chain variable region (e.g., LCDR1, LCDR2 and/or LCDR3) of CLL-1 CAR-1, CLL-1 CAR-2, CLL-1 CAR-3, CLL-1 CAR-4, CLL-1 CAR-5, CLL-1 CAR-6, CL-L1 CAR-7, CLL-1 CAR-8, CLL-1 CAR-9, CLL-1 CAR-10, CLL-1 CAR-11, CLL-1 CAR-12, CLL-1 CAR-13, 181268, provided in Table 6; or a sequence substantially identical (e.g., 95-99% identical, or up to 5, 4, 3, 2, or 1 amino acid changes, e.g., substitutions (e.g., conservative substitutions)) to any of the aforesaid sequences.

The sequences of humanized CDR sequences of the scFv domains are shown in Tables 1, 3, and 5 for the heavy chain variable domains and in Tables 2, 4, and 6 for the light chain variable domains. "ID" stands for the respective SEQ ID NO for each CDR.

The CDRs provided in Tables 1 and 2 are according to a combination of the Kabat and Chothia numbering scheme.

TABLE 1

Heavy Chain Variable Domain CDRs

| Candidate | HCDR1 | ID | HCDR2 | ID | HCDR3 | ID |
|---|---|---|---|---|---|---|
| CLL-1 CAR 9 | ANTFSDHVMH | 125 | YIHAANGGTHYSQKFQD | 138 | GGYNSDAFDI | 151 |
| CLL-1 CAR 6 | GGSFSGYYWS | 122 | EINHSGSTNYNPSLKS | 135 | GSGLVVYAIRVGSGWFDY | 148 |
| CLL-1 CAR 10 | GFTFSSYSMN | 126 | YISSSSSTIYYADSVKG | 139 | DLSVRAIDAFDI | 152 |
| CLL-1 CAR 11 | GFTFNSYGLH | 127 | LIEYDGSNKYYGDSVKG | 140 | EGNEDLAFDI | 153 |
| CLL-1 CAR 12 | GFNVSSNYMT | 128 | VIYSGGATYYGDSVKG | 141 | DRLYCGNNCYLYYYYGMDV | 154 |
| CLL-1 CAR 1 | GGTFSSYAIS | 117 | GIIPIFGTANYAQKFQ | 130 | DLEMATIMGGY | 143 |
| CLL-1 CAR 2 | GFTFDDYAMH | 118 | LISGDGGSTYYADSVKG | 131 | VFDSYYMDV | 144 |
| CLL-1 CAR 3 | GGSISSSSYYWG | 119 | SIYYSGSTYYNPSLKS | 132 | PGTYYDFLSGYYPFY | 145 |

TABLE 1-continued

| Heavy Chain Variable Domain CDRs | | | | | | |
|---|---|---|---|---|---|---|
| Candidate | HCDR1 | ID | HCDR2 | ID | HCDR3 | ID |
| CLL-1 CAR 4 | GFTFSSYWMS | 120 | NINEDGSAKFYVDSV KG | 133 | DLRSGRY | 146 |
| CLL-1 CAR 5 | GGPVRSGSHYWN | 121 | YIYYSGSTNYNPSLEN | 134 | GTATFDWNFPFDS | 147 |
| CLL-1 CAR 7 | GFTFSSYSMN | 123 | SISSSSSYIYYADSVKG | 136 | DPSSSGSYYMEDSYYYGM DV | 149 |
| CLL-1 CAR 8 | GFTFSSYEMN | 124 | YISSSGSTIYYADSVKG | 137 | EALGSSWE | 150 |
| CLL-1 CAR 13 | GYPFTGYYIQ | 129 | WIDPNSGNTGYAQKF QG | 142 | DSYGYYYGMDV | 155 |
| 181268 | GFTFSSYEMN | 199 | YISSSGSTIYYADSVKG | 200 | DPYSSSWHDAFDI | 201 |

TABLE 2

| Light Chain Variable Domain CDRs | | | | | | |
|---|---|---|---|---|---|---|
| Candidate | LCDR1 | ID | LCDR2 | ID | LCDR3 | ID |
| CLL-1 CAR 9 | RASQDISSWLA | 164 | AASSLQS | 177 | QQSYSTPLT | 190 |
| CLL-1 CAR 6 | RASQSISSYLN | 161 | AASSLQS | 174 | QQSYSTPPWT | 187 |
| CLL-1 CAR 10 | QASQDISNYLN | 165 | DASNLET | 178 | QQAYSTPFT | 191 |
| CLL-1 CAR 11 | QASQFIKKNLN | 166 | DASSLQT | 179 | QQHDNLPLT | 192 |
| CLL-1 CAR 12 | RASQSISSYLN | 167 | AASSLQS | 180 | QQSYSTPPLT | 193 |
| CLL-1 CAR 1 | TGTSSDVGGYNYVS | 156 | DVSNRPS | 169 | SSYTSSSTLDVV | 182 |
| CLL-1 CAR 2 | RSSQSLVYTDGNTYLN | 157 | KVSNRDS | 170 | MQGTHWSFT | 183 |
| CLL-1 CAR 3 | RASQGISSYLA | 158 | AASTLQS | 171 | QQLNSYPYT | 184 |
| CLL-1 CAR 4 | RASQSISGSFLA | 159 | GASSRAT | 172 | QQYGSSPPT | 185 |
| CLL-1 CAR 5 | RASQSISSYLN | 160 | AASSLQS | 173 | QQSYSTPWT | 186 |
| CLL-1 CAR 7 | TGSSGSIASNYVQ | 162 | EDNQRPS | 175 | QSYDSSNQVV | 188 |
| CLL-1 CAR 8 | QASQDISNYLN | 163 | DASNLET | 176 | QQYDNLPLT | 189 |
| CLL-1 CAR 13 | RASQGISSALA | 168 | DASSLES | 181 | QQFNNYPLT | 194 |
| 181268 | RASQSVSSSYLA | 202 | GASSRAT | 203 | QQYGSSPLT | 204 |

TABLE 3

| Heavy Chain Variable Domain CDRs according to the Kabat numbering scheme (Kabat et al. (1991), "Sequences of Proteins of Immunological Interest," 5th Ed. Public Health Service, National Institutes of Health, Bethesda, MD) | | | | | | |
|---|---|---|---|---|---|---|
| Candidate | HCDR1 | ID | HCDR2 | ID | HCDR3 | ID |
| 146259-CLL-1-CAR9 | DHVMH | 322 | YIHAANGGTHYSQKF QD | 336 | GGYNSDAFDI | 350 |
| 139119-CLL-1-CAR6 | GYYWS | 319 | EINHSGSTNYNPSLKS | 333 | GSGLVVYAIRVGSG WFDY | 347 |
| 146261-CLL-1-CAR10 | SYSMN | 323 | YISSSSSTIYYADSVKG | 337 | DLSVRAIDAFDI | 351 |

TABLE 3-continued

Heavy Chain Variable Domain CDRs according to the Kabat numbering scheme (Kabat et al. (1991), "Sequences of Proteins of Immunological Interest," 5th Ed. Public Health Service, National Institutes of Health, Bethesda, MD)

| Candidate | HCDR1 | ID | HCDR2 | ID | HCDR3 | ID |
|---|---|---|---|---|---|---|
| 146262-CLL-1-CAR11 | SYGLH | 324 | LIEYDGSNKYYGDSVKG | 338 | EGNEDLAFDI | 352 |
| 146263-CLL-1-CAR12 | SNYMT | 325 | VIYSGGATYYGDSVKG | 339 | DRLYCGNNCYLYYYYGMDV | 353 |
| 139115-CLL-1-CAR1 | SYAIS | 314 | GIIPIFGTANYAQKFQG | 328 | DLEMATIMGGY | 342 |
| 139116-CLL-1-CAR2 | DYAMH | 315 | LISGDGGSTYYADSVKG | 329 | VFDSYYMDV | 343 |
| 139118-CLL-1-CAR3 | SSSYYWG | 316 | SIYYSGSTYYNPSLKS | 330 | PGTYYDFLSGYYPFY | 344 |
| 139122-CLL-1-CAR4 | SYWMS | 317 | NINEDGSAKFYVDSVKG | 331 | DLRSGRY | 345 |
| 139117-CLL-1-CAR5 | SGSHYWN | 318 | YIYYSGSTNYNPSLEN | 332 | GTATFDWNFPFDS | 346 |
| 139120-CLL-1-CAR7 | SYSMN | 320 | SISSSSSYIYYADSVKG | 334 | DPSSSGSYYMEDSYYYGMDV | 348 |
| 139121-CLL-1-CAR8 | SYEMN | 321 | YISSSGSTIYYADSVKG | 335 | EALGSSWE | 349 |
| 146264-CLL-1-CAR13 | GYYIQ | 326 | WIDPNSGNTGYAQKFQG | 340 | DSYGYYYGMDV | 354 |
| 181268 | SYEMN | 327 | YISSSGSTIYYADSVKG | 341 | DPYSSSWHDAFDI | 355 |

TABLE 4

Light Chain Variable Domain CDRs according to the Kabat numbering scheme (Kabat et al. (1991), "Sequences of Proteins of Immunological Interest," 5th Ed. Public Health Service, National Institutes of Health, Bethesda, MD)

| Candidate | LCDR1 | ID | LCDR2 | ID | LCDR3 | ID |
|---|---|---|---|---|---|---|
| 146259-CLL-1-CAR9 | RASQDISSWLA | 364 | AASSLQS | 378 | QQSYSTPLT | 392 |
| 139119-CLL-1-CAR6 | RASQSISSYLN | 361 | AASSLQS | 375 | QQSYSTPPWT | 389 |
| 146261-CLL-1-CAR10 | QASQDISNYLN | 365 | DASNLET | 379 | QQAYSTPFT | 393 |
| 146262-CLL-1-CAR11 | QASQFIKKNLN | 366 | DASSLQT | 380 | QQHDNLPLT | 394 |
| 146263-CLL-1-CAR12 | RASQSISSYLN | 367 | AASSLQS | 381 | QQSYSTPPLT | 395 |
| 139115-CLL-1-CAR1 | TGTSSDVGGYNYVS | 356 | DVSNRPS | 370 | SSYTSSSTLDVV | 384 |
| 139116-CLL-1-CAR2 | RSSQSLVYTDGNTYLN | 357 | KVSNRDS | 371 | MQGTHWSFT | 385 |
| 139118-CLL-1-CAR3 | RASQGISSYLA | 358 | AASTLQS | 372 | QQLNSYPYT | 386 |
| 139122-CLL-1-CAR4 | RASQSISGSFLA | 359 | GASSRAT | 373 | QQYGSSPPT | 387 |

TABLE 4-continued

Light Chain Variable Domain CDRs according to the Kabat numbering scheme (Kabat et al. (1991), "Sequences of Proteins of Immunological Interest," 5th Ed. Public Health Service, National Institutes of Health, Bethesda, MD)

| Candidate | LCDR1 | ID | LCDR2 | ID | LCDR3 | ID |
|---|---|---|---|---|---|---|
| 139117-CLL-1-CAR5 | RASQSISSYLN | 360 | AASSLQS | 374 | QQSYSTPWT | 388 |
| 139120-CLL-1-CAR7 | TGSSGSIASNYVQ | 362 | EDNQRPS | 376 | QSYDSSNQVV | 390 |
| 139121-CLL-1-CAR8 | QASQDISNYLN | 363 | DASNLET | 377 | QQYDNLPLT | 391 |
| 146264-CLL-1-CAR13 | RASQGISSALA | 368 | DASSLES | 382 | QQFNNYPLT | 396 |
| 181268 | RASQSVSSSYLA | 369 | GASSRAT | 383 | QQYGSSPLT | 397 |

TABLE 5

Heavy Chain Variable Domain CDRs according to the Chothia numbering scheme (Al-Lazikani et al., (1997) JMB 273, 927-948)

| Candidate | HCDR1 | ID | HCDR2 | ID | HCDR3 | ID |
|---|---|---|---|---|---|---|
| 146259-CLL-1-CAR9 | ANTFSDH | 406 | HAANGG | 420 | GGYNSDAFDI | 434 |
| 139119-CLL-1-CAR6 | GGSFSGY | 403 | NHSGS | 417 | GSGLVVYAIRVGSGWFDY | 431 |
| 146261-CLL-1-CAR10 | GFTFSSY | 407 | SSSSST | 421 | DLSVRAIDAFDI | 435 |
| 146262-CLL-1-CAR11 | GFTFNSY | 408 | EYDGSN | 422 | EGNEDLAFDI | 436 |
| 146263-CLL-1-CAR12 | GFNVSSN | 409 | YSGGA | 423 | DRLYCGNNCYLYYYYGMDV | 437 |
| 139115-CLL-1-CAR1 | GGTFSSY | 398 | IPIFGT | 412 | DLEMATIMGGY | 426 |
| 139116-CLL-1-CAR2 | GFTFDDY | 399 | SGDGGS | 413 | VFDSYYMDV | 427 |
| 139118-CLL-1-CAR3 | GGSISSSSY | 400 | YYSGS | 414 | PGTYYDFLSGYYPFY | 428 |
| 139122-CLL-1-CAR4 | GFTFSSY | 401 | NEDGSA | 415 | DLRSGRY | 429 |
| 139117-CLL-1-CAR5 | GGPVRSGSH | 402 | YYSGS | 416 | GTATFDWNFPFDS | 430 |
| 139120-CLL-1-CAR7 | GFTFSSY | 404 | SSSSSY | 418 | DPSSSGSYYMEDSYYYGMDV | 432 |
| 139121-CLL-1-CAR8 | GFTFSSY | 405 | SSSGST | 419 | EALGSSWE | 433 |
| 146264-CLL-1-CAR13 | GYPFTGY | 410 | DPNSGN | 424 | DSYGYYYGMDV | 438 |
| 181268 | GFTFSSY | 411 | SSSGST | 425 | DPYSSSWHDAFDI | 439 |

TABLE 6

Light Chain Variable Domain CDRs according to the Chothia numbering scheme (Al-Lazikani et al., (1997) JMB 273, 927-948)

| Candidate | LCDR1 | ID | LCDR2 | ID | LCDR3 | ID |
|---|---|---|---|---|---|---|
| 146259-CLL-1-CAR9 | SQDISSW | 448 | AAS | 462 | SYSTPL | 476 |
| 139119-CLL-1-CAR6 | SQSISSY | 445 | AAS | 459 | SYSTPPW | 473 |
| 146261-CLL-1-CAR10 | SQDISNY | 449 | DAS | 463 | AYSTPF | 477 |
| 146262-CLL-1-CAR11 | SQFIKKN | 450 | DAS | 464 | HDNLPL | 478 |
| 146263-CLL-1-CAR12 | SQSISSY | 451 | AAS | 465 | SYSTPPL | 479 |
| 139115-CLL-1-CAR1 | TSSDVGGYNY | 440 | DVS | 454 | YTSSSTLDV | 468 |
| 139116-CLL-1-CAR2 | SQSLVYTDGNTY | 441 | KVS | 455 | GTHWSF | 469 |
| 139118-CLL-1-CAR3 | SQGISSY | 442 | AAS | 456 | LNSYPY | 470 |
| 139122-CLL-1-CAR4 | SQSISGSF | 443 | GAS | 457 | YGSSPP | 471 |
| 139117-CLL-1-CAR5 | SQSISSY | 444 | AAS | 458 | SYSTPW | 472 |
| 139120-CLL-1-CAR7 | SSGSIASNY | 446 | EDN | 460 | YDSSNQV | 474 |
| 139121-CLL-1-CAR8 | SQDISNY | 447 | DAS | 461 | YDNLPL | 475 |
| 146264-CLL-1-CAR13 | SQGISSA | 452 | DAS | 466 | FNNYPL | 480 |
| 181268 | SQSVSSSY | 453 | GAS | 467 | YGSSPL | 481 |

In certain embodiments, the CAR molecule described herein (e.g., the CAR nucleic acid or the CAR polypeptide) includes:

(1) one, two, or three light chain (LC) CDRs chosen from one of the following:

(i) a LC CDR1 of SEQ ID NO: 156, LC CDR2 of SEQ ID NO: 169 and LC CDR3 of SEQ ID NO: 182 of CLL-1 CAR-1;

(ii) a LC CDR1 of SEQ ID NO: 157, LC CDR2 of SEQ ID NO: 170 and LC CDR3 of SEQ ID NO: 183 of CLL-1 CAR-2;

(iii) a LC CDR1 of SEQ ID NO: 158, LC CDR2 of SEQ ID NO: 171 and LC CDR3 of SEQ ID NO: 184 of CLL-1 CAR-3;

(iv) a LC CDR1 of SEQ ID NO: 159, LC CDR2 of SEQ ID NO: 172 and LC CDR3 of SEQ ID NO: 185 of CLL-1 CAR-4;

(v) a LC CDR1 of SEQ ID NO: 160, LC CDR2 of SEQ ID NO: 173 and LC CDR3 of SEQ ID NO: 186 of CLL-1 CAR-5;

(vi) a LC CDR1 of SEQ ID NO: 161, LC CDR2 of SEQ ID NO: 174 and LC CDR3 of SEQ ID NO: 187 of CLL-1 CAR-6;

(vii) a LC CDR1 of SEQ ID NO: 162, LC CDR2 of SEQ ID NO: 175 and LC CDR3 of SEQ ID NO: 188 of CLL-1 CAR-7;

(viii) a LC CDR1 of SEQ ID NO: 163, LC CDR2 of SEQ ID NO: 176 and LC CDR3 of SEQ ID NO: 189 of CLL-1 CAR-8; or (ix) a LC CDR1 of SEQ ID NO: 164, LC CDR2 of SEQ ID NO: 177 and LC CDR3 of SEQ ID NO: 190 of CLL-1 CAR-9;

(x) a LC CDR1 of SEQ ID NO: 165, LC CDR2 of SEQ ID NO: 178 and LC CDR3 of SEQ ID NO: 191 of CLL-1 CAR-10;

(xi) a LC CDR1 of SEQ ID NO: 166, LC CDR2 of SEQ ID NO: 179 and LC CDR3 of SEQ ID NO: 192 of CLL-1 CAR-11;

(xii) a LC CDR1 of SEQ ID NO: 167, LC CDR2 of SEQ ID NO: 180 and LC CDR3 of SEQ ID NO: 193 of CLL-1 CAR-12;

(xiii) a LC CDR1 of SEQ ID NO: 168, LC CDR2 of SEQ ID NO: 181 and LC CDR3 of SEQ ID NO: 194 of CLL-1 CAR-13;

(xiv) a LC CDR1 of SEQ ID NO: 202, LC CDR2 of SEQ ID NO: 203 and LC CDR3 of SEQ ID NO: 204 of 181286; and/or (2) one, two, or three heavy chain (HC) CDRs from one of the following:

(i) a HC CDR1 of SEQ ID NO: 117, HC CDR2 of SEQ ID NO: 130 and HC CDR3 of SEQ ID NO: 143 of CLL-1 CAR-1;

(ii) a HC CDR1 of SEQ ID NO: 118, HC CDR2 of SEQ ID NO: 131 and HC CDR3 of SEQ ID NO: 144 of CLL-1 CAR-2;

(iii) a HC CDR1 of SEQ ID NO: 119, HC CDR2 of SEQ ID NO: 132 and HC CDR3 of SEQ ID NO: 145 of CLL-1 CAR-3;

(iv) a HC CDR1 of SEQ ID NO: 120, HC CDR2 of SEQ ID NO: 133 and HC CDR3 of SEQ ID NO: 146 of CLL-1 CAR-4;

(v) a HC CDR1 of SEQ ID NO: 121, HC CDR2 of SEQ ID NO: 134 and HC CDR3 of SEQ ID NO: 147 of CLL-1 CAR-5;

(vi) a HC CDR1 of SEQ ID NO: 122, HC CDR2 of SEQ ID NO: 135 and HC CDR3 of SEQ ID NO: 148 of CLL-1 CAR-6;

(vii) a HC CDR1 of SEQ ID NO: 123, HC CDR2 of SEQ ID NO: 136 and HC CDR3 of SEQ ID NO: 149 of CLL-1 CAR-7;

(viii) a HC CDR1 of SEQ ID NO: 124, HC CDR2 of SEQ ID NO: 137 and HC CDR3 of SEQ ID NO: 150 of CLL-1 CAR-8; or (ix) a HC CDR1 of SEQ ID NO: 125, HC CDR2 of SEQ ID NO: 138 and HC CDR3 of SEQ ID NO: 151 of CLL-1 CAR-9;

(x) a HC CDR1 of SEQ ID NO: 126, HC CDR2 of SEQ ID NO: 139 and HC CDR3 of SEQ ID NO: 152 of CLL-1 CAR-10;

(xi) a HC CDR1 of SEQ ID NO: 127, HC CDR2 of SEQ ID NO: 140 and HC CDR3 of SEQ ID NO: 153 of CLL-1 CAR-11;

(xii) a HC CDR1 of SEQ ID NO: 128, HC CDR2 of SEQ ID NO: 141 and HC CDR3 of SEQ ID NO: 154 of CLL-1 CAR-12;

(xiii) a HC CDR1 of SEQ ID NO: 129, HC CDR2 of SEQ ID NO: 142 and HC CDR3 of SEQ ID NO: 155 of CLL-1 CAR-13;

(xiv) a HC CDR1 of SEQ ID NO: 199, HC CDR2 of SEQ ID NO: 200 and HC CDR3 of SEQ ID NO: 201 of 181286.

In certain embodiments, the CAR molecule described herein (e.g., the CAR nucleic acid or the CAR polypeptide) or a CLL-1 binding domain includes:

(1) one, two, or three light chain (LC) CDRs chosen from one of the following:

(i) a LC CDR1 of SEQ ID NO: 356, LC CDR2 of SEQ ID NO: 370 and LC CDR3 of SEQ ID NO: 384 of CLL-1 CAR-1;

(ii) a LC CDR1 of SEQ ID NO: 357, LC CDR2 of SEQ ID NO: 371 and LC CDR3 of SEQ ID NO: 385 of CLL-1 CAR-2;

(iii) a LC CDR1 of SEQ ID NO: 358, LC CDR2 of SEQ ID NO: 372 and LC CDR3 of SEQ ID NO: 386 of CLL-1 CAR-3;

(iv) a LC CDR1 of SEQ ID NO: 359, LC CDR2 of SEQ ID NO: 373 and LC CDR3 of SEQ ID NO: 387 of CLL-1 CAR-4;

(v) a LC CDR1 of SEQ ID NO: 360, LC CDR2 of SEQ ID NO: 374 and LC CDR3 of SEQ ID NO: 388 of CLL-1 CAR-5;

(vi) a LC CDR1 of SEQ ID NO: 361, LC CDR2 of SEQ ID NO: 375 and LC CDR3 of SEQ ID NO: 389 of CLL-1 CAR-6;

(vii) a LC CDR1 of SEQ ID NO: 362, LC CDR2 of SEQ ID NO: 376 and LC CDR3 of SEQ ID NO: 390 of CLL-1 CAR-7;

(viii) a LC CDR1 of SEQ ID NO: 363, LC CDR2 of SEQ ID NO: 377 and LC CDR3 of SEQ ID NO: 391 of CLL-1 CAR-8; or (ix) a LC CDR1 of SEQ ID NO: 364, LC CDR2 of SEQ ID NO: 378 and LC CDR3 of SEQ ID NO: 392 of CLL-1 CAR-9;

(x) a LC CDR1 of SEQ ID NO: 365, LC CDR2 of SEQ ID NO: 379 and LC CDR3 of SEQ ID NO: 393 of CLL-1 CAR-10;

(xi) a LC CDR1 of SEQ ID NO: 366, LC CDR2 of SEQ ID NO: 380 and LC CDR3 of SEQ ID NO: 394 of CLL-1 CAR-11;

(xii) a LC CDR1 of SEQ ID NO: 367, LC CDR2 of SEQ ID NO: 381 and LC CDR3 of SEQ ID NO: 395 of CLL-1 CAR-12;

(xiii) a LC CDR1 of SEQ ID NO: 368, LC CDR2 of SEQ ID NO: 382 and LC CDR3 of SEQ ID NO: 396 of CLL-1 CAR-13;

(xiv) a LC CDR1 of SEQ ID NO: 369, LC CDR2 of SEQ ID NO: 383 and LC CDR3 of SEQ ID NO: 397 of 181286; and/or (2) one, two, or three heavy chain (HC) CDRs from one of the following:

(i) a HC CDR1 of SEQ ID NO: 314, HC CDR2 of SEQ ID NO: 328 and HC CDR3 of SEQ ID NO: 342 of CLL-1 CAR-1;

(ii) a HC CDR1 of SEQ ID NO: 315, HC CDR2 of SEQ ID NO: 329 and HC CDR3 of SEQ ID NO: 343 of CLL-1 CAR-2;

(iii) a HC CDR1 of SEQ ID NO: 316, HC CDR2 of SEQ ID NO: 330 and HC CDR3 of SEQ ID NO: 344 of CLL-1 CAR-3;

(iv) a HC CDR1 of SEQ ID NO: 317, HC CDR2 of SEQ ID NO: 331 and HC CDR3 of SEQ ID NO: 345 of CLL-1 CAR-4;

(v) a HC CDR1 of SEQ ID NO: 318, HC CDR2 of SEQ ID NO: 332 and HC CDR3 of SEQ ID NO: 346 of CLL-1 CAR-5;

(vi) a HC CDR1 of SEQ ID NO: 319, HC CDR2 of SEQ ID NO: 333 and HC CDR3 of SEQ ID NO: 347 of CLL-1 CAR-6;

(vii) a HC CDR1 of SEQ ID NO: 320, HC CDR2 of SEQ ID NO: 334 and HC CDR3 of SEQ ID NO: 348 of CLL-1 CAR-7;

(viii) a HC CDR1 of SEQ ID NO: 321, HC CDR2 of SEQ ID NO: 335 and HC CDR3 of SEQ ID NO: 349 of CLL-1 CAR-8; or (ix) a HC CDR1 of SEQ ID NO: 322, HC CDR2 of SEQ ID NO: 336 and HC CDR3 of SEQ ID NO: 350 of CLL-1 CAR-9;

(x) a HC CDR1 of SEQ ID NO: 323, HC CDR2 of SEQ ID NO: 337 and HC CDR3 of SEQ ID NO: 351 of CLL-1 CAR-10;

(xi) a HC CDR1 of SEQ ID NO: 324, HC CDR2 of SEQ ID NO: 338 and HC CDR3 of SEQ ID NO: 352 of CLL-1 CAR-11;

(xii) a HC CDR1 of SEQ ID NO: 325, HC CDR2 of SEQ ID NO: 339 and HC CDR3 of SEQ ID NO: 353 of CLL-1 CAR-12;

(xiii) a HC CDR1 of SEQ ID NO: 326, HC CDR2 of SEQ ID NO: 340 and HC CDR3 of SEQ ID NO: 354 of CLL-1 CAR-13;

(xiv) a HC CDR1 of SEQ ID NO: 327, HC CDR2 of SEQ ID NO: 341 and HC CDR3 of SEQ ID NO: 355 of 181286.

In certain embodiments, the CAR molecule described herein (e.g., the CAR nucleic acid or the CAR polypeptide) includes:

(1) one, two, or three light chain (LC) CDRs chosen from one of the following:

(i) a LC CDR1 of SEQ ID NO: 440, LC CDR2 of SEQ ID NO: 454 and LC CDR3 of SEQ ID NO: 468 of CLL-1 CAR-1;

(ii) a LC CDR1 of SEQ ID NO: 441, LC CDR2 of SEQ ID NO: 455 and LC CDR3 of SEQ ID NO: 469 of CLL-1 CAR-2;

(iii) a LC CDR1 of SEQ ID NO: 442, LC CDR2 of SEQ ID NO: 456 and LC CDR3 of SEQ ID NO: 470 of CLL-1 CAR-3;

(iv) a LC CDR1 of SEQ ID NO: 443, LC CDR2 of SEQ ID NO: 457 and LC CDR3 of SEQ ID NO: 471 of CLL-1 CAR-4;

(v) a LC CDR1 of SEQ ID NO: 444, LC CDR2 of SEQ ID NO: 458 and LC CDR3 of SEQ ID NO: 472 of CLL-1 CAR-5;

(vi) a LC CDR1 of SEQ ID NO: 445, LC CDR2 of SEQ ID NO: 459 and LC CDR3 of SEQ ID NO: 473 of CLL-1 CAR-6;

(vii) a LC CDR1 of SEQ ID NO: 446, LC CDR2 of SEQ ID NO: 460 and LC CDR3 of SEQ ID NO: 474 of CLL-1 CAR-7;

(viii) a LC CDR1 of SEQ ID NO: 447, LC CDR2 of SEQ ID NO: 461 and LC CDR3 of SEQ ID NO: 475 of CLL-1 CAR-8; or (ix) a LC CDR1 of SEQ ID NO: 448, LC CDR2 of SEQ ID NO: 462 and LC CDR3 of SEQ ID NO: 476 of CLL-1 CAR-9;

(x) a LC CDR1 of SEQ ID NO: 449, LC CDR2 of SEQ ID NO: 463 and LC CDR3 of SEQ ID NO: 477 of CLL-1 CAR-10;

(xi) a LC CDR1 of SEQ ID NO: 450, LC CDR2 of SEQ ID NO: 464 and LC CDR3 of SEQ ID NO: 478 of CLL-1 CAR-11;

(xii) a LC CDR1 of SEQ ID NO: 451, LC CDR2 of SEQ ID NO: 465 and LC CDR3 of SEQ ID NO: 479 of CLL-1 CAR-12;

(xiii) a LC CDR1 of SEQ ID NO: 452, LC CDR2 of SEQ ID NO: 466 and LC CDR3 of SEQ ID NO: 480 of CLL-1 CAR-13;

(xiv) a LC CDR1 of SEQ ID NO: 453, LC CDR2 of SEQ ID NO: 467 and LC CDR3 of SEQ ID NO: 481 of 181286; and/or (2) one, two, or three heavy chain (HC) CDRs from one of the following:

(i) a HC CDR1 of SEQ ID NO: 398, HC CDR2 of SEQ ID NO: 412 and HC CDR3 of SEQ ID NO: 426 of CLL-1 CAR-1;

(ii) a HC CDR1 of SEQ ID NO: 399, HC CDR2 of SEQ ID NO: 413 and HC CDR3 of SEQ ID NO: 427 of CLL-1 CAR-2;

(iii) a HC CDR1 of SEQ ID NO: 400, HC CDR2 of SEQ ID NO: 414 and HC CDR3 of SEQ ID NO: 428 of CLL-1 CAR-3;

(iv) a HC CDR1 of SEQ ID NO: 401, HC CDR2 of SEQ ID NO: 415 and HC CDR3 of SEQ ID NO: 429 of CLL-1 CAR-4;

(v) a HC CDR1 of SEQ ID NO: 402, HC CDR2 of SEQ ID NO: 416 and HC CDR3 of SEQ ID NO: 430 of CLL-1 CAR-5;

(vi) a HC CDR1 of SEQ ID NO: 403, HC CDR2 of SEQ ID NO: 417 and HC CDR3 of SEQ ID NO: 431 of CLL-1 CAR-6;

(vii) a HC CDR1 of SEQ ID NO: 404, HC CDR2 of SEQ ID NO: 418 and HC CDR3 of SEQ ID NO: 432 of CLL-1 CAR-7;

(viii) a HC CDR1 of SEQ ID NO: 405, HC CDR2 of SEQ ID NO: 419 and HC CDR3 of SEQ ID NO: 433 of CLL-1 CAR-8; or (ix) a HC CDR1 of SEQ ID NO: 406, HC CDR2 of SEQ ID NO: 420 and HC CDR3 of SEQ ID NO: 434 of CLL-1 CAR-9;

(x) a HC CDR1 of SEQ ID NO: 407, HC CDR2 of SEQ ID NO: 421 and HC CDR3 of SEQ ID NO: 435 of CLL-1 CAR-10;

(xi) a HC CDR1 of SEQ ID NO: 408, HC CDR2 of SEQ ID NO: 422 and HC CDR3 of SEQ ID NO: 436 of CLL-1 CAR-11;

(xii) a HC CDR1 of SEQ ID NO: 409, HC CDR2 of SEQ ID NO: 423 and HC CDR3 of SEQ ID NO: 437 of CLL-1 CAR-12;

(xiii) a HC CDR1 of SEQ ID NO: 410, HC CDR2 of SEQ ID NO: 424 and HC CDR3 of SEQ ID NO: 438 of CLL-1 CAR-13;

(xiv) a HC CDR1 of SEQ ID NO: 411, HC CDR2 of SEQ ID NO: 425 and HC CDR3 of SEQ ID NO: 439 of 181286.

In embodiments, fully human anti-CLL-1 single chain variable fragments are generated and cloned into lentiviral CAR expression vectors with the intracellular CD3zeta domain and the intracellular co-stimulatory domain of 4-1BBNames of exemplary fully human CLL-1 scFvs are depicted in Table 7.

TABLE 7

CAR-CLL-1 constructs

| Construct ID | Nickname |
|---|---|
| 139115 | CLL-1 (or CLL-1 CAR-1) |
| 139116 | CLL-2 (or CLL-1 CAR-2) |
| 139117 | CLL-3 (or CLL-1 CAR-3) |
| 139118 | CLL-4 (or CLL-1 CAR-4) |
| 139119 | CLL-5 (or CLL-1 CAR-5) |
| 139120 | CLL-6 (or CLL-1 CAR-6) |
| 139121 | CLL-7 (or CLL-1 CAR-7) |
| 139122 | CLL-8 (or CLL-1 CAR-8) |
| 146259 | CLL-9 (or CLL-1 CAR-9) |
| 146261 | CLL-10 (or CLL-1 CAR-10) |
| 146262 | CLL-11 (or CLL-1 CAR-11) |
| 146263 | CLL-12 (or CLL-1 CAR-12) |
| 146264 | CLL-13 (or CLL-1 CAR-13) |

In embodiments, the order in which the VL and VH domains appear in the scFv is varied (i.e., VL-VH, or VH-VL orientation), and where either three or four copies of the "G4S" (SEQ ID NO:25) subunit, in which each subunit comprises the sequence GGGGS (SEQ ID NO:25) (e.g., $(G4S)_3$ (SEQ ID NO:28) or $(G4S)_4$ (SEQ ID NO:27)), connect the variable domains to create the entirety of the scFv domain, as shown in Table 8.

The amino acid and nucleic acid sequences of the CLL-1 scFv domains and CLL-1 CAR molecules are provided in Table 8. The amino acid sequences for the variable heavy chain and variable light chain for each scFv is also provided in Table 8 It is noted that the scFv fragments (SEQ ID NOs: 39-51) with a leader sequence (e.g., the amino acid sequence of SEQ ID NO: 1 or the nucleotide sequence of SEQ ID NO: 12) are also encompassed by the present invention.

```
Leader (amino acid sequence)
                                                    (SEQ ID NO: 1)
MALPVTALLLPLALLLHAARP

Leader (nucleic acid sequence)
                                                    (SEQ ID NO: 12)
ATGGCCCTGCCTGTGACAGCCCTGCTGCTGCCTCTGGCTCTGCTGCTGCATGCCGCTAG

ACCC

CD8 hinge (amino acid sequence)
                                                    (SEQ ID NO: 2)
TTTPAPRPPTPAPTIASQPLSLRPEACRPAAGGAVHTRGLDFACD

CD8 hinge (nucleic acid sequence)
                                                    (SEQ ID NO: 13)
ACCACGACGCCAGCGCCGCGACCACCAACACCGGCGCCCACCATCGCGTCGCAGCCCC

TGTCCCTGCGCCCAGAGGCGTGCCGGCCAGCGGCGGGGGGCGCAGTGCACACGAGGG

GGCTGGACTTCGCCTGTGA

CD8 transmembrane (amino acid sequence)
                                                    (SEQ ID NO: 6)
IYIWAPLAGTCGVLLLSLVITLYC
```

-continued

CD8 transmembrane (nucleic acid sequence)
(SEQ ID NO: 17)
ATCTACATCTGGGCGCCCTTGGCCGGGACTTGTGGGGTCCTTCTCCTGTCACTGGTTATC

ACCCTTTACTGC 4-1BB Intracellular domain (amino acid sequence)
(SEQ ID NO: 7)
KRGRKKLLYIFKQPFMRPVQTTQEEDGCSCRFPEEEEGGCEL 4-1BB Intracellular domain (nucleic acid sequence)
(SEQ ID NO: 18)
AAACGGGGCAGAAAGAAACTCCTGTATATATTCAAACAACCATTTATGAGACCAGTAC

AAACTACTCAAGAGGAAGATGGCTGTAGCTGCCGATTTCCAGAAGAAGAAGAAGGAG

GATGTGAACTG

CD28 Intracellular domain (amino acid sequence)
(SEQ ID NO: 482)
RSKRSRLLHSDYMNMTPRRPGPTRKHYQPYAPPRDFAAYRS (SEQ ID NO: 482)

CD28 Intracellular domain (nucleotide sequence)
(SEQ ID NO: 483)
AGGAGTAAGAGGAGCAGGCTCCTGCACAGTGACTACATGAACATGACTCCCCG

CCGCCCCGGGCCCACCCGCAAGCATTACCAGCCCTATGCCCCACCACGCGACTT

CGCAGCCTATCGCTCC (SEQ ID NO: 483)

ICOS Intracellular domain (amino acid sequence)
(SEQ ID NO: 484)
T K K K Y S S S V H D P N G E Y M F M R A V N T A K K S R L T D V T L
(SEQ ID NO: 484)

ICOS Intracellular domain (nucleotide sequence)
(SEQ ID NO: 485)
ACAAAAAAGAAGTATTCATCCAGTGTGCACGACCCTAACGGTGAATACATGTTCATGA

GAGCAGTGAACACAGCCAAAAAATCCAGACTCACAGATGTGACCCTA (SEQ ID NO:
485)

CD3 zeta domain (amino acid sequence)
(SEQ ID NO: 9)
RVKFSRSADAPAYKQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR

CD3 zeta (nucleic acid sequence)
(SEQ ID NO: 20)
AGAGTGAAGTTCAGCAGGAGCGCAGACGCCCCCGCGTACAAGCAGGGCCAGAACCAG

CTCTATAACGAGCTCAATCTAGGACGAAGAGAGGAGTACGATGTTTTGGACAAGAGAC

GTGGCCGGGACCCTGAGATGGGGGGAAAGCCGAGAAGGAAGAACCCTCAGGAAGGCC

TGTACAATGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGC

CD3 zeta domain (amino acid sequence; NCBI Reference
Sequence NM_000734.3)
(SEQ ID NO: 10)
RVKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR

CD3 zeta (nucleic acid sequence; NCBI Reference
Sequence NM_000734.3);
(SEQ ID NO: 21)
AGAGTGAAGTTCAGCAGGAGCGCAGACGCCCCCGCGTACCAGCAGGGCCAG

AACCAGCTCTATAACGAGCTCAATCTAGGACGAAGAGAGGAGTACGATGTTT

TGGACAAGAGACGTGGCCGGGACCCTGAGATGGGGGGAAAGCCGAGAAGGA

AGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGC

-continued

ACGATGGCCTTTACCAGGGTCTCAGTACAGCCACCAAGGACACCTACGACGC

CCTTCACATGCAGGCCCTGCCCCCTCGC

IgG4 Hinge (amino acid sequence)

(SEQ ID NO: 36)

ESKYGPPCPPCPAPEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKM

IgG4 Hinge (nucleotide sequence)

(SEQ ID NO: 37)

GAGAGCAAGTACGGCCCTCCCTGCCCCCCTTGCCCTGCCCCCGAGTTCCTGGGCGGACC

CAGCGTGTTCCTGTTCCCCCCCAAGCCCAAGGACACCCTGATGATCAGCCGGACCCCCG

AGGTGACCTGTGTGGTGGTGGACGTGTCCCAGGAGGACCCCGAGGTCCAGTTCAACTG

GTACGTGGACGGCGTGGAGGTGCACAACGCCAAGACCAAGCCCCGGGAGGAGCAGTT

CAATAGCACCTACCGGGTGGTGTCCGTGCTGACCGTGCTGCACCAGGACTGGCTGAAC

GGCAAGGAATACAAGTGTAAGGTGTCCAACAAGGGCCTGCCCAGCAGCATCGAGAAA

ACCATCAGCAAGGCCAAGGGCCAGCCTCGGGAGCCCCAGGTGTACACCCTGCCCCCTA

GCCAAGAGGAGATGACCAAGAACCAGGTGTCCCTGACCTGCCTGGTGAAGGGCTTCTA

CCCCAGCGACATCGCCGTGGAGTGGGAGAGCAACGGCCAGCCCGAGAACAACTACAA

GACCACCCCCCCTGTGCTGGACAGCGACGGCAGCTTCTTCCTGTACAGCCGGCTGACCG

TGGACAAGAGCCGGTGGCAGGAGGGCAACGTCTTTAGCTGCTCCGTGATGCACGAGGC

CCTGCACAACCACTACACCCAGAAGAGCCTGAGCCTGTCCCTGGGCAAGATG

In embodiments, these clones (e.g., in Table 8) all contained a Q/K residue change in the signal domain of the co-stimulatory domain derived from CD3zeta chain.

TABLE 8

Amino Acid and Nucleic Acid Sequences of the anti-CLL-1 scFv domains and CLL-1 CAR molecules

| Name/ Description | SEQ ID NO: | Sequence |
|---|---|---|
| | | 146259 |
| 146259-aa ScFv domain CLL-1 CAR 9 | 47 | QVQLVQSGAEVKEPGASVKVSCKAPANTFSDHVMHWVRQAPGQRFEWMGY IHAANGGTHYSQKFQDRVTITRDTSANTVYMDLSSLRSEDTAVYYCARGG YNSDAFDIWGQGTMVTVSSGGGGSGGGGSGGGGSGGGGSDIVMTQSPSSV SASVGDRVTITCRASQDISSWLAWYQQKPGKAPKLLIYAASSLQSGVPSR FNGSGSGTDFTLTISSLQPEDFATYYCQQSYSTPLTFGGGTKVEIK |
| 146259-nt ScFv domain CLL-1 CAR 9 | 60 | CAAGTGCAACTCGTCCAGTCCGGTGCAGAAGTCAAGGAACCCGGAGCCTC CGTGAAAGTGTCCTGCAAAGCTCCTGCCAACACTTTCTCGGACCACGTGA TGCACTGGGTGCGCCAGGCGCCGGGCCAGCGCTTCGAATGGATGGGATAC ATTCATGCCGCCAATGGCGGTACCCACTACTCCCAAAAGTTCCAGGATAG AGTCACCATCACCCGGGACACCAGCGCCAACACCGTGTATATGGATCTGT CCAGCCTGAGGTCCGAGGATACCGCCGTGTACTACTGCGCCCGGGGCGGA TACAACTCAGACGCGTTCGACATTTGGGGACAGGGTACTATGGTCACCGT GTCATCCGGGGGCGGTGGCAGCGGGGGCGGAGGCTCTGGCGGAGGCGGAT CAGGGGGAGGAGGGTCCGACATCGTGATGACCCAGTCCCCGTCATCGGTG TCCGCGTCCGTGGGAGACAGAGTGACCATCACGTGTCGCGCCAGCCAGGA CATCTCCTCGTGGTTGGCATGGTACCAGCAGAAGCCTGGAAAGGCCCCGA AGCTGCTCATCTACGCCGCCTCCTCCCTTCAATCGGGAGTGCCCTCGCGG TTCAACGGAAGCGGAAGCGGGACAGATTTTACCCTGACTATTAGCTCGCT GCAGCCCGAGGACTTCGCTACTTACTACTGCCAACAGAGCTACTCCACCC CACTGACTTTCGGCGGGGGTACCAAGGTCGAGATCAAG |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| 146259-aa VH of ScFv CLL-1 CAR 9 | 73 | QVQLVQSGAEVKEPGASVKVSCKAPANTFSDHVMHWVRQAPGQRFEWMGY IHAANGGTHYSQKFQDRVTITRDTSANTVYMDLSSLRSEDTAVYYCARGG YNSDAFDIWGQGTMVTVSS |
| 146259-aa VL of ScFv CLL-1 CAR 9 | 86 | DIVMTQSPSSVSASVGDRVTITCRASQDISSWLAWYQQKPGKAPKLLIYA ASSLQSGVPSRFNGSGSGTDFTLTISSLQPEDFATYYCQQSYSTPLTFGG GTKVEIK |
| 146259-aa Full CAR CLL-1 CAR 9 | 99 | MALPVTALLLPLALLLHAARPQVQLVQSGAEVKEPGASVKVSCKAPANTF SDHVMHWVRQAPGQRFEWMGYIHAANGGTHYSQKFQDRVTITRDTSANTV YMDLSSLRSEDTAVYYCARGGYNSDAFDIWGQGTMVTVSSGGGGSGGGGS GGGGSGGGGSDIVMTQSPSSVSASVGDRVTITCRASQDISSWLAWYQQKP GKAPKLLIYAASSLQSGVPSRFNGSGSGTDFTLTISSLQPEDFATYYCQQ SYSTPLTFGGGTKVEIKTTTPAPRPPTPAPTIASQPLSLRPEACRPAAGG AVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYN ELNLGRREEYDVLDKRRGRDPEMGGKPRRKNPQEGLYNELQKDKMAEAYS EIGMKGERRRGKGHDGLYQGLSTATKDTYDALHMQALPPR |
| 146259-nt Full CAR CLL-1 CAR 9 | 112 | ATGGCCCTCCCTGTCACCGCCCTGCTGCTTCCGCTGGCTCTTCTGCTCCA CGCCGCTCGGCCCCAAGTGCAACTCGTCCAGTCCGGTGCAGAAGTCAAGG AACCCGGAGCCTCCGTGAAAGTGTCCTGCAAAGCTCCTGCCAACACTTTC TCGGACCACGTGATGCACTGGGTGCGCCAGGCGCCGGGCCAGCGCTTCGA ATGGATGGGATACATTCATGCCGCCAATGGCGGTACCCACTACTCCCAAA AGTTCCAGGATAGAGTCACCATCACCCGGGACACCAGCGCCAACACCGTG TATATGGATCTGTCCAGCCTGAGGTCCGAGGATACCGCCGTGTACTACTG CGCCCGGGGCGGATACAACTCAGACGCGTTCGACATTTGGGGACAGGGTA CTATGGTCACCGTGTCATCCGGGGGCGGTGGCAGCGGGGGCGGAGGCTCT GGCGGAGGCGGATCAGGGGGAGGAGGGTCCGACATCGTGATGACCCAGTC CCCGTCATCGGTGTCCGCGTCCGTGGGAGACAGAGTGACCATCACGTGTC GCGCCAGCCAGGACATCTCCTCGTGGTTGGCATGGTACCAGCAGAAGCCT GGAAAGGCCCCGAAGCTGCTCATCTACGCCGCCTCCTCCCTTCAATCGGG AGTGCCCTCGCGGTTCAACGGAAGCGGAAGCGGGACAGATTTTACCCTGA CTATTAGCTCGCTGCAGCCCGAGGACTTCGCTACTTACTACTGCCAACAG AGCTACTCCACCCCACTGACTTTCGGCGGGGGTACCAAGGTCGAGATCAA GACCACTACCCCAGCACCGAGGCCACCCACCCCGGCTCCTACCATCGCCT CCCAGCCTCTGTCCCTGCGTCCGGAGGCATGTAGACCCGCAGCTGGTGGG GCCGTGCATACCCGGGGTCTTGACTTCGCCTGCGATATCTACATTTGGGC CCCTCTGGCTGGTACTTGCGGGGTCCTGCTGCTTTCACTCGTGATCACTC TTTACTGTAAGCGCGGTCGGAAGAAGCTGCTGTACATCTTTAAGCAACCC TTCATGAGGCCTGTGCAGACTACTCAAGAGGAGGACGGCTGTTCATGCCG GTTCCCAGAGGAGGAGGAAGGCGGCTGCGAACTGCGCGTGAAATTCAGCC GCAGCGCAGATGCTCCAGCCTACAAGCAGGGGCAGAACCAGCTCTACAAC GAACTCAATCTTGGTCGGAGAGAGGAGTACGACGTGCTGGACAAGCGGAG AGGACGGGACCCAGAAATGGGCGGGAAGCCGCGCAGAAAGAATCCCCAAG AGGGCCTGTACAACGAGCTCCAAAAGGATAAGATGGCAGAAGCCTATAGC GAGATTGGTATGAAAGGGGAACGCAGAAGAGGCAAAGGCCACGACGGACT GTACCAGGGACTCAGCACCGCCACCAAGGACACCTATGACGCTCTTCACA TGCAGGCCCTGCCGCCTCGG |
| | | **139119** |
| 139119-aa ScFv domain CLL-1 CAR 6 | 44 | QVQLQESGAGLLKPSETLSLTCAVYGGSFSGYYWSWIRQPPGKGLEWVGE INHSGSTNYNPSLKSRVTISVDTSKNQFSLKLSSVTAADTAVYYCARGSG LVVYAIRVGSGWFDYWGQGTLVTVSSGGGGSGGGDSGGGGSDIQMTQSPS SLSASVGDRVTITCRASQSISSYLNWYQQKPGKAPKLLMYAASSLQSGVP SRFSGSGSGTDFTLTISSLQPEDFATYYCQQSYSTPPWTFGQGTKVDIK |
| 139119-nt ScFv domain CLL-1 CAR 6 | 57 | CAAGTGCAACTTCAAGAATCAGGCGCAGGACTTCTCAAGCCATCCGAAAC ACTCTCCCTCACTTGCGCGGTGTACGGGGGAAGCTTCTCGGGATACTACT GGTCCTGGATTAGGCAGCCTCCCGGCAAAGGCCTGGAATGGGTCGGGGAG ATCAACCACTCCGGTTCAACCAACTACAACCCGTCGCTGAAGTCCCGCGT GACCATTTCCGTGGACACCTCTAAGAATCAGTTCAGCCTGAAGCTCTCGT CCGTGACCGCGGCGGACACCGCCGTCTACTACTGCGCTCGGGGATCAGGA CTGGTGGTGTACGCCATCCGCGTGGGCTCGGGCTGGTTCGATTACTGGGG CCAGGGAACCCTGGTCACTGTGTCGTCCGGCGGAGGAGGTTCGGGGGGCG GAGACAGCGGTGGAGGGGGTAGCGACATCCAGATGACCCAGTCCCCGTCC TCGCTGTCCGCCTCCGTGGGAGATAGAGTGACCATCACCTGTCGGGCATC CCAGAGCATTTCCAGCTACCTGAACTGGTATCAGCAGAAGCCCGGAAAGG CCCCTAAGCTGTTGATGTACGCCGCCAGCAGCTTGCAGTCGGGCGTGCCG AGCCGGTTTTCCGGTTCCGGCTCCGGGACTGACTTCACCCTGACTATCTC |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | ATCCCTGCAACCCGAGGACTTCGCCACTTATTACTGCCAGCAGTCCTACT CAACCCCTCCCTGGACGTTCGGACAGGGCACCAAGGTCGATATCAAG |
| 139119-aa VH of ScFv CLL-1 CAR 6 | 70 | QVQLQESGAGLLKPSETLSLTCAVYGGSFSGYYWSWIRQPPGKGLEWVGE INHSGSTNYNPSLKSRVTISVDTSKNQFSLKLSSVTAADTAVYYCARGSG LVVYAIRVGSGWFDYWGQGTLVTVSS |
| 139119-aa VL of ScFv CLL-1 CAR 6 | 83 | DIQMTQSPSSLSASVGDRVTITCRASQSISSYLNWYQQKPGKAPKLLMYA ASSLQSGVPSRFSGSGSGTDFTLTISSLQPEDFATYYCQQSYSTPPWTFG QGTKVDIK |
| 139119-aa Full CAR CLL-1 CAR 6 | 96 | MALPVTALLLPLALLLHAARPQVQLQESGAGLLKPSETLSLTCAVYGGSF SGYYWSWIRQPPGKGLEWVGEINHSGSTNYNPSLKSRVTISVDTSKNQFS LKLSSVTAADTAVYYCARGSGLVVYAIRVGSGWFDYWGQGTLVTVSSGGG GSGGGDSGGGGSDIQMTQSPSSLSASVGDRVTITCRASQSISSYLNWYQQ KPGKAPKLLMYAASSLQSGVPSRFSGSGSGTDFTLTISSLQPEDFATYYC QQSYSTPPWTFGQGTKVDIKTTTPAPRPPTPAPTIASQPLSLRPEACRPA AGGAVHTRGLDFACDIYIWAPLAGTCGVLLLSLVITLYCKRGRKKLLYIF KQPFMRPVQTTQEEDGCSCRFPEEEEGGCELRVKFSRSADAPAYKQGQNQ LYNELNLGRREEYDVLDKRRGRDPEMGGKPRRKNPQEGLYNELQKDKMAE AYSEIGMKGERRRGKGHDGLYQGLSTATKDTYDALHMQALPPR |
| 139119-nt Full CAR CLL-1 CAR 6 | 109 | ATGGCCCTCCCTGTCACCGCCCTGCTGCTTCCGCTGGCTCTTCTGCTCCA CGCCGCTCGGCCCCAAGTGCAACTTCAAGAATCAGGCGCAGGACTTCTCA AGCCATCCGAAACACTCTCCCTCACTTGCGCGGTGTACGGGGGAAGCTTC TCGGGATACTACTGGTCCTGGATTAGGCAGCCTCCCGGCAAAGGCCTGGA ATGGGTCGGGGAGATCAACCACTCCGGTTCAACCAACTACAACCCGTCGC TGAAGTCCCGCGTGACCATTTCCGTGGACACCTCTAAGAATCAGTTCAGC CTGAAGCTCTCGTCCGTGACCGCGGCGGACACCGCCGTCTACTACTGCGC TCGGGGATCAGGACTGGTGGTGTACGCCATCCGCGTGGGCTCGGGCTGGT TCGATTACTGGGGCCAGGGAACCCTGGTCACTGTGTCGTCCGGCGGAGGA GGTTCGGGGGGCGGAGACAGCGGTGGAGGGGGTAGCGACATCCAGATGAC CCAGTCCCCGTCCTCGCTGTCCGCCTCCGTGGGAGATAGAGTGACCATCA CCTGTCGGGCATCCCAGAGCATTTCCAGCTACCTGAACTGGTATCAGCAG AAGCCCGGAAAGGCCCCTAAGCTGTTGATGTACGCCGCCAGCAGCTTGCA GTCGGGCGTGCCGAGCCGGTTTTCCGGTTCCGGCTCCGGGACTGACTTCA CCCTGACTATCTCATCCCTGCAACCCGAGGACTTCGCCACTTATTACTGC CAGCAGTCCTACTCAACCCCTCCCTGGACGTTCGGACAGGGCACCAAGGT CGATATCAAGACCACTACCCCAGCACCGAGGCCACCCACCCCGGCTCCTA CCATCGCCTCCCAGCCTCTGTCCCTGCGTCCGGAGGCATGTAGACCCGCA GCTGGTGGGGCCGTGCATACCCGGGGTCTTGACTTCGCCTGCGATATCTA CATTTGGGCCCCTCTGGCTGGTACTTGCGGGGTCCTGCTGCTTTCACTCG TGATCACTCTTTACTGTAAGCGCGGTCGGAAGAAGCTGCTGTACATCTTT AAGCAACCCTTCATGAGGCCTGTGCAGACTACTCAAGAGGAGGACGGCTG TTCATGCCGGTTCCCAGAGGAGGAGGAAGGCGGCTGCGAACTGCGCGTGA AATTCAGCCGCAGCGCAGATGCTCCAGCCTACAAGCAGGGGCAGAACCAG CTCTACAACGAACTCAATCTTGGTCGGAGAGAGGAGTACGACGTGCTGGA CAAGCGGAGAGGACGGGACCCAGAAATGGGCGGGAAGCCGCGCAGAAAGA ATCCCCAAGAGGGCCTGTACAACGAGCTCCAAAAGGATAAGATGGCAGAA GCCTATAGCGAGATTGGTATGAAAGGGGAACGCAGAAGAGGCAAAGGCCA CGACGGACTGTACCAGGGACTCAGCACCGCCACCAAGGACACCTATGACG CTCTTCACATGCAGGCCCTGCCGCCTCGG |
| | | 146261 |
| 146261-aa ScFv domain CLL-1 CAR 10 | 48 | QVQLVQSGGGLVQPGGSLRLSCAASGFTFSSYSMNWVRQAPGKGLEWVSY ISSSSSTIYYADSVKGRFTISRDNAKNSLYLQMNSLRAEDTAVYYCARDL SVRAIDAFDIWGQGTMVTVSSGGGGSGGGGSGGGGSGGGGSDIVLTQSPS SLSASVGDRVTITCQASQDISNYLNWYQQKPGKAPKLLIYDASNLETGVP SRFSGSGSGTDFTFTISSLQPEDFATYYCQQAYSTPFTFGPGTKVEIK |
| 146261-nt ScFv domain CLL-1 CAR 10 | 61 | CAAGTGCAACTTGTTCAATCCGGTGGAGGTCTTGTGCAGCCCGGAGGATC ACTCAGACTGTCGTGCGCCGCCTCTGGGTTCACTTTCTCCTCATACTCGA TGAACTGGGTGCGCCAGGCGCCGGGAAAGGGCCTGGAATGGGTGTCATAC ATCTCCTCCTCATCCTCCACCATCTACTACGCCGATTCCGTGAAGGGCCG CTTCACTATTTCCCGGGACAACGCGAAAAACTCGCTCTATCTGCAAATGA ACTCCCTGCGCGCCGAGGACACCGCCGTGTACTACTGCGCCCGGGACCTG AGCGTGCGGGCTATTGATGCGTTCGACATCTGGGGACAGGGCACCATGGT CACAGTGTCCAGCGGAGGCGGCGGCAGCGGTGGAGGAGGATCAGGGGGAG GAGGTTCGGGGGGCGGTGGCTCCGATATCGTGCTGACCCAGAGCCCGTCG AGCCTCTCCGCCTCCGTCGGCGACAGAGTGACCATCACGTGTCAGGCATC CCAGGACATTAGCAACTACCTGAATTGGTACCAGCAGAAGCCTGGAAAGG CACCCAAGTTGCTGATCTACGACGCCTCCAACCTGGAAACCGGAGTGCCA |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | TCCAGGTTCTCGGGCAGCGGCTCGGGAACCGACTTCACTTTTACTATCTC CTCCCTGCAACCCGAGGATTTCGCGACCTACTACTGCCAGCAGGCCTACA GCACCCCTTTCACCTTCGGGCCGGGAACTAAGGTCGAAATCAAG |
| 146261-aa VH of ScFv CLL-1 CAR 10 | 74 | QVQLVQSGGGLVQPGGSLRLSCAASGFTFSSYSMNWVRQAPGKGLEWVSY ISSSSSTIYYADSVKGRFTISRDNAKNSLYLQMNSLRAEDTAVYYCARDL SVRAIDAFDIWGQGTMVTVSS |
| 146261-aa VL of ScFv CLL-1 CAR 10 | 87 | DIVLTQSPSSLSASVGDRVTITCQASQDISNYLNWYQQKPGKAPKLLIYD ASNLETGVPSRFSGSGSGTDFTFTISSLQPEDFATYYCQQAYSTPFTFGP GTKVEIK |
| 146261-aa Full CAR CLL-1 CAR 10 | 100 | MALPVTALLLPLALLLHAARPQVQLVQSGGGLVQPGGSLRLSCAASGFTF SSYSMNWVRQAPGKGLEWVSYISSSSSTIYYADSVKGRFTISRDNAKNSL YLQMNSLRAEDTAVYYCARDLSVRAIDAFDIWGQGTMVTVSSGGGGSGGG GSGGGGSGGGGSDIVLTQSPSSLSASVGDRVTITCQASQDISNYLNWYQQ KPGKAPKLLIYDASNLETGVPSRFSGSGSGTDFTFTISSLQPEDFATYYC QQAYSTPFTFGPGTKVEIKTTTPAPRPPTPAPTIASQPLSLRPEACRPAA GGAVHTRGLDFACDIYIWAPLAGTCGVLLLSLVITLYCKRGRKKLLYIFK QPFMRPVQTTQEEDGCSCRFPEEEEGGCELRVKFSRSADAPAYKQGQNQL YNELNLGRREEYDVLDKRRGRDPEMGGKPRRKNPQEGLYNELQKDKMAEA YSEIGMKGERRRGKGHDGLYQGLSTATKDTYDALHMQALPPR |
| 146261-nt Full CAR CLL-1 CAR 10 | 113 | ATGGCCCTCCCTGTCACCGCCCTGCTGCTTCCGCTGGCTCTTCTGCTCCA CGCCGCTCGGCCCCAAGTGCAACTTGTTCAATCCGGTGGAGGTCTTGTGC AGCCCGGAGGATCACTCAGACTGTCGTGCGCCGCCTCTGGGTTCACTTTC TCCTCATACTCGATGAACTGGGTGCGCCAGGCGCCGGGAAAGGGCCTGGA ATGGGTGTCATACATCTCCTCCTCATCCTCCACCATCTACTACGCCGATT CCGTGAAGGGCCGCTTCACTATTTCCCGGGACAACGCGAAAAACTCGCTC TATCTGCAAATGAACTCCCTGCGCGCCGAGGACACCGCCGTGTACTACTG CGCCCGGGACCTGAGCGTGCGGGCTATTGATGCGTTCGACATCTGGGGAC AGGGCACCATGGTCACAGTGTCCAGCGGAGGCGGCGGCAGCGGTGGAGGA GGATCAGGGGGAGGAGGTTCGGGGGGCGGTGGCTCCGATATCGTGCTGAC CCAGAGCCCGTCGAGCCTCTCCGCCTCCGTCGGCGACAGAGTGACCATCA CGTGTCAGGCATCCCAGGACATTAGCAACTACCTGAATTGGTACCAGCAG AAGCCTGGAAAGGCACCCAAGTTGCTGATCTACGACGCCTCCAACCTGGA AACCGGAGTGCCATCCAGGTTCTCGGGCAGCGGCTCGGGAACCGACTTCA CTTTTACTATCTCCTCCCTGCAACCCGAGGATTTCGCGACCTACTACTGC CAGCAGGCCTACAGCACCCCTTTCACCTTCGGGCCGGGAACTAAGGTCGA AATCAAGACCACTACCCCAGCACCGAGGCCACCCACCCCGGCTCCTACCA TCGCCTCCCAGCCTCTGTCCCTGCGTCCGGAGGCATGTAGACCCGCAGCT GGTGGGGCCGTGCATACCCGGGGTCTTGACTTCGCCTGCGATATCTACAT TTGGGCCCCTCTGGCTGGTACTTGCGGGGTCCTGCTGCTTTCACTCGTGA TCACTCTTTACTGTAAGCGCGGTCGGAAGAAGCTGCTGTACATCTTTAAG CAACCCTTCATGAGGCCTGTGCAGACTACTCAAGAGGAGGACGGCTGTTC ATGCCGGTTCCCAGAGGAGGAGGAAGGCGGCTGCGAACTGCGCGTGAAAT TCAGCCGCAGCGCAGATGCTCCAGCCTACAAGCAGGGGCAGAACCAGCTC TACAACGAACTCAATCTTGGTCGGAGAGAGGAGTACGACGTGCTGGACAA GCGGAGAGGACGGGACCCAGAAATGGGCGGGAAGCCGCGCAGAAAGAATC CCCAAGAGGGCCTGTACAACGAGCTCCAAAAGGATAAGATGGCAGAAGCC TATAGCGAGATTGGTATGAAAGGGGAACGCAGAAGAGGCAAAGGCCACGA CGGACTGTACCAGGGACTCAGCACCGCCACCAAGGACACCTATGACGCTC TTCACATGCAGGCCCTGCCGCCTCGG |
| | | 146262 |
| 146262-aa ScFv domain CLL-1 CAR 11 | 49 | EVQLVQSGGGVVRSGRSLRLSCAASGFTFNSYGLHWVRQAPGKGLEWVAL IEYDGSNKYYGDSVKGRFTISRDKSKSTLYLQMDNLRAEDTAVYYCAREG NEDLAFDIWGQGTLVTVSSGGGGSGGGGSGGGGSGGGGSEIVLTQSPSSL SASVGDRVTITCQASQFIKKNLNWYQHKPGKAPKLLIYDASSLQTGVPSR FSGNRSGTTFSFTISSLQPEDVATYYCQQHDNLPLTFGGGTKVEIK |
| 146262-nt ScFv domain CLL-1 CAR 11 | 62 | GAAGTGCAATTGGTGCAATCAGGAGGAGGAGTGGTCAGATCTGGAAGAAG CCTGAGACTGTCATGCGCGGCTTCGGGCTTTACCTTCAACTCCTACGGCC TCCACTGGGTGCGCCAGGCCCCCGGAAAAGGCCTCGAATGGGTCGCACTG ATTGAGTACGACGGGTCCAACAAGTACTACGGAGATAGCGTGAAGGGCCG CTTCACCATCTCACGGGACAAGTCCAAGTCCACCCTGTATCTGCAAATGG ACAACCTGAGGGCCGAGGATACTGCCGTGTACTACTGCGCCCGCGAAGGA AACGAAGATCTGGCCTTCGATATTTGGGGCCAGGGTACTCTTGTGACCGT GTCGAGCGGAGGCGGAGGCTCCGGTGGAGGAGGATCGGGGGGTGGTGGTT CCGGCGGCGGGGGGAGCGAAATCGTGCTGACCCAGTCGCCTTCCTCCCTC TCCGCTTCCGTGGGGGACCGGGTCACTATTACGTGTCAGGCGTCCCAATT CATCAAGAAGAATCTGAACTGGTACCAGCACAAGCCGGGAAAGGCCCCCA |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | AACTGCTCATCTACGACGCCAGCTCGCTGCAGACTGGCGTGCCTTCCCGG TTTTCCGGGAACCGGTCGGGAACCACCTTCTCATTCACCATCAGCAGCCT CCAGCCGGAGGACGTGGCGACCTACTACTGCCAGCAGCATGACAACCTTC CACTGACTTTCGGCGGGGGCACCAAGGTCGAGATTAAG |
| 146262-aa VH of ScFv CLL-1 CAR 11 | 75 | EVQLVQSGGGVVRSGRSLRLSCAASGFTFNSYGLHWVRQAPGKGLEWVAL IEYDGSNKYYGDSVKGRFTISRDKSKSTLYLQMDNLRAEDTAVYYCAREG NEDLAFDIWGQGTLVTVSS |
| 146262-aa VL of ScFv CLL-1 CAR 11 | 88 | EIVLTQSPSSLSASVGDRVTITCQASQFIKKNLNWYQHKPGKAPKLLIYD ASSLQTGVPSRFSGNRSGTTFSFTISSLQPEDVATYYCQQHDNLPLTFGG GTKVEIK |
| 146262-aa Full CAR CLL-1 CAR 11 | 101 | MALPVTALLLPLALLLHAARPEVQLVQSGGGVVRSGRSLRLSCAASGFTF NSYGLHWVRQAPGKGLEWVALIEYDGSNKYYGDSVKGRFTISRDKSKSTL YLQMDNLRAEDTAVYYCAREGNEDLAFDIWGQGTLVTVSSGGGGSGGGGS GGGGSGGGGSEIVLTQSPSSLSASVGDRVTITCQASQFIKKNLNWYQHKP GKAPKLLIYDASSLQTGVPSRFSGNRSGTTFSFTISSLQPEDVATYYCQQ HDNLPLTFGGGTKVEIKTTTPAPRPPTPAPTIASQPLSLRPEACRPAAGG AVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYN ELNLGRREEYDVLDKRRGRDPEMGGKPRRKNPQEGLYNELQKDKMAEAYS EIGMKGERRRGKGHDGLYQGLSTATKDTYDALHMQALPPR |
| 146262-nt Full CAR CLL-1 CAR 11 | 114 | ATGGCCCTCCCTGTCACCGCCCTGCTGCTTCCGCTGGCTCTTCTGCTCCA CGCCGCTCGGCCCGAAGTGCAATTGGTGCAATCAGGAGGAGGAGTGGTCA GATCTGGAAGAAGCCTGAGACTGTCATGCGCGGCTTCGGGCTTTACCTTC AACTCCTACGGCCTCCACTGGGTGCGCCAGGCCCCCGGAAAAGGCCTCGA ATGGGTCGCACTGATTGAGTACGACGGGTCCAACAAGTACTACGGAGATA GCGTGAAGGGCCGCTTCACCATCTCACGGGACAAGTCCAAGTCCACCCTG TATCTGCAAATGGACAACCTGAGGGCCGAGGATACTGCCGTGTACTACTG CGCCCGCGAAGGAAACGAAGATCTGGCCTTCGATATTTGGGGCCAGGGTA CTCTTGTGACCGTGTCGAGCGGAGGCGGAGGCTCCGGTGGAGGAGGATCG GGGGGTGGTGGTTCCGGCGGCGGGGGGAGCGAAATCGTGCTGACCCAGTC GCCTTCCTCCCTCTCCGCTTCCGTGGGGGACCGGGTCACTATTACGTGTC AGGCGTCCCAATTCATCAAGAAGAATCTGAACTGGTACCAGCACAAGCCG GGAAAGGCCCCCAAACTGCTCATCTACGACGCCAGCTCGCTGCAGACTGG CGTGCCTTCCCGGTTTTCCGGGAACCGGTCGGGAACCACCTTCTCATTCA CCATCAGCAGCCTCCAGCCGGAGGACGTGGCGACCTACTACTGCCAGCAG CATGACAACCTTCCACTGACTTTCGGCGGGGGCACCAAGGTCGAGATTAA GACCACTACCCCAGCACCGAGGCCACCCACCCCGGCTCCTACCATCGCCT CCCAGCCTCTGTCCCTGCGTCCGGAGGCATGTAGACCCGCAGCTGGTGGG GCCGTGCATACCCGGGGTCTTGACTTCGCCTGCGATATCTACATTTGGGC CCCTCTGGCTGGTACTTGCGGGGTCCTGCTGCTTTCACTCGTGATCACTC TTTACTGTAAGCGCGGTCGGAAGAAGCTGCTGTACATCTTTAAGCAACCC TTCATGAGGCCTGTGCAGACTACTCAAGAGGAGGACGGCTGTTCATGCCG GTTCCCAGAGGAGGAGGAAGGCGGCTGCGAACTGCGCGTGAAATTCAGCC GCAGCGCAGATGCTCCAGCCTACAAGCAGGGGCAGAACCAGCTCTACAAC GAACTCAATCTTGGTCGGAGAGAGGAGTACGACGTGCTGGACAAGCGGAG AGGACGGGACCCAGAAATGGGCGGGAAGCCGCGCAGAAAGAATCCCCAAG AGGGCCTGTACAACGAGCTCCAAAAGGATAAGATGGCAGAAGCCTATAGC GAGATTGGTATGAAAGGGGAACGCAGAAGAGGCAAAGGCCACGACGGACT GTACCAGGGACTCAGCACCGCCACCAAGGACACCTATGACGCTCTTCACA TGCAGGCCCTGCCGCCTCGG |
| | | 146263 |
| 146263-aa ScFv domain CLL-1 CAR 12 | 50 | QVQLVESGGGLVQPGGSLRLSCAASGFNVSSNYMTWVRQAPGKGLEWVSV IYSGGATYYGDSVKGRFTVSRDNSKNTVYLQMNRLTAEDTAVYYCARDRL YCGNNCYLYYYYGMDVWGQGTLVTVSSGGGGSGGGGSGGGGSGGGGSDIQ VTQSPSSLSASVGDRVTITCRASQSISSYLNWYQQKPGKAPKLLIYAASS LQSGVPSRFSGSGSGTDFTLTISSLQPEDFATYYCQQSYSTPPLTFGQGT KVEIK |
| 146263-nt ScFv domain CLL-1 CAR 12 | 63 | CAAGTGCAACTCGTGGAATCAGGCGGAGGACTCGTGCAACCCGGAGGTTC CCTTAGACTGTCATGTGCCGCTTCCGGGTTCAATGTGTCCAGCAACTACA TGACCTGGGTCAGACAGGCGCCGGGAAAGGGACTTGAATGGGTGTCCGTG ATCTACTCCGGTGGAGCAACATACTACGGAGACTCCGTGAAAGGCCGCTT TACCGTGTCCCGCGATAACTCGAAGAACACCGTGTACTTGCAGATGAACA GGCTGACTGCCGAGGACACCGCCGTGTATTATTGCGCCCGGGACAGGCTG TACTGTGGAAACAACTGCTACCTGTACTACTACTACGGGATGGACGTGTG GGGACAGGGCACTCTCGTCACTGTGTCATCCGGGGGGGGCGGTAGCGGTG GCGGAGGGTCCGGCGGAGGAGGCTCAGGGGGAGGCGGAAGCGATATCCAG |

TABLE 8-continued

| Amino Acid and Nucleic Acid Sequences of the anti-CLL-1 scFv domains and CLL-1 CAR molecules | | |
|---|---|---|
| Name/ Description | SEQ ID NO: | Sequence |
| | | GTCACCCAGTCTCCCTCCTCGCTGTCCGCCTCCGTGGGCGACCGCGTCAC CATTACTTGCCGGGCGTCGCAGTCGATCAGCTCCTACCTGAACTGGTACC AGCAGAAGCCTGGAAAGGCCCCGAAGCTGCTGATCTACGCGGCCTCGTCC CTGCAAAGCGGCGTCCCGTCGCGGTTCAGCGGTTCCGGTTCGGGAACCGA CTTCACCCTGACTATTTCCTCCCTGCAACCCGAGGATTTCGCCACTTACT ACTGCCAGCAGTCCTACTCCACCCCACCTCTGACCTTCGGCCAAGGAACC AAGGTCGAAATCAAG |
| 146263-aa VH of ScFv CLL-1 CAR 12 | 76 | QVQLVESGGGLVQPGGSLRLSCAASGFNVSSNYMTWVRQAPGKGLEWVSV IYSGGATYYGDSVKGRFTVSRDNSKNTVYLQMNRLTAEDTAVYYCARDRL YCGNNCYLYYYYGMDVWGQGTLVTVSS |
| 146263-aa VL of ScFv CLL-1 CAR 12 | 89 | DIQVTQSPSSLSASVGDRVTITCRASQSISSYLNWYQQKPGKAPKLLIYA ASSLQSGVPSRFSGSGSGTDFTLTISSLQPEDFATYYCQQSYSTPPLTFG QGTKVEIK |
| 146263-aa Full CAR CLL-1 CAR 12 | 102 | MALPVTALLLPLALLLHAARPQVQLVESGGGLVQPGGSLRLSCAASGFNV SSNYMTWVRQAPGKGLEWVSVIYSGGATYYGDSVKGRFTVSRDNSKNTVY LQMNRLTAEDTAVYYCARDRLYCGNNCYLYYYYGMDVWGQGTLVTVSSGG GGSGGGGSGGGGSGGGGSDIQVTQSPSSLSASVGDRVTITCRASQSISSY LNWYQQKPGKAPKLLIYAASSLQSGVPSRFSGSGSGTDFTLTISSLQPED FATYYCQQSYSTPPLTFGQGTKVEIKTTTPAPRPPTPAPTIASQPLSLRP EACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR |
| 146263-nt Full CAR CLL-1 CAR 12 | 115 | ATGGCCCTCCCTGTCACCGCCCTGCTGCTTCCGCTGGCTCTTCTGCTCCA CGCCGCTCGGCCCCAAGTGCAACTCGTGGAATCAGGCGGAGGACTCGTGC AACCCGGAGGTTCCCTTAGACTGTCATGTGCCGCTTCCGGGTTCAATGTG TCCAGCAACTACATGACCTGGGTCAGACAGGCGCCGGGAAAGGGACTTGA ATGGGTGTCCGTGATCTACTCCGGTGGAGCAACATACTACGGAGACTCCG TGAAAGGCCGCTTTACCGTGTCCCGCGATAACTCGAAGAACACCGTGTAC TTGCAGATGAACAGGCTGACTGCCGAGGACACCGCCGTGTATTATTGCGC CCGGGACAGGCTGTACTGTGGAAACAACTGCTACCTGTACTACTACTACG GGATGGACGTGTGGGGACAGGGCACTCTCGTCACTGTGTCATCCGGGGGG GGCGGTAGCGGTGGCGGAGGGTCCGGCGGAGGAGGCTCAGGGGGAGGCGG AAGCGATATCCAGGTCACCCAGTCTCCCTCCTCGCTGTCCGCCTCCGTGG GCGACCGCGTCACCATTACTTGCCGGGCGTCGCAGTCGATCAGCTCCTAC CTGAACTGGTACCAGCAGAAGCCTGGAAAGGCCCCGAAGCTGCTGATCTA CGCGGCCTCGTCCCTGCAAAGCGGCGTCCCGTCGCGGTTCAGCGGTTCCG GTTCGGGAACCGACTTCACCCTGACTATTTCCTCCCTGCAACCCGAGGAT TTCGCCACTTACTACTGCCAGCAGTCCTACTCCACCCCACCTCTGACCTT CGGCCAAGGAACCAAGGTCGAAATCAAGACCACTACCCCAGCACCGAGGC CACCCACCCCGGCTCCTACCATCGCCTCCCAGCCTCTGTCCCTGCGTCCG GAGGCATGTAGACCCGCAGCTGGTGGGGCCGTGCATACCCGGGGTCTTGA CTTCGCCTGCGATATCTACATTTGGGCCCCTCTGGCTGGTACTTGCGGGG TCCTGCTGCTTTCACTCGTGATCACTCTTTACTGTAAGCGCGGTCGGAAG AAGCTGCTGTACATCTTTAAGCAACCCTTCATGAGGCCTGTGCAGACTAC TCAAGAGGAGGACGGCTGTTCATGCCGGTTCCCAGAGGAGGAGGAAGGCG GCTGCGAACTGCGCGTGAAATTCAGCCGCAGCGCAGATGCTCCAGCCTAC AAGCAGGGGCAGAACCAGCTCTACAACGAACTCAATCTTGGTCGGAGAGA GGAGTACGACGTGCTGGACAAGCGGAGAGGACGGGACCCAGAAATGGGCG GGAAGCCGCGCAGAAAGAATCCCCAAGAGGGCCTGTACAACGAGCTCCAA AAGGATAAGATGGCAGAAGCCTATAGCGAGATTGGTATGAAAGGGGAACG CAGAAGAGGCAAAGGCCACGACGGACTGTACCAGGGACTCAGCACCGCCA CCAAGGACACCTATGACGCTCTTCACATGCAGGCCCTGCCGCCTCGG |
| | | 139115 |
| 139115-aa ScFv domain CLL-1 CAR 1 | 39 | EVQLQQSGAEVKKPGSSVKVSCKASGGTFSSYAISWVRQAPGQGLEWMGG IIPIFGTANYAQKFQGRVTITADESTSTAYMELSSLRSEDTAVYYCARDL EMATIMGGYWGQGTLVTVSSGGGGSGGGGSGGGGSQSALTQPASVSGSPG QSITISCTGTSSDVGGYNYVSWYQQHPGKAPKLMIYDVSNRPSGVSNRFS GSKSGNTASLTISGLQAEDEADYYCSSYTSSSTLDVVFGGGTKLTVL |
| 139115-nt ScFv domain CLL-1 CAR 1 | 52 | GAAGTGCAACTCCAACAGTCAGGCGCAGAAGTCAAGAAGCCCGGATCGTC AGTGAAAGTGTCCTGCAAAGCCTCCGGCGGAACCTTCAGCTCCTACGCAA TCAGCTGGGTGCGGCAGGCGCCCGGACAGGGACTGGAGTGGATGGGCGGT ATCATTCCGATCTTTGGCACCGCCAATTACGCCCAGAAGTTCCAGGGACG CGTCACAATCACCGCCGACGAATCGACTTCCACCGCCTACATGGAGCTGT CGTCCTTGAGGAGCGAAGATACCGCCGTGTACTACTGCGCTCGGGATCTG GAGATGGCCACTATCATGGGGGGTTACTGGGGCCAGGGGACCCTGGTCAC |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | TGTGTCCTCGGGAGGAGGGGGATCAGGCGGCGGCGGTTCCGGGGGAGGAG GAAGCCAGTCCGCGCTGACTCAGCCAGCTTCCGTGTCTGGTTCGCCGGGA CAGTCCATCACTATTAGCTGTACCGGCACCAGCAGCGACGTGGGCGGCTA CAACTATGTGTCATGGTACCAGCAGCACCCGGGGAAGGCGCCTAAGCTGA TGATCTACGACGTGTCCAACCGCCCTAGCGGAGTGTCCAACAGATTCTCC GGTTCGAAGTCAGGGAACACTGCCTCCCTCACGATTAGCGGGCTGCAAGC CGAGGATGAAGCCGACTACTACTGCTCCTCCTATACCTCCTCCTCGACCC TGGACGTGGTGTTCGGAGGAGGCACCAAGCTCACCGTCCTT |
| 139115-aa VH of ScFv CLL-1 CAR 1 | 65 | EVQLQQSGAEVKKPGSSVKVSCKASGGTFSSYAISWVRQAPGQGLEWMGG IIPIFGTANYAQKFQGRVTITADESTSTAYMELSSLRSEDTAVYYCARDL EMATIMGGYWGQGTLVTVSS |
| 139115-aa VL of ScFv CLL-1 CAR 1 | 78 | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTLD VVFGGGTKLTVL |
| 139115-aa Full CAR CLL-1 CAR 1 | 91 | MALPVTALLLPLALLLHAARPEVQLQQSGAEVKKPGSSVKVSCKASGGTF SSYAISWVRQAPGQGLEWMGGIIPIFGTANYAQKFQGRVTITADESTSTA YMELSSLRSEDTAVYYCARDLEMATIMGGYWGQGTLVTVSSGGGGSGGGG SGGGGSQSALTQPASVSGSPGQSITISCTGTSSDVGGYNYVSWYQQHPGK APKLMIYDVSNRPSGVSNRFSGSKSGNTASLTISGLQAEDEADYYCSSYT SSSTLDVVFGGGTKLTVLTTTPAPRPPTPAPTIASQPLSLRPEACRPAAG GAVHTRGLDFACDIYIWAPLAGTCGVLLLSLVITLYCKRGRKKLLYIFKQ PFMRPVQTTQEEDGCSCRFPEEEEGGCELRVKFSRSADAPAYKQGQNQLY NELNLGRREEYDVLDKRRGRDPEMGGKPRRKNPQEGLYNELQKDKMAEAY SEIGMKGERRRGKGHDGLYQGLSTATKDTYDALHMQALPPR |
| 139115-nt Full CAR CLL-1 CAR 1 | 104 | ATGGCCCTCCCTGTCACCGCCCTGCTGCTTCCGCTGGCTCTTCTGCTCCA CGCCGCTCGGCCCGAAGTGCAACTCCAACAGTCAGGCGCAGAAGTCAAGA AGCCCGGATCGTCAGTGAAAGTGTCCTGCAAAGCCTCCGGCGGAACCTTC AGCTCCTACGCAATCAGCTGGGTGCGGCAGGCGCCCGGACAGGGACTGGA GTGGATGGGCGGTATCATTCCGATCTTTGGCACCGCCAATTACGCCCAGA AGTTCCAGGGACGCGTCACAATCACCGCCGACGAATCGACTTCCACCGCC TACATGGAGCTGTCGTCCTTGAGGAGCGAAGATACCGCCGTGTACTACTG CGCTCGGGATCTGGAGATGGCCACTATCATGGGGGGTTACTGGGGCCAGG GGACCCTGGTCACTGTGTCCTCGGGAGGAGGGGGATCAGGCGGCGGCGGT TCCGGGGGAGGAGGAAGCCAGTCCGCGCTGACTCAGCCAGCTTCCGTGTC TGGTTCGCCGGGACAGTCCATCACTATTAGCTGTACCGGCACCAGCAGCG ACGTGGGCGGCTACAACTATGTGTCATGGTACCAGCAGCACCCGGGGAAG GCGCCTAAGCTGATGATCTACGACGTGTCCAACCGCCCTAGCGGAGTGTC CAACAGATTCTCCGGTTCGAAGTCAGGGAACACTGCCTCCCTCACGATTA GCGGGCTGCAAGCCGAGGATGAAGCCGACTACTACTGCTCCTCCTATACC TCCTCCTCGACCCTGGACGTGGTGTTCGGAGGAGGCACCAAGCTCACCGT CCTTACCACTACCCCAGCACCGAGGCCACCCACCCCGGCTCCTACCATCG CCTCCCAGCCTCTGTCCCTGCGTCCGGAGGCATGTAGACCCGCAGCTGGT GGGGCCGTGCATACCCGGGGTCTTGACTTCGCCTGCGATATCTACATTTG GGCCCCTCTGGCTGGTACTTGCGGGGTCCTGCTGCTTTCACTCGTGATCA CTCTTTACTGTAAGCGCGGTCGGAAGAAGCTGCTGTACATCTTTAAGCAA CCCTTCATGAGGCCTGTGCAGACTACTCAAGAGGAGGACGGCTGTTCATG CCGGTTCCCAGAGGAGGAGGAAGGCGGCTGCGAACTGCGCGTGAAATTCA GCCGCAGCGCAGATGCTCCAGCCTACAAGCAGGGGCAGAACCAGCTCTAC AACGAACTCAATCTTGGTCGGAGAGAGGAGTACGACGTGCTGGACAAGCG GAGAGGACGGGACCCAGAAATGGGCGGGAAGCCGCGCAGAAAGAATCCCC AAGAGGGCCTGTACAACGAGCTCCAAAAGGATAAGATGGCAGAAGCCTAT AGCGAGATTGGTATGAAAGGGGAACGCAGAAGAGGCAAAGGCCACGACGG ACTGTACCAGGGACTCAGCACCGCCACCAAGGACACCTATGACGCTCTTC ACATGCAGGCCCTGCCGCCTCGG |
| | | 139116 |
| 139116-aa ScFv domain CLL-1 CAR 2 | 40 | EVQLVESGGGVVQPGGSLRLSCAASGFTFDDYAMHWVRQAPGKGLEWVSL ISGDGGSTYYADSVKGRFTISRDNSKNTLYLQMNSLRVEDTAVYYCARVF DSYYMDVWGKGTTVTVSSGGGGSGGGGSGSGGSEIVLTQSPLSLPVTPGQ PASISCRSSQSLVYTDGNTYLNWFQQRPGQSPRRLIYKVSNRDSGVPDRF SGSGSDTDFTLKISRVEAEDVGIYYCMQGTHWSFTFGQGTRLEIK |
| 139116-nt ScFv domain CLL-1 CAR 2 | 53 | GAAGTGCAATTGGTGGAAAGCGGAGGAGGAGTGGTGCAACCTGGAGGAAG CCTGAGACTGTCATGTGCCGCCTCGGGATTCACTTTCGATGACTACGCAA TGCACTGGGTCCGCCAGGCCCCCGGAAAGGGTCTGGAATGGGTGTCCCTC ATCTCCGGCGATGGGGGTTCCACTTACTATGCGGATTCTGTGAAGGGCCG CTTCACAATCTCCCGGGACAATTCCAAGAACACTCTGTACCTTCAAATGA ACTCCCTGAGGGTGGAGGACACCGCTGTGTACTACTGCGCGAGAGTGTTT |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | GACTCGTACTATATGGACGTCTGGGGAAAGGGCACCACCGTGACCGTGTC<br>CAGCGGTGGCGGTGGATCGGGGGGCGGCGGCTCCGGGAGCGGAGGTTCCG<br>AGATTGTGCTGACTCAGTCGCCGTTGTCACTGCCTGTCACCCCCGGGCAG<br>CCGGCCTCCATTTCATGCCGGTCCAGCCAGTCCCTGGTCTACACCGATGG<br>GAACACTTACCTCAACTGGTTCCAGCAGCGCCCAGGACAGTCCCCGCGGA<br>GGCTGATCTACAAAGTGTCAAACCGGGACTCCGGCGTCCCCGATCGGTTC<br>TCGGGAAGCGGCAGCGACACCGACTTCACGCTGAAGATTTCCCGCGTGGA<br>AGCCGAGGACGTGGGCATCTACTACTGTATGCAGGGCACCCACTGGTCGT<br>TTACCTTCGGACAAGGAACTAGGCTCGAGATCAAG |
| 139116-aa<br>VH of ScFv<br>CLL-1 CAR 2 | 66 | EVQLVESGGGVVQPGGSLRLSCAASGFTFDDYAMHWVRQAPGKGLEWVSL<br>ISGDGGSTYYADSVKGRFTISRDNSKNTLYLQMNSLRVEDTAVYYCARVF<br>DSYYMDVWGKGTTVTVSS |
| 139116-aa<br>VL of ScFv<br>CLL-1 CAR 2 | 79 | EIVLTQSPLSLPVTPGQPASISCRSSQSLVYTDGNTYLNWFQQRPGQSPR<br>RLIYKVSNRDSGVPDRFSGSGSDTDFTLKISRVEAEDVGIYYCMQGTHWS<br>FTFGQGTRLEIK |
| 139116-aa<br>Full CAR<br>CLL-1 CAR 2 | 92 | MALPVTALLLPLALLLHAARPEVQLVESGGGVVQPGGSLRLSCAASGFTF<br>DDYAMHWVRQAPGKGLEWVSLISGDGGSTYYADSVKGRFTISRDNSKNTL<br>YLQMNSLRVEDTAVYYCARVFDSYYMDVWGKGTTVTVSSGGGGSGGGGSG<br>SGGSEIVLTQSPLSLPVTPGQPASISCRSSQSLVYTDGNTYLNWFQQRPG<br>QSPRRLIYKVSNRDSGVPDRFSGSGSDTDFTLKISRVEAEDVGIYYCMQG<br>THWSFTFGQGTRLEIKTTTPAPRPPTPAPTIASQPLSLRPEACRPAAGGA<br>VHTRGLDFACDIYIWAPLAGTCGVLLLSLVITLYCKRGRKKLLYIFKQPF<br>MRPVQTTQEEDGCSCRFPEEEEGGCELRVKFSRSADAPAYKQGQNQLYNE<br>LNLGRREEYDVLDKRRGRDPEMGGKPRRKNPQEGLYNELQKDKMAEAYSE<br>IGMKGERRRGKGHDGLYQGLSTATKDTYDALHMQALPPR |
| 139116-nt<br>Full CAR<br>CLL-1 CAR 2 | 105 | ATGGCCCTCCCTGTCACCGCCCTGCTGCTTCCGCTGGCTCTTCTGCTCCA<br>CGCCGCTCGGCCCGAAGTGCAATTGGTGGAAAGCGGAGGAGGAGTGGTGC<br>AACCTGGAGGAAGCCTGAGACTGTCATGTGCCGCCTCGGGATTCACTTTC<br>GATGACTACGCAATGCACTGGGTCCGCCAGGCCCCCGGAAAGGGTCTGGA<br>ATGGGTGTCCCTCATCTCCGGCGATGGGGGTTCCACTTACTATGCGGATT<br>CTGTGAAGGGCCGCTTCACAATCTCCCGGGACAATTCCAAGAACACTCTG<br>TACCTTCAAATGAACTCCCTGAGGGTGGAGGACACCGCTGTGTACTACTG<br>CGCGAGAGTGTTTGACTCGTACTATATGGACGTCTGGGGAAAGGGCACCA<br>CCGTGACCGTGTCCAGCGGTGGCGGTGGATCGGGGGGCGGCGGCTCCGGG<br>AGCGGAGGTTCCGAGATTGTGCTGACTCAGTCGCCGTTGTCACTGCCTGT<br>CACCCCCGGGCAGCCGGCCTCCATTTCATGCCGGTCCAGCCAGTCCCTGG<br>TCTACACCGATGGGAACACTTACCTCAACTGGTTCCAGCAGCGCCCAGGA<br>CAGTCCCCGCGGAGGCTGATCTACAAAGTGTCAAACCGGGACTCCGGCGT<br>CCCCGATCGGTTCTCGGGAAGCGGCAGCGACACCGACTTCACGCTGAAGA<br>TTTCCCGCGTGGAAGCCGAGGACGTGGGCATCTACTACTGTATGCAGGGC<br>ACCCACTGGTCGTTTACCTTCGGACAAGGAACTAGGCTCGAGATCAAGAC<br>CACTACCCCAGCACCGAGGCCACCCACCCCGGCTCCTACCATCGCCTCCC<br>AGCCTCTGTCCCTGCGTCCGGAGGCATGTAGACCCGCAGCTGGTGGGGCC<br>GTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTT<br>ACTGTAAGCGCGGTCGGAAGAAGCTGCTGTACATCTTTAAGCAACCCTTC<br>ATGAGGCCTGTGCAGACTACTCAAGAGGAGGACGGCTGTTCATGCCGGTT<br>CCCAGAGGAGGAGGAAGGCGGCTGCGAACTGCGCGTGAAATTCAGCCGCA<br>GCGCAGATGCTCCAGCCTACAAGCAGGGGCAGAACCAGCTCTACAACGAA<br>CTCAATCTTGGTCGGAGAGAGGAGTACGACGTGCTGGACAAGCGGAGAGG<br>ACGGGACCCAGAAATGGGCGGGAAGCCGCGCAGAAAGAATCCCCAAGAGG<br>GCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTA<br>CCAGGGACTCAGCACCGCCACCAAGGACACCTATGACGCTCTTCACATGC<br>AGGCCCTGCCGCCTCGG |
| | | 139118 |
| 139118-aa<br>ScFv domain<br>CLL-1 CAR 3 | 41 | QVQLQESGPGLVKPSETLSLTCTVSGGSISSSSYYWGWIRQPPGKGLEWI<br>GSIYYSGSTYYNPSLKSRVSISVDTSKNQFSLKLKYVTAADTAVYYCATP<br>GTYYDFLSGYYPFYWGQGTLVTVSSGGGGSGGGGSGGGGSDIVMTQSPSS<br>LSASVGDRVTITCRASQGISSYLAWYQQKPGKAPKLLIYAASTLQSGVPS<br>RFSGSGSGTDFTLTISSLQPEDFATYYCQQLNSYPYTFGQGTKLEIK |
| 139118-nt<br>ScFv domain<br>CLL-1 CAR 3 | 54 | CAAGTGCAGCTTCAAGAAAGCGGTCCAGGACTCGTCAAGCCATCAGAAAC<br>TCTTTCCCTCACTTGTACCGTGTCGGGAGGCAGCATCTCCTCGAGCTCCT<br>ACTACTGGGGTTGGATTAGACAGCCCCCGGGAAAGGGGTTGGAGTGGATC<br>GGTTCCATCTACTACTCCGGGTCGACCTACTACAACCCTTCCCTGAAATC<br>TCGGGTGTCCATCTCCGTCGACACCTCCAAGAACCAGTTCAGCCTGAAGC |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | TGAAATATGTGACCGCGGCCGATACTGCCGTGTACTATTGCGCCACCCCG<br>GGAACCTACTACGACTTCCTCTCGGGGTACTACCCGTTTTACTGGGGACA<br>GGGGACTCTCGTGACCGTGTCCTCGGGCGGCGGAGGTTCAGGCGGTGGCG<br>GATCGGGGGGAGGAGGCTCAGACATTGTGATGACCCAGAGCCCGTCCAGC<br>CTGAGCGCCTCCGTGGGCGATAGGGTCACGATTACTTGCCGGGCGTCCCA<br>GGGAATCTCAAGCTACCTGGCCTGGTACCAACAGAAGCCCGGAAAGGCAC<br>CCAAGTTGCTGATCTATGCCGCTAGCACTCTGCAGTCCGGGGTGCCTTCC<br>CGCTTCTCCGGCTCCGGCTCGGGCACCGACTTCACCCTGACCATTTCCTC<br>ACTGCAACCCGAGGACTTCGCCACTTACTACTGCCAGCAGCTGAACTCCT<br>ACCCTTACACATTCGGACAGGGAACCAAGCTGGAAATCAAG |
| 139118-aa VH of ScFv CLL-1 CAR 3 | 67 | QVQLQESGPGLVKPSETLSLTCTVSGGSISSSSYYWGWIRQPPGKGLEWI<br>GSIYYSGSTYYNPSLKSRVSISVDTSKNQFSLKLKYVTAADTAVYYCATP<br>GTYYDFLSGYYPFYWGQGTLVTVSS |
| 139118-aa VL of ScFv CLL-1 CAR 3 | 80 | DIVMTQSPSSLSASVGDRVTITCRASQGISSYLAWYQQKPGKAPKLLIYA<br>ASTLQSGVPSRFSGSGSGTDFTLTISSLQPEDFATYYCQQLNSYPYTFGQ<br>GTKLEIK |
| 139118-aa Full CAR CLL-1 CAR 3 | 93 | MALPVTALLLPLALLLHAARPQVQLQESGPGLVKPSETLSLTCTVSGGSI<br>SSSSYYWGWIRQPPGKGLEWIGSIYYSGSTYYNPSLKSRVSISVDTSKNQ<br>FSLKLKYVTAADTAVYYCATPGTYYDFLSGYYPFYWGQGTLVTVSSGGGG<br>SGGGGSGGGGSDIVMTQSPSSLSASVGDRVTITCRASQGISSYLAWYQQK<br>PGKAPKLLIYAASTLQSGVPSRFSGSGSGTDFTLTISSLQPEDFATYYCQ<br>QLNSYPYTFGQGTKLEIKTTTPAPRPPTPAPTIASQPLSLRPEACRPAAG<br>GAVHTRGLDFACDIYIWAPLAGTCGVLLLSLVITLYCKRGRKKLLYIFKQ<br>PFMRPVQTTQEEDGCSCRFPEEEEGGCELRVKFSRSADAPAYKQGQNQLY<br>NELNLGRREEYDVLDKRRGRDPEMGGKPRRKNPQEGLYNELQKDKMAEAY<br>SEIGMKGERRRGKGHDGLYQGLSTATKDTYDALHMQALPPR |
| 139118-nt Full CAR CLL-1 CAR 3 | 106 | ATGGCCCTCCCTGTCACCGCCCTGCTGCTTCCGCTGGCTCTTCTGCTCCA<br>CGCCGCTCGGCCCCAAGTGCAGCTTCAAGAAAGCGGTCCAGGACTCGTCA<br>AGCCATCAGAAACTCTTTCCCTCACTTGTACCGTGTCGGGAGGCAGCATC<br>TCCTCGAGCTCCTACTACTGGGGTTGGATTAGACAGCCCCCGGGAAAGGG<br>GTTGGAGTGGATCGGTTCCATCTACTACTCCGGGTCGACCTACTACAACC<br>CTTCCCTGAAATCTCGGGTGTCCATCTCCGTCGACACCTCCAAGAACCAG<br>TTCAGCCTGAAGCTGAAATATGTGACCGCGGCCGATACTGCCGTGTACTA<br>TTGCGCCACCCCGGGAACCTACTACGACTTCCTCTCGGGGTACTACCCGT<br>TTTACTGGGGACAGGGGACTCTCGTGACCGTGTCCTCGGGCGGCGGAGGT<br>TCAGGCGGTGGCGGATCGGGGGGAGGAGGCTCAGACATTGTGATGACCCA<br>GAGCCCGTCCAGCCTGAGCGCCTCCGTGGGCGATAGGGTCACGATTACTT<br>GCCGGGCGTCCCAGGGAATCTCAAGCTACCTGGCCTGGTACCAACAGAAG<br>CCCGGAAAGGCACCCAAGTTGCTGATCTATGCCGCTAGCACTCTGCAGTC<br>CGGGGTGCCTTCCCGCTTCTCCGGCTCCGGCTCGGGCACCGACTTCACCC<br>TGACCATTTCCTCACTGCAACCCGAGGACTTCGCCACTTACTACTGCCAG<br>CAGCTGAACTCCTACCCTTACACATTCGGACAGGGAACCAAGCTGGAAAT<br>CAAGACCACTACCCCAGCACCGAGGCCACCCACCCCGGCTCCTACCATCG<br>CCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTG<br>GGCCCCTCTGGCTGGTACTTGCGGGGTCCTGCTGCTTTCACTCGTGATCA<br>CTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATG<br>CCGGTTCCCAGAGGAGGAGGAAGGCGGCTGCGAACTGCGCGTGAAATTCA<br>GCCGCAGCGCAGATGCTCCAGCCTACAAGCAGGGGCAGAACCAGCTCTAC<br>AACGAACTCAATCTTGGTCGGAGAGAGGAGTACGACGTGCTGGACAAGCG<br>GAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGG<br>ACTGTACCAGGGACTCAGCACCGCCACCAAGGACACCTATGACGCTCTTC<br>ACATGCAGGCCCTGCCGCCTCGG |
| | | 139122 |
| 139122-aa ScFv domain CLL-1 CAR 4 | 42 | QVQLVESGGGLVQPGGSLRLSCAASGFTFSSYWMSWVRQAPGKGLEWVAN<br>INEDGSAKFYVDSVKGRFTISRDNAKNSLYLQMNSLRAEDTAVYFCARDL<br>RSGRYWGQGTLVTVSSGGGGSGGGGSGGGGSEIVLTQSPGTLSLSPGGRA<br>TLSCRASQSISGSFLAWYQQKPGQAPRLLIYGASSRATGIPDRFSGSGSG<br>TDFTLTISRLEPEDFAVYYCQQYGSSPPTFGLGTKLEIK |
| 139122-nt ScFv domain CLL-1 CAR 4 | 55 | CAAGTGCAACTCGTGGAATCTGGTGGAGGACTCGTGCAACCCGGAGGATC<br>ATTGCGACTCTCGTGTGCGGCATCCGGCTTTACCTTTTCATCCTACTGGA<br>TGTCCTGGGTCAGACAGGCCCCCGGGAAGGGACTGGAATGGGTCGCGAAC<br>ATCAACGAGGACGGCTCGGCCAAGTTCTACGTGGACTCCGTGAAGGGCCG |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| | | CTTCACGATCTCACGGGATAACGCCAAGAATTCCCTGTATCTGCAAATGAACAGCCTGAGGGCCGAGGACACTGCGGTGTACTTCTGCGCACGCGACCTGAGGTCCGGGAGATACTGGGGACAGGGCACCCTCGTGACCGTGTCGAGCGGAGGAGGGGGGTCGGGCGGCGGCGGTTCCGGTGGCGGCGGTAGCGAAATTGTGTTGACCCAGTCCCCTGGAACCCTGAGCCTGTCACCTGGAGGACGCGCCACCCTGTCCTGCCGGGCCAGCCAGAGCATCTCAGGGTCCTTCCTGGCTTGGTACCAGCAGAAGCCGGGACAGGCTCCGAGACTTCTGATCTACGGCGCCTCCTCGCGGGCGACCGGAATCCCGGATCGGTTCTCCGGCTCGGGAAGCGGAACTGACTTCACTCTTACCATTTCCCGCCTGGAGCCGGAAGATTTCGCCGTGTACTACTGCCAGCAGTACGGGTCATCCCCTCCAACCTTCGGCCTGGGAACTAAGCTGGAAATCAAA |
| 139122-aa VH of ScFv CLL-1 CAR 4 | 68 | QVQLVESGGGLVQPGGSLRLSCAASGFTFSSYWMSWVRQAPGKGLEWVANINEDGSAKFYVDSVKGRFTISRDNAKNSLYLQMNSLRAEDTAVYFCARDLRSGRYWGQGTLVTVSS |
| 139122-aa VL of ScFv CLL-1 CAR 4 | 81 | EIVLTQSPGTLSLSPGGRATLSCRASQSISGSFLAWYQQKPGQAPRLLIYGASSRATGIPDRFSGSGSGTDFTLTISRLEPEDFAVYYCQQYGSSPPTFGLGTKLEIK |
| 139122-aa Full CAR CLL-1 CAR 4 | 94 | MALPVTALLLPLALLLHAARPQVQLVESGGGLVQPGGSLRLSCAASGFTFSSYWMSWVRQAPGKGLEWVANINEDGSAKFYVDSVKGRFTISRDNAKNSLYLQMNSLRAEDTAVYFCARDLRSGRYWGQGTLVTVSSGGGGSGGGGSGGGGSEIVLTQSPGTLSLSPGGRATLSCRASQSISGSFLAWYQQKPGQAPRLLIYGASSRATGIPDRFSGSGSGTDFTLTISRLEPEDFAVYYCQQYGSSPPTFGLGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 139122-nt Full CAR CLL-1 CAR 4 | 107 | ATGGCCCTCCCTGTCACCGCCCTGCTGCTTCCGCTGGCTCTTCTGCTCCACGCCGCTCGGCCCCAAGTGCAACTCGTGGAATCTGGTGGAGGACTCGTGCAACCCGGAGGATCATTGCGACTCTCGTGTGCGGCATCCGGCTTTACCTTTTCATCCTACTGGATGTCCTGGGTCAGACAGGCCCCCGGGAAGGGACTGGAATGGGTCGCGAACATCAACGAGGACGGCTCGGCCAAGTTCTACGTGGACTCCGTGAAGGGCCGCTTCACGATCTCACGGGATAACGCCAAGAATTCCCTGTATCTGCAAATGAACAGCCTGAGGGCCGAGGACACTGCGGTGTACTTCTGCGCACGCGACCTGAGGTCCGGGAGATACTGGGGACAGGGCACCCTCGTGACCGTGTCGAGCGGAGGAGGGGGGTCGGGCGGCGGCGGTTCCGGTGGCGGCGGTAGCGAAATTGTGTTGACCCAGTCCCCTGGAACCCTGAGCCTGTCACCTGGAGGACGCGCCACCCTGTCCTGCCGGGCCAGCCAGAGCATCTCAGGGTCCTTCCTGGCTTGGTACCAGCAGAAGCCGGGACAGGCTCCGAGACTTCTGATCTACGGCGCCTCCTCGCGGGCGACCGGAATCCCGGATCGGTTCTCCGGCTCGGGAAGCGGAACTGACTTCACTCTTACCATTTCCCGCCTGGAGCCGGAAGATTTCGCCGTGTACTACTGCCAGCAGTACGGGTCATCCCCTCCAACCTTCGGCCTGGGAACTAAGCTGGAAATCAAAACCACTACCCCAGCACCGAGGCCACCCACCCCGGCTCCTACCATCGCCTCCCAGCCTCTGTCCCTGCGTCCGGAGGCATGTAGACCCGCAGCTGGTGGGGCCGTGCATACCCGGGGTCTTGACTTCGCCTGCGATATCTACATTTGGGCCCCTCTGGCTGGTACTTGCGGGGTCCTGCTGCTTTCACTCGTGATCACTCTTTACTGTAAGCGCGGTCGGAAGAAGCTGCTGTACATCTTTAAGCAACCCTTCATGAGGCCTGTGCAGACTACTCAAGAGGAGGACGGCTGTTCATGCCGGTTCCCAGAGGAGGAGGAAGGCGGCTGCGAACTGCGCGTGAAATTCAGCCGCAGCGCAGATGCTCCAGCCTACAAGCAGGGGCAGAACCAGCTCTACAACGAACTCAATCTTGGTCGGAGAGAGGAGTACGACGTGCTGGACAAGCGGAGAGGACGGGACCCAGAAATGGGCGGGAAGCCGCGCAGAAAGAATCCCCAAGAGGGCCTGTACAACGAGCTCCAAAAGGATAAGATGGCAGAAGCCTATAGCGAGATTGGTATGAAAGGGGAACGCAGAAGAGGCAAAGGCCACGACGGACTGTACCAGGGACTCAGCACCGCCACCAAGGACACCTATGACGCTCTTCACATGCAGGCCCTGCCGCCTCGG |
| | | 139117 |
| 139117-aa ScFv domain CLL-1 CAR 5 | 43 | EVQLQQSGPGLVRPSETLSLTCTVSGGPVRSGSHYWNWIRQPPGRGLEWIGYIYYSGSTNYNPSLENRVTISIDTSNNHFSLKLSSVTAADTALYFCARGTATFDWNFPFDSWGQGTLVTVSSGGGGSGGGGSGSGGSDIQMTQSPSSLSASIGDRVTITCRASQSISSYLNWYQQKPGKAPKLLIYAASSLQSGVPSRFSGSGSGTDFTLTISSLQPEDFATYYCQQSYSTPWTFGQGTKLEIK |
| 139117-nt ScFv domain CLL-1 CAR 5 | 56 | GAAGTGCAACTCCAACAATCCGGTCCAGGACTCGTCAGACCCTCCGAAACTCTCTCGCTTACATGCACTGTGTCCGGCGGCCCTGTGCGGTCCGGCTCTCATTACTGGAACTGGATTCGCCAGCCCCCGGGACGCGGACTGGAGTGGATCGGCTACATCTATTACTCGGGGTCGACTAACTACAACCCGAGCCTGGAAAA |

TABLE 8-continued

| Amino Acid and Nucleic Acid Sequences of the anti-CLL-1 scFv domains and CLL-1 CAR molecules | | |
|---|---|---|
| Name/ Description | SEQ ID NO: | Sequence |
| | | TAGAGTGACCATCTCAATCGACACGTCCAACAACCACTTCTCGCTGAAGT TGTCCTCCGTGACTGCCGCCGATACTGCCCTGTACTTCTGTGCTCGCGGA ACCGCCACCTTCGACTGGAACTTCCCTTTTGACTCATGGGGCCAGGGGAC CCTTGTGACCGTGTCCAGCGGAGGAGGAGGCTCCGGTGGTGGCGGGAGCG GTAGCGGCGGAAGCGACATCCAGATGACCCAGTCACCGTCCTCGCTGTCC GCATCCATTGGGGATCGGGTCACTATTACTTGCCGGGCGTCCCAGTCCAT CTCGTCCTACCTGAACTGGTATCAGCAGAAGCCAGGGAAAGCCCCCAAGC TGCTGATCTACGCGGCCAGCAGCCTGCAGTCAGGAGTGCCTTCAAGGTTT AGCGGCAGCGGATCGGGAACCGACTTCACCCTGACCATTTCCTCCCTCCA ACCCGAGGATTTCGCCACCTACTACTGCCAGCAGTCCTACTCCACCCCGT GGACCTTCGGACAGGGAACCAAGCTGGAGATCAAG |
| 139117-aa VH of ScFv CLL-1 CAR 5 | 69 | EVQLQQSGPGLVRPSETLSLTCTVSGGPVRSGSHYWNWIRQPPGRGLEWI GYIYYSGSTNYNPSLENRVTISIDTSNNHFSLKLSSVTAADTALYFCARG TATFDWNFPFDSWGQGTLVTVSS |
| 139117-aa VL of ScFv CLL-1 CAR 5 | 82 | DIQMTQSPSSLSASIGDRVTITCRASQSISSYLNWYQQKPGKAPKLLIYA ASSLQSGVPSRFSGSGSGTDFTLTISSLQPEDFATYYCQQSYSTPWTFGQ GTKLEIK |
| 139117-aa Full CAR CLL-1 CAR 5 | 95 | MALPVTALLLPLALLLHAARPEVQLQQSGPGLVRPSETLSLTCTVSGGPV RSGSHYWNWIRQPPGRGLEWIGYIYYSGSTNYNPSLENRVTISIDTSNNH FSLKLSSVTAADTALYFCARGTATFDWNFPFDSWGQGTLVTVSSGGGGSG GGGSGSGGSDIQMTQSPSSLSASIGDRVTITCRASQSISSYLNWYQQKPG KAPKLLIYAASSLQSGVPSRFSGSGSGTDFTLTISSLQPEDFATYYCQQS YSTPWTFGQGTKLEIKTTTPAPRPPTPAPTIASQPLSLRPEACRPAAGGA VHTRGLDFACDIYIWAPLAGTCGVLLLSLVITLYCKRGRKKLLYIFKQPF MRPVQTTQEEDGCSCRFPEEEEGGCELRVKFSRSADAPAYKQGQNQLYNE LNLGRREEYDVLDKRRGRDPEMGGKPRRKNPQEGLYNELQKDKMAEAYSE IGMKGERRRGKGHDGLYQGLSTATKDTYDALHMQALPPR |
| 139117-nt Full CAR CLL-1 CAR 5 | 108 | ATGGCCCTCCCTGTCACCGCCCTGCTGCTTCCGCTGGCTCTTCTGCTCCA CGCCGCTCGGCCCGAAGTGCAACTCCAACAATCCGGTCCAGGACTCGTCA GACCCTCCGAAACTCTCTCGCTTACATGCACTGTGTCCGGCGGCCCTGTG CGGTCCGGCTCTCATTACTGGAACTGGATTCGCCAGCCCCCGGGACGCGG ACTGGAGTGGATCGGCTACATCTATTACTCGGGGTCGACTAACTACAACC CGAGCCTGGAAAATAGAGTGACCATCTCAATCGACACGTCCAACAACCAC TTCTCGCTGAAGTTGTCCTCCGTGACTGCCGCCGATACTGCCCTGTACTT CTGTGCTCGCGGAACCGCCACCTTCGACTGGAACTTCCCTTTTGACTCAT GGGGCCAGGGGACCCTTGTGACCGTGTCCAGCGGAGGAGGAGGCTCCGGT GGTGGCGGGAGCGGTAGCGGCGGAAGCGACATCCAGATGACCCAGTCACC GTCCTCGCTGTCCGCATCCATTGGGGATCGGGTCACTATTACTTGCCGGG CGTCCCAGTCCATCTCGTCCTACCTGAACTGGTATCAGCAGAAGCCAGGG AAAGCCCCCAAGCTGCTGATCTACGCGGCCAGCAGCCTGCAGTCAGGAGT GCCTTCAAGGTTTAGCGGCAGCGGATCGGGAACCGACTTCACCCTGACCA TTTCCTCCCTCCAACCCGAGGATTTCGCCACCTACTACTGCCAGCAGTCC TACTCCACCCCGTGGACCTTCGGACAGGGAACCAAGCTGGAGATCAAGAC CACTACCCCAGCACCGAGGCCACCCACCCCGGCTCCTACCATCGCCTCCC AGCCTCTGTCCCTGCGTCCGGAGGCATGTAGACCCGCAGCTGGTGGGGCC GTGCATACCCGGGGTCTTGACTTCGCCTGCGATATCTACATTTGGGCCCC TCTGGCTGGTACTTGCGGGGTCCTGCTGCTTTCACTCGTGATCACTCTTT ACTGTAAGCGCGGTCGGAAGAAGCTGCTGTACATCTTTAAGCAACCCTTC ATGAGGCCTGTGCAGACTACTCAAGAGGAGGACGGCTGTTCATGCCGGTT CCCAGAGGAGGAGGAAGGCGGCTGCGAACTGCGCGTGAAATTCAGCCGCA GCGCAGATGCTCCAGCCTACAAGCAGGGGCAGAACCAGCTCTACAACGAA CTCAATCTTGGTCGGAGAGAGGAGTACGACGTGCTGGACAAGCGGAGAGG ACGGGACCCAGAAATGGGCGGGAAGCCGCGCAGAAAGAATCCCCAAGAGG GCCTGTACAACGAGCTCCAAAAGGATAAGATGGCAGAAGCCTATAGCGAG ATTGGTATGAAAGGGGAACGCAGAAGAGGCAAAGGCCACGACGGACTGTA CCAGGGACTCAGCACCGCCACCAAGGACACCTATGACGCTCTTCACATGC AGGCCCTGCCGCCTCGG |
| 139120 | | |
| 139120-aa ScFv domain CLL-1 CAR 7 | 45 | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARDP SSSGSYYMEDSYYYGMDVWGQGTTVTVSSGGGGSGGGGSGGGGSNFMLTQ PHSVSESPGKTVTISCTGSSGSIASNYVQWYQQRPGSAPTTVIYEDNQRP SGVPDRFSGSIDSSSNSASLTISGLKTEDEADYYCQSYDSSNQVVFGGGT KLTVL |
| 139120-nt ScFv domain | 58 | GAAGTGCAATTGGTGGAATCTGGAGGAGGACTTGTGAAACCTGGTGGAAG CCTGAGACTTTCCTGTGCGGCCTCGGGATTCACTTTCTCCTCCTACTCCA |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| CLL-1 CAR 7 | | TGAACTGGGTCAGACAGGCCCCTGGGAAGGGACTGGAATGGGTGTCATCC ATCTCCTCCTCATCGTCGTACATCTACTACGCCGATAGCGTGAAGGGGCG GTTCACCATTTCCCGGGACAACGCTAAGAACAGCCTCTATCTGCAAATGA ATTCCCTCCGCGCCGAGGACACTGCCGTGTACTACTGCGCGAGGGACCCC TCATCAAGCGGCAGCTACTACATGGAGGACTCGTATTACTACGGAATGGA CGTCTGGGGCCAGGGAACCACTGTGACGGTGTCCTCCGGTGGAGGGGGCT CCGGGGGCGGGGGATCTGGCGGAGGAGGCTCCAACTTCATGCTGACCCAG CCGCACTCCGTGTCCGAAAGCCCCGGAAAGACCGTGACAATTTCCTGCAC CGGGTCCTCCGGCTCGATCGCATCAAACTACGTGCAGTGGTACCAGCAGC GCCCGGGCAGCGCCCCCACCACTGTCATCTACGAGGATAACCAGCGGCCG TCGGGTGTCCCAGACCGGTTTTCCGGTTCGATCGATAGCAGCAGCAACAG CGCCTCCCTGACCATTTCCGGCCTCAAGACCGAGGATGAGGCTGACTACT ACTGCCAGTCGTATGACTCCTCGAACCAAGTGGTGTTCGGTGGCGGCACC AAGCTGACTGTGCTG |
| 139120-aa VH of ScFv CLL-1 CAR 7 | 71 | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARDP SSSGSYYMEDSYYYGMDVWGQGTTVTVSS |
| 139120-aa VL of ScFv CLL-1 CAR 7 | 84 | NFMLTQPHSVSESPGKTVTISCTGSSGSIASNYVQWYQQRPGSAPTTVIY EDNQRPSGVPDRFSGSIDSSSNSASLTISGLKTEDEADYYCQSYDSSNQV VFGGGTKLTVL |
| 139120-aa Full CAR CLL-1 CAR 7 | 97 | MALPVTALLLPLALLLHAARPEVQLVESGGGLVKPGGSLRLSCAASGFTF SSYSMNWVRQAPGKGLEWVSSISSSSSYIYYADSVKGRFTISRDNAKNSL YLQMNSLRAEDTAVYYCARDPSSSGSYYMEDSYYYGMDVWGQGTTVTVSS GGGGSGGGGSGGGGSNFMLTQPHSVSESPGKTVTISCTGSSGSIASNYVQ WYQQRPGSAPTTVIYEDNQRPSGVPDRFSGSIDSSSNSASLTISGLKTED EADYYCQSYDSSNQVVFGGGTKLTVLTTTPAPRPPTPAPTIASQPLSLRP EACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR |
| 139120-nt Full CAR CLL-1 CAR 7 | 110 | ATGGCCCTCCCTGTCACCGCCCTGCTGCTTCCGCTGGCTCTTCTGCTCCA CGCCGCTCGGCCCGAAGTGCAATTGGTGGAATCTGGAGGAGGACTTGTGA AACCTGGTGGAAGCCTGAGACTTTCCTGTGCGGCCTCGGGATTCACTTTC TCCTCCTACTCCATGAACTGGGTCAGACAGGCCCCTGGGAAGGGACTGGA ATGGGTGTCATCCATCTCCTCCTCATCGTCGTACATCTACTACGCCGATA GCGTGAAGGGGCGGTTCACCATTTCCCGGGACAACGCTAAGAACAGCCTC TATCTGCAAATGAATTCCCTCCGCGCCGAGGACACTGCCGTGTACTACTG CGCGAGGGACCCCTCATCAAGCGGCAGCTACTACATGGAGGACTCGTATT ACTACGGAATGGACGTCTGGGGCCAGGGAACCACTGTGACGGTGTCCTCC GGTGGAGGGGGCTCCGGGGGCGGGGGATCTGGCGGAGGAGGCTCCAACTT CATGCTGACCCAGCCGCACTCCGTGTCCGAAAGCCCCGGAAAGACCGTGA CAATTTCCTGCACCGGGTCCTCCGGCTCGATCGCATCAAACTACGTGCAG TGGTACCAGCAGCGCCCGGGCAGCGCCCCCACCACTGTCATCTACGAGGA TAACCAGCGGCCGTCGGGTGTCCCAGACCGGTTTTCCGGTTCGATCGATA GCAGCAGCAACAGCGCCTCCCTGACCATTTCCGGCCTCAAGACCGAGGAT GAGGCTGACTACTACTGCCAGTCGTATGACTCCTCGAACCAAGTGGTGTT CGGTGGCGGCACCAAGCTGACTGTGCTGACCACTACCCCAGCACCGAGGC CACCCACCCCGGCTCCTACCATCGCCTCCCAGCCTCTGTCCCTGCGTCCG GAGGCATGTAGACCCGCAGCTGGTGGGGCCGTGCATACCCGGGGTCTTGA CTTCGCCTGCGATATCTACATTTGGGCCCCTCTGGCTGGTACTTGCGGGG TCCTGCTGCTTTCACTCGTGATCACTCTTTACTGTAAGCGCGGTCGGAAG AAGCTGCTGTACATCTTTAAGCAACCCTTCATGAGGCCTGTGCAGACTAC TCAAGAGGAGGACGGCTGTTCATGCCGGTTCCCAGAGGAGGAGGAAGGCG GCTGCGAACTGCGCGTGAAATTCAGCCGCAGCGCAGATGCTCCAGCCTAC AAGCAGGGGCAGAACCAGCTCTACAACGAACTCAATCTTGGTCGGAGAGA GGAGTACGACGTGCTGGACAAGCGGAGAGGACGGGACCCAGAAATGGGCG GGAAGCCGCGCAGAAAGAATCCCCAAGAGGGCCTGTACAACGAGCTCCAA AAGGATAAGATGGCAGAAGCCTATAGCGAGATTGGTATGAAAGGGGAACG CAGAAGAGGCAAAGGCCACGACGGACTGTACCAGGGACTCAGCACCGCCA CCAAGGACACCTATGACGCTCTTCACATGCAGGCCCTGCCGCCTCGG |
| 139121 | | |
| 139121-aa ScFv domain CLL-1 CAR 8 | 46 | QVNLRESGGGLVQPGGSLRLSCAASGFTFSSYEMNWVRQAPGKGLEWVSY ISSSGSTIYYADSVKGRFTISRDNAKNSLYLQMNSLRAEDTAVYYCAREA LGSSWEWGQGTTVTVSSGGGGSGGGGSGGGGSDIQMTQSPSSLSASVGDR VTITCQASQDISNYLNWYQQKPGKAPKLLIYDASNLETGVPSRFSGSGSG TDFTFTISSLQPEDIATYYCQQYDNLPLTFGGGTKLEIK |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| 139121-nt ScFv domain CLL-1 CAR 8 | 59 | CAAGTGAACCTGAGAGAAAGCGGCGGAGGACTTGTGCAACCTGGAGGAAGCCTGAGACTGTCATGTGCCGCGTCCGGCTTCACCTTCTCGTCCTACGAGATGAACTGGGTCCGCCAGGCACCGGGCAAAGGACTGGAATGGGTGTCCTACATTTCCTCGTCCGGGTCCACCATCTATTACGCCGACTCCGTGAAGGGACGGTTCACCATCTCCCGGGACAACGCCAAGAACTCCCTCTACCTCCAAATGAACTCACTGAGGGCAGAGGACACTGCGGTCTACTACTGCGCCCGCGAAGCTTTGGGTAGCTCCTGGGAGTGGGGCCAGGGAACCACTGTGACCGTGTCCTCGGGTGGAGGGGGCTCCGGTGGCGGGGGTTCAGGGGGTGGCGGAAGCGATATCCAGATGACTCAGTCACCAAGCTCCCTGAGCGCCTCAGTGGGAGATCGGGTCACAATCACGTGCCAGGCGTCCCAGGACATTTCTAACTACCTCAATTGGTACCAGCAGAAGCCGGGGAAGGCCCCCAAGCTTCTGATCTACGATGCCTCCAACCTGGAAACCGGCGTGCCCTCCCGCTTCTCGGGATCGGGCAGCGGCACTGACTTCACCTTTACCATCTCGTCCCTGCAACCTGAGGACATCGCCACCTATTACTGCCAGCAGTACGATAACCTCCCGCTGACTTTCGGAGGCGGAACTAAGCTGGAGATTAAG |
| 139121-aa VH of ScFv CLL-1 CAR 8 | 72 | QVNLRESGGGLVQPGGSLRLSCAASGFTFSSYEMNWVRQAPGKGLEWVSYISSSGSTIYYADSVKGRFTISRDNAKNSLYLQMNSLRAEDTAVYYCAREALGSSWEWGQGTTVTVSS |
| 139121-aa VL of ScFv CLL-1 CAR 8 | 85 | DIQMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKLEIK |
| 139121-aa Full CAR CLL-1 CAR 8 | 98 | MALPVTALLLPLALLLHAARPQVNLRESGGGLVQPGGSLRLSCAASGFTFSSYEMNWVRQAPGKGLEWVSYISSSGSTIYYADSVKGRFTISRDNAKNSLYLQMNSLRAEDTAVYYCAREALGSSWEWGQGTTVTVSSGGGGSGGGGSGGGGSDIQMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 139121-nt Full CAR CLL-1 CAR 8 | 111 | ATGGCCCTCCCTGTCACCGCCCTGCTGCTTCCGCTGGCTCTTCTGCTCCACGCCGCTCGGCCCCAAGTGAACCTGAGAGAAAGCGGCGGAGGACTTGTGCAACCTGGAGGAAGCCTGAGACTGTCATGTGCCGCGTCCGGCTTCACCTTCTCGTCCTACGAGATGAACTGGGTCCGCCAGGCACCGGGCAAAGGACTGGAATGGGTGTCCTACATTTCCTCGTCCGGGTCCACCATCTATTACGCCGACTCCGTGAAGGGACGGTTCACCATCTCCCGGGACAACGCCAAGAACTCCCTCTACCTCCAAATGAACTCACTGAGGGCAGAGGACACTGCGGTCTACTACTGCGCCCGCGAAGCTTTGGGTAGCTCCTGGGAGTGGGGCCAGGGAACCACTGTGACCGTGTCCTCGGGTGGAGGGGGCTCCGGTGGCGGGGGTTCAGGGGGTGGCGGAAGCGATATCCAGATGACTCAGTCACCAAGCTCCCTGAGCGCCTCAGTGGGAGATCGGGTCACAATCACGTGCCAGGCGTCCCAGGACATTTCTAACTACCTCAATTGGTACCAGCAGAAGCCGGGGAAGGCCCCCAAGCTTCTGATCTACGATGCCTCCAACCTGGAAACCGGCGTGCCCTCCCGCTTCTCGGGATCGGGCAGCGGCACTGACTTCACCTTTACCATCTCGTCCCTGCAACCTGAGGACATCGCCACCTATTACTGCCAGCAGTACGATAACCTCCCGCTGACTTTCGGAGGCGGAACTAAGCTGGAGATTAAGACCACTACCCCAGCACCGAGGCCACCCACCCCGGCTCCTACCATCGCCTCCCAGCCTCTGTCCCTGCGTCCGGAGGCATGTAGACCCGCAGCTGGTGGGGCCGTGCATACCCGGGGTCTTGACTTCGCCTGCGATATCTACATTTGGGCCCCTCTGGCTGGTACTTGCGGGGTCCTGCTGCTTTCACTCGTGATCACTCTTTACTGTAAGCGCGGTCGGAAGAAGCTGCTGTACATCTTTAAGCAACCCTTCATGAGGCCTGTGCAGACTACTCAAGAGGAGGACGGCTGTTCATGCCGGTTCCCAGAGGAGGAGGAAGGCGGCTGCGAACTGCGCGTGAAATTCAGCCGCAGCGCAGATGCTCCAGCCTACAAGCAGGGGCAGAACCAGCTCTACAACGAACTCAATCTTGGTCGGAGAGAGGAGTACGACGTGCTGGACAAGCGGAGAGGACGGGACCCAGAAATGGGCGGGAAGCCGCGCAGAAAGAATCCCCAAGAGGGCCTGTACAACGAGCTCCAAAAGGATAAGATGGCAGAAGCCTATAGCGAGATTGGTATGAAAGGGGAACGCAGAAGAGGCAAAGGCCACGACGGACTGTACCAGGGACTCAGCACCGCCACCAAGGACACCTATGACGCTCTTCACATGCAGGCCCTGCCGCCTCGG |
| 146264 | | |
| 146264-aa ScFv domain CLL-1 CAR 13 | 51 | QVQLVQSGAEVKKSGASVKVSCKASGYPFTGYYIQWVRQAPGQGLEWMGWIDPNSGNTGYAQKFQGRVTMTRNTSISTAYMELSSLRSEDTAVYYCASDSYGYYYGMDVWGQGTLVTVSSGGGGSGGGGSGGGGSGGGGSDIQMTQSPSSLSASVGDRVTFTCRASQGISSALAWYQQKPGKPPKLLIYDASSLESGVPSRFSGSGSGTDFTLTISSLQPEDFATYYCQQFNNYPLTFGGGTKVEIK |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| 146264-nt ScFv domain CLL-1 CAR 13 | 64 | CAAGTGCAACTCGTCCAGTCCGGTGCAGAAGTGAAAAAGAGCGGAGCCTC AGTGAAAGTGTCCTGCAAGGCCTCCGGTTACCCCTTCACTGGATACTACA TTCAGTGGGTCCGCCAAGCCCCGGGACAGGGTCTGGAGTGGATGGGGTGG ATTGACCCTAACTCGGGAAATACGGGATACGCGCAGAAGTTCCAGGGCCG CGTGACCATGACCAGGAACACCTCGATCAGCACCGCCTACATGGAACTGT CCTCCCTGCGGTCGGAGGATACTGCCGTGTACTACTGCGCCTCCGATTCC TATGGGTACTACTACGGAATGGACGTCTGGGGACAGGGCACCCTCGTGAC CGTGTCCTCGGGAGGCGGAGGGAGCGGCGGGGGTGGATCGGGAGGAGGCG GCTCCGGCGGCGGCGGTAGCGACATCCAGATGACCCAGTCACCATCAAGC CTTAGCGCCTCCGTGGGCGACAGAGTGACATTCACTTGTCGGGCGTCCCA GGGAATCTCCTCCGCTCTGGCTTGGTATCAGCAGAAGCCTGGGAAGCCTC CGAAGCTGTTGATCTACGACGCGAGCAGCCTGGAATCAGGGGTGCCCTCC CGGTTTTCCGGGTCCGGTTCTGGCACCGATTTCACCCTGACCATTTCGTC CCTCCAACCCGAGGACTTCGCCACTTACTACTGCCAGCAGTTCAACAACT ACCCGCTGACCTTCGGAGGAGGCACTAAGGTCGAGATCAAG |
| 146264-aa VH of ScFv CLL-1 CAR 13 | 77 | QVQLVQSGAEVKKSGASVKVSCKASGYPFTGYYIQWVRQAPGQGLEWMGW IDPNSGNTGYAQKFQGRVTMTRNTSISTAYMELSSLRSEDTAVYYCASDS YGYYYGMDVWGQGTLVTVSS |
| 146264-aa VL of ScFv CLL-1 CAR 13 | 90 | DIQMTQSPSSLSASVGDRVTFTCRASQGISSALAWYQQKPGKPPKLLIYD ASSLESGVPSRFSGSGSGTDFTLTISSLQPEDFATYYCQQFNNYPLTFGG GTKVEIK |
| 146264-aa Full CAR CLL-1 CAR 13 | 103 | MALPVTALLLPLALLLHAARPQVQLVQSGAEVKKSGASVKVSCKASGYPF TGYYIQWVRQAPGQGLEWMGWIDPNSGNTGYAQKFQGRVTMTRNTSISTA YMELSSLRSEDTAVYYCASDSYGYYYGMDVWGQGTLVTVSSGGGGSGGGG SGGGGSGGGGSDIQMTQSPSSLSASVGDRVTFTCRASQGISSALAWYQQK PGKPPKLLIYDASSLESGVPSRFSGSGSGTDFTLTISSLQPEDFATYYCQ QFNNYPLTFGGGTKVEIKTTTPAPRPPTPAPTIASQPLSLRPEACRPAAG GAVHTRGLDFACDIYIWAPLAGTCGVLLLSLVITLYCKRGRKKLLYIFKQ PFMRPVQTTQEEDGCSCRFPEEEEGGCELRVKFSRSADAPAYKQGQNQLY NELNLGRREEYDVLDKRRGRDPEMGGKPRRKNPQEGLYNELQKDKMAEAY SEIGMKGERRRGKGHDGLYQGLSTATKDTYDALHMQALPPR |
| 146264-nt Full CAR CLL-1 CAR 13 | 116 | ATGGCCCTCCCTGTCACCGCCCTGCTGCTTCCGCTGGCTCTTCTGCTCCA CGCCGCTCGGCCCCAAGTGCAACTCGTCCAGTCCGGTGCAGAAGTGAAAA AGAGCGGAGCCTCAGTGAAAGTGTCCTGCAAGGCCTCCGGTTACCCCTTC ACTGGATACTACATTCAGTGGGTCCGCCAAGCCCCGGGACAGGGTCTGGA GTGGATGGGGTGGATTGACCCTAACTCGGGAAATACGGGATACGCGCAGA AGTTCCAGGGCCGCGTGACCATGACCAGGAACACCTCGATCAGCACCGCC TACATGGAACTGTCCTCCCTGCGGTCGGAGGATACTGCCGTGTACTACTG CGCCTCCGATTCCTATGGGTACTACTACGGAATGGACGTCTGGGGACAGG GCACCCTCGTGACCGTGTCCTCGGGAGGCGGAGGGAGCGGCGGGGGTGGA TCGGGAGGAGGCGGCTCCGGCGGCGGCGGTAGCGACATCCAGATGACCCA GTCACCATCAAGCCTTAGCGCCTCCGTGGGCGACAGAGTGACATTCACTT GTCGGGCGTCCCAGGGAATCTCCTCCGCTCTGGCTTGGTATCAGCAGAAG CCTGGGAAGCCTCCGAAGCTGTTGATCTACGACGCGAGCAGCCTGGAATC AGGGGTGCCCTCCCGGTTTTCCGGGTCCGGTTCTGGCACCGATTTCACCC TGACCATTTCGTCCCTCCAACCCGAGGACTTCGCCACTTACTACTGCCAG CAGTTCAACAACTACCCGCTGACCTTCGGAGGAGGCACTAAGGTCGAGAT CAAGACCACTACCCCAGCACCGAGGCCACCCACCCCGGCTCCTACCATCG CCTCCCAGCCTCTGTCCCTGCGTCCGGAGGCATGTAGACCCGCAGCTGGT GGGGCCGTGCATACCCGGGGTCTTGACTTCGCCTGCGATATCTACATTTG GGCCCCTCTGGCTGGTACTTGCGGGGTCCTGCTGCTTTCACTCGTGATCA CTCTTTACTGTAAGCGCGGTCGGAAGAAGCTGCTGTACATCTTTAAGCAA CCCTTCATGAGGCCTGTGCAGACTACTCAAGAGGAGGACGGCTGTTCATG CCGGTTCCCAGAGGAGGAGGAAGGCGGCTGCGAACTGCGCGTGAAATTCA GCCGCAGCGCAGATGCTCCAGCCTACAAGCAGGGGCAGAACCAGCTCTAC AACGAACTCAATCTTGGTCGGAGAGAGGAGTACGACGTGCTGGACAAGCG GAGAGGACGGGACCCAGAAATGGGCGGGAAGCCGCGCAGAAAGAATCCCC AAGAGGGCCTGTACAACGAGCTCCAAAAGGATAAGATGGCAGAAGCCTAT AGCGAGATTGGTATGAAAGGGGAACGCAGAAGAGGCAAAGGCCACGACGG ACTGTACCAGGGACTCAGCACCGCCACCAAGGACACCTATGACGCTCTTC ACATGCAGGCCCTGCCGCCTCGG |
| | | 181268 |
| 181268-aa VH of ScFv | 195 | EVQLVESGGGLVQPGGSLRLSCAASGFTFSSYEMNWVRQAPGKGLEWVSY ISSSGSTIYYADSVKGRFTISRDNAKNSLYLQMNSLRAEDTAVYYCARDP YSSSWHDAFDIWGQGTMVTVSS |
| 181268-aa | 196 | EIVLTQSPGTLSLSPGERATLSCRASQSVSSSYLAWYQQKPGQAPRLLIY |

TABLE 8-continued

Amino Acid and Nucleic Acid Sequences of the anti-CLL-1 scFv domains and CLL-1 CAR molecules

| Name/ Description | SEQ ID NO: | Sequence |
|---|---|---|
| VL of ScFv | | GASSRATGIPDRFSGSGSGTDFTLTISRLEPEDFAVYYCQQYGSSPLTFG GGTKVDIK |
| 181268-aa Full CAR | 197 | MALPVTALLLPLALLLHAARPEVQLVESGGGLVQPGGSLRLSCAASGFTF SSYEMNWVRQAPGKGLEWVSYISSSGSTIYYADSVKGRFTISRDNAKNSL YLQMNSLRAEDTAVYYCARDPYSSSWHDAFDIWGQGTMVTVSSGGGGSGG GGSGGGGSEIVLTQSPGTLSLSPGERATLSCRASQSVSSSYLAWYQQKPG QAPRLLIYGASSRATGIPDRFSGSGSGTDFTLTISRLEPEDFAVYYCQQY GSSPLTFGGGTKVDIKTTTPAPRPPTPAPTIASQPLSLRPEACRPAAGGA VHTRGLDFACDIYIWAPLAGTCGVLLLSLVITLYCKRGRKKLLYIFKQPF MRPVQTTQEEDGCSCRFPEEEEGGCELRVKFSRSADAPAYKQGQNQLYNE LNLGRREEYDVLDKRRGRDPEMGGKPRRKNPQEGLYNELQKDKMAEAYSE IGMKGERRRGKGHDGLYQGLSTATKDTYDALHMQALPPR |
| 181268-nt Full CAR | 198 | ATGGCCCTCCCTGTCACCGCCCTGCTGCTTCCGCTGGCTCTTCTGCTCCA CGCCGCTCGGCCCGAAGTGCAACTCGTGGAAAGCGGTGGAGGTCTTGTGC AACCTGGAGGTTCCTTGCGCCTGTCATGTGCAGCTTCCGGCTTCACTTTC TCCTCGTACGAGATGAATTGGGTGCGGCAGGCGCCTGGAAAGGGGCTGGA ATGGGTGTCCTACATCTCAAGCTCCGGCTCGACCATCTACTACGCGGACA GCGTGAAGGGGCGGTTCACGATTTCGAGGGACAACGCCAAGAACTCGCTC TATCTGCAAATGAACTCCCTGAGAGCCGAGGACACCGCTGTGTATTACTG CGCCCGGGACCCCTACTCCTCCTCATGGCACGACGCCTTTGATATCTGGG GCCAGGGAACCATGGTCACCGTCAGCAGCGGGGGCGGAGGTTCCGGGGGA GGGGGCTCCGGCGGAGGAGGCTCCGAGATTGTGTTGACTCAGAGCCCGGG TACCCTGTCGCTGAGCCCCGGAGAGCGGGCCACCCTTTCATGCCGCGCCA GCCAGTCCGTGTCCTCATCCTACCTCGCGTGGTACCAGCAGAAACCTGGC CAGGCCCCGCGGCTGCTGATCTACGGCGCCTCCTCGCGCGCAACCGGAAT CCCCGACCGGTTCTCCGGGTCTGGCAGCGGAACCGACTTCACTCTCACCA TTTCGAGGCTGGAGCCGGAAGATTTCGCCGTGTACTACTGCCAGCAGTAC GGCTCCTCGCCACTGACTTTCGGCGGAGGAACCAAGGTCGATATCAAGAC CACTACCCCAGCACCGAGGCCACCCACCCCGGCTCCTACCATCGCCTCCC AGCCTCTGTCCCTGCGTCCGGAGGCATGTAGACCCGCAGCTGGTGGGGCC GTGCATACCCGGGGTCTTGACTTCGCCTGCGATATCTACATTTGGGCCCC TCTGGCTGGTACTTGCGGGGTCCTGCTGCTTTCACTCGTGATCACTCTTT ACTGTAAGCGCGGTCGGAAGAAGCTGCTGTACATCTTTAAGCAACCCTTC ATGAGGCCTGTGCAGACTACTCAAGAGGAGGACGGCTGTTCATGCCGGTT CCCAGAGGAGGAGGAAGGCGGCTGCGAACTGCGCGTGAAATTCAGCCGCA GCGCAGATGCTCCAGCCTACAAGCAGGGGCAGAACCAGCTCTACAACGAA CTCAATCTTGGTCGGAGAGAGGAGTACGACGTGCTGGACAAGCGGAGAGG ACGGGACCCAGAAATGGGCGGGAAGCCGCGCAGAAAGAATCCCCAAGAGG GCCTGTACAACGAGCTCCAAAAGGATAAGATGGCAGAAGCCTATAGCGAG ATTGGTATGAAAGGGGAACGCAGAAGAGGCAAAGGCCACGACGGACTGTA CCAGGGACTCAGCACCGCCACCAAGGACACCTATGACGCTCTTCACATGC AGGCCCTGCCGCCTCGG |

In embodiments, the CAR scFv fragments were then cloned into lentiviral vectors to create a full length CAR construct in a single coding frame, and using the EF1 alpha promoter for expression (SEQ ID NO: 11).

EF1 Alpha Promoter

CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

-continued

GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGGAGGGGTTTTATGCGATGGAGTTTCCCCACACTGAGTGGGTGG

-continued

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA

Gly/Ser (SEQ ID NO: 25)

GGGGS

Gly/Ser (SEQ ID NO: 26): This sequence may encompass 1-6 "Gly Gly Gly Gly Ser" repeating units

GGGGSGGGGS GGGGSGGGGS GGGGSGGGGS

Gly/Ser (SEQ ID NO: 27)

GGGGSGGGGS GGGGSGGGGS

Gly/Ser (SEQ ID NO: 28)

GGGGSGGGGS GGGGS

Gly/Ser (SEQ ID NO: 29)

GGGS

PolyA: $(A)_{5000}$ (SEQ ID NO: 30)

This sequence may encompass 50-5000 adenines.

PolyA: $(T)_{100}$ (SEQ ID NO: 31)

PolyA: $(T)_{5000}$ (SEQ ID NO: 32)

This sequence may encompass 50-5000 thymines.

PolyA: $(A)_{5000}$ (SEQ ID NO: 33)

This sequence may encompass 100-5000 adenines.

PolyA: $(A)_{400}$ (SEQ ID NO: 34)

PolyA: $(A)_{2000}$ (SEQ ID NO: 35)

Gly/Ser (SEQ ID NO: 38): This sequence may encompass 1-10 "Gly Gly Gly Ser" repeating units

GGGSGGGSGG GSGGGSGGGS GGGSGGGSGG GSGGGSGGGS

In one embodiment, the CLL-1 CAR may comprise one or more, e.g., one, two, or three, CDRs of the heavy chain variable domain and/or one or more, e.g., one, two, or three, CDRs of the light chain variable domain, or the variable heavy chain (VH) or the variable light chain (VL) of the anti-CLL-1 (CLEC12A) antibody disclosed in PCT Publication WO2014/051433, the entire contents of which are hereby incorporated by reference.

The CAR scFv fragments can be cloned into lentiviral vectors to create a full length CAR construct in a single coding frame, and using the EF1 alpha promoter for expression (SEQ ID NO: 11).

The CAR construct can include a Gly/Ser linker having one or more of the following sequences: GGGGS (SEQ ID NO:25); encompassing 1-6 "Gly Gly Gly Gly Ser" repeating units, e.g., GGGGSGGGGS GGGGSGGGGS GGGGSGGGGS (SEQ ID NO:26); GGGGSGGGGS GGGGSGGGGS (SEQ ID NO:27); GGGGSGGGGS GGGGS (SEQ ID NO:28); GGGS (SEQ ID NO:29); or encompassing 1-10 "Gly Gly Gly Ser" repeating units, e.g., GGGSGGGSGG GSGGGSGGGS GGGSGGGSGG GSGGGSGGGS (SEQ ID NO:38). In embodiments, the CAR construct include a poly A sequence, e.g., a sequence encompassing 50-5000 or 100-5000 adenines (e.g., SEQ ID NO:30, SEQ ID NO:33, SEQ ID NO:34 or SEQ ID NO:35), or a sequence encompassing 50-5000 thymines (e.g., SEQ ID NO:31, SEQ ID NO:32). Alternatively, the CAR construct can include, for example, a linker including the sequence GSTSGSGKPGSGEGSTKG (SEQ ID NO: 486)

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254;

bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, U.S. Pat. Nos. 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 64). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for CLL-1, e.g., comprises a scFv as described herein, e.g., as described in Table 8, or comprises the light chain CDRs and/or heavy chain CDRs from a CLL-1 scFv described herein, and a second immunoglobulin variable domain sequence that has binding specificity for a second epitope on a different antigen. In some aspects the second immunoglobulin variable domain sequence has binding specificity for an antigen expressed on AML cells, e.g., an antigen other than CLL-1. For example, the second immunoglobulin variable domain sequence has binding specificity for CD123. As another example, the second immunoglobulin variable domain sequence has binding specificity for CD33. As another example, the second immunoglobulin variable domain sequence has binding specificity for CD34. As another example, the second immunoglobulin variable domain sequence has binding specificity for FLT3. For example, the second immunoglobulin variable domain sequence has binding specificity for folate receptor beta. In some aspects, the second immunoglobulin variable domain sequence has binding specificity for an antigen expressed on B-cells, for example, CD19, CD20, CD22 or ROR1.

Chimeric TCR

In one aspect, the CLL-1 antibodies and antibody fragments of the present invention (for example, those disclosed in Tables 8) can be grafted to one or more constant domain of a T cell receptor ("TCR") chain, for example, a TCR alpha or TCR beta chain, to create an chimeric TCR that binds specificity to CLL-1. Without being bound by theory, it is believed that chimeric TCRs will signal through the TCR complex upon antigen binding. For example, a CLL-1 scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a CLL-1 antibody fragment, for example a VL domain as described herein, can be grafted to the constant domain of a TCR alpha chain, and a CLL-1 antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of a CLL-1 antibody or antibody fragment, e.g., the CDRs of a CLL-1 antibody or antibody fragment as described in Tables 1, 2, 3, 4, 5, or 6 may be grafted into a TCR alpha and/or beta chain to create a chimeric TCR that binds specifically to CLL-1. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CART cell surface. In a different aspect the amino acid sequence of the transmembrane domain may be modified or substituted so as to minimize interactions with the binding domains of the native binding partner present in the same CART.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of a costimulatory molecule, e.g., a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLPS SIEK TISKAKGQPREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLSLSLGKM (SEQ ID NO:3). In some embodiments, the hinge or spacer comprises a hinge encoded by a nucleotide sequence of (SEQ ID NO: 14)

```
GAGAGCAAGTACGGCCCTCCCTGCCCCCCTTGCCCTGCCCCCGAGTTCCT
GGGCGGACCCAGCGTGTTCCTGTTCCCCCCCAAGCCCAAGGACACCCTGA
TGATCAGCCGGACCCCCGAGGTGACCTGTGTGGTGGTGGACGTGTCCCAG
GAGGACCCCGAGGTCCAGTTCAACTGGTACGTGGACGGCGTGGAGGTGCA
CAACGCCAAGACCAAGCCCCGGGAGGAGCAGTTCAATAGCACCTACCGGG
TGGTGTCCGTGCTGACCGTGCTGCACCAGGACTGGCTGAACGGCAAGGAA
TACAAGTGTAAGGTGTCCAACAAGGGCCTGCCCAGCAGCATCGAGAAAAC
CATCAGCAAGGCCAAGGGCCAGCCTCGGGAGCCCCAGGTGTACACCCTGC
CCCCTAGCCAAGAGGAGATGACCAAGAACCAGGTGTCCCTGACCTGCCTG
GTGAAGGGCTTCTACCCCAGCGACATCGCCGTGGAGTGGGAGAGCAACGG
CCAGCCCGAGAACAACTACAAGACCACCCCCCCTGTGCTGGACAGCGACG
GCAGCTTCTTCCTGTACAGCCGGCTGACCGTGGACAAGAGCCGGTGGCAG
GAGGGCAACGTCTTTAGCTGCTCCGTGATGCACGAGGCCCTGCACAACCA
CTACACCCAGAAGAGCCTGAGCCTGTCCCTGGGCAAGATG.
```

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQEERET KTPECPSHTQPLGVYLLTPAVQDLWLRDKATFTCFVVGSDLKDAHLTWEVAGK VPTG GVEEGLLERHSNGSQSQHSRLTLPRSLWNAGTSVTCTLNHPSLPPQRLMALREPAAQA PVKLSLNLLASSDPPEAASWLLCEVSGFSPPNILLMWLEDQREVNTSGFAPARPPPQPG STTFWAWSVLRVPAPPSPQPATYTCVVSHEDSRTLLNASRSLEVSYVTDH (SEQ ID NO:4). In some embodiments, the hinge or spacer comprises a hinge encoded by a nucleotide sequence of (SEQ ID NO: 15)

```
AGGTGGCCCGAAAGTCCCAAGGCCCAGGCATCTAGTGTTCCTACTGCACA
GCCCCAGGCAGAAGGCAGCCTAGCCAAAGCTACTACTGCACCTGCCACTA
CGCGCAATACTGGCCGTGGCGGGGAGGAGAAGAAAAAGGAGAAAGAGAAA
GAAGAACAGGAAGAGAGGGAGACCAAGACCCCTGAATGTCCATCCCATAC
CCAGCCGCTGGGCGTCTATCTCTTGACTCCCGCAGTACAGGACTTGTGGC
TTAGAGATAAGGCCACCTTTACATGTTTCGTCGTGGGCTCTGACCTGAAG
GATGCCCATTTGACTTGGGAGGTTGCCGGAAAGGTACCCACAGGGGGGGT
TGAGGAAGGGTTGCTGGAGCGCCATTCCAATGGCTCTCAGAGCCAGCACT
CAAGACTCACCCTTCCGAGATCCCTGTGGAACGCCGGGACCTCTGTCACA
TGTACTCTAAATCATCCTAGCCTGCCCCCACAGCGTCTGATGGCCCTTAG
AGAGCCAGCCGCCCAGGCACCAGTTAAGCTTAGCCTGAATCTGCTCGCCA
GTAGTGATCCCCCAGAGGCCGCCAGCTGGCTCTTATGCGAAGTGTCCGGC
TTTAGCCCGCCCAACATCTTGCTCATGTGGCTGGAGGACCAGCGAGAAGT
GAACACCAGCGGCTTCGCTCCAGCCCGGCCCCCACCCCAGCCGGGTTCTA
CCACATTCTGGGCCTGGAGTGTCTTAAGGGTCCCAGCACCACCTAGCCCC
CAGCCAGCCACATACACCTGTGTTGTGTCCCATGAAGATAGCAGGACCCT
GCTAAATGCTTCTAGGAGTCTGGAGGTTTCCTACGTGACTGACCATT.
```

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of GGTGGCGGAGGTTCTGGAGGTGGAGGTTCC (SEQ ID NO:16).

In one aspect, the hinge or spacer comprises a KIR2DS2 hinge.

Cytoplasmic Domain

The cytoplasmic domain or region of a CAR of the present invention includes an intracellular signaling domain. An intracellular signaling domain is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular signalling domain of the CAR can comprise the primary signalling domain, e.g., CD3-zeta signaling domain, by itself or it can be combined with any other desired intracellular signaling domain(s) useful in the context of a CAR of the invention. For example, the intracellular signaling domain of the CAR can comprise a primary signalling domain, e.g., CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9 (mutant CD3 zeta) or SEQ ID NO: 10 (wild-type human CD3 zeta).

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO:8). In one aspect, the signaling domain of CD27 is encoded by a nucleic acid sequence of

```
                                          (SEQ ID NO: 19)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.
```

In one aspect, the intracellular is designed to comprise the signaling domain of CD3-zeta and the signaling domain of CD28. In one aspect, the signaling domain of CD28 comprises an amino acid sequence of SEQ ID NO: 482. In one aspect, the signaling domain of CD28 is encoded by a nucleic acid sequence of SEQ ID NO: 483.

In one aspect, the intracellular is designed to comprise the signaling domain of CD3-zeta and the signaling domain of ICOS. In one aspect, the signaling domain of CD28 comprises an amino acid sequence of SEQ ID NO: 484. In one aspect, the signaling domain of ICOS is encoded by a nucleic acid sequence of SEQ ID NO: 485.

In one aspect, the CAR-expressing cell described herein can further comprise a second CAR, e.g., a second CAR that includes a different antigen binding domain, e.g., to the same target (CLL-1) or a different target (e.g., CD123, CD33, CD34, FLT3, or folate receptor beta). In one embodiment, the second CAR includes an antigen binding domain to a target expressed on acute myeloid leukemia cells, such as, e.g., CD123, CD33, CD34, FLT3, or folate receptor beta. In one embodiment, the CAR-expressing cell comprises a first CAR that specifically binds a first antigen and includes an intracellular signaling domain having a costimulatory signaling domain but not a primary signaling domain, and a second CAR that specifically binds a second, different, antigen and includes an intracellular signaling domain having a primary signaling domain but not a costimulatory signaling domain. While not wishing to be bound by theory, placement of a co stimulatory signaling domain, e.g., 4-1BB, CD28, CD27, ICOS, or OX-40, onto the first CAR, and the primary signaling domain, e.g., CD3 zeta, on the second CAR can limit the CAR activity to cells where both targets are expressed. In one embodiment, the CAR expressing cell comprises a first CLL-1 CAR that includes a CLL-1 binding domain, a transmembrane domain and a costimulatory domain and a second CAR that specifically binds an antigen other than CLL-1 (e.g., an antigen expressed on AML cells, e.g., CD123, CD33, CD34, FLT3, or folate receptor beta) and includes an antigen binding domain, a transmembrane domain and a primary signaling domain. In another embodiment, the CAR expressing cell comprises a first CLL-1 CAR that includes a CLL-1 binding domain, a transmembrane domain and a primary signaling domain and a second CAR that specifically binds an antigen other than CLL-1 (e.g., an antigen expressed on AML cells, e.g., CD123, CD33, CD34, FLT3, or folate receptor beta) and includes an antigen binding domain to the antigen, a transmembrane domain and a costimulatory signaling domain.

In one embodiment, the CAR-expressing cell comprises a CLL-1 CAR described herein and an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising a antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of the first CAR or the second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 4-1BB, CD27, ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). In embodiments, the CAR-expressing cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a CLL-1 CAR described herein, improves the persistence of the CAR-expressing cell, e.g., T cell or NK cell. In one embodiment, the CAR is a PD1 CAR comprising the extracellular domain of PD1 indicated as underlined in SEQ ID NO: 24. In one embodiment, the PD1 CAR comprises the amino acid sequence of SEQ ID NO:24.

```
                                                (SEQ ID NO: 24)
Malpvtalllplalllhaarppgwfldspdrpwnpptfspallvvtegdn

atftcsfsntsesfvlnwyrmspsnqtdklaafpedrsqpgqdcrfrvtq

lpngrdfhmsvvrarrndsgtylcgaislapkaqikeslraelrvterra

evptahpspsprpagqfqtlvtttpaprpptpaptiasqplslrpeacrp

aaggavhtrgldfacdiyiwaplagtcgvlllslvitlyckrgrkkllyi

fkqpfmrpvqttqeedgcscrfpeeeeggcelrvkfsrsadapaykqgqn

qlynelnlgrreeydvldkrrgrdpemggkprrknpqeglynelqkdkma

eayseigmkgerrrgkghdglyqglstatkdtydalhmqalppr.
```

In one embodiment, the PD1 CAR comprises the amino acid sequence provided below (SEQ ID NO:22).

```
                                                (SEQ ID NO: 22)
pgwfldspdrpwnpptfspallvvtegdnatftcsfsntsesfvlnwyrm

spsnqtdklaafpedrsqpgqdcrfrvtqlpngrdfhmsvvrarrndsgt

ylcgaislapkaqikeslraelrvterraevptahpspsprpagqfqtlv

tttpaprpptpaptiasqplslrpeacrpaaggavhtrgldfacdiyiwa

plagtcgvlllslvitlyckrgrkkllyifkqpfmrpvqttqeedgcscr
```

-continued

```
fpeeeeggcelrvkfsrsadapaykqgqnqlynelnlgrreeydvldkrr

grdpemggkprrknpqeglynelqkdkmaeayseigmkgerrrgkghdgl

yqglstatkdtydalhmqalppr.
```

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 23

```
                                                (SEQ ID NO: 23)
atggccctccctgtcactgccctgcttctccccctcgcactcctgctcca

cgccgctagaccacccggatggtttctggactctccggatcgcccgtgga

atcccccaaccttctcaccggcactcttggttgtgactgagggcgataat

gcgaccttcacgtgctcgttctccaacacctccgaatcattcgtgctgaa

ctggtaccgcatgagcccgtcaaaccagaccgacaagctcgccgcgtttc

cggaagatcggtcgcaaccgggacaggattgtcggttccgcgtgactcaa

ctgccgaatggcagagacttccacatgagcgtggtccgcgctaggcgaaa

cgactccgggacctacctgtgcggagccatctcgctggcgcctaaggccc

aaatcaaagagagcttgagggccgaactgagagtgaccgagcgcagagct

gaggtgccaactgcacatccatccccatcgcctcggcctgcggggcagtt

tcagaccctggtcacgaccactccggcgccgcgcccaccgactccggccc

caactatcgcgagccagcccctgtcgctgaggccggaagcatgccgccct

gccgccggaggtgctgtgcatacccggggattggacttcgcatgcgacat

ctacatttgggctcctctcgccggaacttgtggcgtgctccttctgtccc

tggtcatcaccctgtactgcaagcggggtcggaaaaagcttctgtacatt

ttcaagcagcccttcatgaggcccgtgcaaaccacccaggaggaggacgg

ttgctcctgccggttccccgaagaggaagaaggaggttgcgagctgcgcg

tgaagttctcccggagcgccgacgcccccgcctataagcagggccagaac

cagctgtacaacgaactgaacctgggacggcgggaagagtacgatgtgct

ggacaagcggcgcggccgggaccccgaaatgggcgggaagcctagaagaa

agaaccctcaggaaggcctgtataacgagctgcagaaggacaagatggcc

gaggcctactccgaaattgggatgaagggagagcggcggaggggaaaggg

gcacgacggcctgtaccaaggactgtccaccgccaccaaggacacatacg

atgccctgcacatgcaggcccttccccctcgc.
```

In another aspect, the present invention provides a population of CAR-expressing cells, e.g., CART cells or CAR-expressing NK cells. In some embodiments, the population of CAR-expressing cells comprises a mixture of cells expressing different CARs. For example, in one embodiment, the population of CAR-expressing cells (e.g., CART cells or CAR-expressing NK cells) can include a first cell expressing a CAR having an anti-CLL-1 binding domain described herein, and a second cell expressing a CAR having a different anti-CLL-1 binding domain, e.g., an anti-CLL-1 binding domain described herein that differs from the anti-CLL-1 binding domain in the CAR expressed by the first cell. As another example, the population of CAR-expressing cells can include a first cell expressing a CAR that includes an anti-CLL-1 binding domain, e.g., as described herein, and a second cell expressing a CAR that includes an antigen binding domain to a target other than CLL-1 (e.g., CD123, CD33, CD34, FLT3, or folate receptor beta). In one embodiment, the population of CAR-expressing cells includes, e.g., a first cell expressing a CAR that includes a primary intracellular signaling domain, and a second cell expressing a CAR that includes a secondary signaling domain, e.g., a costimulatory signaling domain.

In another aspect, the present invention provides a population of cells wherein at least one cell in the population expresses a CAR having an anti-CLL-1 domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 4-1BB, CD27 ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells (e.g., CART cells or CAR-expressing NK cells), e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an anti-cancer associated antigen binding domain as described herein, and a second cell expressing another agent, e.g., an agent which enhances the activity of a CAR-expressing cell, in combination with another agent, e.g., a kinase inhibitor, such as a kinase inhibitor described herein.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI3/4β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/lgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In some embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain.

Additional description and exemplary configurations of such regulatable CARs are provided herein and in International Publication No. WO 2015/090229, hereby incorporated by reference in its entirety.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that specifically binds a tumor antigen described herein, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 4-1BB, CD28, CD27, ICOS, and OX40, and in embodiments, no primary intracellular signaling domain. In an embodiment, the antigen binding member comprises the following costimulatory signaling domains, from the extracellular to intracellular direction: 4-1BB-CD27; 4-1BB-CD27; CD27-4-1BB; 4-1BB-CD28; CD28-4-1BB; OX40-CD28; CD28-OX40; CD28-4-1BB; or 4-1BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 4-1BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

(SEQ ID NO: 205)
D V P D Y A S L G G P S S P K K K R K V S R G V Q
V E T I S P G D G R T F P KR G Q T C V V H Y T G M
L E D G K K F D S S R D R N K P F K F M L G K Q E
V I R GW E E G V A Q M S V G Q R A K L T I S P D
Y A Y G A T G H P G I I P P H A T L V F DV E L L K
L E T S Y

In embodiments, an FKBP switch domain can comprise a fragment of FKBP having the ability to bind with FRB, or a fragment or analog thereof, in the presence of rapamycin or a rapalog, e.g., the underlined portion of SEQ ID NO: 205, which is:

(SEQ ID NO: 206)
V Q V E T I S P G D G R T F P K R G Q T C V V H Y
T G M L E D G K K F D S S RD R N K P F K F M L G K
Q E V I R G W E E G V A Q M S V G Q R A K L T I S
P D Y AY G A T G H P G I I P P H A T L V F D V E
L L K L E T S

The amino acid sequence of FRB is as follows:

(SEQ ID NO: 207)
ILWHEMWHEG LEEASRLYFG ERNVKGMFEV LEPLHAMMER GPQTLKETSF NQAYGRDLME AQEWCRKYMK SGNVKDLTQA WDLYYHVFRR ISK

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 54 or 55; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 56. In an embodiment, a RCAR described herein comprises one switch domain comprises amino acid residues disclosed in SEQ ID NO: 205 (or SEQ ID NO: 206), and one switch domain comprises amino acid residues disclosed in SEQ ID NO: 207.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, 52035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 208, or leucine (E2032L), e.g., SEQ ID NO: 209. In an embodiment, a mutant FRB comprises a mutation at T2098, where T2098 is mutated to phenylalanine (T2098F) or leucine (T2098L), e.g., SEQ ID NO: 210. In an embodiment, a mutant FRB comprises a mutation at E2032 and at T2098, where E2032 is mutated to any amino acid, and where T2098 is mutated to any amino acid, e.g., SEQ ID NO: 211. In an embodiment, a mutant FRB comprises an E2032I and a T2098L mutation, e.g., SEQ ID NO: 212. In an embodiment, a mutant FRB comprises an E2032L and a T2098L mutation, e.g., SEQ ID NO: 213.

TABLE 9

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAY GRDLMEAQEWCRKYMKSGNVKDLTQAWDLYYHVFRRISKTS | 208 |
| E2032L mutant | ILWHEMWHEGLLEASRLYFGERNVKGMFEVLEPLHAMMERGPQTLKETSFNQAY GRDLMEAQEWCRKYMKSGNVKDLTQAWDLYYHVFRRISKTS | 209 |
| T2098L mutant | ILWHEMWHEGLEEASRLYFGERNVKGMFEVLEPLHAMMERGPQTLKETSFNQAY GRDLMEAQEWCRKYMKSGNVKDLLQAWDLYYHVFRRISKTS | 210 |
| E2032, T2098 mutant | ILWHEMWHEGLXEASRLYFGERNVKGMFEVLEPLHAMMERGPQTLKETSFNQAY GRDLMEAQEWCRKYMKSGNVKDLXQAWDLYYHVFRRISKTS | 211 |
| E2032I, T2098L mutant | ILWHEMWHEGLIEASRLYFGERNVKGMFEVLEPLHAMMERGPQTLKETSFNQAY GRDLMEAQEWCRKYMKSGNVKDLLQAWDLYYHVFRRISKTS | 212 |
| E2032L, T2098L mutant | ILWHEMWHEGLLEASRLYFGERNVKGMFEVLEPLHAMMERGPQTLKETSFNQAY GRDLMEAQEWCRKYMKSGNVKDLLQAWDLYYHVFRRISKTS | 213 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Combination with a low dose mTOR inhibitor".

Split CAR

In some embodiments, the CAR-expressing cell uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes CLL-1, e.g., comprises an antigen binding domain described herein, and the second antigen binding domain recognizes an antigen expressed on acute myeloid leukemia cells, e.g., CD123, CD33, CD34, FLT3, or folate receptor beta. In embodiments the first antigen binding domain recognizes CLL-1, e.g., comprises an antigen binding domain described herein, and the second antigen binding domain recognizes an antigen expressed on B-cells, e.g., CD19, CD20, CD22 or ROR1.

Stability and Mutations

The stability of a CLL-1 binding domain, e.g., scFv molecules (e.g., soluble scFv) can be evaluated in reference to the biophysical properties (e.g., thermal stability) of a conventional control scFv molecule or a full length antibody. In one embodiment, the human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the anti-CLL-1 binding domain, e.g., scFv is subsequently conferred to the entire CLL-1 CAR construct, leading to improved therapeutic properties of the CLL-1 CAR construct. The thermal stability of the anti-CLL-1 binding domain, e.g., scFv can be improved by at least about 2° C. or 3° C. as compared to a conventional antibody. In one embodiment, the anti-CLL-1 binding domain, e.g., scFv has a 1° C. improved thermal stability as compared to a conventional antibody. In another embodiment, the anti-CLL-1 binding domain, e.g., scFv has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and full length antibodies. Thermal stability can be measured using methods known in the art. For example, in one embodiment, Tm can be measured. Methods for measuring Tm and other methods of determining protein stability are described in more detail below.

Mutations in scFv alter the stability of the scFv and improve the overall stability of the scFv and the CART CLL-1 construct. Stability of the human scFv is determined using measurements such as Tm, temperature denaturation and temperature aggregation.

The binding capacity of the mutant scFvs can be determined using assays described in the Examples.

In one embodiment, the anti-CLL-1 binding domain, e.g., scFv comprises at least one mutation such that the mutated scFv confers improved stability to the CLL-1 CAR construct.

In another embodiment, the anti-CLL-1 binding domain, e.g., scFv comprises at least 1, 2, 3, 4, 5, 6, 7, 8, 9, 10 mutations arising from the humanization process such that the mutated scFv confers improved stability to the CLL-1 CAR construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of anti-CLL-1 binding domain, e.g., scFv variants may be created using methods known in the art. Anti-CLL-1 binding domain, e.g., scFv expression may be induced and the anti-CLL-1 binding domain, e.g., scFv may be subjected to thermal challenge. The challenged test samples may be assayed for binding and those anti-CLL-1 binding domain, e.g., scFvs which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an anti-CLL-1 binding domain, e.g., scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the $T_C$ value) at which 50% of the composition retains its activity (e.g. binding activity).

In addition, mutations to the anti-CLL-1 binding domain, e.g., scFv alter the thermal stability of the anti-CLL-1 binding domain, e.g., scFv compared with the unmutated anti-CLL-1 binding domain, e.g., scFv. In one embodiment, the anti-CLL-1 binding domain, e.g., scFv comprises a single mutation that confers thermal stability to the anti-CLL-1 binding domain, e.g., scFv. In another embodiment, the anti-CLL-1 binding domain, e.g., scFv comprises multiple mutations that confer thermal stability to the anti-CLL-1 binding domain, e.g., scFv. In one embodiment, the multiple mutations in the anti-CLL-1 binding domain, e.g., scFv have an additive effect on thermal stability of the anti-CLL-1 binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the anti-CLL-1 antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-CLL-1 binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-CLL-1 binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

In one aspect the anti-CLL-1 CAR is encoded by a messenger RNA (mRNA). In one aspect the mRNA encoding the anti-CLL-1 CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. “Substantially complementary,” as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. “Forward primers” are primers that contain a region of nucleotides that are substantially complementary to nucleotides on the DNA template that are upstream of the DNA sequence that is to be amplified. “Upstream” is used herein to refer to a location 5, to the DNA sequence to be amplified relative to the coding strand. “Reverse primers” are primers that contain a region of nucleotides that are substantially complementary to a double-stranded DNA template that are downstream of the DNA sequence that is to be amplified. “Downstream” is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15 (2008):2961-2971; Huang et al. Mol. Ther. 16 (2008):580-589; Grabundzija et al. Mol. Ther. 18 (2010):1200-1209; Kebriaei et al. Blood. 122.21 (2013): 166; Williams. Molecular Therapy 16.9 (2008):1515-16; Bell et al. Nat. Protoc. 2.12 (2007):3153-65; and Ding et al. Cell. 122.3 (2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises a anti-CLL-1 binding domain (e.g., a human anti-CLL-1 binding domain), a transmembrane domain, and an intracellular signaling domain comprising a stimulatory domain, e.g., a costimulatory signaling domain and/or a primary signaling domain, e.g., zeta chain. In one embodiment, the anti-CLL-1 binding domain is an anti-CLL-1 binding domain described herein, e.g., an anti-CLL-1 binding domain which comprises a sequence selected from a group consisting of SEQ ID NO:39-51, or a sequence with 95-99% identity thereof. In one embodiment, the transmembrane domain is transmembrane domain of a protein described herein, e.g., selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6, or a sequence with 95-99% identity thereof. In one embodiment, the anti-CLL-1 binding domain is connected to the transmembrane domain by a hinge region, e.g., a hinge described herein. In one embodiment, the hinge region comprises SEQ ID NO:2 or SEQ ID NO:3 or SEQ ID NO:4 or SEQ ID NO:5, or a sequence with 95-99% identity thereof. In one embodiment, the isolated nucleic acid molecule further comprises a sequence encoding a costimulatory domain. In one embodiment, the costimulatory domain is a functional signaling domain of a protein described herein, e.g., selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one embodiment, the costimulatory domain comprises a sequence of SEQ ID NO:7, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 7 or SEQ ID NO:8, or a sequence with 95-99% identity thereof, and the sequence of SEQ ID NO: 9 or SEQ ID NO:10, or a sequence with 95-99% identity thereof, wherein the sequences comprising the intracellular signaling domain are expressed in the same frame and as a single polypeptide chain.

In another aspect, the invention pertains to an isolated nucleic acid molecule encoding a CAR construct comprising a leader sequence of SEQ ID NO: 1, a scFv domain having a sequence selected from the group consisting of SEQ ID NO:39-51, (or a sequence with 95-99% identity thereof), a hinge region of SEQ ID NO:2 or SEQ ID NO:3 or SEQ ID NO:4 or SEQ ID NO:5 (or a sequence with 95-99% identity thereof), a transmembrane domain having a sequence of SEQ ID NO: 6 (or a sequence with 95-99% identity thereof), a 4-1BB costimulatory domain having a sequence of SEQ ID NO:7 or a CD27 costimulatory domain having a sequence of SEQ ID NO:8 (or a sequence with 95-99% identity thereof) or a CD28 costimulatory domain having a sequence of SEQ ID NO:482 (or a sequence with 95-99% identity thereof) or a ICOS costimulatory domain having a sequence of SEQ ID NO: 483 (or a sequence with 95-99% identity thereof), and a CD3 zeta stimulatory domain having a sequence of SEQ ID NO:9 or SEQ ID NO:10 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:91-103, or a sequence with 95-99% identity thereof.

In another aspect, the invention pertains to a nucleic acid molecule encoding a chimeric antigen receptor (CAR) molecule that comprises an anti-CLL-1 binding domain, a transmembrane domain, and an intracellular signaling domain comprising a stimulatory domain, and wherein said anti-CLL-1 binding domain comprises a sequence selected from the group consisting of SEQ ID NO:39-51, or a sequence with 95-99% identity thereof.

In one embodiment, the encoded CAR molecule further comprises a sequence encoding a costimulatory domain. In one embodiment, the costimulatory domain is a functional signaling domain of a protein selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In one embodiment, the 4-1BB costimulatory domain comprises an amino acid sequence of SEQ ID NO:7. In one embodiment, the CD27 costimulatory domain comprises an amino acid sequence of SEQ ID NO:8. In one embodiment, the CD28 costimulatory domain comprises an amino acid sequence of SEQ ID NO:482. In one embodiment, the ICOS costimulatory domain comprises an amino acid sequence of SEQ ID NO:484.

In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In one embodiment, the transmembrane domain comprises a sequence of SEQ ID NO:6. In one embodiment, the intracellular signaling domain comprises a functional signaling domain of 4-1BB and a functional signaling domain of zeta. In one embodiment, the intracellular signaling domain comprises the sequence of SEQ ID NO: 7 and the sequence of SEQ ID NO: 9, wherein the sequences comprising the intracellular signaling domain are expressed in the same frame and as a single polypeptide chain. In one embodiment, the anti-CLL-1 binding domain is connected to the transmembrane domain by a hinge region. In one embodiment, the hinge region comprises SEQ ID NO:2. In one embodiment, the hinge region comprises SEQ ID NO:3 or SEQ ID NO:4 or SEQ ID NO:5.

In another aspect, the invention pertains to an encoded CAR molecule comprising a leader sequence of SEQ ID NO: 1, a scFv domain having a sequence selected from the group consisting of SEQ ID NO:59-51, or a sequence with 95-99% identity thereof, a hinge region of SEQ ID NO:2 or SEQ ID NO:3 or SEQ ID NO:4 or SEQ ID NO:5, a transmembrane domain having a sequence of SEQ ID NO: 6, a 4-1BB costimulatory domain having a sequence of SEQ ID NO:7 or a CD27 costimulatory domain having a sequence of SEQ ID NO:8, and a CD3 zeta stimulatory domain having a sequence of SEQ ID NO:9 or SEQ ID NO:10. In one embodiment, the encoded CAR molecule comprises a sequence selected from a group consisting of SEQ ID NO:91-103, or a sequence with 95-99% identity thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

```
WT PGK Promoter
                                        (SEQ ID NO: 487)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT

Exemplary truncated PGK Promoters:
PGK100:
                                        (SEQ ID NO: 488)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
                                        (SEQ ID NO: 489)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:
                                        (SEQ ID NO: 490)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:
                                        (SEQ ID NO: 491)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC
```

-continued

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector can further comprise a nucleic acid encoding a second CAR. In one embodiment, the second CAR includes an antigen binding domain to a target expressed on acute myeloid leukemia cells, such as, e.g., CD123, CD33, CD34, FLT3, or folate receptor beta. In one embodiment, the vector comprises a nucleic acid sequence encoding a first CAR that specifically binds a first antigen and includes an intracellular signaling domain having a costimulatory signaling domain but not a primary signaling domain, and a nucleic acid encoding a second CAR that specifically binds a second, different, antigen and includes an intracellular signaling domain having a primary signaling domain but not a costimulatory signaling domain. In one embodiment, the vector comprises a nucleic acid encoding a first CLL-1 CAR that includes a CLL-1 binding domain, a transmembrane domain and a costimulatory domain and a nucleic acid encoding a second CAR that specifically binds an antigen other than CLL-1 (e.g., an antigen expressed on AML cells, e.g., CD123, CD33, CD34, FLT3, or folate receptor beta) and includes an antigen binding domain, a transmembrane domain and a primary signaling domain. In another embodiment, the vector comprises a nucleic acid encoding a first CLL-1 CAR that includes a CLL-1 binding domain, a transmembrane domain and a primary signaling domain and a nucleic acid encoding a second CAR that specifically binds an antigen other than CLL-1 (e.g., an antigen expressed on AML cells, e.g., CD123, CD33, CD34, FLT3, or folate receptor beta) and includes an antigen binding domain to the antigen, a transmembrane domain and a costimulatory signaling domain.

In one embodiment, the vector comprises a nucleic acid encoding a CLL-1 CAR described herein and a nucleic acid encoding an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In embodiments, the vector may comprise two or more nucleic acid sequences encoding a CAR, e.g., a CLL-1 CAR described herein and a second CAR, e.g., an inhibitory CAR or a CAR that specifically binds to an antigen other than CLL-1 (e.g., an antigen expressed on AML cells, e.g., CD123, CD33, CD34, FLT3, or folate receptor beta). In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include the following, wherein the GSG residues are optional:

T2A:

(SEQ ID NO: 492)
(GSG) E G R G S L L T C G D V E E N P G P

P2A:

(SEQ ID NO: 493)
(GSG) A T N F S L L K Q A G D V E E N P G P

E2A:

(SEQ ID NO: 494)
(GSG) Q C T N Y A L L K L A G D V E S N P G P

F2A:

(SEQ ID NO: 495)
(GSG) V K Q T L N F D L L K L A G D V E S N P G P

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., an immune effector cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of Cells

Prior to expansion and genetic modification, a source of cells (e.g., immune effector cells, e.g., T cells or NK cells) is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present invention, any number of immune effector cell (e.g., T cell or NK cell) lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-7, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as immune effector cells, e.g., T cells or NK cells, isolated and frozen for later use in cell therapy, e.g., T cell therapy, for any number of diseases or conditions that would benefit from cell therapy, e.g., T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the immune effector cells, e.g., T cells or NK cells, may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some aspects, downregulation of HLA may be accomplished by reducing or eliminating expression of beta-2 microglobulin (B2M).

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g., a cell engineered by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in

*Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797 and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA and/or TCR can be constructed using any method known in the art. See, e.g., Provasi (2011) Nature Med. 18: 807-815; Torikai (2013) Blood 122: 1341-1349; Cathomen et al. (2008) *Mol. Ther.* 16: 1200-7; Guo et al. (2010) *J. Mol. Biol.* 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

(SEQ ID NO: 214)

```
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG
```

-continued

```
FALLDGARGGPPEAFTTSVRSYLPNTVTDALRGSGAWGLLLRRVGDDVLV

HLLARCALFVLVAPSCAYQVCGPPLYQLGAATQARPPPHASGPRRRLGCE

RAWNHSVREAGVPLGLPAPGARRRGGSASRSLPLPKRPRRGAAPEPERTP

VGQGSWAHPGRTRGPSDRGFCVVSPARPAEEATSLEGALSGTRHSHPSVG

RQHHAGPPSTSRPPRPWDTPCPPVYAETKHFLYSSGDKEQLRPSFLLSSL

RPSLTGARRLVETIFLGSRPWMPGTPRRLPRLPQRYWQMRPLFLELLGNH

AQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKH

AKLSLQELTWKMSVRGCAWLRRSPGVGCVPAAEHRLREEILAKFLHWLMS

VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD
```

In an embodiment, the hTERT has a sequence at least 80%, 85%, 90%, 95%, 96ˆ, 97%, 98%, or 99% identical to the sequence of SEQ ID NO: 214. In an embodiment, the hTERT has a sequence of SEQ ID NO: 214. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 215)

```
  1 caggcagcgt ggtcctgctg cgcacgtggg aagccctggc cccggccacc cccgcgatgc

 61 cgcgcgctcc ccgctgccga gccgtgcgct ccctgctgcg cagccactac cgcgaggtgc

121 tgccgctggc cacgttcgtg cggcgcctgg ggccccaggg ctggcggctg gtgcagcgcg

181 gggacccggc ggctttccgc gcgctggtgg cccagtgcct ggtgtgcgtg ccctgggacg

241 cacggccgcc ccccgccgcc ccctccttcc gccaggtgtc ctgcctgaag gagctggtgg

301 cccgagtgct gcagaggctg tgcgagcgcg gcgcgaagaa cgtgctggcc ttcggcttcg

361 cgctgctgga cggggcccgc gggggccccc ccgaggcctt caccaccagc gtgcgcagct

421 acctgcccaa cacggtgacc gacgcactgc gggggagcgg ggcgtggggg ctgctgttgc
```

-continued 481 gccgcgtggg cgacgacgtg ctggttcacc tgctggcacg ctgcgcgctc tttgtgctgg 541 tggctcccag ctgcgcctac caggtgtgcg ggccgccgct gtaccagctc ggcgctgcca 601 ctcaggcccg gcccccgcca cacgctagtg gaccccgaag gcgtctggga tgcgaacggg 661 cctggaacca tagcgtcagg gaggccgggg tcccccctggg cctgccagcc ccgggtgcga 721 ggaggcgcgg gggcagtgcc agccgaagtc tgccgttgcc caagaggccc aggcgtggcg 781 ctgcccctga gccggagcgg acgcccgttg ggcaggggtc ctgggcccac ccgggcagga 841 cgcgtggacc gagtgaccgt ggtttctgtg tggtgtcacc tgccagaccc gccgaagaag 901 ccacctcttt ggagggtgcg ctctctggca cgcgccactc ccacccatcc gtgggccgcc 961 agcaccacgc gggcccccca tccacatcgc ggccaccacg tccctgggac acgccttgtc 1021 ccccggtgta cgccgagacc aagcacttcc tctactcctc aggcgacaag gagcagctgc 1081 ggccctcctt cctactcagc tctctgaggc ccagcctgac tggcgctcgg aggctcgtgg 1141 agaccatctt tctgggttcc aggccctgga tgccagggac tccccgcagg ttgccccgcc 1201 tgccccagcg ctactggcaa atgcggcccc tgtttctgga gctgcttggg aaccacgcgc 1261 agtgccccta cggggtgctc ctcaagacgc actgcccgct gcgagctgcg gtcaccccag 1321 cagccggtgt ctgtgcccgg gagaagcccc agggctctgt ggcggccccc gaggaggagg 1381 acacagaccc ccgtcgcctg gtgcagctgc tccgccagca cagcagcccc tggcaggtgt 1441 acggcttcgt gcgggcctgc ctgcgccggc tggtgccccc aggcctctgg ggctccaggc 1501 acaacgaacg ccgcttcctc aggaacacca agaagttcat ctccctgggg aagcatgcca 1561 agctctcgct gcaggagctg acgtggaaga tgagcgtgcg gggctgcgct tggctgcgca 1621 ggagcccagg ggttggctgt gttccggccg cagagcaccg tctgcgtgag gagatcctgg 1681 ccaagttcct gcactggctg atgagtgtgt acgtcgtcga gctgctcagg tctttctttt 1741 atgtcacgga gaccacgttt caaaagaaca ggctcttttt ctaccggaag agtgtctgga 1801 gcaagttgca aagcattgga atcagacagc acttgaagag ggtgcagctg cgggagctgt 1861 cggaagcaga ggtcaggcag catcgggaag ccaggcccgc cctgctgacg tccagactcc 1921 gcttcatccc caagcctgac gggctgcggc cgattgtgaa catggactac gtcgtgggag 1981 ccagaacgtt ccgcagagaa aagagggccg agcgtctcac ctcgagggtg aaggcactgt 2041 tcagcgtgct caactacgag cgggcgcggc gccccggcct cctgggcgcc tctgtgctgg 2101 gcctggacga tatccacagg gcctggcgca ccttcgtgct gcgtgtgcgg gcccaggacc 2161 cgccgcctga gctgtacttt gtcaaggtgg atgtgacggg cgcgtacgac accatccccc 2221 aggacaggct cacggaggtc atcgccagca tcatcaaacc ccagaacacg tactgcgtgc 2281 gtcggtatgc cgtggtccag aaggccgccc atgggcacgt ccgcaaggcc ttcaagagcc 2341 acgtctctac cttgacagac ctccagccgt acatgcgaca gttcgtggct cacctgcagg 2401 agaccagccc gctgagggat gccgtcgtca tcgagcagag ctcctccctg aatgaggcca 2461 gcagtggcct cttcgacgtc ttcctacgct tcatgtgcca ccacgccgtg cgcatcaggg 2521 gcaagtccta cgtccagtgc caggggatcc cgcagggctc catcctctcc acgctgctct 2581 gcagcctgtg ctacggcgac atggagaaca agctgtttgc ggggattcgg cgggacgggc 2641 tgctcctgcg tttggtggat gatttcttgt tggtgacacc tcacctcacc cacgcgaaaa 2701 ccttcctcag gaccctggtc cgaggtgtcc ctgagtatgg ctgcgtggtg aacttgcgga 2761 agacagtggt gaacttccct gtagaagacg aggccctggg tggcacggct tttgttcaga 2821 tgccggccca cggcctattc ccctggtgcg gcctgctgct ggatacccgg accctggagg -continued

```
2881 tgcagagcga ctactccagc tatgcccgga cctccatcag agccagtctc accttcaacc
2941 gcggcttcaa ggctgggagg aacatgcgtc gcaaactctt tggggtcttg cggctgaagt
3001 gtcacagcct gtttctggat ttgcaggtga acagcctcca gacggtgtgc accaacatct
3061 acaagatcct cctgctgcag gcgtacaggt ttcacgcatg tgtgctgcag ctcccatttc
3121 atcagcaagt ttggaagaac cccacatttt tcctgcgcgt catctctgac acggcctccc
3181 tctgctactc catcctgaaa gccaagaacg cagggatgtc gctgggggcc aagggcgccg
3241 ccggccctct gccctccgag gccgtgcagt ggctgtgcca ccaagcattc ctgctcaagc
3301 tgactcgaca ccgtgtcacc tacgtgccac tcctggggtc actcaggaca gcccagacgc
3361 agctgagtcg gaagctcccg gggacgacgc tgactgccct ggaggccgca gccaacccgg
3421 cactgccctc agacttcaag accatcctgg actgatggcc acccgcccac agccaggccg
3481 agagcagaca ccagcagccc tgtcacgccg ggctctacgt cccagggagg gaggggcggc
3541 ccacacccag gcccgcaccg ctgggagtct gaggcctgag tgagtgtttg gccgaggcct
3601 gcatgtccgg ctgaaggctg agtgtccggc tgaggcctga gcgagtgtcc agccaagggc
3661 tgagtgtcca gcacacctgc cgtcttcact tccccacagg ctggcgctcg gctccacccc
3721 agggccagct tttcctcacc aggagcccgg cttccactcc ccacatagga atagtccatc
3781 cccagattcg ccattgttca cccctcgccc tgccctcctt tgccttccac ccccaccatc
3841 caggtggaga ccctgagaag gaccctggga gctctgggaa tttggagtga ccaaaggtgt
3901 gccctgtaca caggcgagga ccctgcacct ggatgggggt ccctgtgggt caaattgggg
3961 ggaggtgctg tgggagtaaa atactgaata tatgagtttt tcagttttga aaaaaaaaaa
4021 aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 215. In an embodiment, the hTERT is encoded by a nucleic acid of SEQ ID NO: 215.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CLL-1 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CLL-1 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CLL-1 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CLL-1 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CLL-1 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CLL-1 CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-t chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures can be re-stimulated with CLL-1 expressing cells.

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human CLL-1-specific $CAR^+$ T cells to treat a primary human AML in immunodeficient mice can be used. Very briefly, after establishment of the tumors, mice are randomized as to treatment groups. CLL-1 CART cells are injected into the immunodeficient mice, e.g., intravenously. Animals are assessed for cancer cells at weekly intervals. Peripheral blood CLL-1-expressing AML cell counts are measured in mice that are injected with CLL-1 CART cells or mock-transduced T cells. Survival curves for the groups are compared using the log-rank test.

Cytotoxicity can be assessed by a standard 51Cr-release assay. See, e.g., Milone et al., Molecular Therapy 17(8): 1453-1464 (2009). Briefly, target cells are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of $CAR^+$ T cells in Nalm-6 xenograft model can be measured as the following: NSG mice are injected with Nalm-6 transduced to stably express firefly luciferase, followed by a single tail-vein injection of T cells electroporated with CLL-1 CAR 7 days later. Animals are imaged at various time points post injection. For example, photon-density heat maps of firefly luciferasepositive leukemia in representative mice at day 5 (2 days before treatment) and day 8 (24 hr post $CAR^+$ PBLs) can be generated.

Other assays, including those described in the Example section herein as well as those that are known in the art can also be used to evaluate the CLL-1 CAR constructs of the invention.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

acquiring the CAR-expressing cell (e.g., acquiring a sample containing CAR-expressing cells, such as a manufacturing sample or a clinical sample);

contacting the CAR-expressing cell with the CAR ligand under conditions where binding occurs, thereby detecting the level (e.g., amount) of the CAR-expressing cells present. Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference. In one embodiment, the anti-idiotypic antibody molecule recognizes an anti-CD19 antibody molecule, e.g., an anti-CD19 scFv. For instance, the anti-idiotypic antibody molecule can compete for binding with the CD19-specific CAR mAb clone no. 136.20.1 described in Jena et al., PLOS March 2013 8:3 e57838; may have the same CDRs (e.g., one or more of, e.g., all of, VH CDR1, VH CDR2, CH CDR3, VL CDR1, VL CDR2, and VL CDR3, using the Kabat definition, the Chothia definition, or a combination of the Kabat and Chothia definitions) as the CD19-specific CAR mAb clone no. 136.20.1; may have one or more (e.g., 2) variable regions as the CD19-specific CAR mAb clone no. 136.20.1, or may comprise the CD19-specific CAR mAb clone no. 136.20.1. In some embodiments, the anti-idiotypic antibody was made according to a method described in Jena et al. In another embodiment, the anti-idiotypic antibody molecule is an anti-idiotypic antibody molecule described in WO 2014/190273. In some embodiments, the anti-idiotypic antibody molecule has the same CDRs (e.g., one or more of, e.g., all of, VH CDR1, VH CDR2, CH CDR3, VL CDR1, VL CDR2, and VL CDR3) as an antibody molecule of WO 2014/190273 such as 136.20.1; may have one or more (e.g., 2) variable regions of an antibody molecule of WO 2014/190273, or may comprise an antibody molecule of WO 2014/190273 such as 136.20.1. In other embodiments, the anti-CAR antibody binds to a constant region of the extracellular binding domain of the CAR molecule, e.g., as described in WO 2014/190273. In some embodiments, the anti-CAR antibody binds to a constant region of the extracellular binding domain of the CAR molecule, e.g., a heavy chain constant region (e.g., a CH2-CH3 hinge region) or light chain constant region. For instance, in some embodiments the anti-CAR antibody competes for binding with the 2D3 monoclonal antibody described in WO 2014/190273, has the same CDRs (e.g., one or more of, e.g., all of, VH CDR1, VH CDR2, CH CDR3, VL CDR1, VL CDR2, and VL CDR3) as 2D3, or has one or more (e.g., 2) variable regions of 2D3, or comprises 2D3 as described in WO 2014/190273.

In some aspects and embodiments, the compositions and methods herein are optimized for a specific subset of T cells, e.g., as described in U.S. Ser. No. 62/031,699 filed Jul. 31, 2014, the contents of which are incorporated herein by reference in their entirety. In some embodiments, the optimized subsets of T cells display an enhanced persistence compared to a control T cell, e.g., a T cell of a different type (e.g., $CD8^+$ or $CD4^+$) expressing the same construct.

In some embodiments, a $CD4^+$ T cell comprises a CAR described herein, which CAR comprises an intracellular signaling domain suitable for (e.g., optimized for, e.g., leading to enhanced persistence in) a $CD4^+$ T cell, e.g., an ICOS domain. In some embodiments, a $CD8^+$ T cell comprises a CAR described herein, which CAR comprises an intracellular signaling domain suitable for (e.g., optimized for, e.g., leading to enhanced persistence of) a $CD8^+$ T cell, e.g., a 4-1BB domain, a CD28 domain, or another costimulatory domain other than an ICOS domain. In some embodiments, the CAR described herein comprises an antigen binding domain described herein, e.g., a CAR comprising an antigen binding domain that specifically binds CLL-1, e.g., a CAR of Table 8.

In an aspect, described herein is a method of treating a subject, e.g., a subject having cancer. The method includes administering to said subject, an effective amount of:

1) a $CD4^+$ T cell comprising a CAR (the $CAR^{CD4+}$) comprising:

an antigen binding domain, e.g., an antigen binding domain described herein, e.g., an antigen binding domain that specifically binds CLL-1, e.g., an antigen-binding domain of Table 8;

a transmembrane domain; and an intracellular signaling domain, e.g., a first costimulatory domain, e.g., an ICOS domain; and 2) a $CD8^+$ T cell comprising a CAR (the $CAR^{CD8+}$) comprising:

an antigen binding domain, e.g., an antigen binding domain described herein, e.g., an antigen binding domain that specifically binds CLL-1, e.g., an antigen-binding domain of Table 8;

a transmembrane domain; and an intracellular signaling domain, e.g., a second co stimulatory domain, e.g., a 4-1BB domain, a CD28 domain, or another costimulatory domain other than an ICOS domain;

wherein the $CAR^{CD4+}$ and the $CAR^{CD8+}$ differ from one another.

Optionally, the method further includes administering:

3) a second CD8+ T cell comprising a CAR (the second $CAR^{CD8+}$) comprising:

an antigen binding domain, e.g., an antigen binding domain described herein, e.g., an antigen binding domain that specifically binds CLL-1, e.g., an antigen-binding domain of Table 8;

a transmembrane domain; and an intracellular signaling domain, wherein the second $CAR^{CD8+}$ comprises an intracellular signaling domain, e.g., a costimulatory signaling domain, not present on the $CAR^{CD8+}$, and, optionally, does not comprise an ICOS signaling domain.

Therapeutic Application

CLL-1 Associated Diseases and/or Disorders

The present invention provides, among other things, compositions and methods for treating cancer. In one aspect, the cancer is a hematologic cancer including but is not limited to leukemia (such as acute myelogenous leukemia (AML), chronic myelogenous leukemia (CML), acute lymphoid leukemia, chronic lymphoid leukemia, acute lymphoblastic B-cell leukemia (B-cell acute lymphoid leukemia, BALL), acute lymphoblastic T-cell leukemia (T-cell acute lymphoid leukemia (TALL), B-cell prolymphocytic leukemia, plasma cell myeloma, and myelodysplastic syndrome) and malignant lymphoproliferative conditions, including lymphoma (such as multiple myeloma, non-Hodgkin's lymphoma, Burkitt's lymphoma, and small cell- and large cell-follicular lymphoma).

Therapeutic Applications

In one aspect, the invention provides methods for treating a disease associated with CLL-1 expression. In one aspect, the invention provides methods for treating a disease wherein part of the tumor is negative for CLL-1 and part of the tumor is positive for CLL-1. For example, the CAR of the invention is useful for treating subjects that have undergone treatment for a disease associated with elevated expression of CLL-1, wherein the subject that has undergone treatment for elevated levels of CLL-1 exhibits a disease associated with elevated levels of CLL-1. In embodiments, the CAR of the invention is useful for treating subjects that have undergone treatment for a disease associated with expression of CLL-1, wherein the subject that has undergone treatment related to expression of CLL-1 exhibits a disease associated with expression of CLL-1.

In one aspect, the invention pertains to a vector comprising CLL-1 CAR operably linked to promoter for expression in mammalian immune effector cells, e.g., T cells or NK cells. In one aspect, the invention provides a recombinant immune effector cells, e.g., T cells or NK cells expressing the CLL-1 CAR for use in treating CLL-1-expressing tumors, wherein the recombinant immune effector cells, e.g., T cells or NK cells expressing the CLL-1 CAR is termed a CLL-1 CAR-expressing cell (e.g., CLL-1 CART or CLL-1 CAR-expressing NK cell). In one aspect, the CLL-1 CAR-expressing cell (e.g., CLL-1 CART or CLL-1 CAR-expressing NK cell). of the invention is capable of contacting a tumor cell with at least one CLL-1 CAR of the invention expressed on its surface such that the CLL-1 CAR-expressing cell (e.g., CLL-1 CART or CLL-1 CAR-expressing NK cell). targets the tumor cell and growth of the tumor is inhibited.

In one aspect, the invention pertains to a method of inhibiting growth of a CLL-1-expressing tumor cell, comprising contacting the tumor cell with a CLL-1 CAR-expressing cell (e.g., CLL-1 CART or CLL-1 CAR-expressing NK cell). cell of the present invention such that the CLL-1 CAR-expressing cell (e.g., CLL-1 CART or CLL-1 CAR-expressing NK cell). is activated in response to the antigen and targets the cancer cell, wherein the growth of the tumor is inhibited.

In one aspect, the invention pertains to a method of treating cancer in a subject. The method comprises administering to the subject a CLL-1 CAR-expressing cell (e.g., CLL-1 CART or CLL-1 CAR-expressing NK cell) of the present invention such that the cancer is treated in the subject. An example of a cancer that is treatable by the CLL-1 CAR-expressing cell (e.g., CLL-1 CART or CLL-1 CAR-expressing NK cell) of the invention is a cancer associated with expression of CLL-1. In one aspect, the cancer associated with expression of CLL-1 is a hematological cancer. In one aspect, a hematologic cancer including but is not limited to leukemia (such as acute myelogenous leukemia, chronic myelogenous leukemia, acute lymphoid leukemia, chronic lymphoid leukemia and myelodysplastic syndrome) and malignant lymphoproliferative conditions, including lymphoma (such as multiple myeloma, non-Hodgkin's lymphoma, Burkitt's lymphoma, and small cell- and large cell-follicular lymphoma). In other embodiments, a hematologic cancer can include minimal residual disease, MRD, e.g., of a leukemia, e.g., of AML or MDS.

The invention includes a type of cellular therapy where immune effector cell, e.g., T cells or NK cells, are genetically modified to express a chimeric antigen receptor (CAR) and the CLL-1 CAR-expressing cell (e.g., CLL-1 CART or CLL-1 CAR-expressing NK cell). is infused to a recipient in need thereof. The infused cell is able to kill tumor cells in the recipient. Unlike antibody therapies, CAR-modified cells (e.g., T cells or NK cells) are able to replicate in vivo resulting in long-term persistence that can lead to sustained tumor control. In various aspects, the immune effector cells (e.g., T cells or NK cells), administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the immune effector cell (e.g., T cell or NK cell) to the patient.

The invention also includes a type of cellular therapy where immune effector cells (e.g., T cells or NK cells) are modified, e.g., by in vitro transcribed RNA, to transiently express a chimeric antigen receptor (CAR) and the CLL-1 CAR expressing cell (e.g., CLL-1 CAR T cell or CLL-1 CAR-expressing NK cell) is infused to a recipient in need thereof. The infused cell is able to kill tumor cells in the recipient. Thus, in various aspects, the immune effector cells (e.g., T cells or NK cells) administered to the patient, is present for less than one month, e.g., three weeks, two weeks, one week, after administration of the immune effector cells (e.g., T cells or NK cells) to the patient.

Without wishing to be bound by any particular theory, the anti-tumor immunity response elicited by the CAR-modified immune effector cells (e.g., T cells or NK cells) may be an active or a passive immune response, or alternatively may be due to a direct vs indirect immune response. In one aspect, the CAR transduced immune effector cells (e.g., T cells or NK cells) exhibit specific proinflammatory cytokine secretion and potent cytolytic activity in response to human cancer cells expressing the CLL-1, resist soluble CLL-1 inhibition, mediate bystander killing and mediate regression of an established human tumor. For example, antigen-less tumor cells within a heterogeneous field of CLL-1-expressing tumor may be susceptible to indirect destruction by CLL-1-redirected immune effector cells (e.g., T cells or NK cells) that has previously reacted against adjacent antigen-positive cancer cells.

In one aspect, the fully-human CAR-modified immune effector cells (e.g., T cells or NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No.

5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells or NK cells) of the invention are used in the treatment of diseases, disorders and conditions associated with expression of CLL-1. In certain aspects, the cells of the invention are used in the treatment of patients at risk for developing diseases, disorders and conditions associated with expression of CLL-1. Thus, the present invention provides methods for the treatment or prevention of diseases, disorders and conditions associated with expression of CLL-1 comprising administering to a subject in need thereof, a therapeutically effective amount of the CAR-modified immune effector cells (e.g., T cells or NK cells) of the invention. In one aspect the CAR-expressing cells, e.g., CART cells or CAR-expressing NK cells) of the inventions may be used to treat a proliferative disease such as a cancer or malignancy or is a precancerous condition such as a myelodysplasia, a myelodysplastic syndrome or a preleukemia hyperproliferative disorder, hyperplasia or a dysplasia, which is characterized by abnormal growth of cells.

In one aspect, the CAR-expressing cells (e.g., CART cells or CAR-expressing NK cells) of the invention are used to treat a cancer, wherein the cancer is a hematological cancer. Hematological cancer conditions are the types of cancer such as leukemia and malignant lymphoproliferative conditions that affect blood, bone marrow and the lymphatic system.

In one aspect, the compositions and CAR-expressing cells (e.g., CART cells or CAR-expressing NK cells) of the present invention are particularly useful for treating myeloid leukemias, AML and its subtypes, chronic myeloid leukemia (CML), and myelodysplastic syndrome (MDS).

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Existing treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15;17), t(8;21), and inv16 (p13;q22). Negative factors include increasing age, a preceding myelodysplastic phase, secondary leukemia, high WBC count, and absence of Auer rods.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

Chronic myelogenous (or myeloid) leukemia (CML) is also known as chronic granulocytic leukemia, and is characterized as a cancer of the white blood cells. Common treatment regimens for CML include Bcr-Abl tyrosine kinase inhibitors, imatinib (Gleevec®), dasatinib and nilotinib. Bcr-Abl tyrosine kinase inhibitors are specifically useful for CML patients with the Philadelphia chromosome translocation.

Myelodysplastic syndromes (MDS) are hematological medical conditions characterized by disorderly and ineffective hematopoiesis, or blood production. Thus, the number and quality of blood-forming cells decline irreversibly. Some patients with MDS can develop severe anemia, while others are asymptomatic.

The classification scheme for MDS is known in the art, with criteria designating the ratio or frequency of particular blood cell types, e.g., myeloblasts, monocytes, and red cell precursors. MDS includes refractory anemia, refractory anemia with ring sideroblasts, refractory anemia with excess blasts, refractory anemia with excess blasts in transformation, chronic myelomonocytic leukemia (CMML).

Treatment for MDS vary with the severity of the symptoms. Aggressive forms of treatment for patients experiencing severe symptoms include bone marrow transplants and supportive care with blood product support (e.g., blood transfusions) and hematopoietic growth factors (e.g., erythropoietin). Other agents are frequently used to treat MDS: 5-azacytidine, decitabine, and lenalidomide. In some cases, iron chelators deferoxamine (Desferal®) and deferasirox (Exjade®) may also be administered.

In another embodiment, the CAR-expressing cells (e.g., CART cells or CAR-expressing NK cells) of the present invention are used to treat cancers or leukemias with leukemia stem cells. For example, the leukemia stem cells are $CD34^+/CD38^-$ leukemia cells.

The present invention provides, among other things, compositions and methods for treating cancer. In one aspect, the cancer is a hematologic cancer including but is not limited to leukemia (such as acute myelogenous leukemia, chronic myelogenous leukemia, acute lymphoid leukemia, chronic lymphoid leukemia and myelodysplastic syndrome) and malignant lymphoproliferative conditions, including lymphoma (such as multiple myeloma, non-Hodgkin's lymphoma, Burkitt's lymphoma, and small cell- and large cell-follicular lymphoma).

In one aspect, the CAR-expressing cells (e.g., CART cells or CAR-expressing NK cells) of the invention may be used to treat other cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. The CAR-modified immune effector cells (e.g., T cells or NK cells) of the present invention may be administered either alone, or as a pharmaceutical composition in combination with diluents and/or with other components such as IL-2 or other cytokines or cell populations.

The present invention also provides methods for inhibiting the proliferation or reducing a CLL-1-expressing cell population, the methods comprising contacting a population of cells comprising a CLL-1-expressing cell with an CLL-1 CAR-expressing cell (e.g., CLL-1 CART cell or CLL-1 CAR-expressing NK cell) of the invention that binds to the CLL-1-expressing cell. In a specific aspect, the present invention provides methods for inhibiting the proliferation or reducing the population of cancer cells expressing CLL-1, the methods comprising contacting the CLL-1-expressing cancer cell population with a CLL-1 CAR-expressing cell (e.g., CLL-1 CART cell or CLL-1 CAR-expressing NK cell) of the invention that binds to the CLL-1-expressing cell. In one aspect, the present invention provides methods for inhibiting the proliferation or reducing the population of cancer cells expressing CLL-1, the methods comprising contacting the CLL-1-expressing cancer cell population with a CLL-1 CAR-expressing cell (e.g., CLL-1 CART cell or CLL-1 CAR-expressing NK cell) of the invention that binds to the CLL-1-expressing cell. In certain aspects, the CLL-1 CAR-expressing cell (e.g., CLL-1 CART cell or CLL-1 CAR-expressing NK cell) cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CLL-1-expressing cells relative to a negative control. In one aspect, the subject is a human.

The present invention also provides methods for preventing, treating and/or managing a disease associated with CLL-1-expressing cells (e.g., a hematologic cancer or atypical cancer expressing CLL-1), the methods comprising administering to a subject in need a CLL-1 CAR-expressing cell (e.g., CLL-1 CART cell or CLL-1 CAR-expressing NK cell) of the invention that binds to the CLL-1-expressing cell. In one aspect, the subject is a human. Non-limiting examples of disorders associated with CLL-1-expressing cells include autoimmune disorders (such as lupus), inflammatory disorders (such as allergies and asthma) and cancers (such as hematological cancers or atypical cancers expressing CLL-1).

The present invention also provides methods for preventing, treating and/or managing a disease associated with CLL-1-expressing cells, the methods comprising administering to a subject in need an a CLL-1 CAR-expressing cell (e.g., CLL-1 CART cell or CLL-1 CAR-expressing NK cell) of the invention that binds to the CLL-1-expressing cell. In one aspect, the subject is a human.

The present invention provides methods for preventing relapse of cancer associated with CLL-1-expressing cells, the methods comprising administering to a subject in need thereof a CLL-1 CAR-expressing cell (e.g., CLL-1 CART cell or CLL-1 CAR-expressing NK cell) of the invention that binds to the CLL-1-expressing cell. In one aspect, the methods comprise administering to the subject in need thereof an effective amount of a CLL-1 CAR-expressing cell (e.g., CLL-1 CART cell or CLL-1 CAR-expressing NK cell) described herein that binds to the CLL-1-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Treatment with a combination of a chemotherapeutic agent and a cell expressing a CLL-1 CAR molecule described herein can be used to treat a hematologic cancer described herein, e.g., AML. In embodiments, the combination of a chemotherapeutic agent and a CLL-1 CAR-expressing cell is useful for targeting, e.g., killing, cancer stem cells, e.g., leukemic stem cells, e.g., in subjects with AML. In embodiments, the combination of a chemotherapeutic agent and a CLL-1 CAR-expressing cell is useful for treating minimal residual disease (MRD). MRD refers to the small number of cancer cells that remain in a subject during treatment, e.g., chemotherapy, or after treatment. MRD is often a major cause for relapse. The present invention provides a method for treating cancer, e.g., MRD, comprising administering a chemotherapeutic agent in combination with a CLL-1 CAR-expressing cell, e.g., as described herein.

In an embodiment, the chemotherapeutic agent is administered prior to administration of the cell expressing a CAR molecule, e.g., a CAR molecule described herein. In chemotherapeutic regimens where more than one administration of the chemotherapeutic agent is desired, the chemotherapeutic regimen is initiated or completed prior to administration of a cell expressing a CAR molecule, e.g., a CAR molecule described herein. In embodiments, the chemotherapeutic agent is administered at least 1 day, 2 days, 3 days, 4 days, 5 days, 6 days, 7 days, 8 days, 9 days, 10 days, 11 days, 12 days, 13 days, 14 days, 15 days, 20 days, 25 days, or 30 days prior to administration of the cell expressing the CAR molecule. In embodiments, the chemotherapeutic regimen is initiated or completed at least 1 day, 2 days, 3 days, 4 days, 5 days, 6 days, 7 days, 8 days, 9 days, 10 days, 11 days, 12 days, 13 days, 14 days, 15 days, 20 days, 25 days, or 30 days prior to administration of the cell expressing the CAR molecule. In embodiments, the chemotherapeutic agent is a chemotherapeutic agent that increases CLL-1 expression on the cancer cells, e.g., the tumor cells, e.g., as compared to CLL-1 expression on normal or non-cancer cells. CLL-1 expression can be determined, for example, by immunohistochemical staining or flow cytometry analysis. For example, the chemotherapeutic agent is cytarabine (Ara-C).

Anti-cancer agents of particular interest for combinations with the compounds of the present invention include: anti-metabolites; drugs that inhibit either the calcium dependent phosphatase calcineurin or the p70S6 kinase FK506) or inhibit the p70S6 kinase; alkylating agents; mTOR inhibitors; immunomodulators; anthracyclines; vinca alkaloids; proteosome inhibitors; GITR agonists; protein tyrosine phosphatase inhibitors; a CDK4 kinase inhibitor; a BTK kinase inhibitor; a MKN kinase inhibitor; a DGK kinase inhibitor; or an oncolytic virus.

Exemplary antimetabolites include, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®) and gemcitabine (Gemzar®). Preferred antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In embodiments, a CAR-expressing cell described herein is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the fludarabine is administered at a dosage of about 10-50 mg/m$^2$ (e.g., about 10-15, 15-20, 20-25, 25-30, 30-35, 35-40, 40-45, or 45-50 mg/m$^2$), e.g., intravenously. In embodiments, the cyclophosphamide is administered at a dosage of about 200-300 mg/m$^2$ (e.g., about 200-225, 225-250, 250-275, or 275-300 mg/m$^2$), e.g., intravenously. In embodiments, the rituximab is administered at a dosage of about 400-600 mg/m2 (e.g., 400-450, 450-500, 500-550, or 550-600 mg/m$^2$), e.g., intravenously.

In embodiments, a CAR-expressing cell described herein is administered to a subject in combination with bendamustine and rituximab. In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the bendamustine is administered at a dosage of about 70-110 mg/m2 (e.g., 70-80, 80-90, 90-100, or 100-110 mg/m2), e.g., intravenously. In embodiments, the rituximab is administered at a dosage of about 400-600 mg/m2 (e.g., 400-450, 450-500, 500-550, or 550-600 mg/m$^2$), e.g., intravenously.

In embodiments, a CAR-expressing cell described herein is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 mg/m$^2$ (e.g., 350-375, 375-400, 400-425, 425-450, 450-475, or 475-500 mg/m$^2$), e.g., intravenously.

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.0$^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 313), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/m$^2$ (e.g., about 300-325, 325-350, 350-375, 375-400, 400-425, or 425-450 mg/m$^2$), e.g., intravenously. In embodiments, bendamustine is administered at a dosage of about 75-125 mg/m2 (e.g., 75-100 or 100-125 mg/m$^2$, e.g., about 90 mg/m$^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1 (2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s5311lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m$^2$ to 750 mg/m$^2$, e.g., about 150-175 mg/m$^2$, 175-200 mg/m$^2$, 200-225 mg/m$^2$, 225-250 mg/m$^2$, 250-300 mg/m$^2$, 300-325 mg/m$^2$, 325-350 mg/m$^2$, 350-375 mg/m$^2$, 375-400 mg/m$^2$, 400-425 mg/m$^2$, 425-450 mg/m$^2$, 450-475 mg/m$^2$, 475-500 mg/m$^2$, 500-525 mg/m$^2$, 525-550 mg/m$^2$, 550-575 mg/m$^2$, 575-600 mg/m$^2$, 600-625 mg/m$^2$, 625-650 mg/m$^2$, 650-675 mg/m$^2$, or 675-700 mg/m$^2$, where m$^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378 (2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or R05072759) is a humanized and glyco-engineered anti-CD20 monoclonal antibody. See, e.g., Robak. Curr. Opin. Investig. Drugs. 10.6 (2009):588-96; Clinical Trial Identifier Numbers: NCT01995669, NCT01889797, NCT02229422, and NCT01414205; and www.accessdata.fda.gov/drugsatfda_docs/label/2013/125486s0001bl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1 (2011):13-25; and Forero-Torres et al. Clin Cancer Res. 18.5 (2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1 (2011):13-25; and Casulo et al. Clin Immunol. 154.1 (2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1 (2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

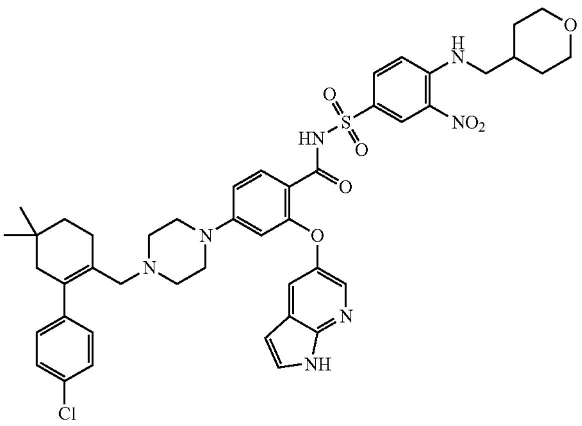 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3 (2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18 (2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Catala d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmucosally, orally, intranasally, or via pulmonary administration.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, a CAR expressing cell described herein is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to aphersis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In an embodiment, the subject has CLL. In embodiments, the subject has ALL. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No.

7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor, e.g., an SHP-2 inhibitor described herein.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d]pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102. In one embodiment, the kinase inhibitor is a DGK inhibitor, e.g., a DGK inhibitor described herein, such as, e.g., DGKinh1 (D5919) or DGKinh2 (D5794). In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

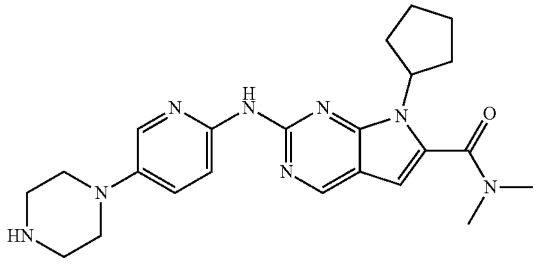 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

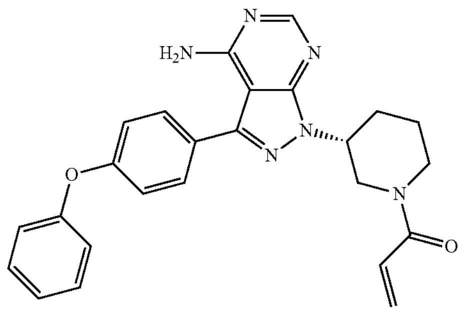 [SMILES: C=CC(=O)N1CCC[C@@H](n2nc(-c3ccc(Oc4ccccc4)cc3)c3c(N)ncnc32)C1]

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered. In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at 55$^{th}$ ASH Annual Meeting and Exposition, New Orleans, La. 7-10 December Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

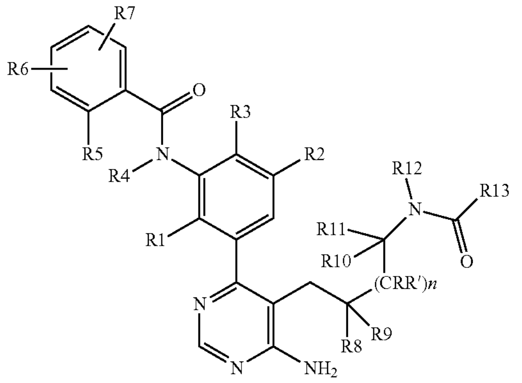

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2—, —CH2—CH2—, —CH═CH—, —CH═CH—CH2—; —CH2—CH═CH—; or —CH2—CH2—CH2—;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but- 2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl) azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido) ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl) pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy) pyrimidin-4-yl)-5-fluoro-2-methylphenyl)-4-cyclopropyl-2-fluorobenzamide; N-(3-(5-((1-Acrylamidocyclopropyl) methoxy)-6-aminopyrimidin-4-yl)-5-fluoro-2-methylphenyl)-4-cyclopropyl-2-fluorobenzamide; (S)-N-(3-(5-(2-Acrylamidopropoxy)-6-aminopyrimidin-4-yl)-5-fluoro-2-methylphenyl)-4-cyclopropyl-2-fluorobenzamide; (S)-N-(3-(6-Amino-5-(2-(but-2-ynamido)propoxy)pyrimidin-4-yl)-5-fluoro-2-methylphenyl)-4-cyclopropyl-2-fluorobenzamide; (S)-N-(3-(6-Amino-5-(2-(N-methylacrylamido)propoxy)pyrimidin-4-yl)-5-fluoro-2-methylphenyl)-4-cyclopropyl-2-fluorobenzamide; (S)-N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)-N-(3-(5-((1-Acryloylpyrrolidin-2-yl) methoxy)-6-aminopyrimidin-4-yl)-5-fluoro-2-methylphenyl)-4-cyclopropyl-2-fluorobenzamide; (S)-N-(3-(6-Amino-5-((1-(but-2-ynoyl)pyrrolidin-2-yl)methoxy) pyrimidin-4-yl)-5-fluoro-2-methylphenyl)-4-cyclopropyl-2-fluorobenzamide; (S)-2-(3-(5-((l-Acryloylpyrrolidin-2-yl) methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy) ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy) pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)-N-(3-(5-((l-Acryloylazetidin-2-yl)methoxy)-6-aminopyrimidin-4-yl)-5-fluoro-2-methylphenyl)-4-cyclopropyl-2-fluorobenzamide; (S)-N-(3-(6-Amino-5-((1-propioloylazetidin-2-yl)methoxy) pyrimidin-4-yl)-5-fluoro-2-methylphenyl)-4-cyclopropyl-2-fluorobenzamide; (S)-2-(3-(5-((1-Acryloylazetidin-2-yl) methoxy)-6-aminopyrimidin-4-yl)-5-fluoro-2-(hydroxymethyl)phenyl)-6-cyclopropyl-3,4-dihydroisoquinolin-1(2H)-one; (R)-N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)-N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl) methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety In one embodiment, the kinase inhibitor is an mTOR inhibitor selected from temsirolimus; ridaforolimus (1R,2R, 4S)-4-[(2R)-2 [(1R,9S,12S,15R,16E,18R,19R,21R, 23S, 24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl) methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine-(SEQ ID NO:313), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

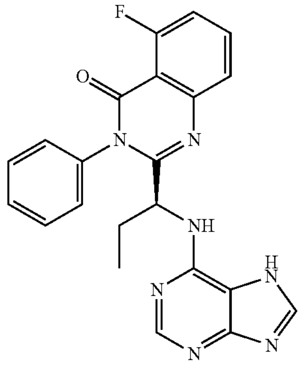 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

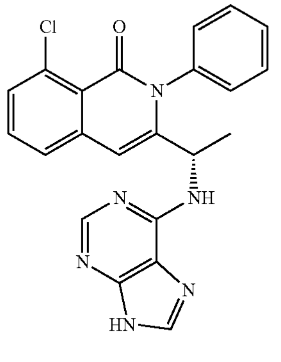 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m$^2$ (e.g., 350-375, 375-400, 400-425, 425-450, 450-475, or 475-500 mg/m$^2$), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-N$^2$-[2-isopropoxy-5-methyl-4-(4-piperidinyl)phenyl]-N$^4$-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-N$^2$-{4-[4-(dimethylamino)-1-piperidinyl]-2-methoxyphenyl}-N$^4$-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N- methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19 (2013): 1264-72. The structure of BLZ945 is shown below.

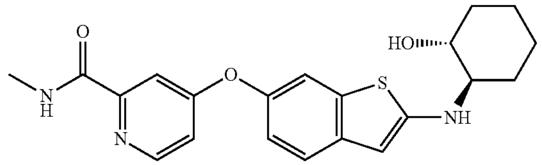 [SMILES: CNC(=O)c1cc(Oc2ccc3cc(N[C@@H]4CCCC[C@H]4O)sc3c2)ccn1]

In embodiments, a CAR-expressing cell described herein is administered to a subject in combination with a CD19 CART cell (e.g., CTL019, e.g., as described in WO2012/079000, incorporated herein by reference). In embodiments, the subject has acute myeloid leukemia (AML), e.g., a CD19 positive AML or a CD19 negative AML. In embodiments, the subject has a CD19+ lymphoma, e.g., a CD19+ Non-Hodgkin's Lymphoma (NHL), a CD19+FL, or a CD19+ DLBCL. In embodiments, the subject has a relapsed or refractory CD19+ lymphoma. In embodiments, a lymphodepleting chemotherapy is administered to the subject prior to, concurrently with, or after administration (e.g., infusion) of CD19 CART cells. In an example, the lymphodepleting chemotherapy is administered to the subject prior to administration of CD19 CART cells. For example, the lymphodepleting chemotherapy ends 1-4 days (e.g, 1, 2, 3, or 4 days) prior to CD19 CART cell infusion. In embodiments, multiple doses of CD19 CART cells are administered, e.g., as described herein. For example, a single dose comprises about $5\times10^8$ CD19 CART cells. In embodiments, a lymphodepleting chemotherapy is administered to the subject prior to, concurrently with, or after administration (e.g., infusion) of a CAR-expressing cell described herein, e.g., a non-CD19 CAR-expressing cell. In embodiments, a CD19 CART is administered to the subject prior to, concurrently with, or after administration (e.g., infusion) of a non-CD19 CAR-expressing cell, e.g., a non-CD19 CAR-expressing cell described herein.

In some embodiments, a CAR-expressing cell described herein is administered to a subject in combination with a CD19 CAR-expressing cell, e.g., CTL019, e.g., as described in WO2012/079000, incorporated herein by reference, for treatment of a disease associated with the expression of CLL-1, e.g., a cancer described herein. Without being bound by theory, it is believed that administering a CD19 CAR-expressing cell in combination with a CAR-expressing cell improves the efficacy of a CAR-expressing cell described herein by targeting early lineage cancer cells, e.g., cancer stem cells, modulating the immune response, depleting regulatory B cells, and/or improving the tumor microenvironment. For example, a CD19 CAR-expressing cell targets cancer cells that express early lineage markers, e.g., cancer stem cells and CD19-expressing cells, while the CAR-expressing cell described herein targets cancer cells that express later lineage markers, e.g., CLL-1. This preconditioning approach can improve the efficacy of the CAR-expressing cell described herein. In such embodiments, the CD19 CAR-expressing cell is administered prior to, concurrently with, or after administration (e.g., infusion) of a CAR-expressing cell described herein.

In embodiments, a CAR-expressing cell described herein also expresses a CAR targeting CD19, e.g., a CD19 CAR. In an embodiment, the cell expressing a CAR described herein and a CD19 CAR is administered to a subject for treatment of a cancer described herein, e.g., AML. In an embodiment, the configurations of one or both of the CAR molecules comprise a primary intracellular signaling domain and a costimulatory signaling domain. In another embodiment, the configurations of one or both of the CAR molecules comprise a primary intracellular signaling domain and two or more, e.g., 2, 3, 4, or 5 or more, costimulatory signaling domains. In such embodiments, the CAR molecule described herein and the CD19 CAR may have the same or a different primary intracellular signaling domain, the same or different costimulatory signaling domains, or the same number or a different number of costimulatory signaling domains. Alternatively, the CAR described herein and the CD19 CAR are configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In embodiments, a subject having a disease described herein, e.g., a hematological disorder, e.g., AML or MDS, is administered a CAR-expressing cell described herein in combination with an agent, e.g., cytotoxic or chemotherapy agent, a biologic therapy (e.g., antibody, e.g., monoclonal antibody, or cellular therapy), or an inhibitor (e.g., kinase inhibitor). In embodiments, the subject is administered a CAR-expressing cell described herein in combination with a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In embodiments, the subject is administered a CAR-expressing cell described herein in combination with a hypomethylating agent, e.g., a DNA methyltransferase inhibitor, e.g., azacitidine or decitabine. In embodiments, the subject is administered a CAR-expressing cell described herein in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). SGN-CD33A is an antibody-drug conjugate (ADC) comprising a pyrrolobenzodiazepine dimer that is attached to an anti-CD33 antibody. Actimab-A is an anti-CD33 antibody (lintuzumab) labeled with actinium. IPH2102 is a monoclonal antibody that targets killer immunoglobulin-like receptors (KIRs). In embodiments, the subject is administered a CAR-expressing cell described herein in combination a FLT3 inhibitor, e.g., sorafenib (Bayer), midostaurin (Novartis), quizartinib (Daiichi Sankyo), crenolanib (Arog Pharmaceuticals), PLX3397 (Daiichi Sankyo), AKN-028 (Akinion Pharmaceuticals), or ASP2215 (Astellas). In embodiments, the subject is administered a CAR-expressing cell described herein in combination with an isocitrate dehydrogenase (IDH) inhibitor, e.g., AG-221 (Celgene/Agios) or AG-120 (Agios/Celgene). In embodiments, the subject is administered a CAR-expressing cell described herein in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In embodiments, the subject is administered a CAR-expressing cell described herein in combination with a B cell receptor signaling network inhibitor, e.g., an inihibitor of B-cell lymphoma 2 (Bcl-2), e.g., venetoclax (Abbvie/Roche); or an inhibitor of Bruton's tyrosine kinase (Btk), e.g., ibrutinib (Pharmacyclics/Johnson & Johnson Janssen Pharmaceutical). In embodiments, the subject is administered a CAR-expressing cell described herein in combination with an inhibitor of M1 aminopeptidase, e.g., tosedostat (CTI BioPharmaNernalis); an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx). In embodiments, the subject is administered a CLL-1-targeting CAR-expressing cell in combination with a CAR-expressing cell that specifically binds an antigen other than CLL-1, e.g., CLL, BCMA, CD123, CD19, FLT-3, or folate receptor beta.

In another embodiment, the subjects receive an infusion of the CLL-1 expressing cell compositions of the present invention prior to transplantation, e.g., allogeneic stem cell transplant, of cells. In a preferred embodiment, CLL-1 expressing cells transiently express CLL-1 CAR, e.g., by electroporation of an mRNA CLL-1 CAR, whereby the expression of the CLL-1 is terminated prior to infusion of donor stem cells to avoid engraftment failure.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symsptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures. Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antibody thereof. Examples of such agents include, but are not limited to a steroid (e.g., corticosteroid), an inhibitor of TNFα, and an inhibitor of IL-6. An example of a TNFα inhibitor is an anti-TNFa antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In one embodiment, the subject can be administered an agent which enhances the activity of a CAR-expressing cell. For example, in one embodiment, the agent can be an agent which inhibits an inhibitory molecule, e.g., the agent is a checkpoint inhibitor. Inhibitory molecules, e.g., Programmed Death 1 (PD1), can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. FIGS. 29A-29E depicts examples of vectors for expressing a component, e.g., all of the components, of the CAR with a dsRNA molecule that inhibits expression of the molecule that modulates or regulates, e.g., inhibits, T-cell function.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided below.

Provided in Table 10 below are the names of PDCD1 (PD1) RNAi agents (derived from their position in the mouse PDCD1 gene sequence NM_008798.2), along with the SEQ ID NOs: 216-263 representing the DNA sequence. Both sense (S) and antisense (AS) sequences are presented as 19mer and 21mer sequences are in this table. Also note that the position (PoS, e.g., 176) is derived from the position number in the mouse PDCD1 gene sequence NM_008798.2. SEQ ID NOs are indicated in groups of 12 that correspond with "sense 19" SEQ ID NOs: 216-227; "sense 21" SEQ ID NOs: 228-239; "asense 21" SEQ ID NOs: 240-251; "asense 19" SEQ ID NOs: 252-263.

TABLE 10

Mouse PDCD1 (PD1) shRNA sequences

| Position on NM_008798.2 | Target region | Sense19 | Sense21 | Asense21 | Asense19 |
|---|---|---|---|---|---|
| 176 | CDS | GGAGGTCCCTCACCTTCTA (SEQ ID NO: 216) | CTGGAGGTCCCTCACCTTCTA (SEQ ID NO: 228) | TAGAAGGTGAGGGACCTCCAG (SEQ ID NO: 240) | TAGAAGGTGAGGGACCTCC (SEQ ID NO: 252) |
| 260 | CDS | CGGAGGATCTTATGCTGAA (SEQ ID NO: 217) | GTCGGAGGATCTTATGCTGAA (SEQ ID NO: 229) | TTCAGCATAAGATCCTCCGAC (SEQ ID NO: 241) | TTCAGCATAAGATCCTCCG (SEQ ID NO: 253) |
| 359 | CDS | CCCGCTTCCAGATCATACA (SEQ ID NO: 218) | TGCCCGCTTCCAGATCATACA (SEQ ID NO: 230) | TGTATGATCTGGAAGCGGGCA (SEQ ID NO: 242) | TGTATGATCTGGAAGCGGG (SEQ ID NO: 254) |

TABLE 10-continued

Mouse PDCD1 (PD1) shRNA sequences

| Position on NM_008798.2 | Target region | Sense19 | Sense21 | Asense21 | Asense19 |
|---|---|---|---|---|---|
| 528 | CDS | GGAGACCTCA ACAAGATAT (SEQ ID NO: 219) | CTGGAGACCT CAACAAGATAT (SEQ ID NO: 231) | ATATCTTGTTG AGGTCTCCAG (SEQ ID NO: 243) | ATATCTTGTT GAGGTCTCC (SEQ ID NO: 255) |
| 581 | CDS | AAGGCATGGT CATTGGTAT (SEQ ID NO: 220) | TCAAGGCATG GTCATTGGTAT (SEQ ID NO: 232) | ATACCAATGA CCATGCCTTGA (SEQ ID NO: 244) | ATACCAATGA CCATGCCTT (SEQ ID NO: 256) |
| 584 | CDS | GCATGGTCAT TGGTATCAT (SEQ ID NO: 221) | AGGCATGGTC ATTGGTATCAT (SEQ ID NO: 233) | ATGATACCAA TGACCATGCCT (SEQ ID NO: 245) | ATGATACCAA TGACCATGC (SEQ ID NO: 257) |
| 588 | CDS | GGTCATTGGT ATCATGAGT (SEQ ID NO: 222) | ATGGTCATTG GTATCATGAGT (SEQ ID NO: 234) | ATGGTCATTG GTATCATGAGT (SEQ ID NO: 246) | ATGGTCATTG GTATCATGA (SEQ ID NO: 258) |
| 609 | CDS | CCTAGTGGGT ATCCCTGTA (SEQ ID NO: 223) | GCCCTAGTGG GTATCCCTGTA (SEQ ID NO: 235) | GCCCTAGTGG GTATCCCTGTA (SEQ ID NO: 247) | GCCCTAGTGG GTATCCCTG (SEQ ID NO: 259) |
| 919 | CDS | GAGGATGGAC ATTGTTCTT (SEQ ID NO: 224) | ATGAGGATGG ACATTGTTCTT (SEQ ID NO: 236) | ATGAGGATGG ACATTGTTCTT (SEQ ID NO: 248) | ATGAGGATGG ACATTGTTC (SEQ ID NO: 260) |
| 1021 | 3'UTR | GCATGCAGGC TACAGTTCA (SEQ ID NO: 225) | GAGCATGCAG GCTACAGTTCA (SEQ ID NO: 237) | GAGCATGCAG GCTACAGTTCA (SEQ ID NO: 249) | GAGCATGCAG GCTACAGTT (SEQ ID NO: 261) |
| 1097 | 3'UTR | CCAGCACATG CACTGTTGA (SEQ ID NO: 226) | TTCCAGCACA TGCACTGTTGA (SEQ ID NO: 238) | TTCCAGCACA TGCACTGTTGA (SEQ ID NO: 250) | TTCCAGCACA TGCACTGTT (SEQ ID NO: 262) |
| 1101 | 3'UTR | CACATGCACT GTTGAGTGA (SEQ ID NO: 227) | AGCACATGCA CTGTTGAGTGA (SEQ ID NO: 239) | AGCACATGCA CTGTTGAGTGA (SEQ ID NO: 251) | AGCACATGCA CTGTTGAGT (SEQ ID NO: 263) |

Provided in Table 11 below are the names of PDCD1 (PD1) RNAi agents (derived from their position in the human PDCD1 gene sequence, along with the SEQ ID NOs. 264-311 representing the DNA sequence. Both sense (S) and antisense (AS) sequences are presented as 19mer and 21mer sequences. SEQ ID NOs are indicated in groups of 12 that correspond with "sense 19" SEQ ID NOs: 264-275; "sense 21" SEQ ID NOs: 276-287; "asense 21" SEQ ID NOs: 288-299; "asense 19" SEQ ID NOs: 300-311.

TABLE 11

Human PDCD1 (PD1) shRNA sequences

| Position on NM_005018.2 | Target region | Sense19 | Asense19 | Sense21 | Asense21 |
|---|---|---|---|---|---|
| 145 | CDS | GGCCAGGATG GTTCTTAGA (SEQ ID NO: 264) | TCTAAGAACC ATCCTGGCC (SEQ ID NO: 276) | GCGGCCAGGA TGGTTCTTAG A (SEQ ID NO: 288) | TCTAAGAACC ATCCTGGCCG C (SEQ ID NO: 300) |
| 271 | CDS | GCTTCGTGCT AAACTGGTA (SEQ ID NO: 265) | TACCAGTTTA GCACGAAGC (SEQ ID NO: 277) | GAGCTTCGTG CTAAACTGGT A (SEQ ID NO: 289) | TACCAGTTTA GCACGAAGCT C (SEQ ID NO: 301) |

TABLE 11-continued

Human PDCD1 (PD1) shRNA sequences

| Position on NM_005018.2 | Target region | Sense19 | Asense19 | Sense21 | Asense21 |
|---|---|---|---|---|---|
| 393 | CDS | GGGCGTGACT TCCACATGA (SEQ ID NO: 266) | TCATGTGGAA GTCACGCCC (SEQ ID NO: 278) | ACGGGCGTGA CTTCCACATG A (SEQ ID NO: 290) | TCATGTGGAA GTCACGCCCG T (SEQ ID NO: 302) |
| 1497 | 3'UTR | CAGGCCTAGA GAAGTTTCA (SEQ ID NO: 267) | TGAAACTTCT CTAGGCCTG (SEQ ID NO: 279) | TGCAGGCCTA GAGAAGTTTC A (SEQ ID NO: 291) | TGAAACTTCT CTAGGCCTGC A (SEQ ID NO: 303) |
| 1863 | 3'UTR | CTTGGAACCC ATTCCTGAA (SEQ ID NO: 268) | TTCAGGAATG GGTTCCAAG (SEQ ID NO: 280) | TCCTTGGAAC CCATTCCTGA A (SEQ ID NO: 292) | TTCAGGAATG GGTTCCAAGG A (SEQ ID NO: 304) |
| 1866 | 3'UTR | GGAACCCATT CCTGAAATT (SEQ ID NO: 269) | AATTTCAGGA ATGGGTTCC (SEQ ID NO: 281) | TTGGAACCCA TTCCTGAAAT T (SEQ ID NO: 293) | AATTTCAGGA ATGGGTTCCA A (SEQ ID NO: 305) |
| 1867 | 3'UTR | GAACCCATTC CTGAAATTA (SEQ ID NO: 270) | TAATTTCAGG AATGGGTTC (SEQ ID NO: 282) | TGGAACCCAT TCCTGAAATT A (SEQ ID NO: 294) | TAATTTCAGG AATGGGTTCC A (SEQ ID NO: 306) |
| 1868 | 3'UTR | AACCCATTCC TGAAATTAT (SEQ ID NO: 271) | ATAATTTCAG GAATGGGTT (SEQ ID NO: 283) | GGAACCCATT CCTGAAATTA T (SEQ ID NO: 295) | ATAATTTCAG GAATGGGTTC C (SEQ ID NO: 307) |
| 1869 | 3'UTR | ACCCATTCCT GAAATTATT (SEQ ID NO: 272) | AATAATTTCA GGAATGGGT (SEQ ID NO: 284) | GAACCCATTC CTGAAATTAT T (SEQ ID NO: 296) | AATAATTTCA GGAATGGGTT C (SEQ ID NO: 308) |
| 1870 | 3'UTR | CCCATTCCTG AAATTATTT (SEQ ID NO: 273) | AAATAATTTC AGGAATGGG (SEQ ID NO: 285) | AACCCATTCC TGAAATTATT T (SEQ ID NO: 297) | AAATAATTTC AGGAATGGGT T (SEQ ID NO: 309) |
| 2079 | 3'UTR | CTGTGGTTCT ATTATATTA (SEQ ID NO: 274) | TAATATAATA GAACCACAG (SEQ ID NO: 286) | CCCTGTGGTT CTATTATATT A (SEQ ID NO: 298) | TAATATAATA GAACCACAGG G (SEQ ID NO: 310) |
| 2109 | 3'UTR | AAATATGAGA GCATGCTAA (SEQ ID NO: 275) | TTAGCATGCT CTCATATTT (SEQ ID NO: 287) | TTAAATATGA GAGCATGCTA A (SEQ ID NO: 299) | TTAGCATGCT CTCATATTTA A (SEQ ID NO: 311) |

In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3. In embodiments, the agent that enhances the activity of a CAR-expressing cell, e.g., inhibitor of an inhibitory molecule, is administered in combination with an allogeneic CAR, e.g., an allogeneic CAR described herein (e.g., described in the Allogeneic CAR section herein).

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75).

Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10:1371/journal-.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) Nature doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein.

In one embodiment, the fusion protein is expressed by the same cell that expressed the CAR. In another embodiment, the fusion protein is expressed by a cell, e.g., a T cell that does not express an anti-CLL-1 CAR.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CAR-expressing cell therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-cancer activity. In a preferred embodiment, the cytokine administered after administration of CAR-expressing cells is IL-7.

Combination with a Low, Immune Enhancing, Dose of an mTOR Inhibitor

Methods described herein use low, immune enhancing, doses of mTOR inhibitors, e.g., allosteric mTOR inhibitors, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CAR-expressing cells, in the subject. Methods for measuring mTOR inhibition, dosages, treatment regimens, and suitable pharmaceutical compositions are described in U.S. Patent Application No. 2015/01240036, hereby incorporated by reference.

In an embodiment, administration of a low, immune enhancing, dose of an mTOR inhibitor can result in one or more of the following:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $CD27^{+}$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

and wherein any of the foregoing, e.g., i), ii), iii), iv), v), vi), or vii), occurs e.g., at least transiently, e.g., as compared to a non-treated subject.

In another embodiment, administration of a low, immune enhancing, dose of an mTOR inhibitor results in increased or prolonged proliferation or persistence of CAR-expressing cells, e.g., in culture or in a subject, e.g., as compared to non-treated CAR-expressing cells or a non-treated subject. In embodiments, increased proliferation is associated with in an increase in the number of CAR-expressing cells. Methods for measuring increased or prolonged proliferation are described in Examples 8 and 9. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume. Methods for measuring increased killing of cancer cells are described in Example 2.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof. In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, at least 70 but no more than 90%, at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, at least 60 but no more than 80%, at least 5 but no more than 70%, at least 10 but no more than 70%, at least 15, but no more than 70%, at least 20 but no more than 70%, at least 30 but no more than 70%, at least 40 but no more than 70%, at least 50 but no more than 70%, at least 5 but no more than 60%, at least 10 but no more than 60%, at least 15, but no more than 60%, at least 20 but no more than 60%, at least 30 but no more than 60%, at least 40 but no more than 60%, at least 5 but no more than 50%, at least 10 but no more than 50%, at least 15, but no more than 50%, at least 20 but no more than 50%, at least 30 but no more than 50%, at least 40 but no more than 50%, at least 5 but no more than 40%, at least 10 but no more than 40%, at least 15, but no more than 40%, at least 20 but no more than 40%, at least 30 but no more than 40%, at least 35 but no more than 40%, at least 5 but no more than 30%, at least 10 but no more than 30%, at least 15, but no more than 30%, at least 20 but no more than 30%, or at least 25 but no more than 30%.

The extent of mTOR inhibition can be conveyed as, or corresponds to, the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by various methods, such as measuring P70 S6 kinase activity by the Boulay assay, as described in U.S. Patent Application No. 2015/01240036, hereby incorporated by reference, or as described in U.S. Pat. No. 7,727,950, hereby incorporated by reference; measuring the level of phosphorylated S6 by western blot; or evaluating a change in the ratio of PD1 negative immune effector cells to PD1 positive immune effector cells.

As used herein, the term "mTOR inhibitor" refers to a compound or ligand, or a pharmaceutically acceptable salt thereof, which inhibits the mTOR kinase in a cell. In an embodiment, an mTOR inhibitor is an allosteric inhibitor. Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity. In an embodiment, an mTOR inhibitor is a catalytic inhibitor.

Rapamycin is a known macrolide antibiotic produced by *Streptomyces hygroscopicus* having the structure shown in Formula A.

(A)

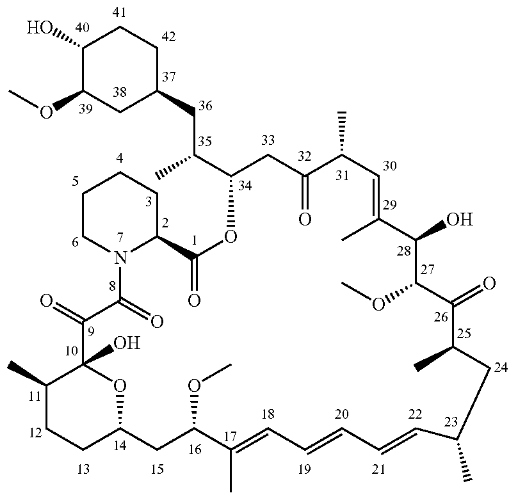

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, 0-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g.

ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the methoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone, as described in U.S. Pat. No. 5,665,772 and WO94/09010, the contents of each are incorporated by reference.

Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (AB T578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in WO2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol; 3-[2,4-bis[(35)-3-methylmorpholin-4-yl]pyrido[2,3-d] pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl) pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Methods and Biomarkers for Evaluating CAR-Effectiveness or Sample Suitability

In another aspect, the invention features a method of evaluating or monitoring the effectiveness of a CAR-expressing cell therapy (e.g., a CLL-1 CAR therapy), in a subject (e.g., a subject having a cancer, e.g., a hematological cancer), or the suitability of a sample (e.g., an apheresis sample) for a CAR therapy (e.g., a CLL-1 CAR therapy). The method includes acquiring a value of effectiveness to the CAR therapy, or sample suitability, wherein said value is indicative of the effectiveness or suitability of the CAR-expressing cell therapy.

In embodiments, the value of effectiveness to the CAR therapy, or sample suitability, comprises a measure of one, two, three, four, five, six or more (all) of the following:

(i) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in a sample (e.g., an apheresis sample or a manufactured CAR-expressing cell product sample);

(ii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a sample (e.g., an apheresis sample or a manufactured CAR-expressing cell product sample);

(iii) the level or activity of an immune cell exhaustion marker, e.g., one, two or more immune checkpoint inhibitors (e.g., PD-1, PD-L1, TIM-3 and/or LAG-3) in a sample (e.g., an apheresis sample or a manufactured CAR-expressing cell product sample). In one embodiment, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3;

(iv) the level or activity of CD27 and/or CD45RO− (e.g., CD27+CD45RO−) immune effector cells, e.g., in a CD4+ or a CD8+ T cell population, in a sample (e.g., an apheresis sample or a manufactured CAR-expressing cell product sample);

(v) the level or activity of one, two, three, four, five, ten, twenty or more of the biomarkers chosen from CCL20, IL-17a and/or IL-6, PD-1, PD-L1, LAG-3, TIM-3, CD57, CD27, CD122, CD62L, KLRG1;

(vi) a cytokine level or activity (e.g., quality of cytokine repertoire) in a CAR-expressing cell product sample, e.g., CLL-1-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (e.g., a population) of CAR-expressing immune effector cells, e.g., a plurality (e.g., a population) of T cells or NK cells, or a combination thereof. In one embodiment, the CAR-expressing cell therapy is a CLL-1 CAR therapy.

In some embodiments of any of the methods disclosed herein, the measure of one or more of (i)-(vii) is obtained from an apheresis sample acquired from the subject. The apheresis sample can be evaluated prior to infusion or re-infusion.

In some embodiments of any of the methods disclosed herein, the measure of one or more of (i)-(vii) is obtained from a manufactured CAR-expressing cell product sample, e.g., CLL-1 CAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of (i)-(vii) evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of (i)-(vii).

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In some embodiments of any of the methods disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods disclosed herein, a complete responder has, or is identified as having, a greater percentage of CD27+CD45RO− immune effector cells, e.g., in the CD8+ population, compared to a reference value, e.g., a non-responder number of CD27+ CD45RO− immune effector cells.

In some embodiments of any of the methods disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods disclosed herein, a complete responder has, or is identified as having, a greater percentage of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, compared to a reference value, e.g., a non-responder number of resting $T_{EFF}$ cells, resting $T_{REG}$ cells, younger T cells (e.g., younger CD4 or CD8 cells), or early memory T cells.

In some embodiments of any of the methods disclosed herein, a non-responder has, or is identified as having, a greater percentage of one, two, three, or more (e.g., all) of activated $T_{EFF}$ cells, activated $T_{REG}$ cells, older T cells (e.g., older CD4 or CD8 cells), or late memory T cells, or a combination thereof, compared to a reference value, e.g., a responder number of activated $T_{EFF}$ cells, activated $T_{REG}$ cells, older T cells (e.g., older CD4 or CD8 cells), or late memory T cells.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In one embodiment, a non-responder has, or is identified as having, a greater percentage of PD-1, PD-L1, or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In one embodiment, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (e.g., a CLL-1 CAR+ cell population) compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population (e.g., a CLL-1 CAR+ cell population).

In some embodiments of any of the methods disclosed herein, a non-responder has, or is identified as having, an exhausted phenotype of PD1/PD-L1+ CAR+ and co-expression of LAG3 in the CAR-expressing cell population (e.g., a CLL-1 CAR+ cell population).

In some embodiments of any of the methods disclosed herein, a non-responder has, or is identified as having, a greater percentage of PD-1/PD-L1+/TIM-3+ cells in the CAR-expressing cell population (e.g., a CLL-1 CAR+ cell population) compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population (e.g., a CLL-1 CAR+ cell population).

In some embodiments of any of the methods disclosed herein, the presence of CD8+CD27+CD45RO− T cells in an apheresis sample is a positive predictor of the subject response to a CAR-expressing cell therapy (e.g., a CLL-1 CAR therapy).

In some embodiments of any of the methods disclosed herein, a high percentage of PD1+ CAR+ and LAG3+ or TIM3+ T cells in an apheresis sample is a poor prognostic predictor of the subject response to a CAR-expressing cell therapy (e.g., a CLL-1 CAR therapy).

In some embodiments of any of the methods disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) (i) has a greater number of CD8+ T cells compared to a reference value, e.g., a non-responder number of CD8+ T cells;

(iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ cells, resting $T_{REG}$ cells, naïve CD4 cells, unstimulated memory cells or early memory T cells, or a combination thereof, compared to a reference value, e.g., a non-responder number of resting $T_{EFF}$ cells, resting $T_{REG}$ cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFa. In one embodiment, an increased level or activity of a cytokine is chosen from one or both of IL-17a and CCL20, is indicative of increased responsiveness or decreased relapse.

In some embodiments of any of the methods disclosed herein, a transduction efficiency of 15% or higher in (vii) is indicative of increased responsiveness or decreased relapse.

In some embodiments of any of the methods disclosed herein, a transduction efficiency of less than 15% in (vii) is indicative of decreased responsiveness or increased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, or Cheson criteria as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

Alternatively, or in combination with the methods disclosed herein, responsive to said value, performing one, two, three four or more of:

administering e.g., to a responder or a non-relapser, a CAR-expressing cell therapy;

administered an altered dosing of a CAR-expressing cell therapy;

altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of younger T cells in the subject prior to treatment with a CAR-expressing cell therapy;

modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder;

administering an alternative therapy, e.g., for a non-responder or partial responder or relapser; or if the subject is, or is identified as, a non-responder or a relapser, decreasing the $T_{REG}$ cell population and/or $T_{REG}$ gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxyhexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology,* 2015, 33:97-101; and WO2014/110591.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks.

In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the CAR-expressing cell (e.g., T cell or NK cell) compositions of the present invention are administered by i.v. injection. The compositions of CAR-expressing cells (e.g., T cell or NK cell) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., immune effector cells (e.g., T cells or NK cells). These immune effector cells (e.g., T cells or NK cells) isolates may be expanded by methods known in the art and treated such that one or more CAR constructs of the invention may be introduced, thereby creating a CAR-expressing cell (e.g., CAR T cell or CAR-expressing NK cell) of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR-expressing cell (e.g., CAR T cell or CAR-expressing NK cell) of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells or NK cells), e.g., using in vitro transcription, and the subject (e.g., human) receives an initial administration of CAR-expressing immune effector cells (e.g., T cells, NK cells) cells of the invention, and one or more subsequent administrations of the CAR-expressing immune effector cells (e.g., T cells, NK cells) cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing immune effector cells (e.g., T cells, NK cells) of the invention are administered to the subject (e.g., human) per week, e.g., 2, 3, or 4 administrations of the CAR-expressing immune effector cells (e.g., T cells, NK cells) of the invention are administered per week. In one embodiment, the subject (e.g., human subject) receives more than one administration of the CAR-expressing immune effector cells (e.g., T cells, NK cells) cells per week (e.g., 2, 3 or 4 administrations per week) (also referred to herein as a cycle), followed by a week of no CAR-expressing immune effector cells (e.g., T cells, NK cells) administrations, and then one or more additional administration of the CAR-expressing immune effector cells (e.g., T cells, NK cells) (e.g., more than one administration of the CAR-expressing immune effector cells (e.g., T cells, NK cells) per week) is administered to the subject. In another embodiment, the subject (e.g., human subject) receives more than one cycle of CAR-expressing immune effector cells (e.g., T cells, NK cells), and the time between each cycle is less than 10, 9, 8, 7, 6, 5, 4, or 3 days. In one embodiment, the CAR-expressing immune effector cells (e.g., T cells, NK cells) are administered every other day for 3 administrations per week. In one embodiment, the CAR-expressing immune effector cells (e.g., T cells, NK cells) of the invention are administered for at least two, three, four, five, six, seven, eight or more weeks.

In one aspect, CLL-1 CAR-expressing cells, e.g., CLL-1 CARTs or CLL-1 CAR-expressing NK cells) are generated using lentiviral viral vectors, such as lentivirus. CAR-expressing cells, e.g., CLL-1 CARTs or CAR expressing NK cells, generated that way will have stable CAR expression.

In one aspect, CAR-expressing cells, e.g., CARTs or CAR-expressing NK cells, are generated using a viral vector such as a gammaretroviral vector, e.g., a gammaretroviral vector described herein. CAR-expressing cells, e.g., CARTs or CAR-expressing NK cells, generated using these vectors can have stable CAR expression.

In one aspect, CAR-expressing cells, e.g., CARTs or CAR-expressing NK cells, transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR-expressing cells, e.g., CARTs or CAR-expressing NK cells, (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Generating CAR Constructs

Fully human anti-CD33 single chain variable fragments (scFv) were generated and cloned into a lentiviral expression vector with the intracellular CD3zeta chain and the intracellular co-stimulatory domain of 4-1BB and given the names depicted in Table 7 (which is shown in the Detailed Description).

The order in which the VL and VH domains appear in the scFv was varied (i.e., VL-VH, or VH-VL orientation), and where either three or four copies of the "G4S" (SEQ ID NO:25) subunit, in which each subunit comprises the sequence GGGGS (SEQ ID NO:25) (e.g., $(G45)_3$ (SEQ ID NO:28) or $(G4S)_4$ (SEQ ID NO:27)), connect the variable domains to create the entirety of the scFv domain, as shown in Table 8.

The sequences of the human scFv fragments (SEQ ID NOS: 39-51) are provided herein in Table 8 (in the Detailed Description). These clones all contained a Q/K residue change in the signal domain of the co-stimulatory domain derived from CD3zeta chain. The CAR scFv fragments were then cloned into lentiviral vectors to create a full length CAR construct in a single coding frame, and using the EF1 alpha promoter for expression (SEQ ID NO: 11).

Sequences of CAR constructs and their domain sequences are listed in the Detailed Description. Analysis of the human CAR constructs was conducted as described in Examples 2-5.

Example 2: Analysis and In Vitro Activity of Human scFv Bearing CARTs

Figure 1B:
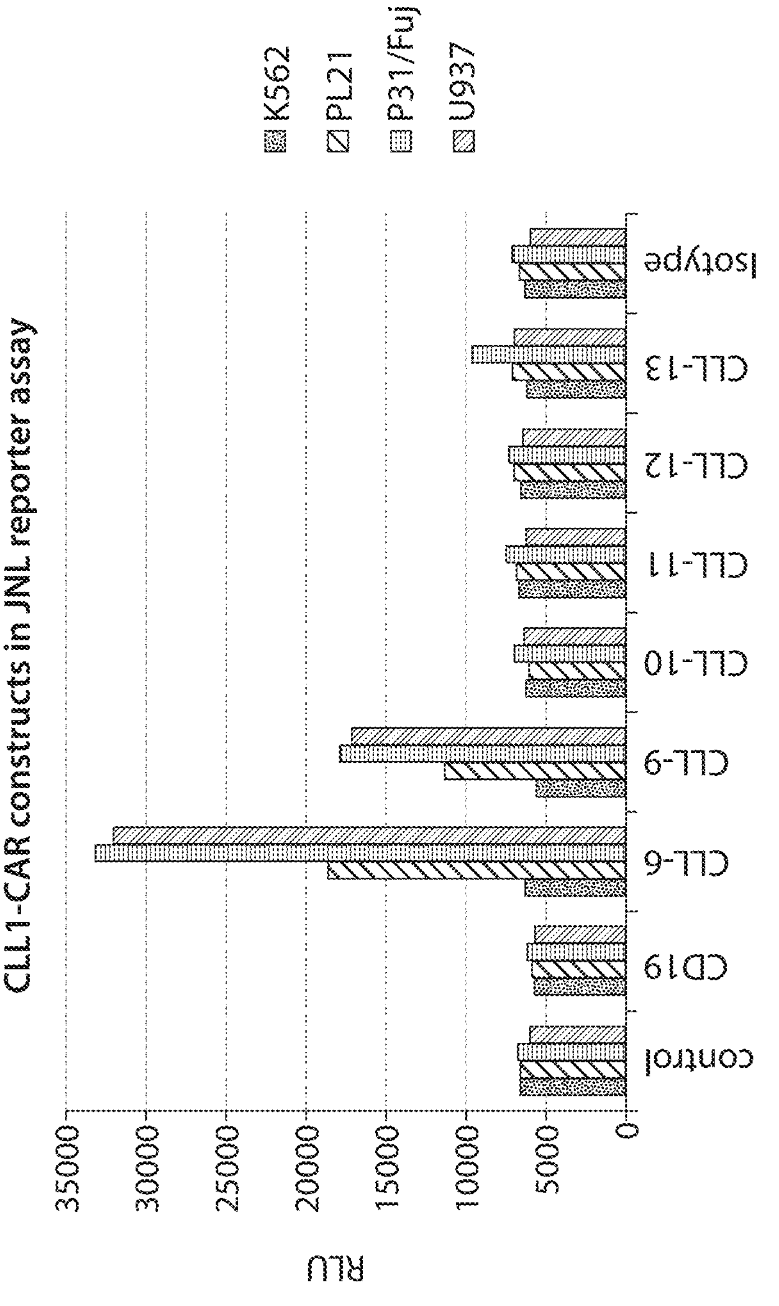
Figure 1C:
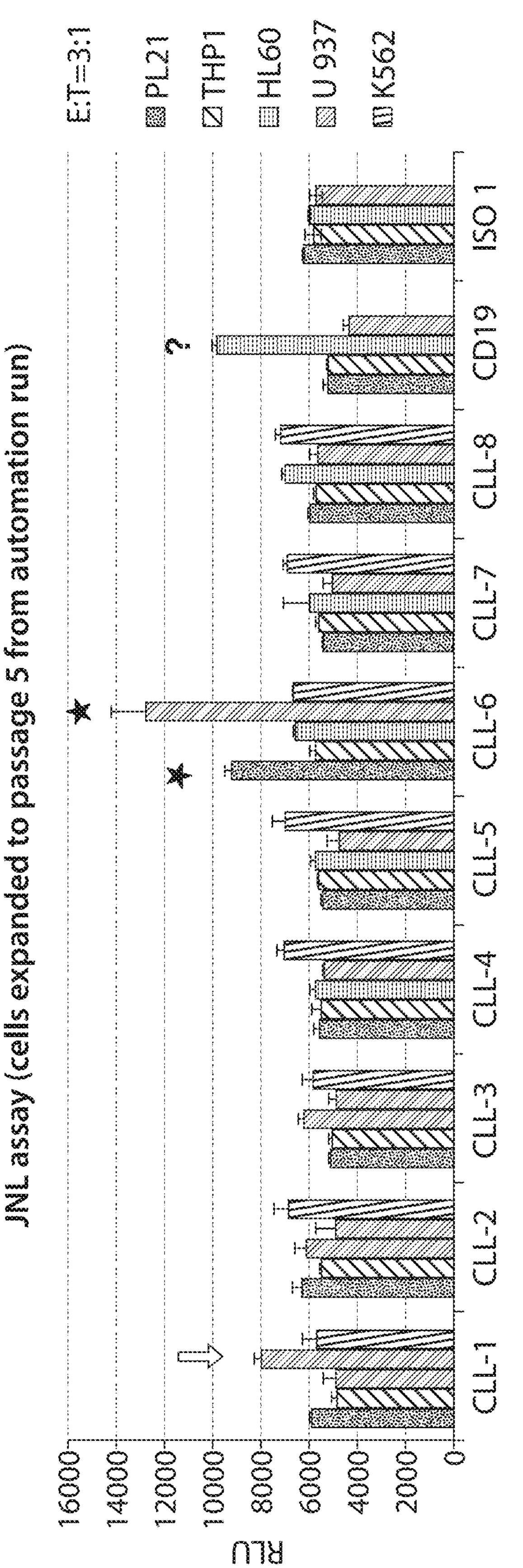
Figure 2A:
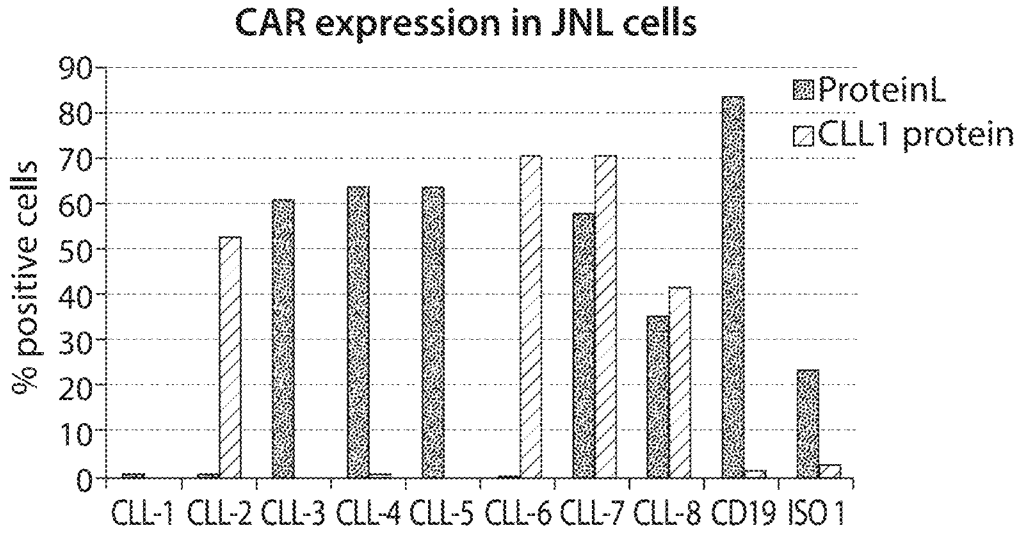
FIGS. 2A, 2B, and 2C, is a series of images demonstrating CAR expression as evaluated by FACS in a JNL cell line transduced with anti-CLL-1 CAR.
Figure 2B:
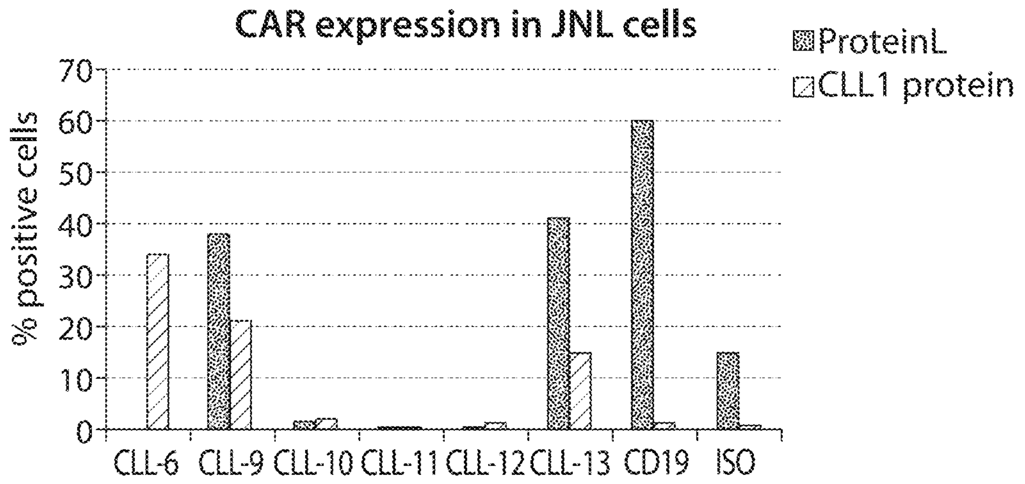
Figure 2C:
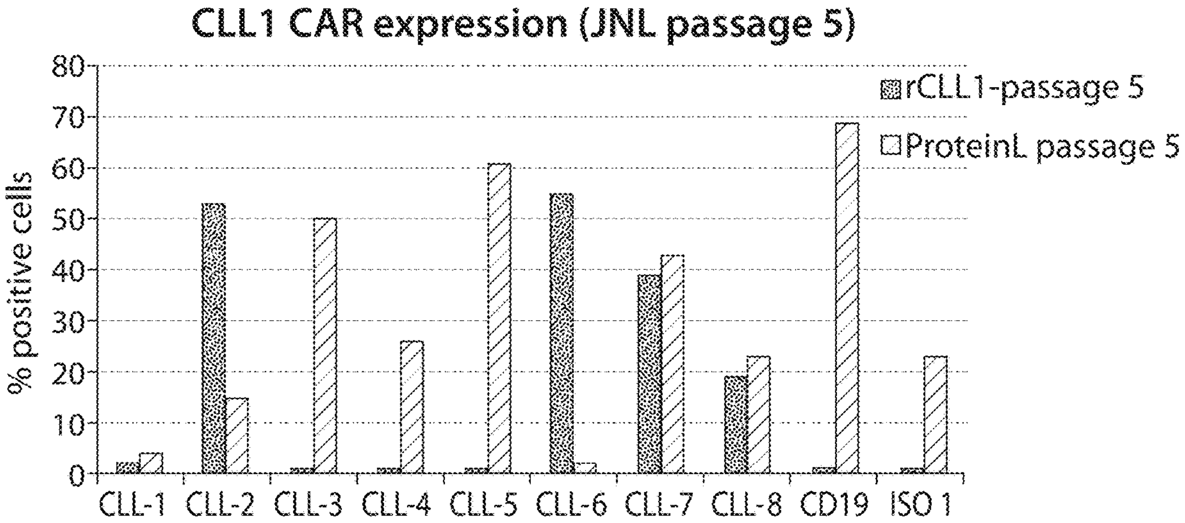

Anti-CLL-1 CAR constructs were evaluated for activity using a Jurkat cell line containing the luciferase reporter driven by the NFAT promoter (termed JNL cells). CAR activity is measured as activation of this NFAT-driven reporter. Lentiviral supernatants containing the CART constructs were added to JNL cells for transduction. 4-6 days after transduction, JNL cells were either evaluated for CAR expression by FACS as described below (FIGS. 2A, 2B, and 2C) or mixed with target-positive (PL21, THP1, HL60, U937) or target-negative (K562) cell lines at the indicated effector (JNL) to target cell line (E:T) ratio to trigger activation. After 20 hours of co-incubation, luciferase signal was measured using the Bright-Glo™ Luciferase Assay on the EnVision instrument (FIGS. 1A, 1B, and 2C).

Optimal anti-CLL-1 CAR constructs are selected based on the quantity and quality of the effector T cell responses of CLL-1 CAR transduced T cells ("CART-CLL-1" or "CART-CLL-1 T cells") in response to CLL-1 expressing ("CLL-1+") targets. Effector T cell responses include, but are not limited to, cellular expansion, proliferation, doubling, cytokine production and target cell killing or cytolytic activity (degranulation).

Generation of CART-CLL-1

The human scFv encoding lentiviral transfer vectors were used to produce the genomic material packaged into the VSVg pseudotyped lentiviral particles. Lentiviral transfer vector DNA was mixed with the three packaging components of VSVg, gag/pol and rev in combination with lipofectamine reagent to transfect them together in to Lenti-X 293T cells (Clontech).

After 30 hours, the media was collected, filtered and stored at −80 C. The therapeutic CART-CLL-1 were generated by starting with the blood from a normal apheresed donor whose naïve T cells are obtained by negative selection for T cells, CD4+ and CD8+ lymphocytes. These cells were activated by CD3×28 beads (Dynabeads® Human T-Expander CD3/CD28, Invitrogen) at a ratio of 1:3 in RPMI 1640, 10% heat-inactivated fetal calf serum (FCS), 2 mM L-glutamine, 1× Penicillin/Streptomycin, 100 μM non-essential amino acids, 1 mM NaPyruvate, 10 mM Hepes, and 55 μM 2-mercaptoethanol at 37° C., 5% $CO_2$ T cells were cultured at $1\times10^6$ T cells in 0.5 mL medium per well of a 24-well plate. After 24 hours, the T cells are blasting and 0.5 mL of viral supernatant was added. The T cells began to divide in a logarithmic growth pattern, which was monitored by measuring the cell counts per mL, and T cells were diluted in fresh medium every two days. As the T cells began to rest down after approximately 10 days, the logarithmic growth waned. The combination of slowing growth rate and T cell size approaching ~300 fl determines the state for T cells to be cryopreserved for later analysis.

Figure 3A:
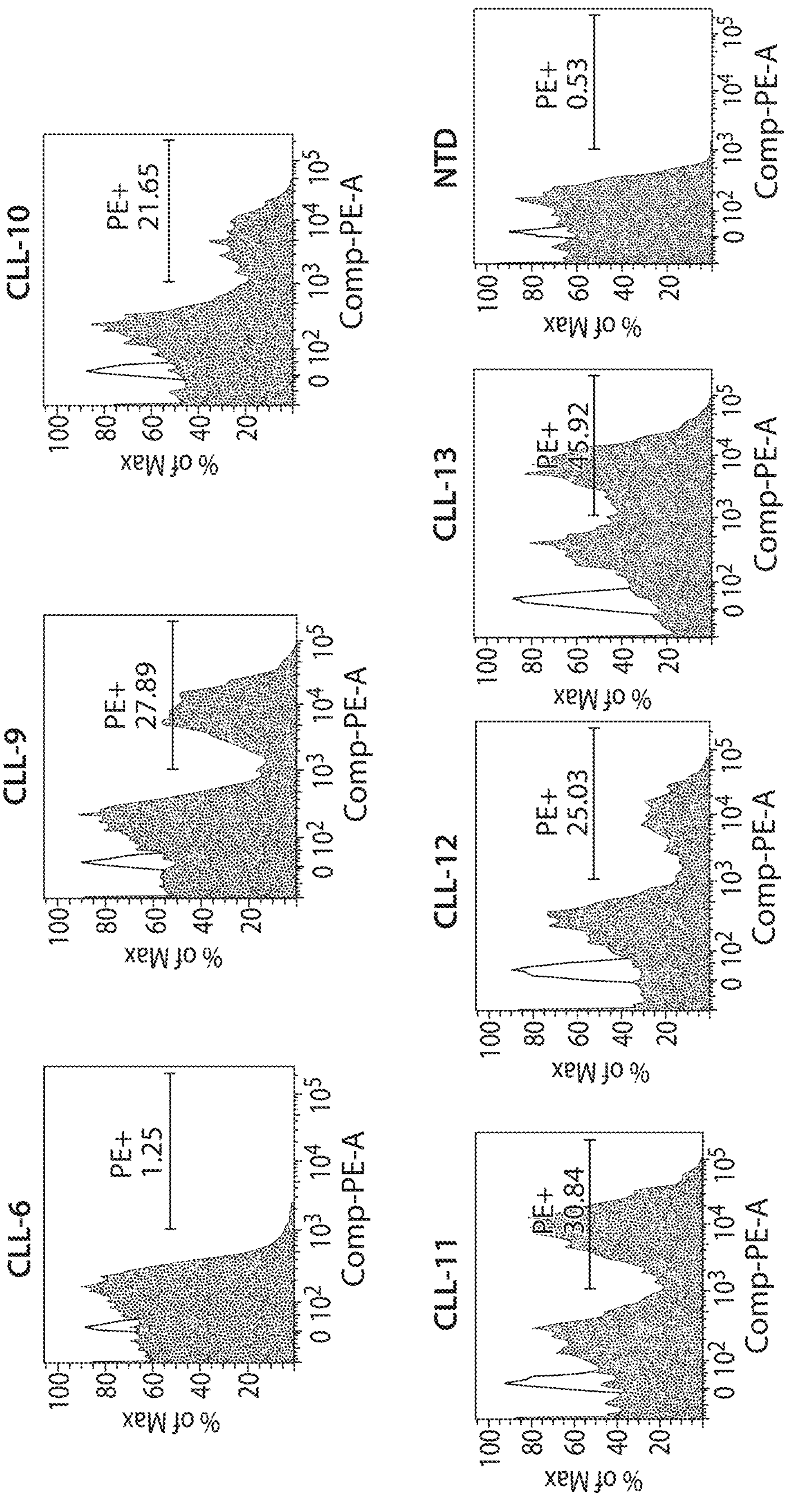
FIGS. 3A and 3B, is a series of images demonstrating histogram plots of relative fluorescent intensity from that FACS showed the percentage of transduced T cells.
Figure 3B:
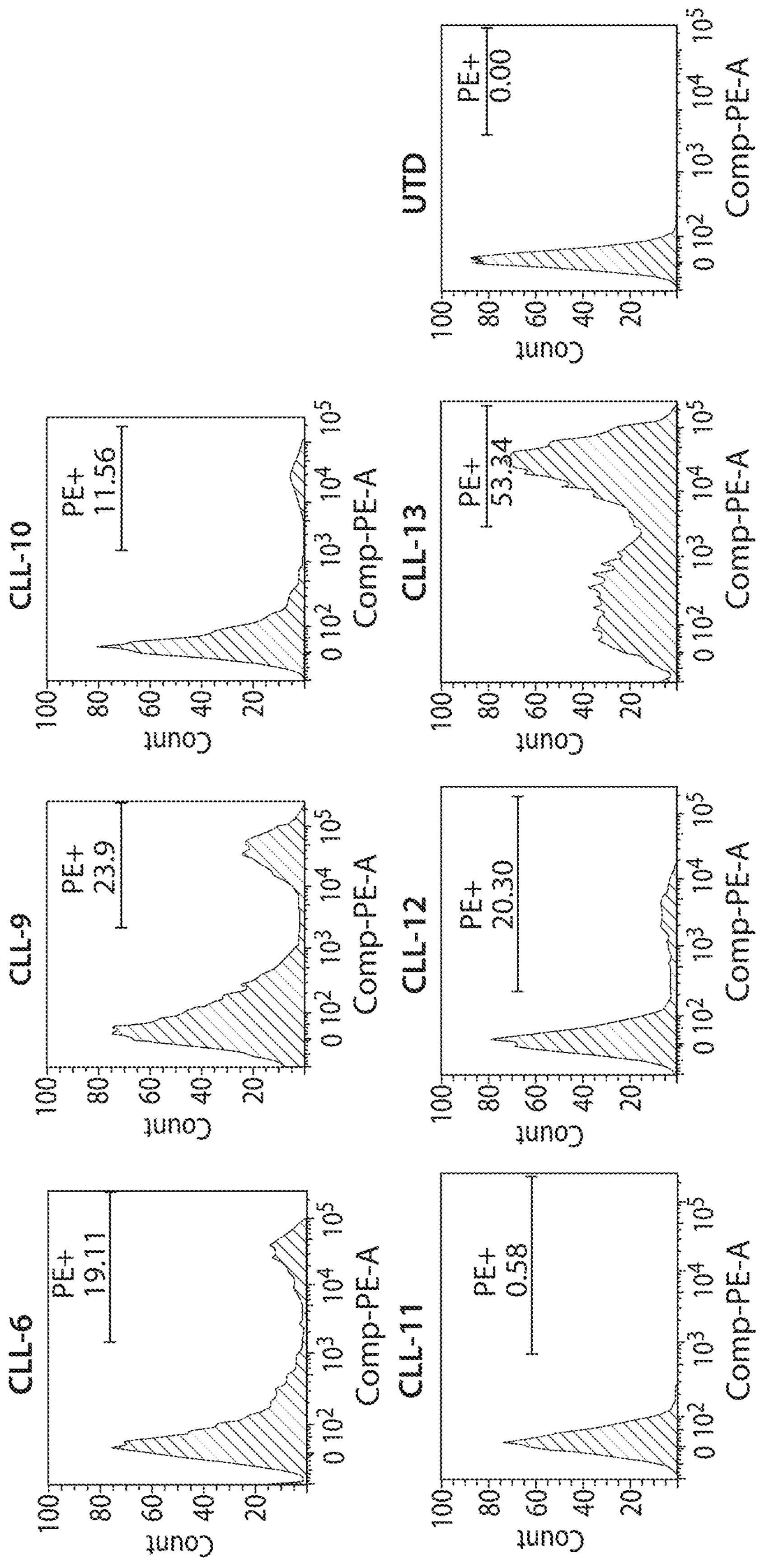
Figure 22A:
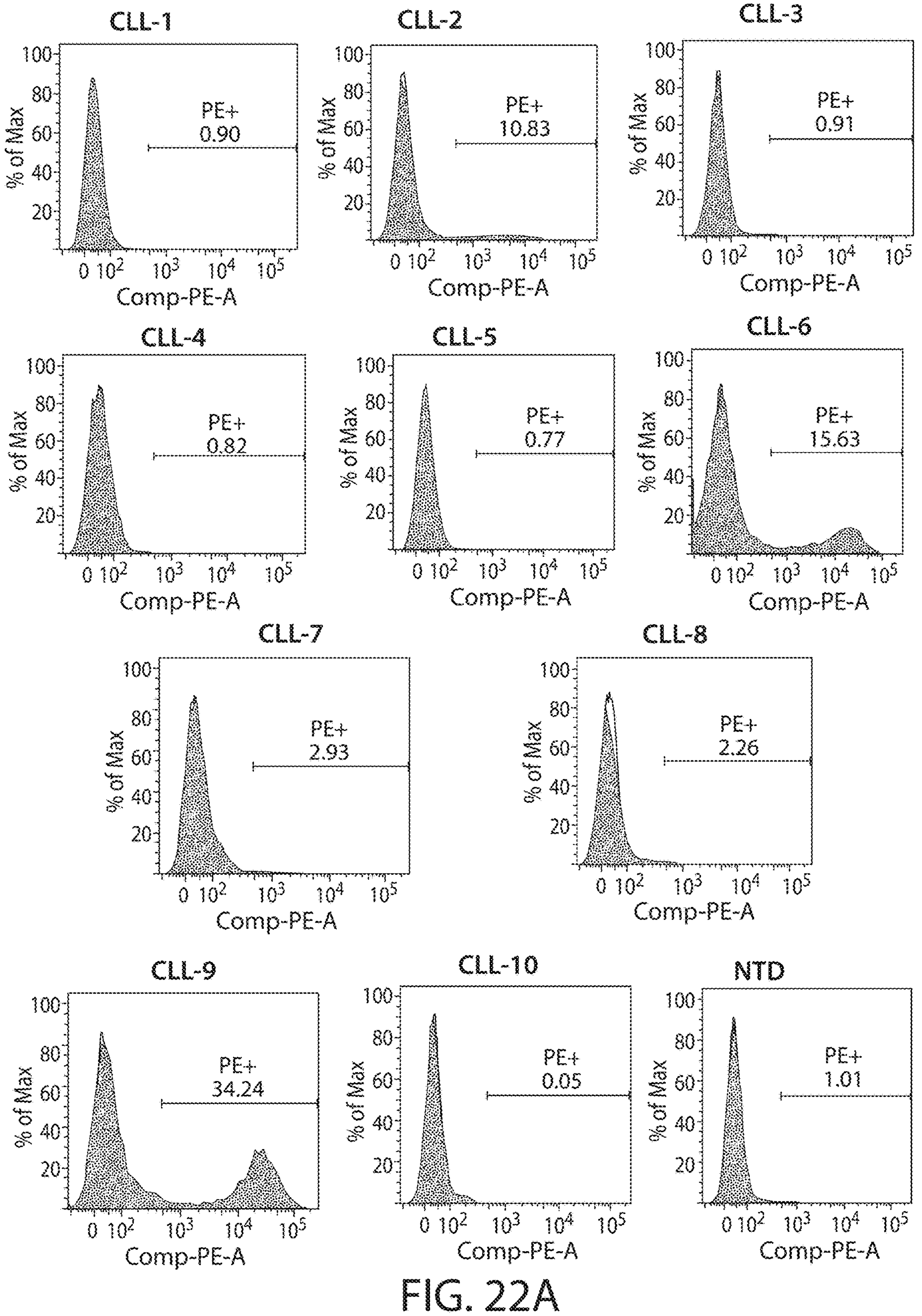
FIGS. 22A and 22B, is a series of histogram plots showing the relative fluorescent intensity from FACS analysis showing the percentage of transduced T cells.
Figure 22B:
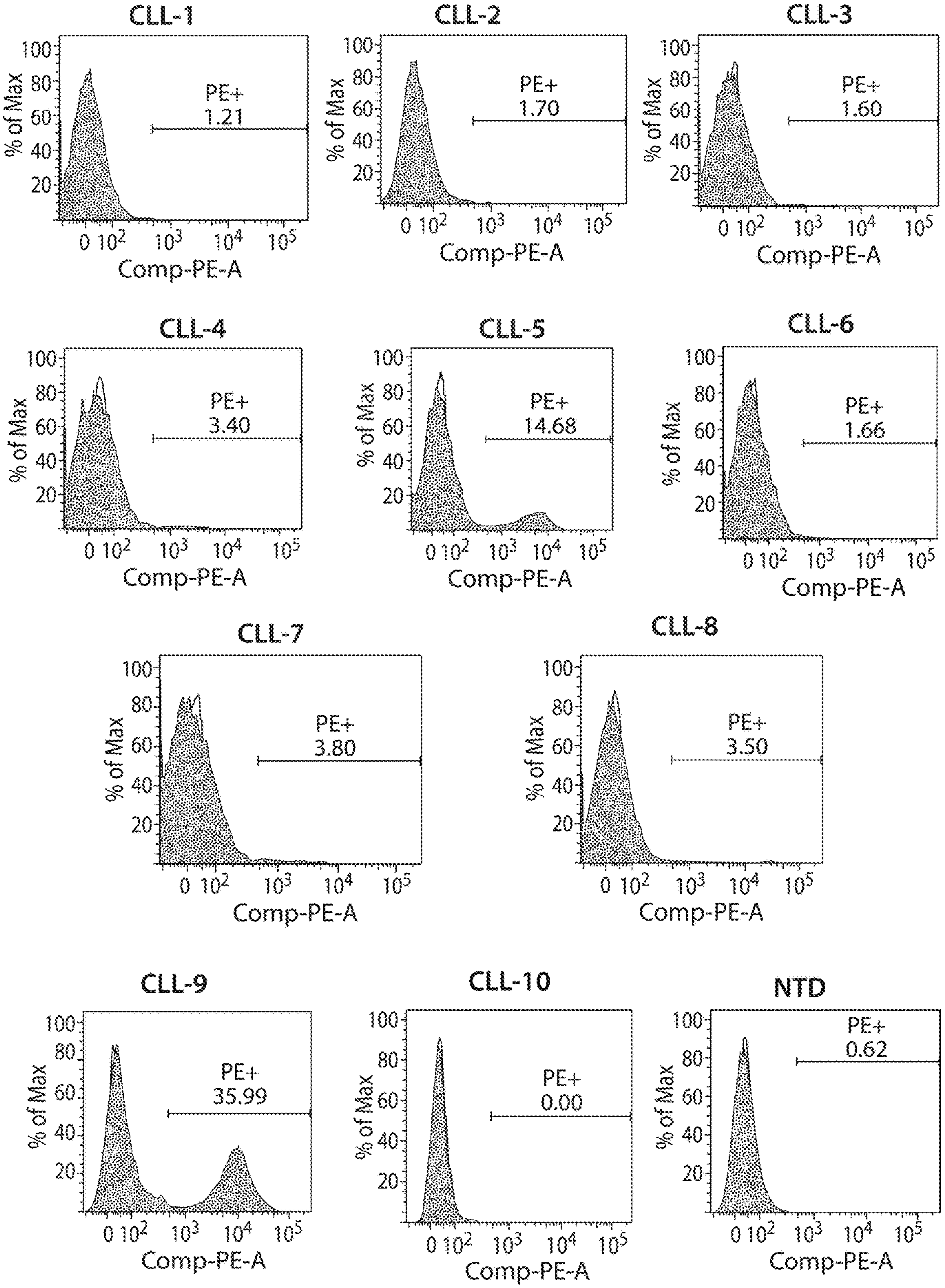

Before cryopreserving, percentage of cells transduced (expressing the anti-CLL-1 CAR on the cell surface) and their relative fluorescence intensity of expression were determined by flow cytometric analysis on a BD LSR-Fortessa or BD-FACSCanto using either Protein L (FIGS. 3A and 22A) or biotinylated recombinant human CLL-1 protein as detection reagents (FIGS. 3B and 22B). Histogram plots of relative fluorescent intensity from that FACS showed the percentage of transduced T cells. Transduction result in a range of CART positive cells from 10-50%.

Evaluating Cytolytic Activity and Cytokine Secretion of CART-CLL-1 Redirected T Cells.

To evaluate the functional abilities of CART-CLL-1 T cells to kill and secrete cytokines, the cells were thawed and allowed to recover overnight.

Figure 4A:
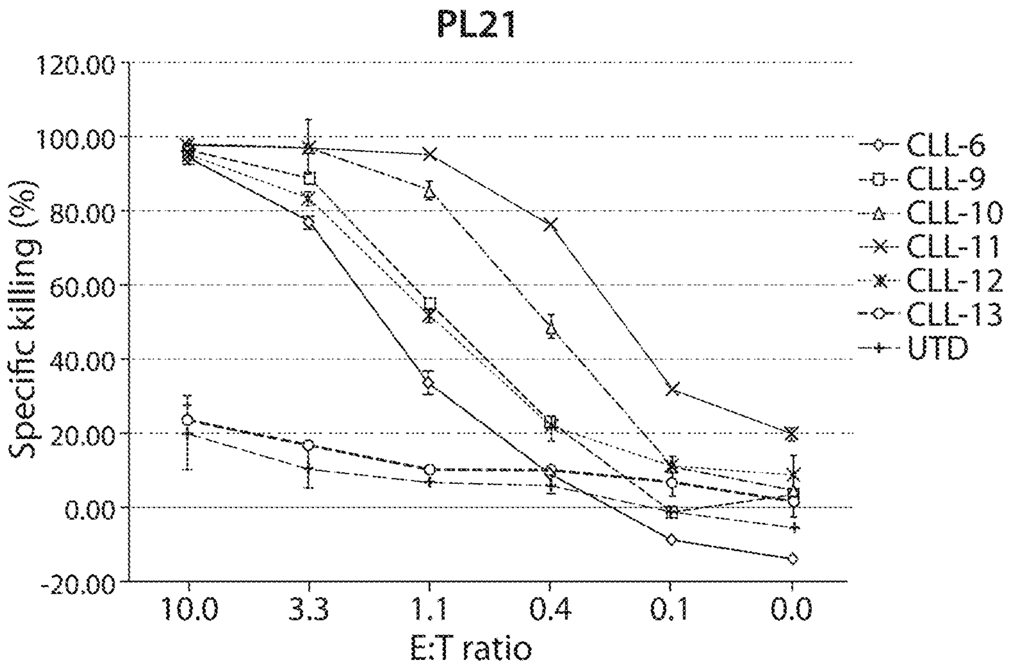
FIGS. 4A, 4B, and 4C, is a series of images demonstrating anti-CLL-1 CART cell killing of luciferized PL21 (FIG. 4A), HL60 (FIG. 4B) and U87 cells (FIG. 4C).
Figure 4B:
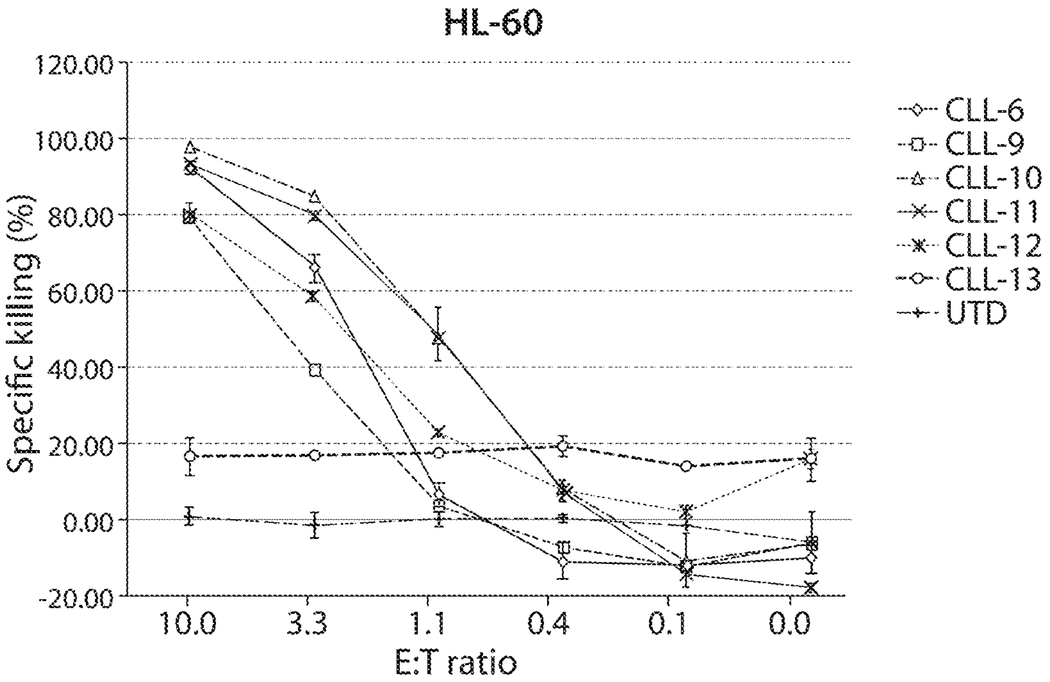
Figure 4C:
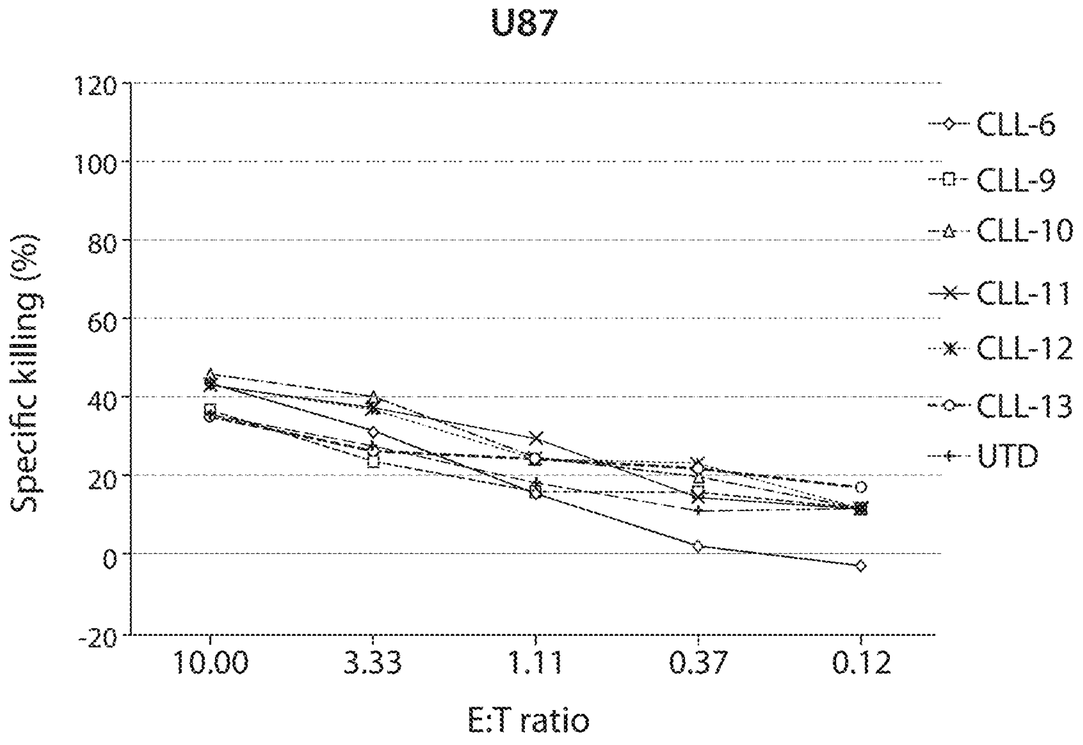

T cell killing was directed towards CLL-1-expressing PL21 (FIG. 4A) and HL-60 (FIG. 4B) acute myelogenous leukemia cell lines stably expressing luciferase. Non-CLL-1 expressing U87 cells were used as a control (FIG. 4C) and untransduced T cells were used to determine non-specific background killing levels. The cytolytic activities of CART-CLL-1 were measured as a titration of effector:target cell ratios of 10:1 and 3-fold downward dilutions of T cells where effectors were defined as T cells expressing the anti-CLL-1 chimeric receptor. Assays were initiated by mixing an appropriate number of T cells with a constant number of targets cells. After 20 hours luciferase signal was measured using the Bright-Glo™ Luciferase Assay on the EnVision instrument.

Comparing these killing curves, titrating the amount of effector cells shows that those cells expressing CLL-1 were destroyed. T cells from the same donor that were transduced with either human scFv bearing CAR-CLL-1 cells were able to kill selectively CLL-1+ targets. Interestingly, not all CART-CLL-1 cells were active. CART cells containing clone 13 were inactive in this assay even in the presence of target-expressing cells.

Figure 5A:
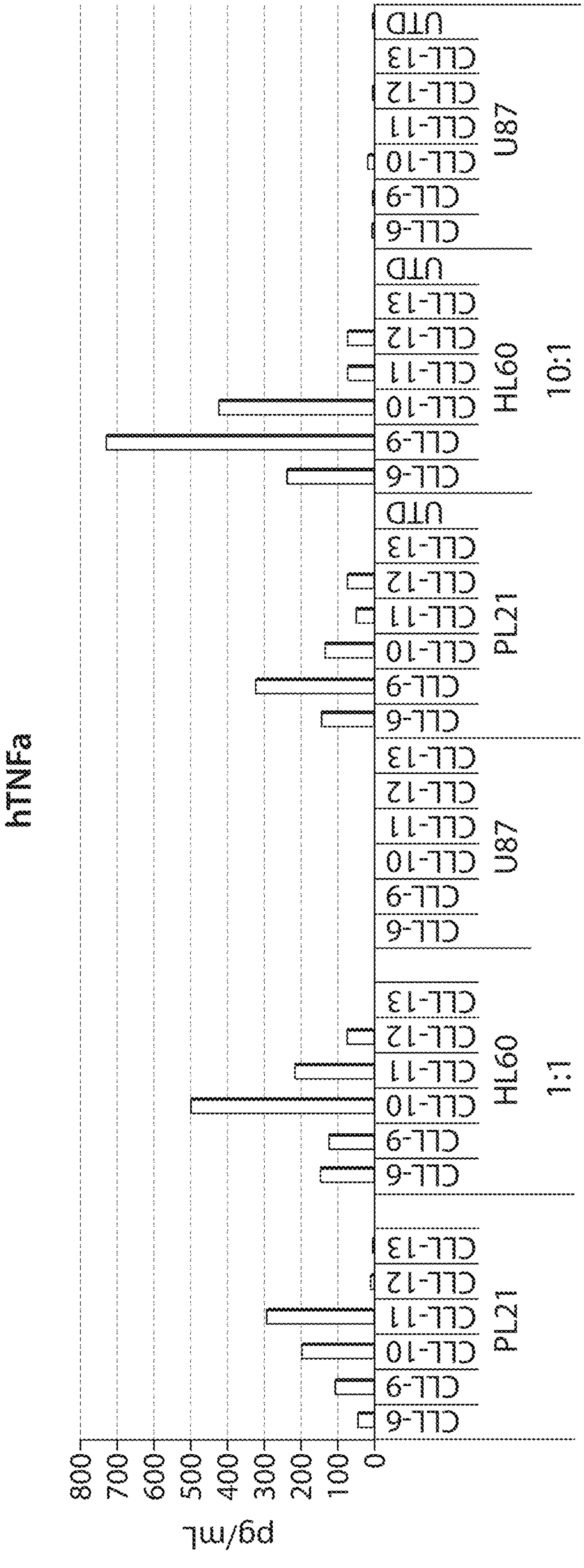
FIGS. 5A, 5B, and 5C, is a series of images demonstrating cytokine production in CART-CLL-1 cells. Untransduced T cells (UTD) were used as a non-specific control for background T cell effects. TNF-alpha (FIG. 5A), IL-2 (FIG. 5B), and interferon (IFN)-gamma (FIG. 5C) were measured.
Figure 5B:
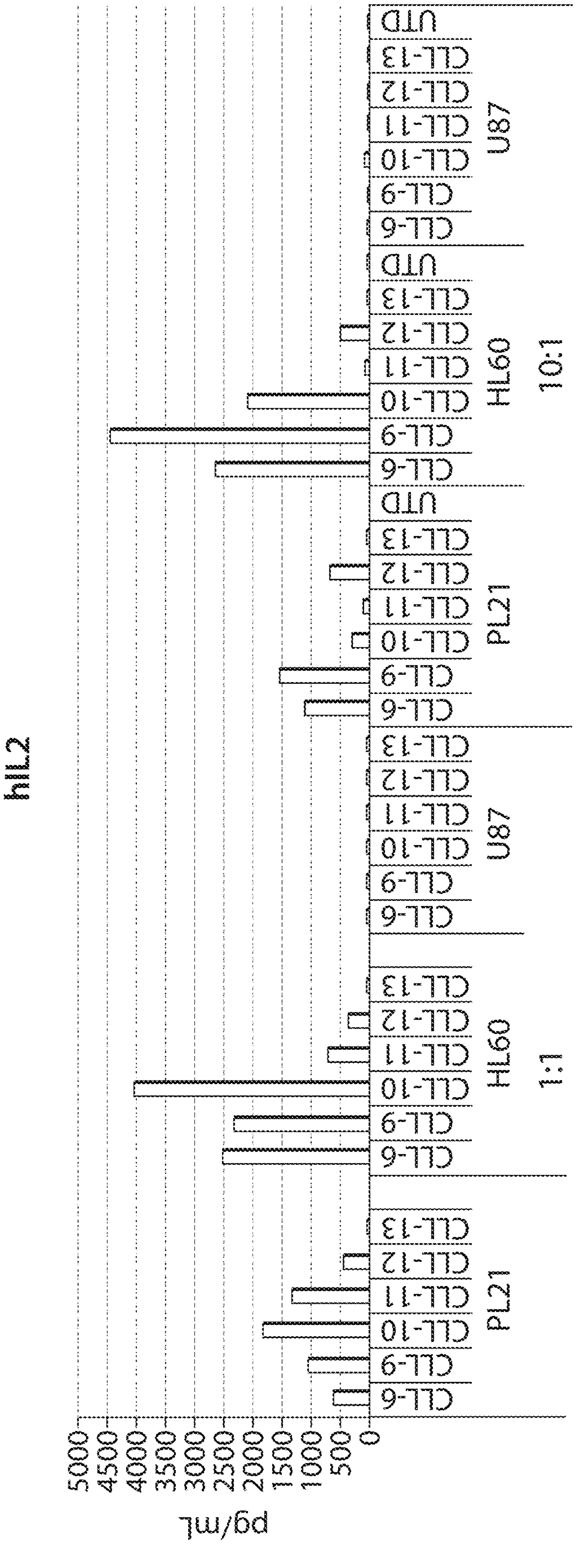
Figure 5C:
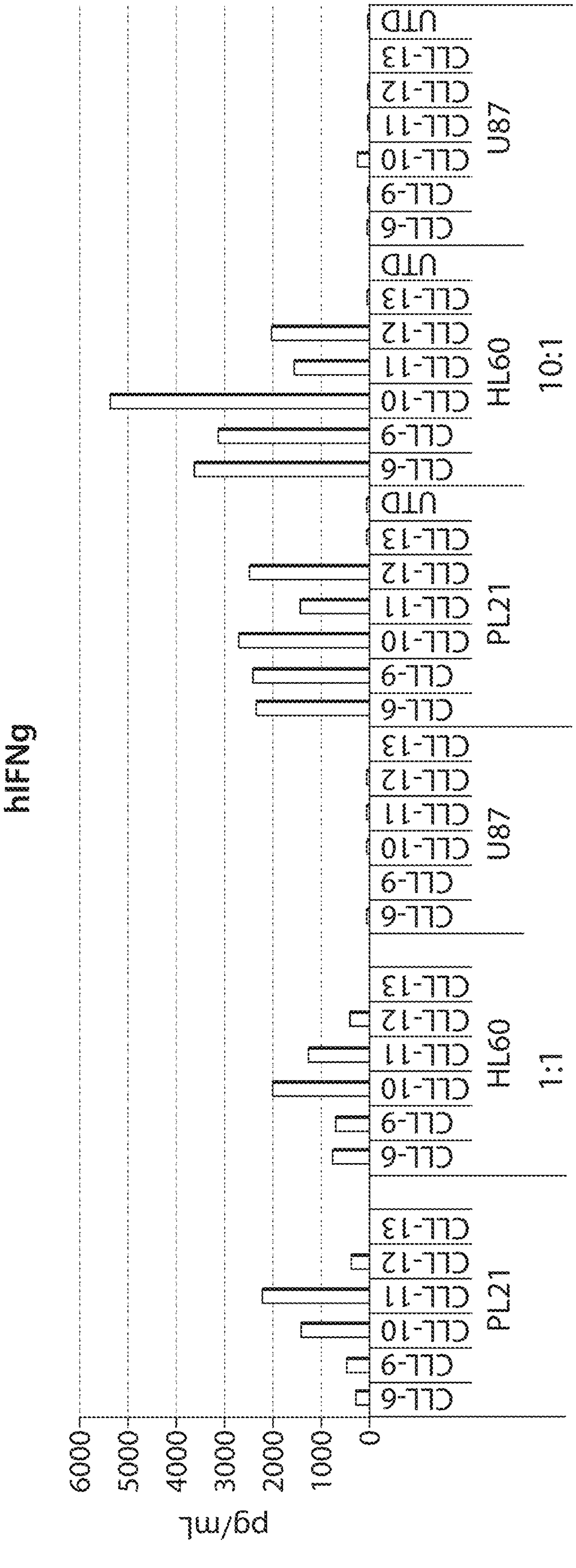

For measuring cytokine production of CART-CLL-1 cells, cells were thawed and allowed to recover overnight. Untransduced T cells (UTD) were used as a non-specific control for background T cell effects. The T cells were directed towards HL-60, PL21, or U87 cells. The assay tested an effector:target ratio of 1:1 or 10:1 as noted where effectors were defined as T cells expressing the anti-CLL-1 CAR. The assay was run 24 hours after mixing of the cells, when the media is removed for analysis of cytokines TNF-alpha (FIG. 5A), IL-2 (FIG. 5B), and INF-gamma (FIG. 5C) using the CBA-Flex kit for human cytokine detection.

When CART-CLL-1 T cells were cultured with cancer cells endogenously expressing CLL-1, all CLL-1-CARTs except CLL-1-13 produced cytokines in response to target-expressing cells. The difference in reactivity of the various CLL-1-CART clones toward low CLL-1-expressing target cells may translate to better clinical efficacy of CART cells transduced with these constructs.

Evaluating Proliferative Capacity of CART-CLL-1

CART-CLL1 T cells were tested for their ability to proliferate in response to exposure to antigen on target cells. Multiple CLL-1 CAR constructs were tested, CLL-6, CLL-9, CLL-10, CLL-11, CLL-12, and CLL-13. Target cells included U937, PL-21, HL60, and Molm13 cells. On the day of assay (Day 0), target cells were counted and transferred to a 50 ml tube in 6 mL of T cell media at 3e6 cells/ml. Target cells were irradiated on ice at 10,000 rad. After irradiation, target cells were washed twice in T cell media, counted, and resuspended to 5e5 cells/ml in T cell media on ice.

Frozen transduced T cells were thawed, washed in 10 mL complete T cell media, spun at 300 g for 10 min, and resuspended gently in 3 mL of complete T cell media at RT. T-cells were then counted in a cellometer and resuspended to 2.5e6/mL in 10 mL of media. In a 96 well U-bottom plate, 25,000 irradiated target cells and 25,000 transduced CAR T cells (1:1 ratio) were combined in duplicate wells. In a separate well, 75,000 Anti-CD3/CD28 beads were added in 100 μl of medium to 25,000 transduced T cells to create a 1:3 cells-to-beads ratio as positive control; in another well, 100 μl of medium was added to 25,000 transduced T cells alone as media-only control. Cells were incubated for 4 days at 37° C., 5% $CO_2$.

On day 4, cells were harvested and duplicates were combined by pipetting and transferring into the same well on the U-bottom plate for staining for FACS of CD4, CD8, and CAR using protein L or recombinant human CLL1 protein. After staining, cells were resuspended in 120 μl MACS+ 0.5% BSA buffer and 20 μl/well countbright beads were added to each well. Proliferation was measured as the number of FACS positive cells detected in the period of time used to count 2500 beads.

Figure 23A:
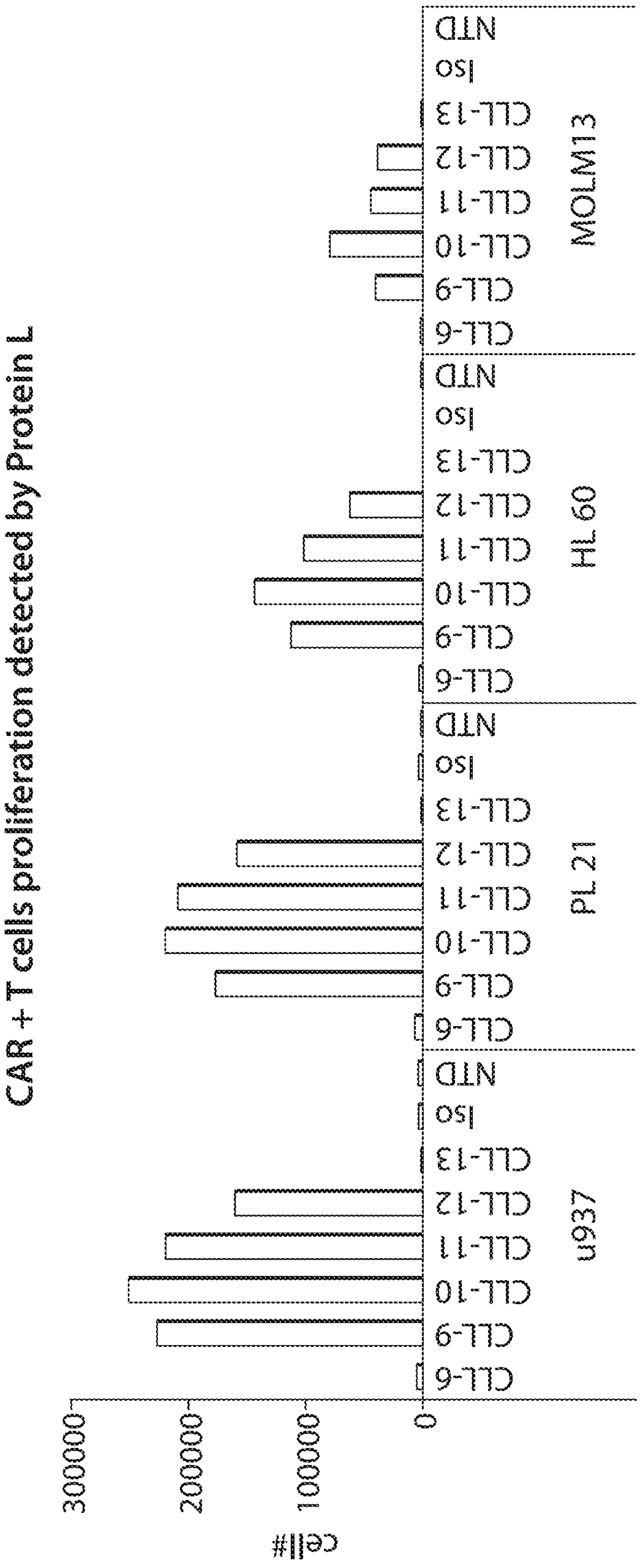
FIGS. 23A and 23B, are two graphs showing the proliferation capacity of the CLL-1 CART cells when cultured with target cells.
Figure 23B:
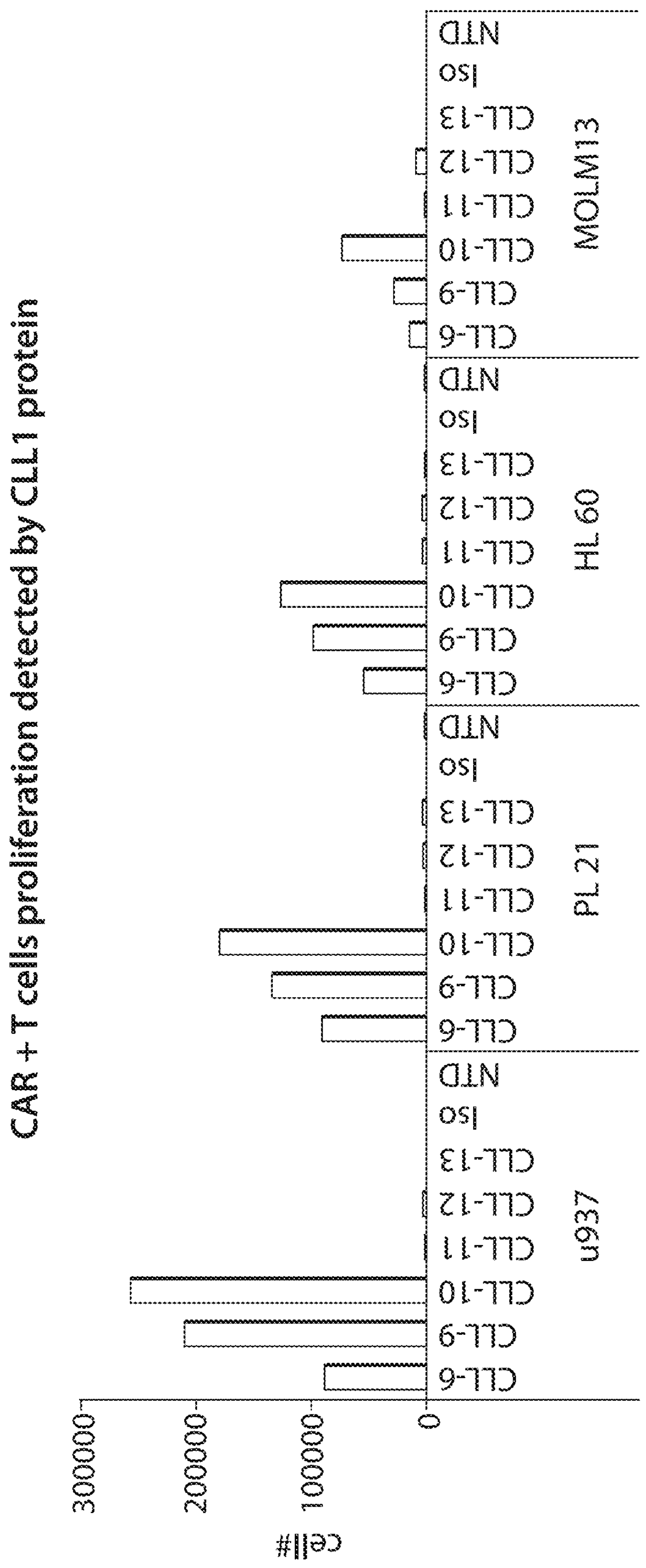

As shown in FIGS. 23A and 23B, cells expressing CLL-1 CAR constructs CLL-6, CLL-9, CLL-10, CLL-11, and CLL-12 proliferated in the presence of different target cells.

Example 3: CLL-1 Toxicity Studies

Figure 6:
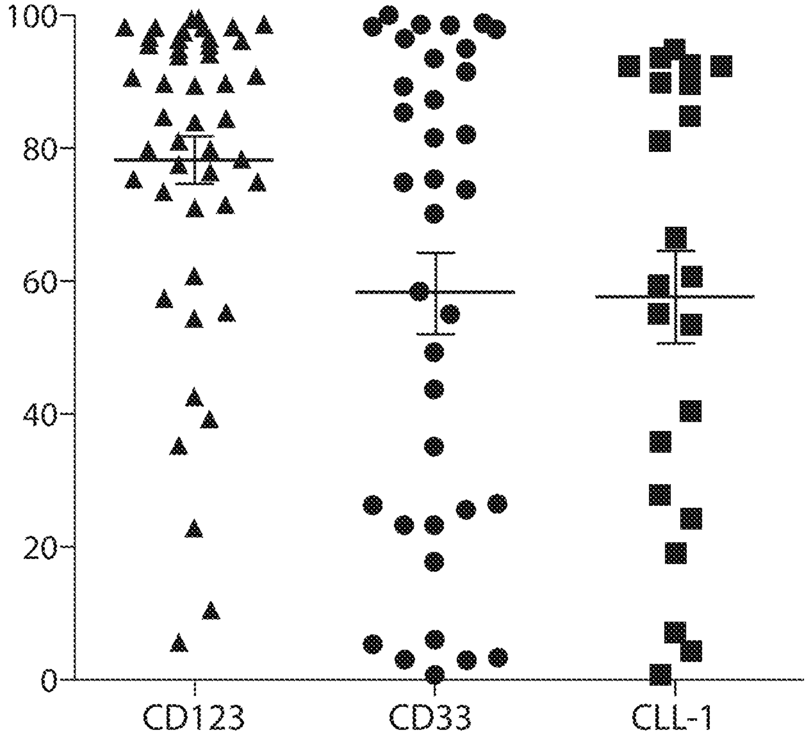
FIG. 6 is an image demonstrating that CLL-1 is expressed in most primary patient samples with AML (AML blasts were gated using standard side scatter $^{low}$ CD45$^{dim}$ characteristics). CLL-1 was measured by flow cytometry using a commercially available antibody (clone HIM3-4, eBioscience)

CLL-1 was measured by flow cytometry using a commercially available antibody (clone HIM3-4, eBioscience). The results herein demonstrate that CLL-1 was expressed in most primary patient samples with AML (AML blasts were gated using standard side scatter low CD45dim characteristics) (FIG. 6).

Figure 7A:
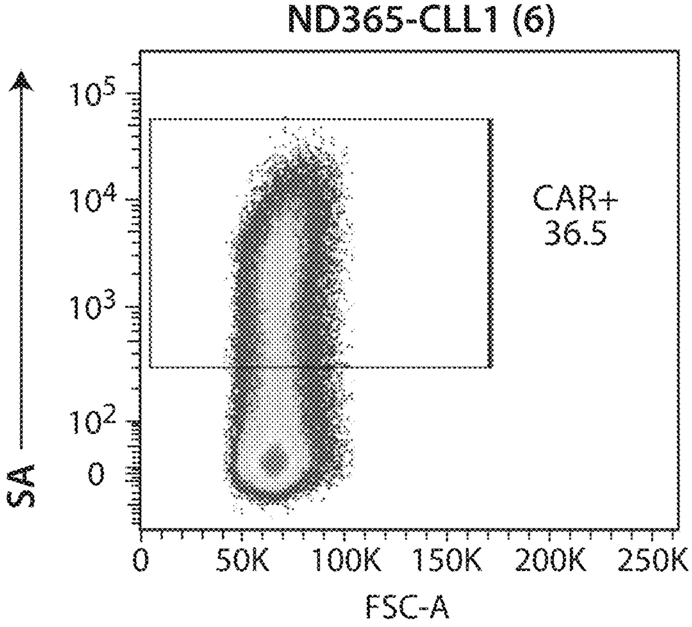
FIGS. 7A and 7B, is a series of images demonstrating the transduction efficiency of T cells transduced with CAR.
Figure 7B:
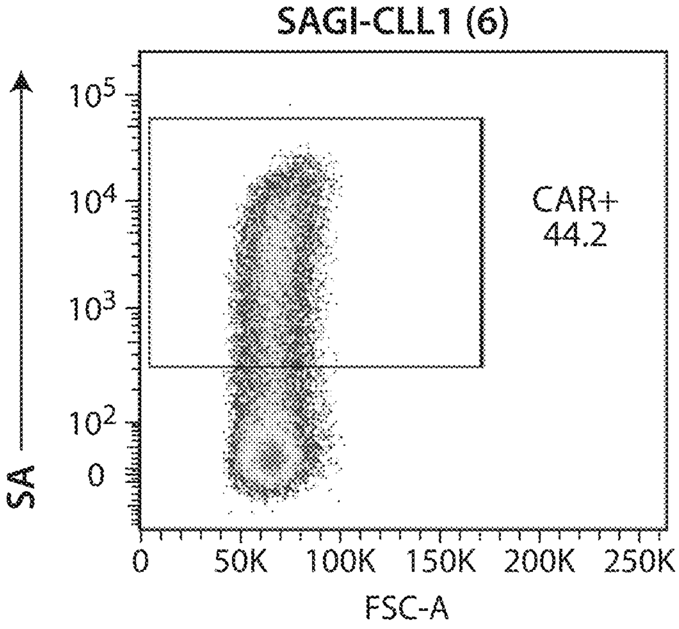

T cells from two different donors were transduced with CLL-1 (FIG. 6) and resulted in transduction efficiency of 35-45%. T cells were first stimulated with CD3/CD28 Dynabeads (Invitrogen) and maintained in serum free T cell media, along with IL-2 support. T cell were then transduced with CLL-1 (FIG. 6) CAR using a lentiviral vector the following day and were expanded in media for about 10 days. T cells were then frozen when the median cell volume approached 300 fl. CAR expression on T cells was detected by flow cytometry using a biotinylated CLL-1 protein (Sino Biological) with secondary staining using streptavidin. The results presented herein demonstrate transduction efficiency of T cells transduced with CAR (FIGS. 7A and 7B).

Figure 8A:
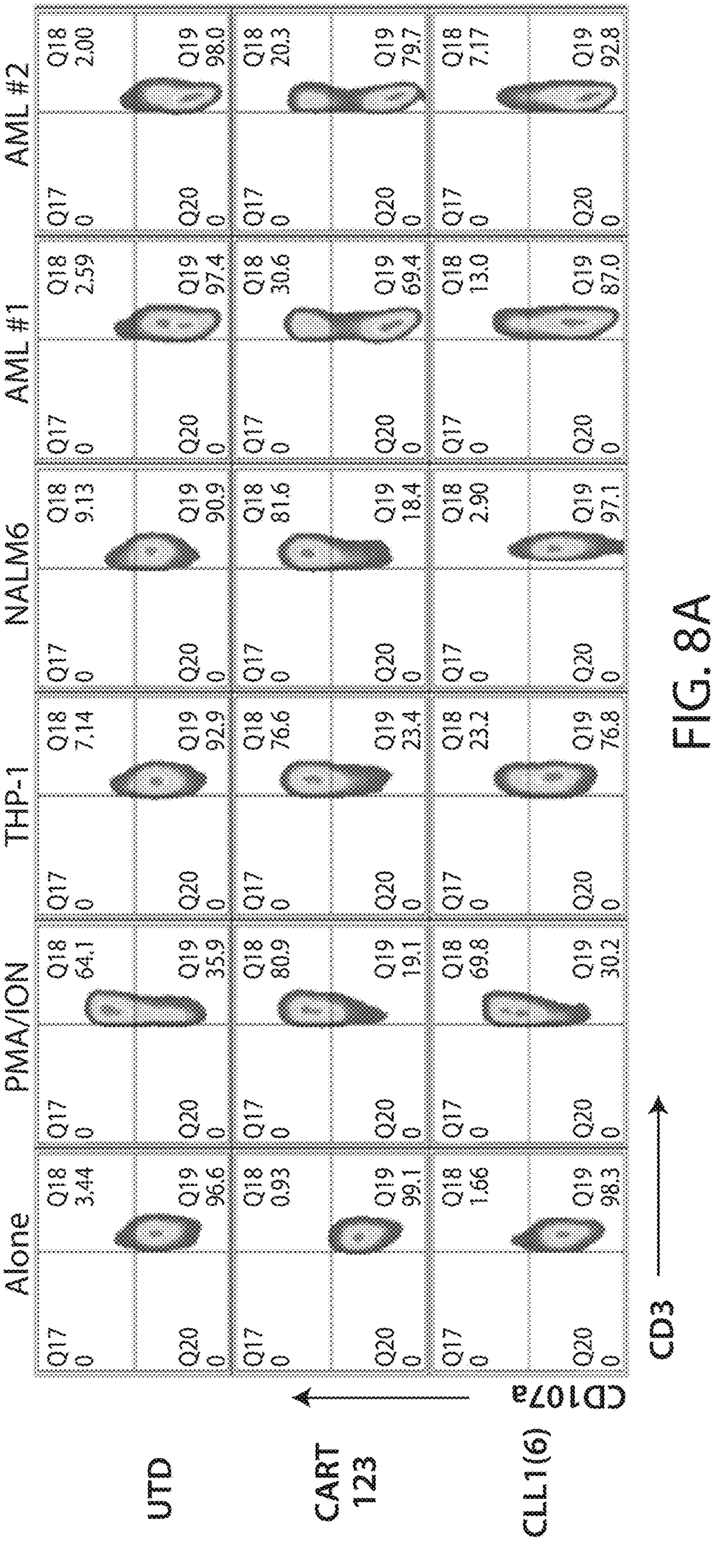
FIGS. 8A and 8B, is a series of images demonstrating that CLL1-CART cells undergo specific degranulation to CLL1+ cell lines and primary AML samples. CD107a degranulation was measured by flow cytometry (FIG. 8A). CLL-1 CART cells underwent specific degranulation to THP1 and primary AML samples and not to the control cell line (FIG. 8B).
Figure 8B:
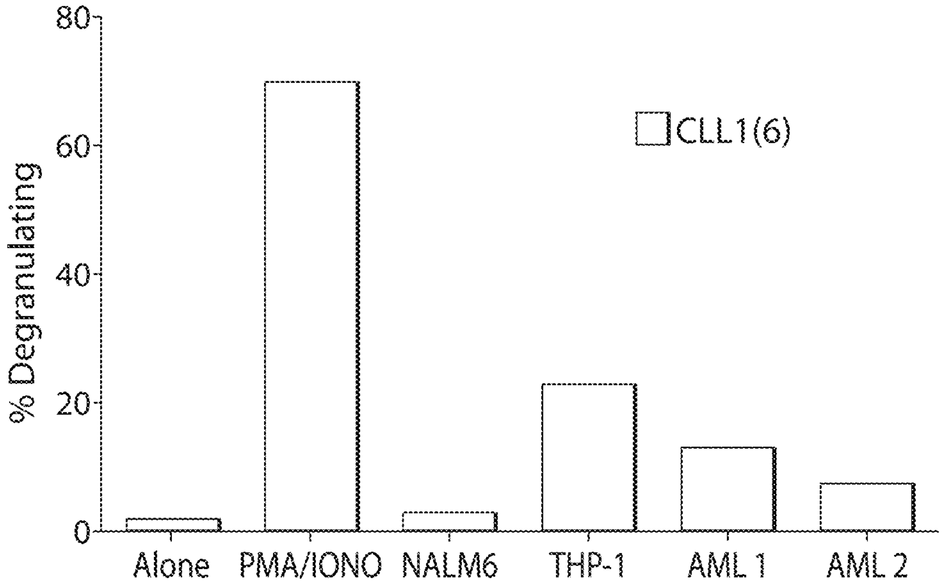

CART123, CLL1-CART cells and untransduced T cells were incubated with the CD123+/CLL1+ cell line THP-1, two primary AML samples that are CLL1+/CD123+ and a control ALL cell line NALM6 for 4 hours. CD107a degranulation was measured by flow cytometry (8A). CLL-1 CART cells underwent specific degranulation to THP1 and primary AML samples and not to the control cell line (FIG. 8B). The results presented herein demonstrate that CLL1-CART cells underwent specific degranulation to CLL1+ cell lines and primary AML samples.

Figure 9A:
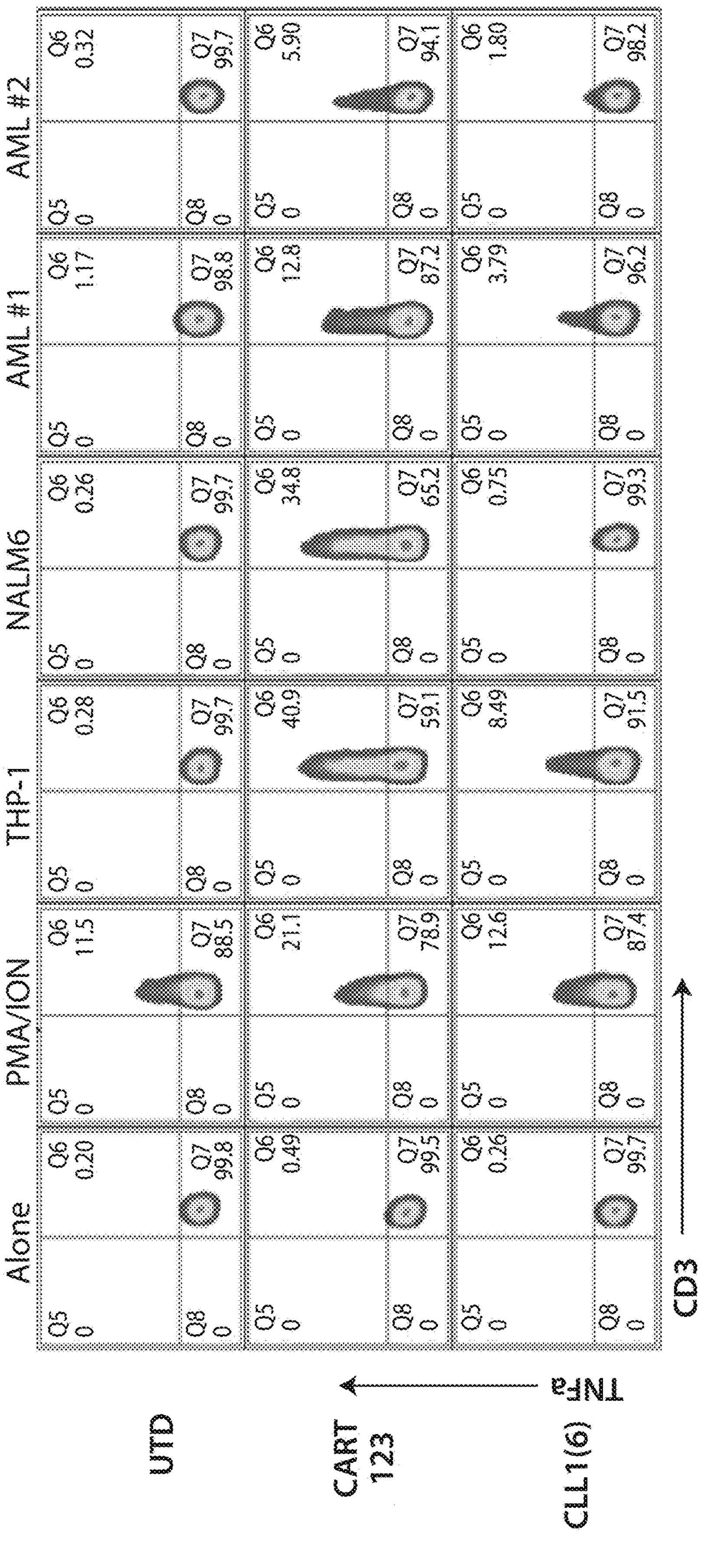
FIGS. 9A and 9B, is a series of images demonstrating CLL1-CART cells produce TNF-α after incubation with CLL1+ cell line and primary AML samples.
Figure 9B:
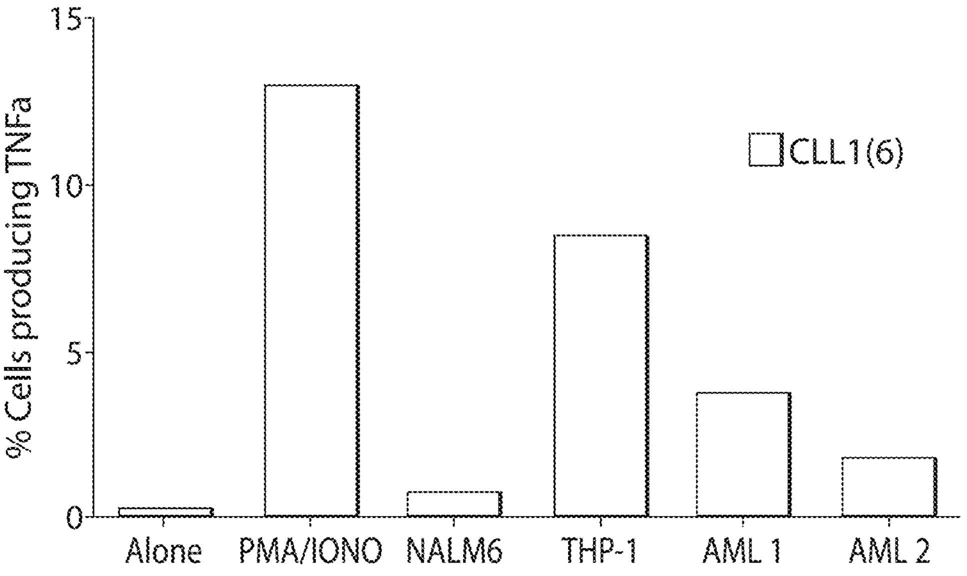

CART123, CLL1-CART cells and untransduced T cells were incubated with the CD123+/CLL1+ cell line THP-1, two primary AML samples that are CLL1+/CD123+ and a control ALL cell line NALM6 for 4 hours. Cells were then harvested and intracytoplasmic TNFα were measured by flow cytometry. More CLL-1 CART cells produced TNF-α after incubation specifically with THP1 and primary AML samples and not to the control cell line. The results presented herein demonstrate that CLL1-CART cells produced TNF-α after incubation with CLL1+ cell line and primary AML samples (FIGS. 9A and 9B).

Figure 10A:
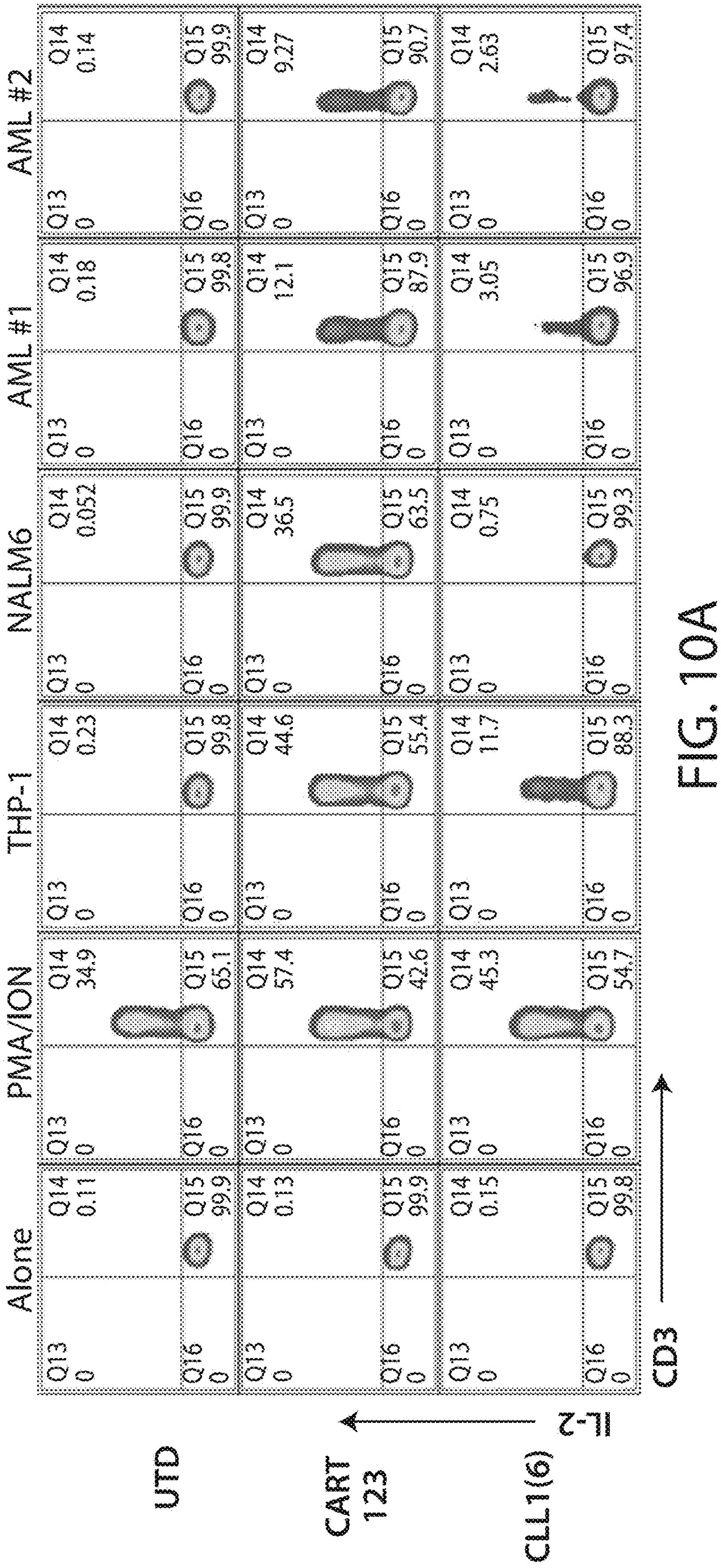
FIGS. 10A and 10B, is a series of images demonstrating CLL1-CART cells produce IL-2 after incubation with CLL1+ cell line and primary AML samples.
Figure 10B:
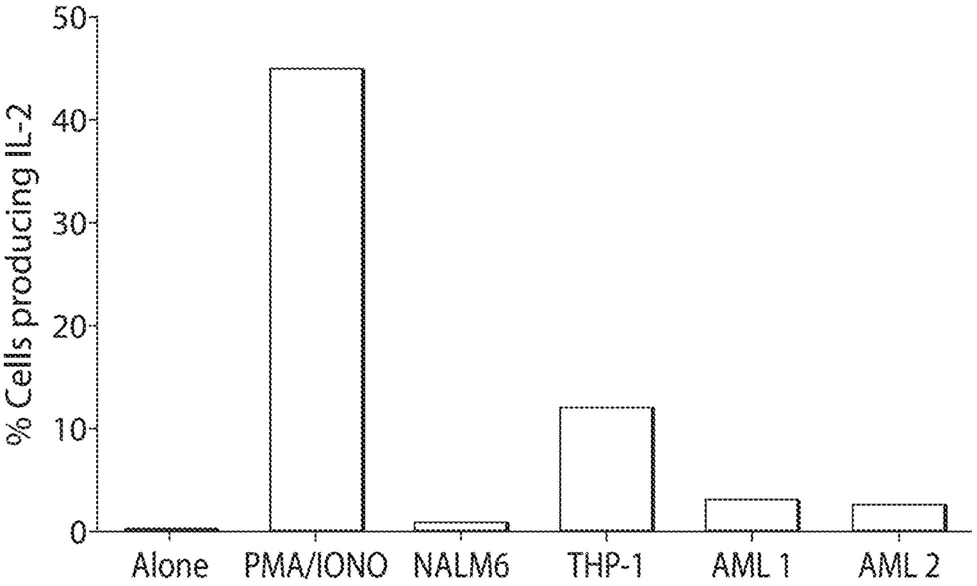
Figure 11A:
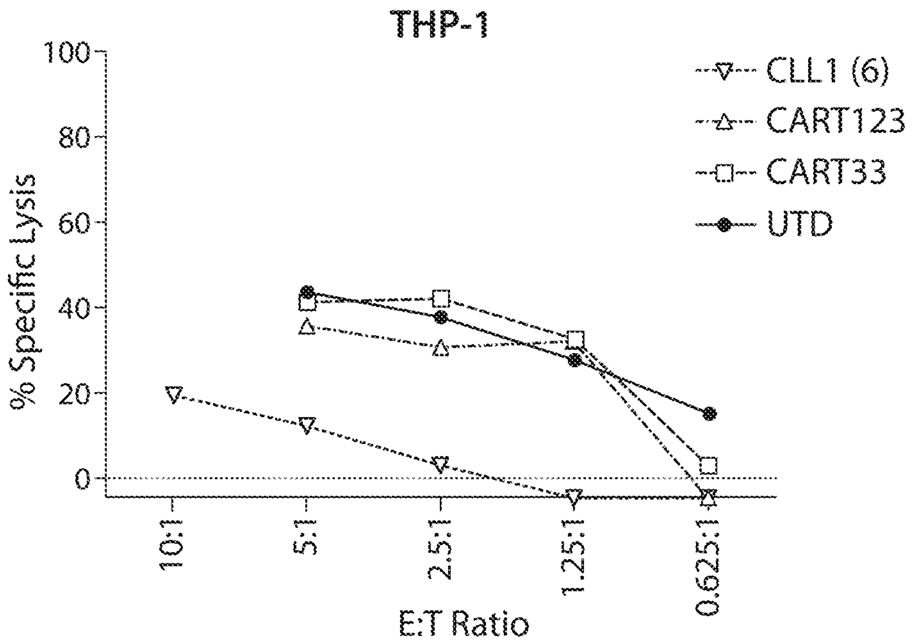
FIGS. 11A-11D, is a series of images demonstrating CLL1-CART cells specifically kill the CLL-1+ cell lines MOLM14 and THP-1 and primary AML samples. CLL1-CART cells results in specific lysis of MOLM14 (FIG. 11D), THP-1 (FIG. 11A) and the primary AML sample (FIG. 11B) and not to the control cell line JEKO (FIG. 11C), at the indicated E:T ratios.
Figure 11B:
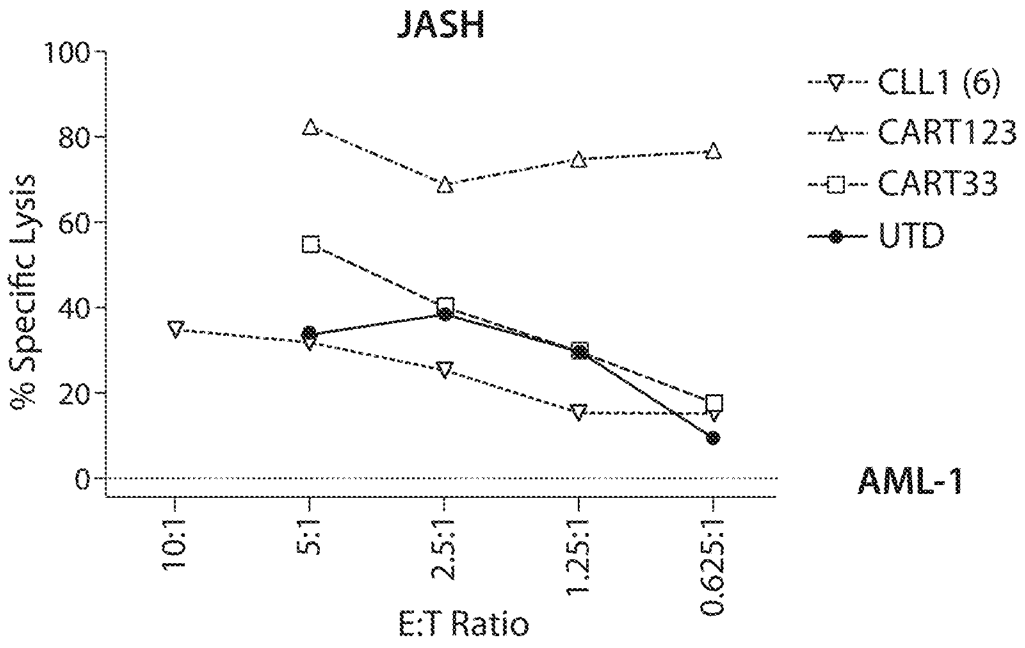
Figure 11C:
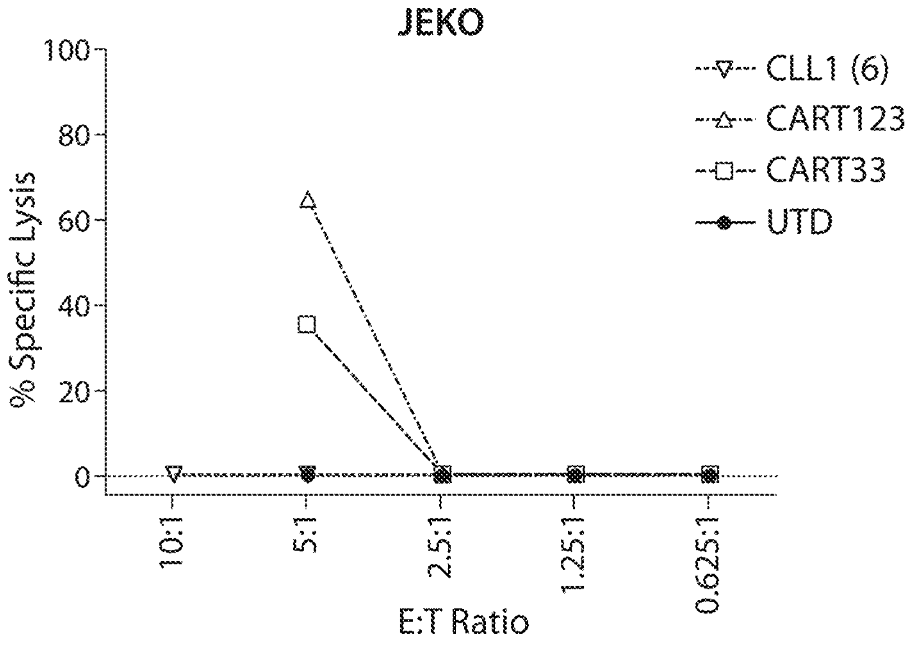
Figure 11D:
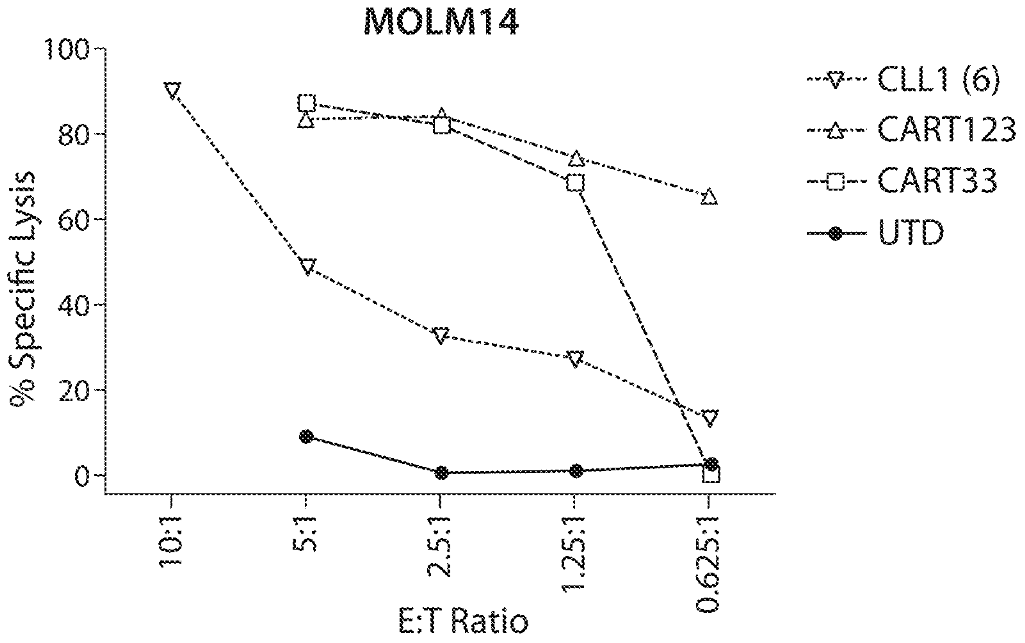

CART123, CLL1-CART cells and untransduced T cells were incubated with the CD123+/CLL1+ cell line THP-1, two primary AML samples that are CLL1+/CD123+ and a control ALL cell line NALM6 for 4 hours. Cells were then harvested and intracytoplasmic IL-2 were measured by flow cytometry. More CLL-1 CART cells produced IL-2 after incubation specifically with THP1 and primary AML samples and not to the control cell line. The results presented herein demonstrate that CLL1-CART cells produced IL-2 after incubation with CLL1+ cell line and primary AML samples (FIGS. 10A and 10B).

CART123, CLL1-CART cells and untransduced T cells were incubated with the CD123+/CLL1+ cell lines THP-1 and MOLM14, a primary AML sample that is CLL1+/CD123+ and a control mantle cell lymphoma cell line JEKO for 24 hours. Cells were then harvested and 7-AAD and counting beads were added. Killing was then measured using a flow cytometry based assay after CFSE-labeling of the tumor cells (e.g. Cao et al, Cytometry Part A 2010; 7&A:534-545) or by incubating CART cells with luciferase-expressing target cells at various effector-to-target ratios for up to 20 hours, followed by optical imaging for photons emitted by the target cells. In this latter assay, number of live target cells correlates positively with the number of photons emitted. CLL1-CART cells results in specific lysis of MOLM14 (FIG. 11D), THP-1 (FIG. 11A) and the primary AML sample (FIG. 11B) and not to the control cell line JEKO (FIG. 11C), at the indicated E:T ratios. The results presented herein demonstrate that CLL1-CART cells specifically killed the CLL-1+ cell lines MOLM14 and THP-1 and primary AML samples (FIG. 11A-11D).

Figure 12A:
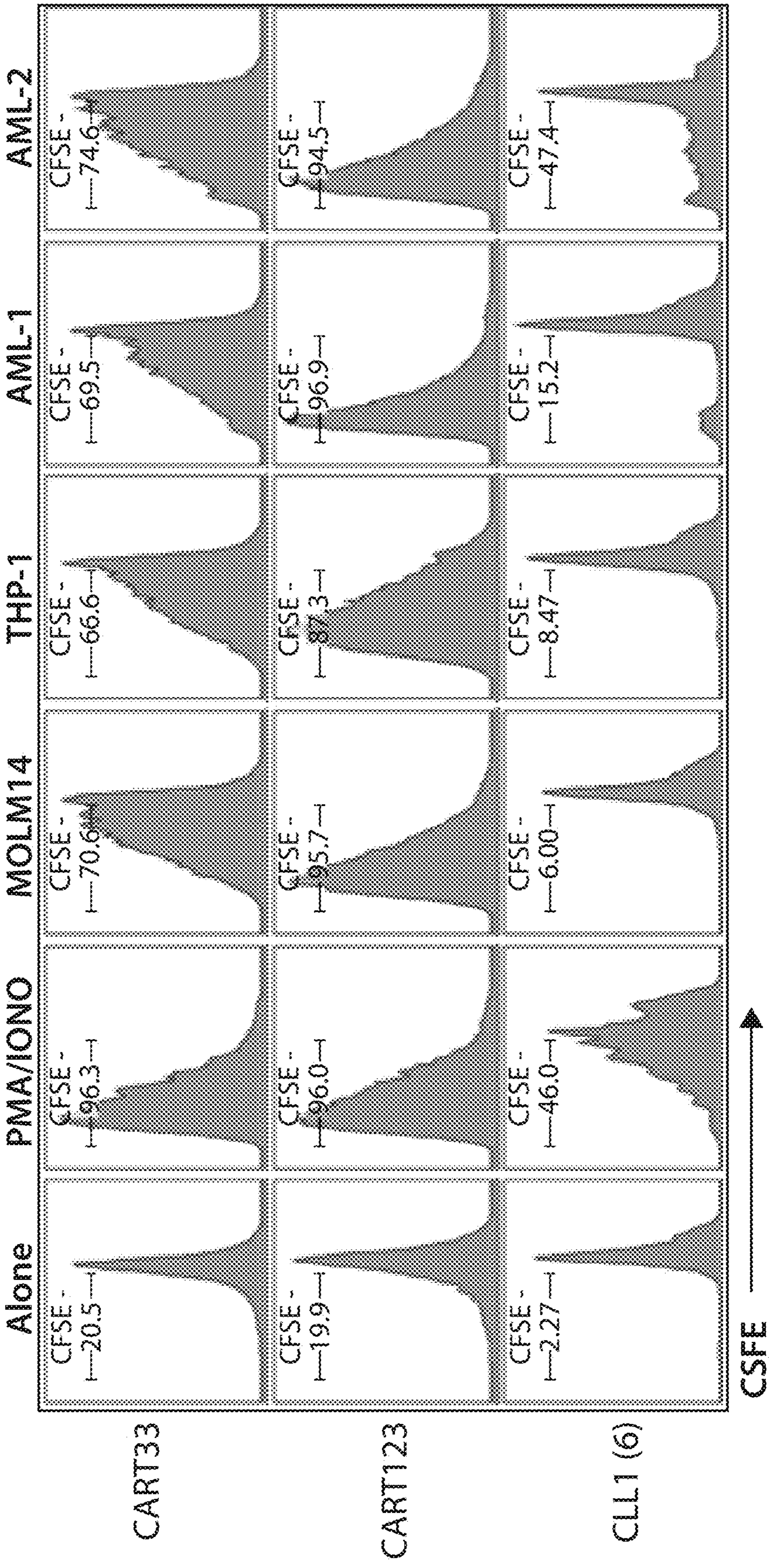
FIGS. 12A and 12B, is a series of images demonstrating CLL1-CART cells proliferate in response to MOLM14, THP-1 and primary AML samples.
Figure 12B:
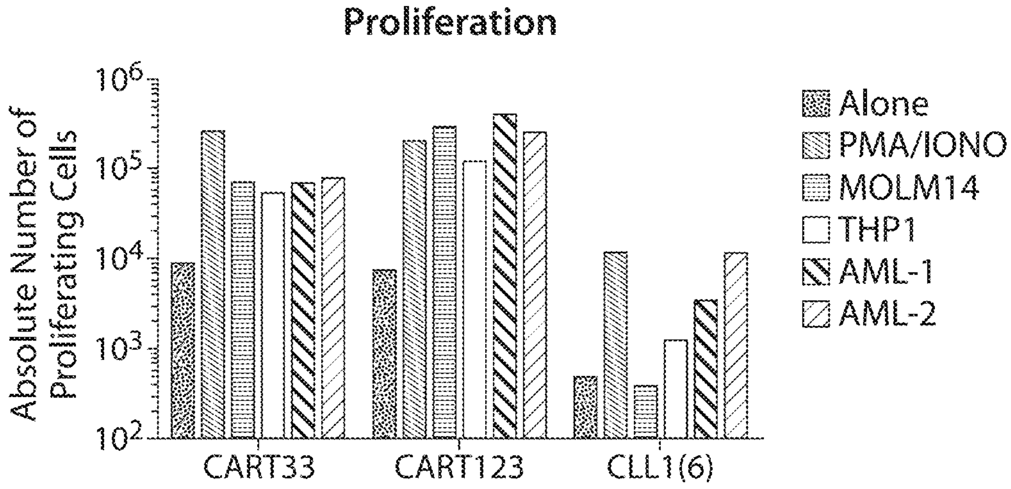

Proliferation of CART123, CART33 and CLL1-CART cells was measured in response to MOLM14, THP-1, and two primary AML samples. T cells were labeled with CFSE and incubated with targets for 120 hour at an effector:target ratio of 1:1. CLL1-CART cells underwent specific proliferation in response to MOLM14, THP1 and primary AML samples. Un-proliferated T cells retained a single bright peak of CFSE expression (by green fluorescence in the FITC channel), whereas proliferating CART cells had more than one CFSE peak and expression that was lower than baseline. The results presented herein demonstrate that CLL1-CART cells proliferated in response to MOLM14, THP-1 and primary AML samples (FIGS. 12A and 12B).

Figure 13:
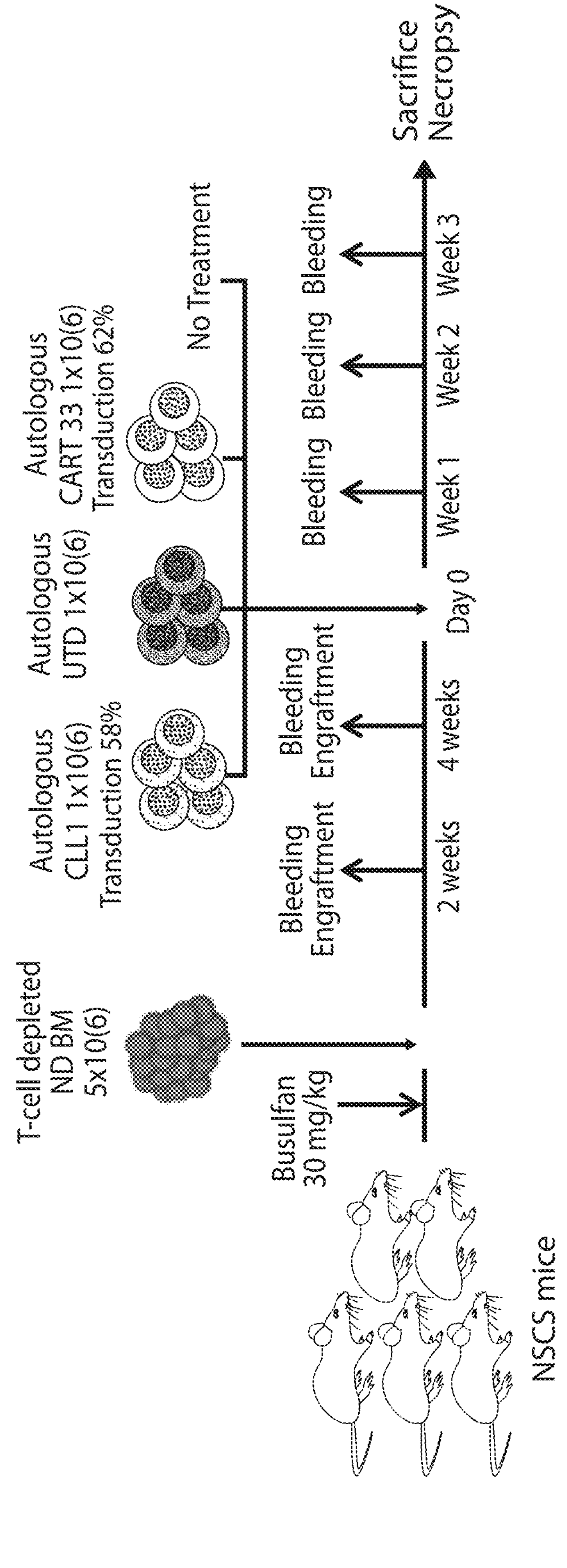
FIG. 13 is an image illustrating a schematic diagram for assaying hematopoietic stem cell toxicity of CLL-1 CART cells using autologous xenografts.

FIG. 13 presents a schematic diagram for assaying hematopoietic stem cell cyoxicity of CLL-1 CART cells using autologous xenografts. NSGS (NOD-SCID-gamma mice that are transgenic for IL-3, GM-CSF, stem cell factor) mice received busulfan i.p. followed by T cell depleted bone marrow from a normal donor the following day. Engraftment was confirmed by flow cytometric analysis of peripheral blood after 4 weeks and defined as circulating CD45 positive cells of >1%. Mice were then treated with autologous T cells by intravenous tail vain injection. T cells were derived from the same donor and were transduced with CART33, CLL1-CAR or UTD. A forth group received no treatment. Mice were then followed with retro-orbital bleeding on day 7, day 14 and day 21.

Figure 14A:
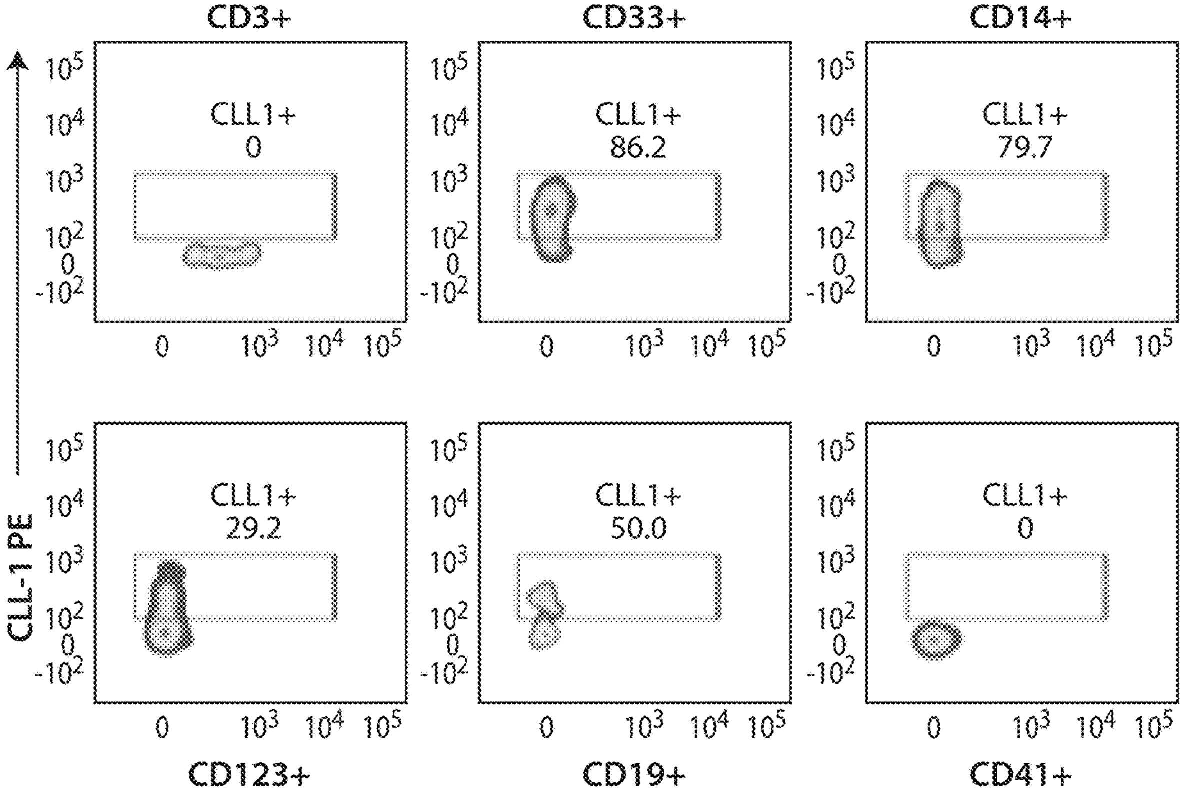
FIGS. 14A, 14B, and 14C, is a series of images demonstrating that CLL-1 is expressed on different myeloid lineage cells and B cells in humanized mice. A representative FACS plots of the peripheral blood analysis of one mouse is shown (FIG. 14A). CLL-1 is expressed on monocytes (CD14+ cells), myeloid cells (CD33+ and CD123+ cells), B cells (CD19+ cells), but not on platelets (CD41+ cells) or T cells (CD3+ cells). A representative histogram presentation is shown (FIG. 14B). A schematic plot representation of peripheral blood analysis from 24 mice is shown (FIG. 14C).
Figure 14B:
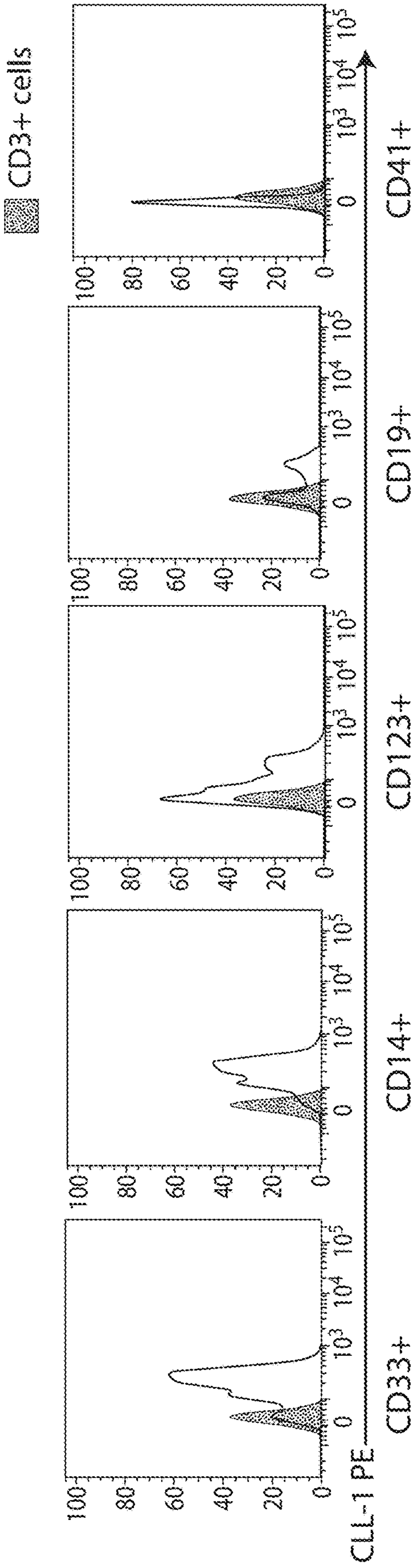
Figure 14C:
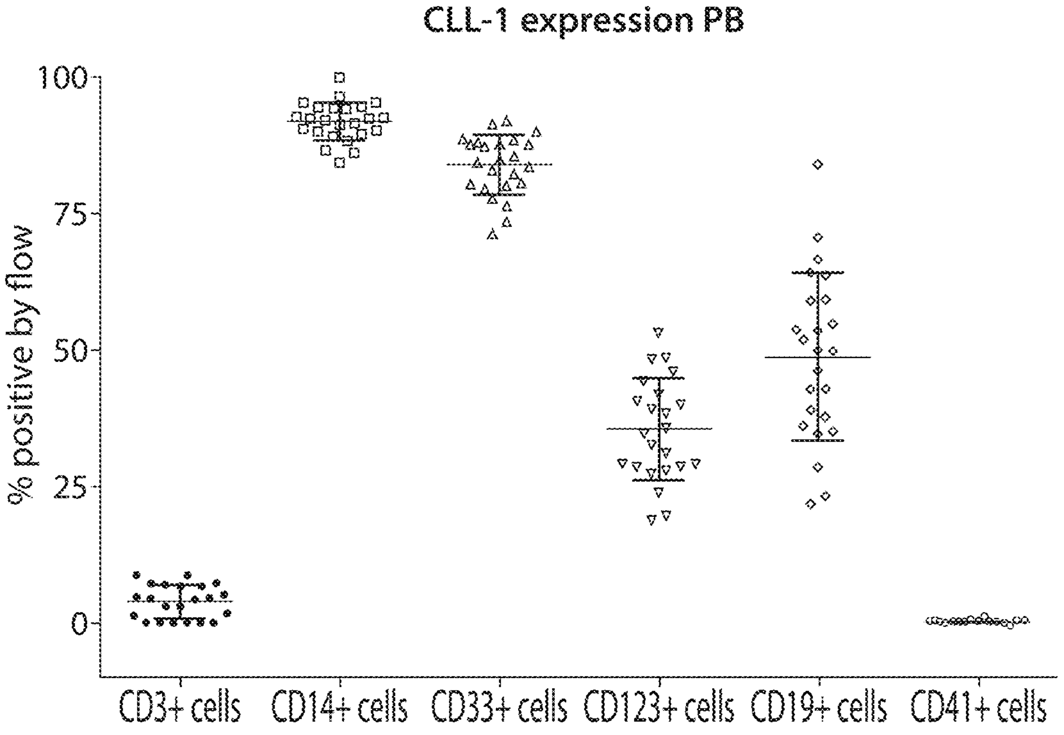
Figure 15A:
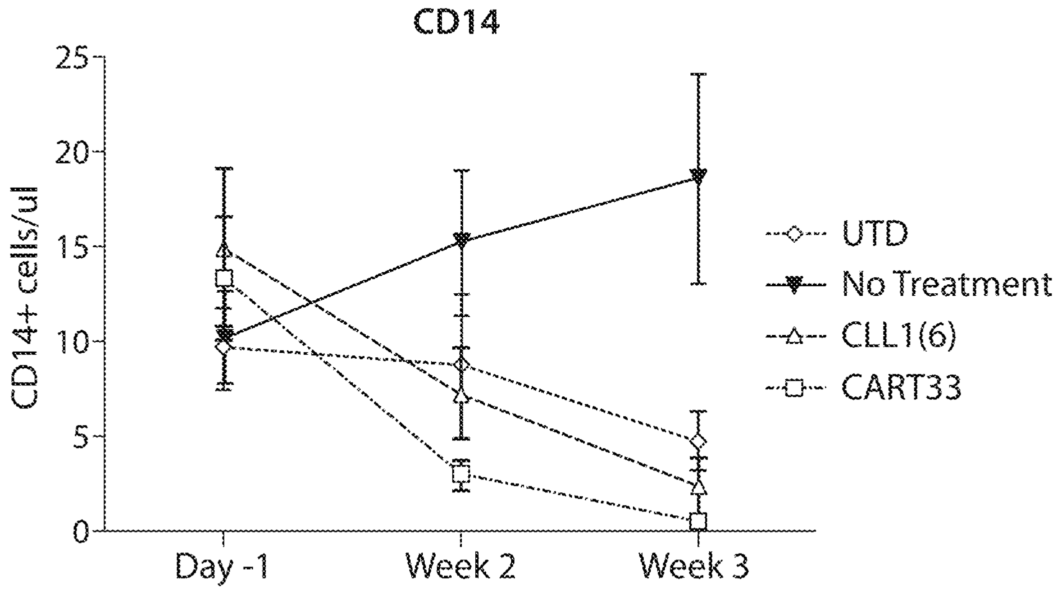
FIGS. 15A, 15B, 15C, and 15D, is a series of images demonstrating CLL-1 is expressed on different myeloid lineage cells and B cells in humanized mice.
Figure 15B:
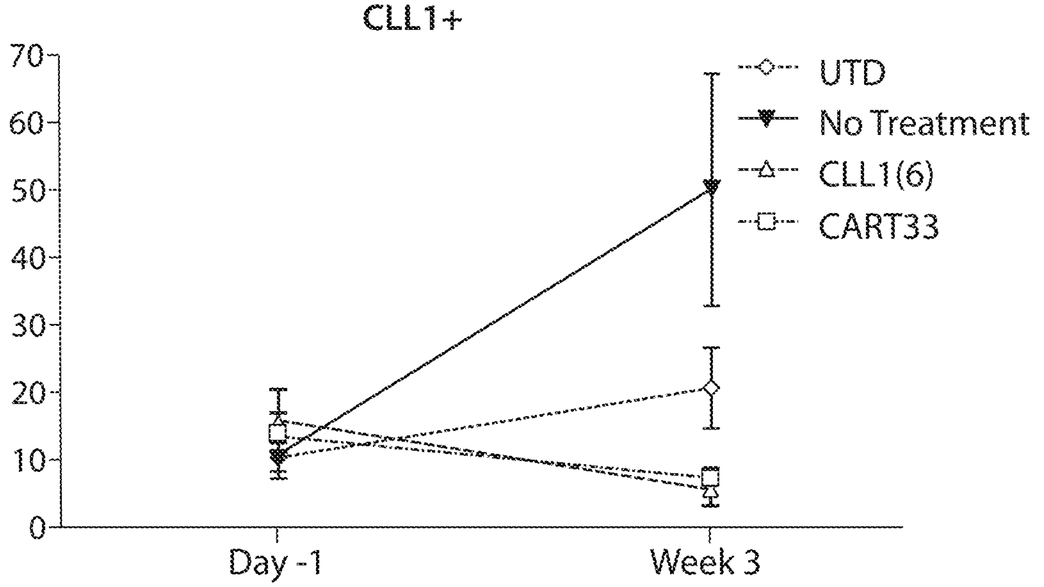
Figure 15C:
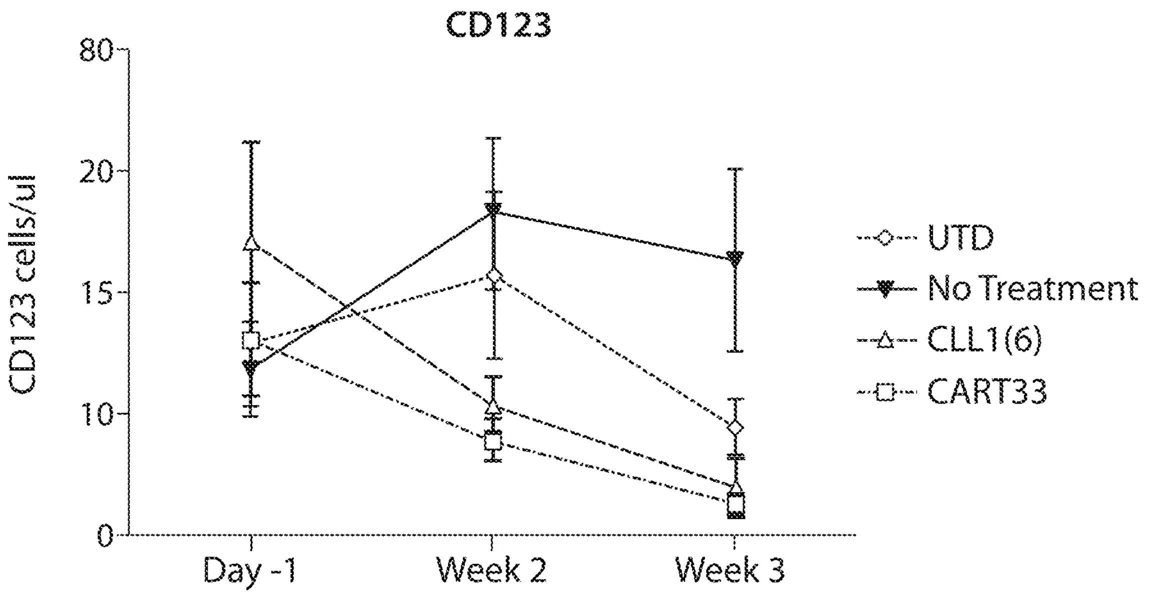
Figure 15D:
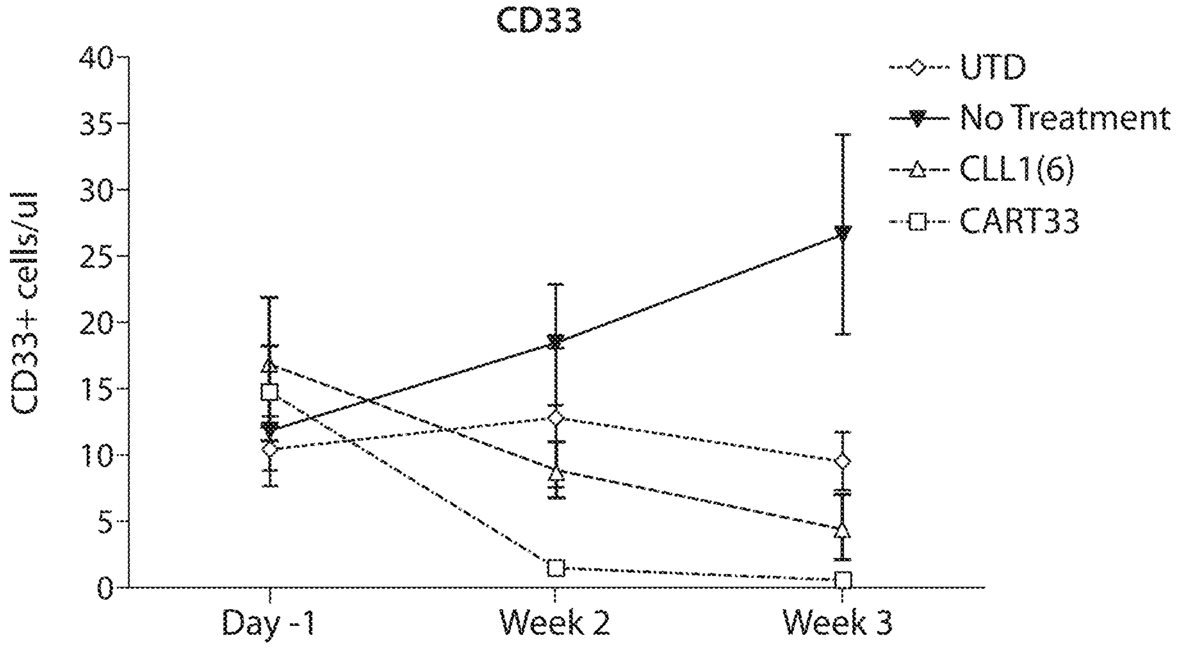
Figure 16A:
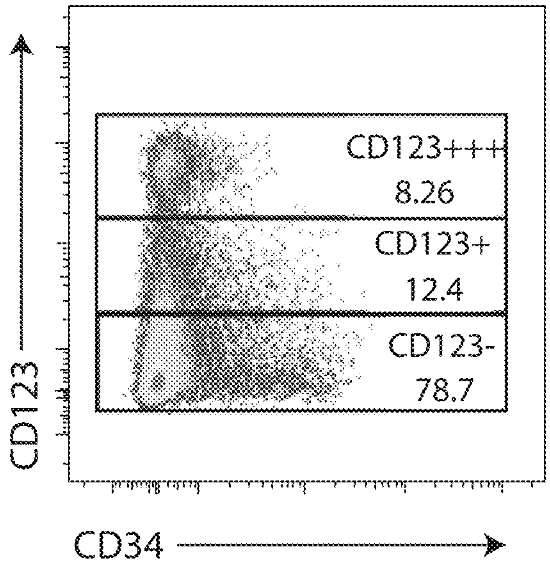
FIGS. 16A, 16B, 16C, and 16D, is a series of images demonstrating that CLL-1 is expressed on different myeloid progenitors and on hematopoietic stem cells in humanized mice.
Figure 16B:
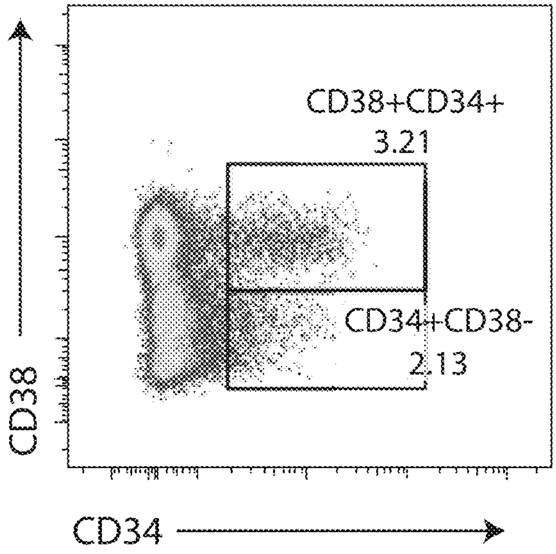
Figure 16C:
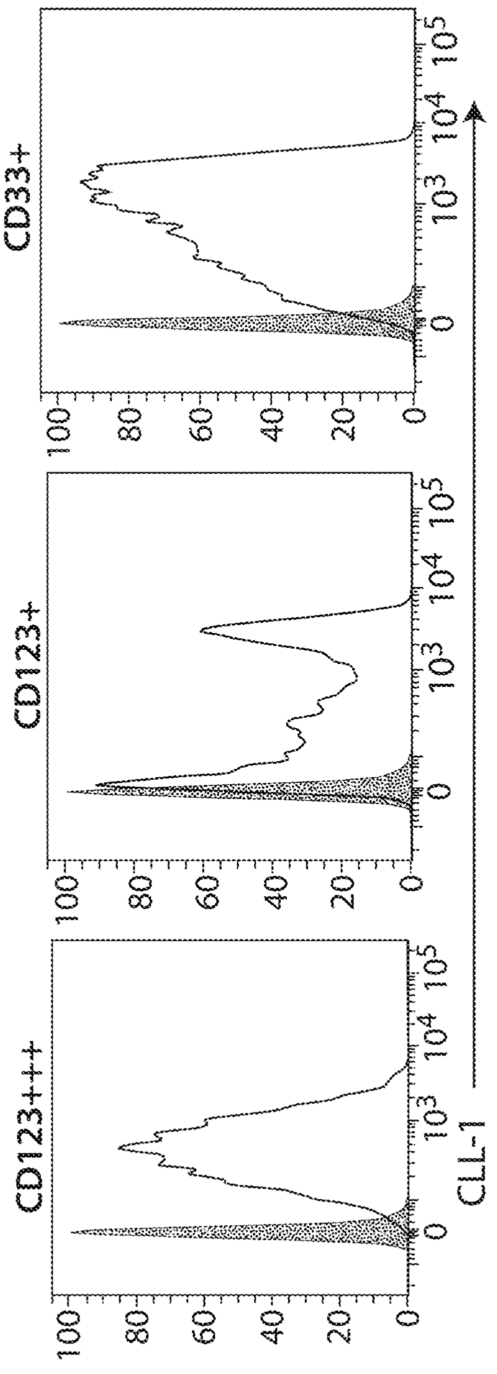
Figure 16D:
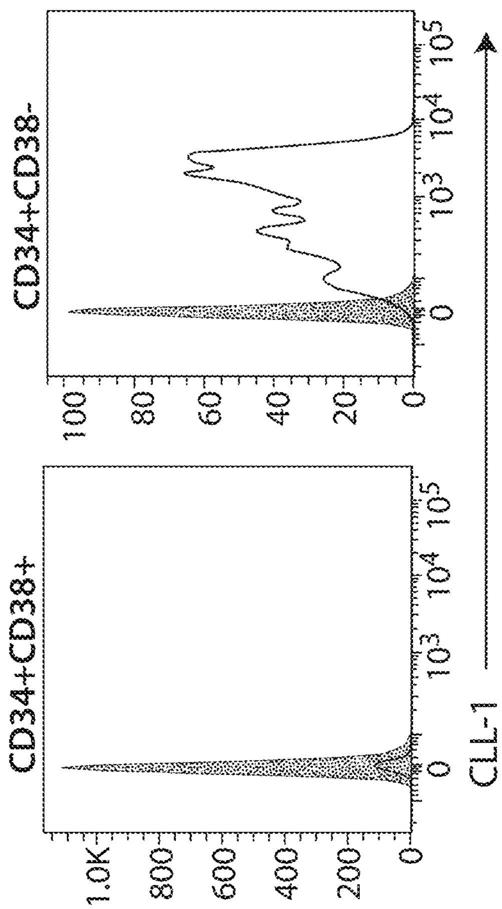

CLL-1 expression was measured on different peripheral blood cells from humanized xenografts. Mice were bled through the retro-orbital vein after being anesthetized, using standard techniques. A standard volume of 50-60 ul blood was then lysed in 1 ml of ACK lysis buffer. The blood was then stained using fluorescently-labelled antibodies and the expression of CLL-1 on different peripheral blood cells was detected using flow cytometry. This analysis was performed at baseline, after engraftment with T cell depleted normal donor bone marrow and prior to any treatments. A representative FACS plots of the peripheral blood analysis of one mouse is shown (FIG. 14A). CLL-1 is expressed on monocytes (CD14+ cells), myeloid cells (CD33+ and CD123+ cells), B cells (CD19+ cells), but not on platelets (CD41+ cells) or T cells (CD3+ cells). A representative histogram presentation is shown (FIG. 14B). A schematic plot representation of peripheral blood analysis from 24 mice is shown (FIG. 14C). The results presented herein demonstrate that CLL-1 was expressed on different myeloid lineage cells and B cells in humanized mice.

Hematopoietic stem cell toxicity of CLL1-CART cells was determined using an autologous model. Representative plot of peripheral blood analysis by flow cytometry. Treatment with CART33 or CLL1-CART cells resulted in significant reduction in Myloid cells (CD123+, CD33+, CLL1+), and in CD14+ monocytes. The results presented herein demonstrate that CLL-1 was expressed on different myeloid lineage cells and B cells in humanized mice.

CLL-1 expression on different bone marrow progenitor cells from humanized xenografts was assayed. After 4 weeks of treatment with T cells, mice were euthanized and bone marrow was harvested and analyzed. Bone marrow was harvested by flushing of the femur bones. Bone marrow samples from the control untreated animals were used as a reference to analyze expression of CLL-1 on different progenitors. The samples were then stained using fluorescently-labelled antibodies and the expression of CLL-1 on different progenitor cells was detected using flow cytometry. CLL-1 was expressed on the CD34+CD38− hematopoietic stem cells, CD123 bright, CD123 dim and CD33 positive cells. Gated on $CD45^{dim}$, $LIN^{-}$, live cells. The results presented herein demonstrate that CLL-1 was expressed on different myeloid progenitors and on hematopoietic stem cells in humanized mice (FIG. 16A-16D).

Figure 17:
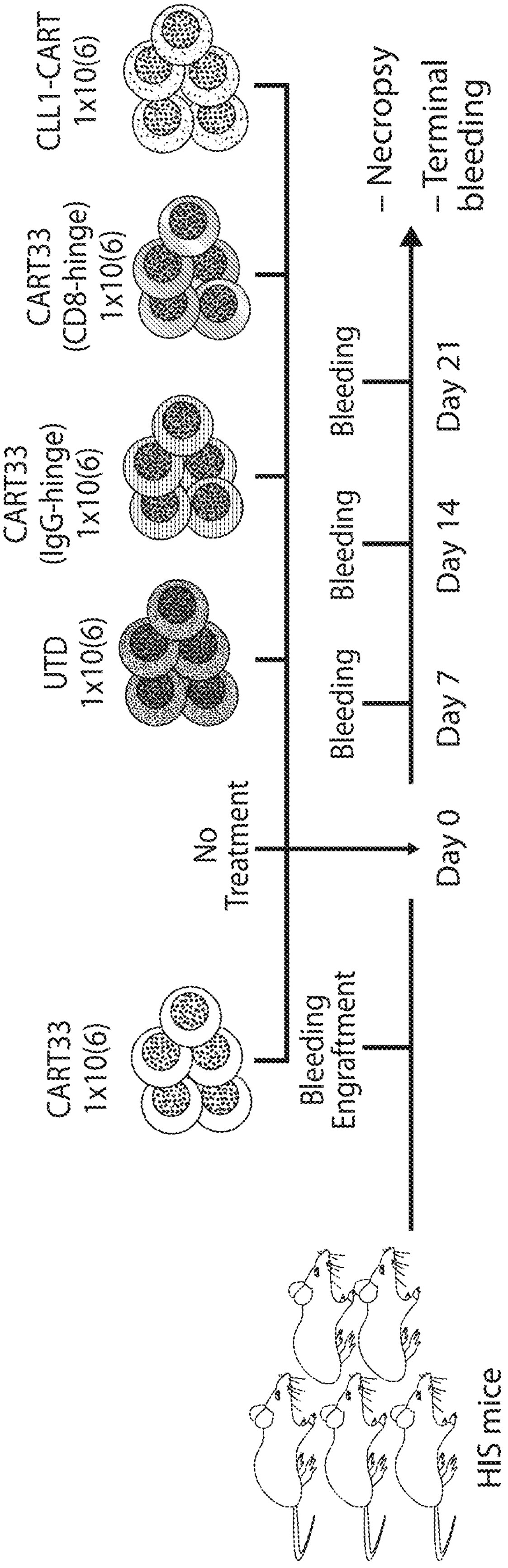
FIG. 17 is an image illustrating a schematic diagram for assaying hematopoietic stem cell toxicity of CLL-1 CART cells using a Humanized Immune System (HIS) xenografts.

FIG. 17 illustrates a schematic diagram for assaying hematopoietic stem cell toxicity of CLL-1 CART cells using a Humanized Immune System (HIS) xenografts. HIS mice were bled retro-orbitally 6-8 weeks after injection of CD34+ fetal liver, to confirm engraftment of human cells and then treated with either CLL1-CARTs, CART123, CART33-CD8 hinge, CART33-IgG4 hinge, untransduced T cells or with no treatment. Mice were then followed by serial weekly retro-orbital bleedings. Mice were then euthanized on day 28 and organs were harvested and analyzed.

Figure 18A:
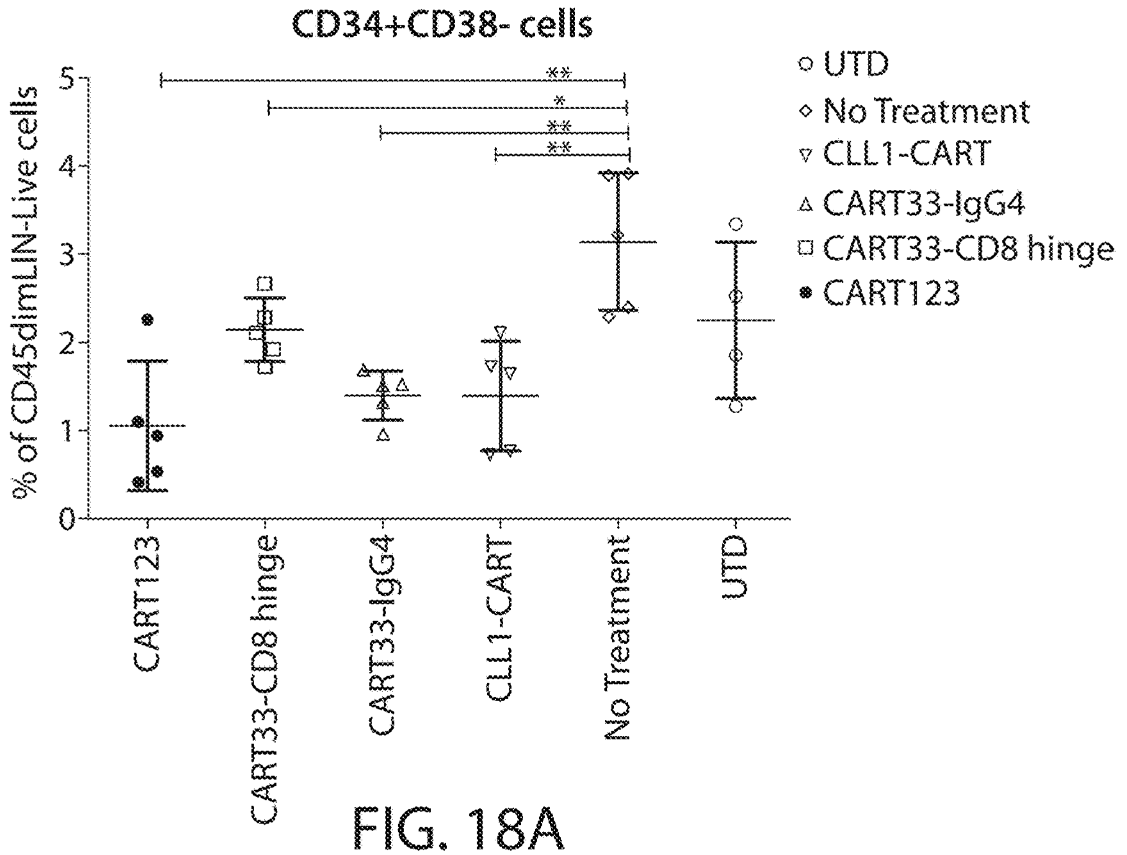
FIGS. 18A and 18B, is a series of images demonstrating bone marrow analysis 4 weeks post CLL-1 CAR T cell infusions. Flow cytometry analysis was performed in the CD34+CD38− component (hematopoietic stem cells) (FIG. 18A) and CD34+CD38+ component (Progenitor cells) (FIG. 18B).
Figure 18B:
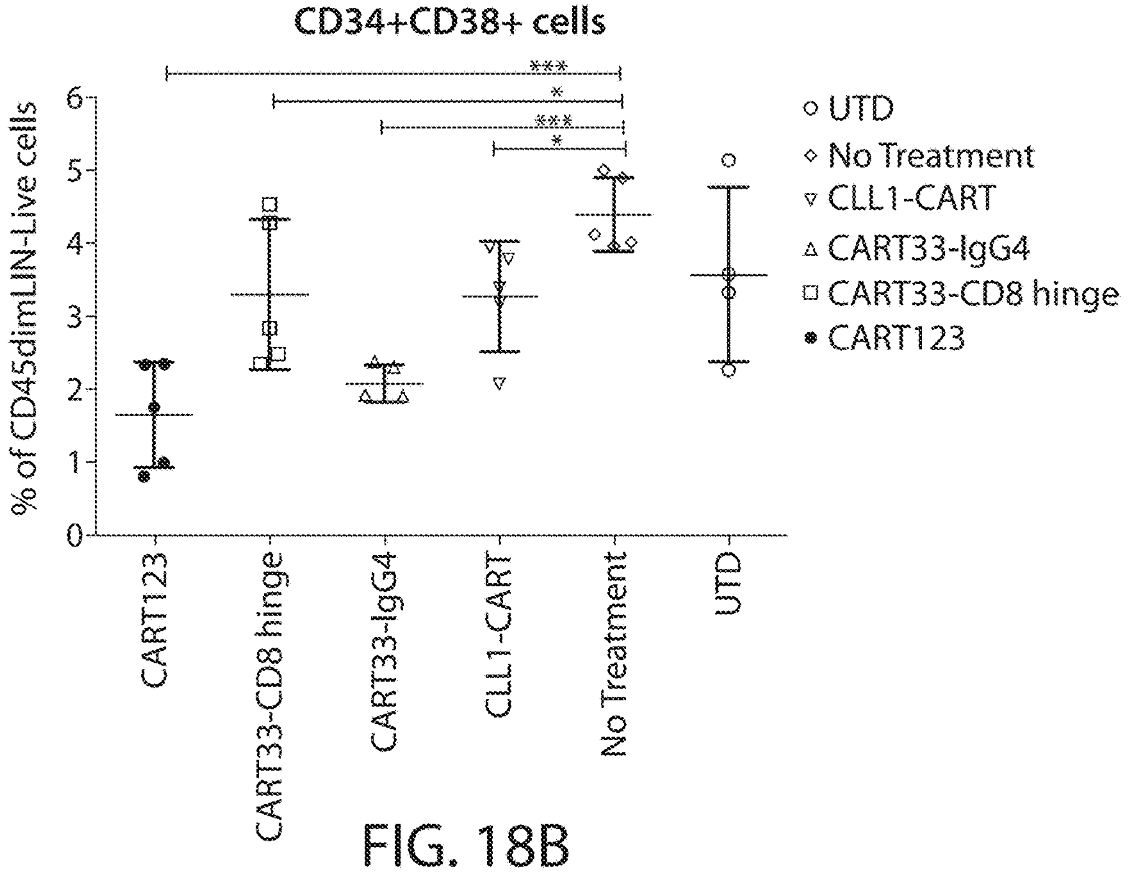

Bone marrow was analyzed 4 weeks post T cell infusion. Hematopoietic stem cell toxicity of CLL1-CART cells was measured using HIS xenografts. Mice were euthanized 4 weeks after T cell infusion, femur bones were harvested and flushed for bone marrow. The samples were then stained using fluorescently-labelled antibodies. Schematic plots of all mice treated with different CART cells. Treatment with CLL1-CART cells resulted in significant reduction in the CD34+CD38− component (hematopoietic stem cells) (FIG. 18A) and CD34+CD38+ component (Progenitor cells) (FIG. 18B). Representative plots of bone marrows from mice treated with different CART cells are shown. Gated on live CD45dim LIN− cells (FIG. 19A-19E).

Figure 20:
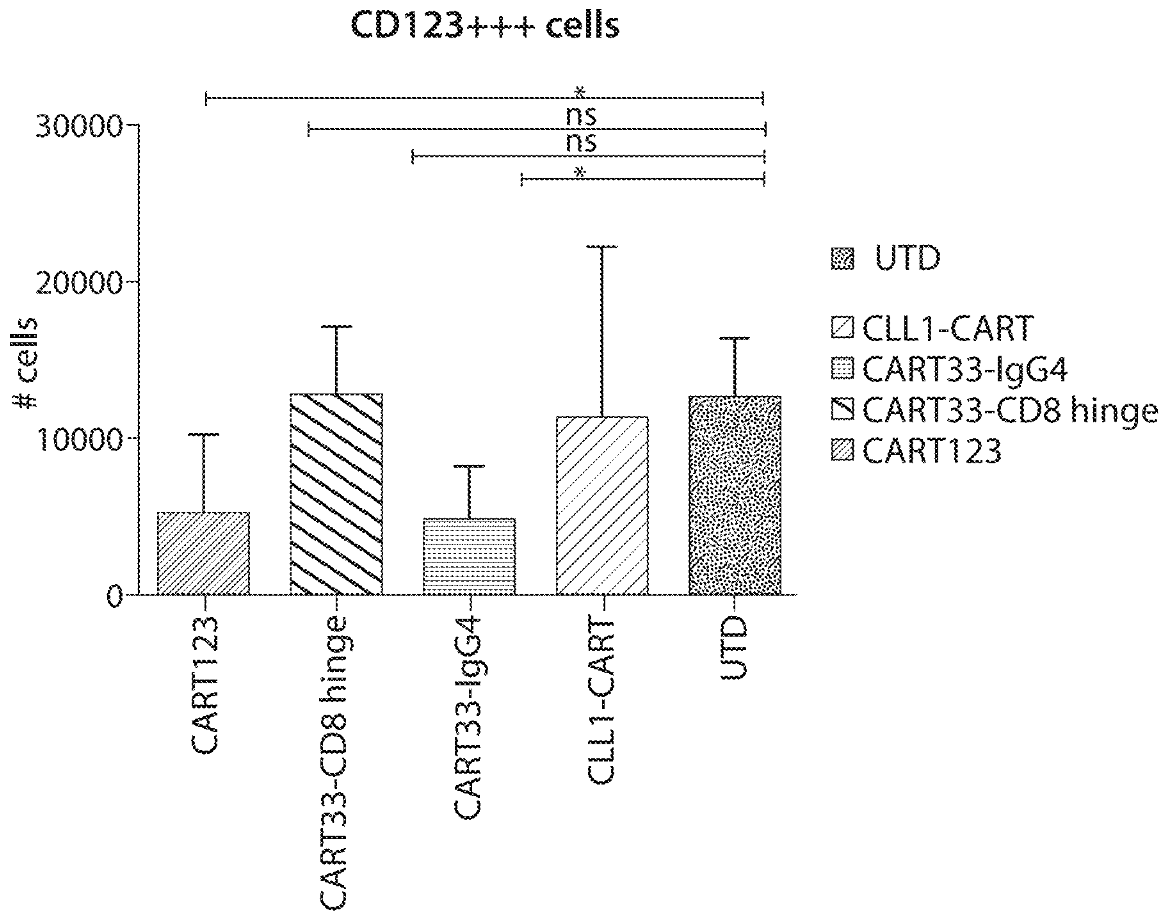
FIG. 20 is an image demonstrating bone marrow analysis in HIS mice 4 weeks post T cells. Hematopoietic stem cell toxicity of CLL1-CART cells using HIS xenografts.
Figure 21A:
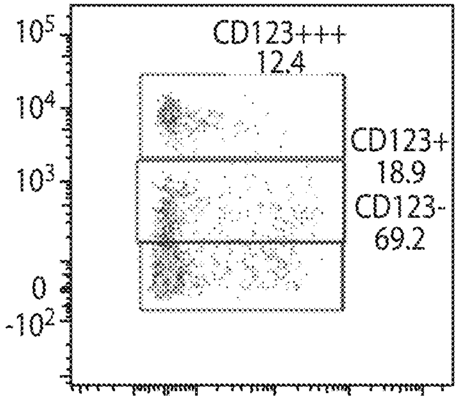
FIGS. 21A, 21B, 21C, 21D, and 21E, is a series of images demonstrating bone marrow analysis in HIS mice 4 weeks post T cells. Representative plots of bone marrows from mice treated with different CART cells are shown.
Figure 21B:
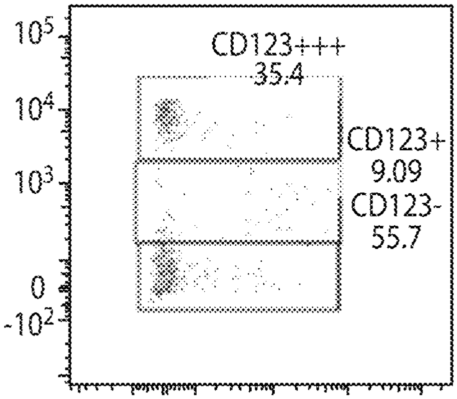
Figure 21C:
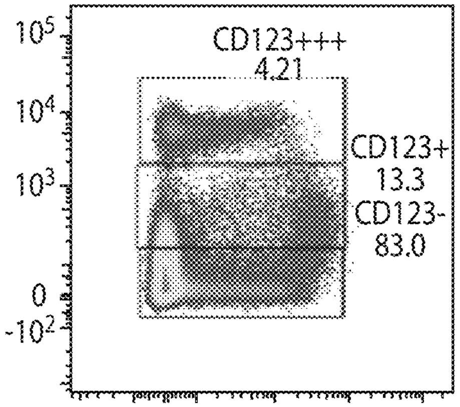
Figure 21D:
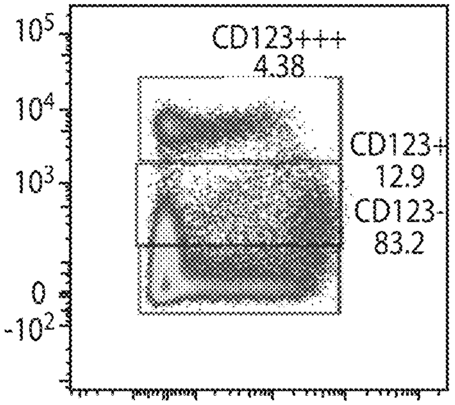
Figure 21E:
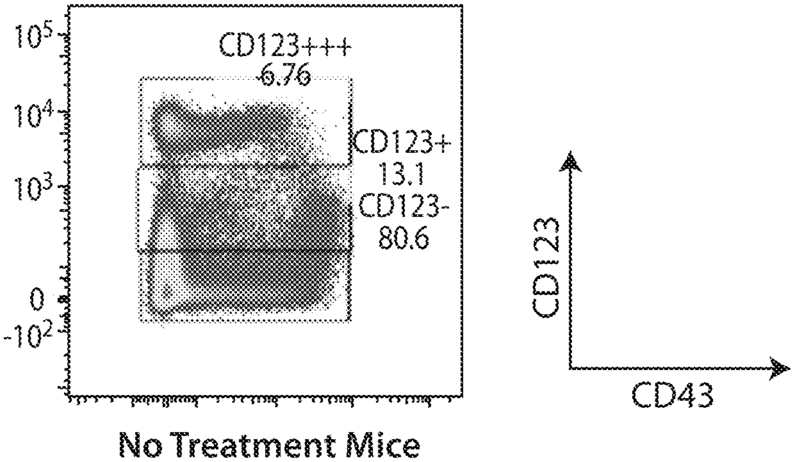

Bone marrow was analyzed in HIS mice 4 weeks post T cell infusion. Hematopoietic stem cell toxicity of CLL1-CART cells using HIS xenografts. Mice were euthanized 4 weeks after T cell infusion, femur bones were harvested and flushed for bone marrow. The samples were then stained using fluorescently-labelled antibodies. A schematic plots is shown of all mice treated with different CART cells (FIG. 20). Treatment with CLL1-CART cells did not result in significant reduction in the CD123 bright population. The samples were then stained using fluorescently-labelled antibodies. Representative plots of bone marrows from mice treated with different CART cells are shown (FIG. 21).

Example 4: Evaluation of CLL-1 CART Cells In Vivo

PL-21 is a human acute myeloid leukemia cell line isolated from the peripheral blood of a 24 year old male patient with refractory acute promyelocytic leukemia, and can be grown as a xenograft in immune compromised mice. The xenograft mimics disease in the bone marrow as seen in humans, establishing a model with which to test the efficacy of therapies on AMLs in the bone. These mice can be used to test the efficacy of chimeric antigen receptor (CAR) T cells specific for cellular markers found on acute myeloid (or promyelocytic) leukemia cells, such as CLL-1 (a C-type lectin-type molecule). PL-21 cells were tagged with a firefly luciferase reporter gene and used in an orthotopic model of acute myeloid leukemia (AML) in NOD.Cg-$Prkdc^{scid}Il2rg^{tm1Wjl}$/SzJ (NSG) mice to test the efficacy of CAR T cells specific for CLL-1.

CLL-1 expression was tested on PL-21 cells and these cells were used in in vitro assays to look at the ability of CLL-1-specific CAR T cells to recognize and respond to the target. In vivo PL-21 cells grow when implanted intravenously via the tail vein and growth is limited primarily to the bone marrow. One week after the tumor cells are implanted, the disease shifts fully to the bones and begins to grow at an exponential rate. Left untreated, mice will start to display clinical symptoms and hind limb paralysis 4-6 weeks after tumor implantation. The study described in this example investigates whether any of the CLL-1 specific scFv clones from the in vitro screen show activity against tumors in this in vivo xenograft model.

The following materials and methods were used in the experiments described herein.

Materials and Methods:

PL-21 Cell Line:

The PL-21 human AML cell line was developed from the peripheral blood of a patient with acute promyelocytic leukemia. The cells were then tagged with firefly luciferase. These suspension cells grow in RPMI supplemented with 10% heat inactivated fetal bovine serum.

Mice:

6 week old NSG (NOD.Cg-Prkdc$^{scid}$Il2rg$^{tm1Wjl}$/SzJ) mice were received from the Jackson Laboratory (stock number 005557). Animals were allowed to acclimate to the Novartis NIBRI animal facility for at least 3 days prior to experimentation. Animals were handled in accordance with Novartis ACUC regulations and guidelines.

Tumor Implantation:

PL-21-luc cells were grown and expanded in vitro in RPMI supplemented with 10% heat inactivated fetal bovine serum. The cells were then transferred to a 50 ml conical tube and washed twice with cold sterile PBS. The PL-21-luc cells were then counted and resuspended at a concentration of $10\times10^6$ cells per milliliter of PBS. The cells were placed on ice and immediately (within one hour) implanted in mice. PL-21-luc cells were injected intravenously via the tail vein in a 100 μl volume, for a total of $1\times10^6$ cells per mouse.

CAR T Cell Dosing:

Mice were administered $5\times10^6$ CAR$^+$ T cells 8 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. The CAR T cells were normalized for CAR transduction so that each group has the same percentage of CAR$^+$ T cells. The $5\times10^6$ CAR$^+$ T cells were then resuspended at a concentration of $50\times10^6$ CAR$^+$ T cells per ml of cold PBS and kept on ice until the mice were dosed. The mice were injected intravenously via the tail vein with 100 μl of the CAR T cells for a dose of $5\times10^6$ CAR$^+$ T cells per mouse.

Eight mice per group were treated either with 100 μl of PBS alone (PBS), CD19 control CAR T cells (CD19), CLL-1-6 (clone 6) CAR T cells, CLL-1-9 (clone 9) CAR T cells, CLL-1-10 (clone 10) CART cells, CLL-1-11 (clone 11) CART cells, and CLL-1-12 (clone 12) CAR T cells. The T cells were all prepared from the same human donor in parallel.

Animal Monitoring:

The health status of the mice was monitored daily, including twice weekly body weight measurements. The percent change in body weight was calculated as $(BW_{current}-BW_{initial})/(BW_{initial})\times100\%$. Tumor burden was monitored twice weekly by bioluminescent imaging. Mice were intraperitoneally injected with D-luciferin 10 minutes prior to anesthetizing and imaging the mice with a Xenogen. Disease burden was calculated by calculating the bioluminescence of the tumor cells (photons/second).

Percent treatment/control (T/C) values were calculated using the following formula:

$$\%\ T/C=100\times\Delta T/\Delta C \text{ if } \Delta T\geq0;$$

$$\%\ \text{Regression}=100\times\Delta T/T_{initial} \text{ if } \Delta T<0;$$

where T=mean bioluminescence of the drug-treated group on the final day of the study; $T_{initial}$=mean bioluminescence of the drug-treated group on initial day of dosing; ΔT=mean bioluminescence of the drug-treated group on the final day of the study=mean bioluminescence of the drug treated group on the initial day of dosing; C=mean bioluminescence of the control group on the final day of the study; and ΔC=mean bioluminescence of the control group on the final day of the study=mean bioluminescence of the control group on the initial day of dosing.

T/C values in the range of 100% to 42% are interpreted to have no or minimal anti-tumor activity; T/C values that are ≤42% and ≤10% are interpreted to have anti-tumor activity or tumor growth inhibition. T/C values ≤10% or regression values ≥−10% are interpreted to be tumor stasis. Regression values <−10% are reported as regression.

Peripheral Blood FACS Analysis:

T cells in the peripheral blood of the mice were also monitored. Mice were bled weekly via the tail vein into EDTA coated tubes that were kept on ice. 10 μl of blood was plated from the tubes into 96 well plates on ice. Red blood cells were lysed with ACK red blood cell lysis buffer (Life Technologies, catalog number A10492-01) and then washed twice with cold PBS. The cells were incubated with an Fc blocking mix of human and mouse Fc block (Miltenyi Biotec, catalog numbers 130-059-901 and 130-092-575) for 30 minutes and then incubated with anti-mouse CD11b, anti-human CD45, anti-human CD4, anti-human CD8, and CLL-1-Fc or Protein L antibodies, followed by a secondary. The cells were fixed with a 2% paraformaldehyde solution for 20 minutes, washed and stored in PBS+2% FBS overnight prior to analysis on a BD Fortessa, followed by further analysis using the FlowJo FACS analysis software. The cells were analyzed to determine the number of CAR$^+$ CD4$^+$ and CD8$^+$ T cells per milliliter of blood in the PL-21-luc tumor-bearing NSG mice. T cell numbers in the blood are reported as the mean±standard error of the mean (SEM).

Results:

The anti-tumor activity of a panel of CLL-1 specific CAR T cells (clone 6, 9 10, 11, and 12) were evaluated and directly compared in the PL-21 model of human AML. Following tumor implantation on day 0, mice were randomized into treatment groups and treated with $5\times10^6$ CAR$^+$ T cells intravenously on day 8. AML disease burden and animal health were monitored until animals achieved endpoint. The mice in the control PBS and CD19 groups along with the CLL-1-11 and CLL-1-12 groups were euthanized on day 18 post-CART cell dosing (26 days post-tumor implantation) when disease burden in the control groups was nearing maximum luminescence via imaging. The mice in the remaining CLL-1 CAR T cell treated groups (CLL-1-6, CLL-1-9, and CLL-1-10) were euthanized on day 25 post-CAR T cell dosing (33 days post-tumor implantation) to enable comparison of all of the groups terminal samples.

A delay in disease progression was observed between the control groups and the CLL-1-6, CLL-1-9, and CLL-1-10 treated groups and slowing in tumor growth at late time points with the CLL-1-11 and CLL-1-12 CAR T cell treated groups. Calculated at the last time point with all the groups represented (day 18 post CAR T cell dose), all of the CLL-1 CAR T cells groups were significantly different from the control groups. Compared to the PBS treated mice, the CD19 CAR T cell treated group did not demonstrate significance with a P value of 0.496. All of the CLL-1 CAR T cell treated groups compared to PBS had a P≤0.01 (clone 6 P=0.0008; clone 9 P=0.0006; clone 10 P=0.0006; clone 11 P=0.0013; clone 12 P=0.0109). The three CLL-1 clones that showed an initial delay in tumor progression, clones 6, 9, and 10, showed stasis in tumor growth on day 18 post CAR T cell dose. The other two CLL-1 clones, clones 11 and 12, showed anti-tumor activity by this time point, although at the earlier time points they did not show any delay in disease progression. Calculated on day 18 post-T cell dose, the percent delta T/C values for each treatment group compared to the PBS control group were as follows: 98.38% for CD19, 3.15% for CLL-1-6, 2.04% for CLL-1-9, 4.92% for CLL-1-10, 13.42% for CLL-1-11, and 25.19% for CLL-1-12.

Based on these values, the CD19 CAR T cell treated group showed no activity, the CLL-1-6, -9, and -10 CAR T cell treated groups showed stasis in tumor growth, and the CLL-1-11, and -12 CAR T cell treated groups demonstrated anti-tumor activity.

Figure 24:
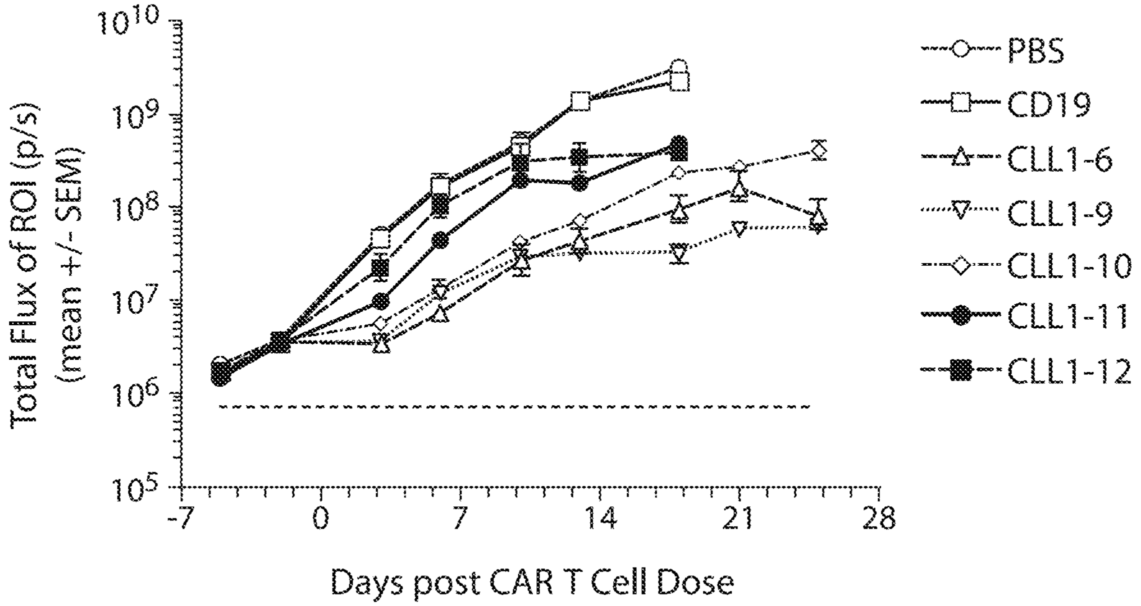
FIG. 24 is a graphic representation demonstrating AML disease progression in the PL-21-luc xenograft model after treatment with CLL-1 CAR T cells. Mean bioluminescence (+/− SEM) of the tumor cells show disease burden in the whole animal is shown as photons/second (p/s) of the ROI (region of interest), which is the whole mouse.

The bioluminescence imaging results of this study are shown in FIG. 24. The PBS treatment group, which did not receive any T cells, demonstrated baseline PL-21 tumor growth kinetics in intravenously implanted NSG mice. The CD19 treatment group received control CD19 CAR T cells, not specific for PL-21 cells, which underwent the same in vitro expansion process as the CAR T cells. These cells served as a T cell control to show the non-specific response of the T cells in this tumor model. Both the PBS and the CD19 CAR T cell treatment groups demonstrated continuous tumor progression throughout the experiment.

Figure 25A:
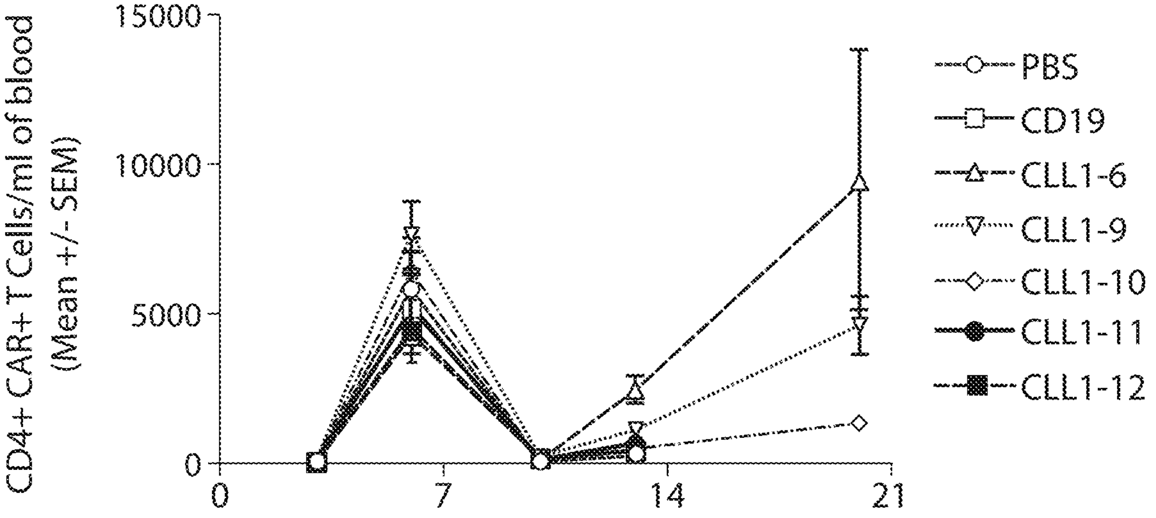
FIGS. 25A and 25B, are two graphs showing the quantification of $CD4^+$ (FIG. 25A) and $CD8^+$ (FIG. 25B) $CAR^+$ T cells in the peripheral blood of PL-21-luc tumor-bearing mice.
Figure 25B:
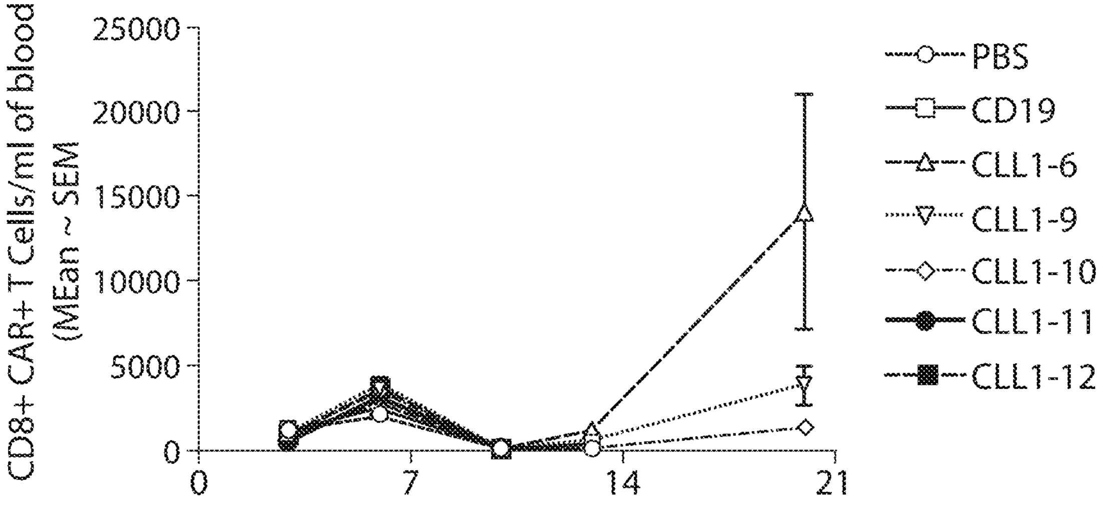
Figure 26A:
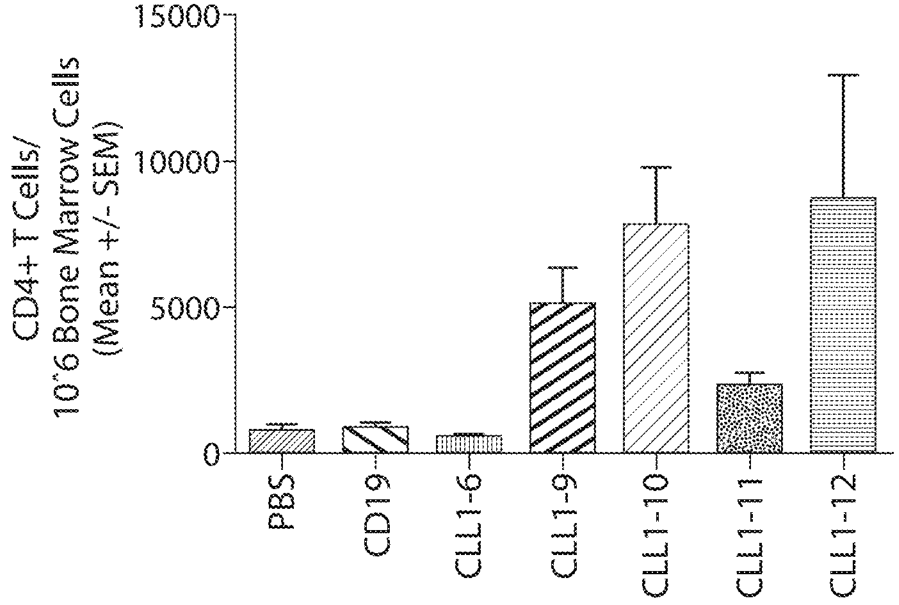
FIGS. 26A, 26B, 26C, and 26D, are bar graphs quantifying the $CD4^+$ T cells (FIG. 26A), $CD4^+$ CLL-1 CAR-expressing T cells (FIG. 26B), $CD8^+$ T cells (FIG. 26C), and the $CD8^+$ CLL-1 CAR-expressing T cells (FIG. 26D) in the bone marrow of the PL-21-luc tumor-bearing mice. Mean T cell number (+/−SEM) per million bone marrow cells is shown. Significance is calculated by one way ANOVA and is denoted as * $P<0.05$ and **$P<0.01$.
Figure 26B:
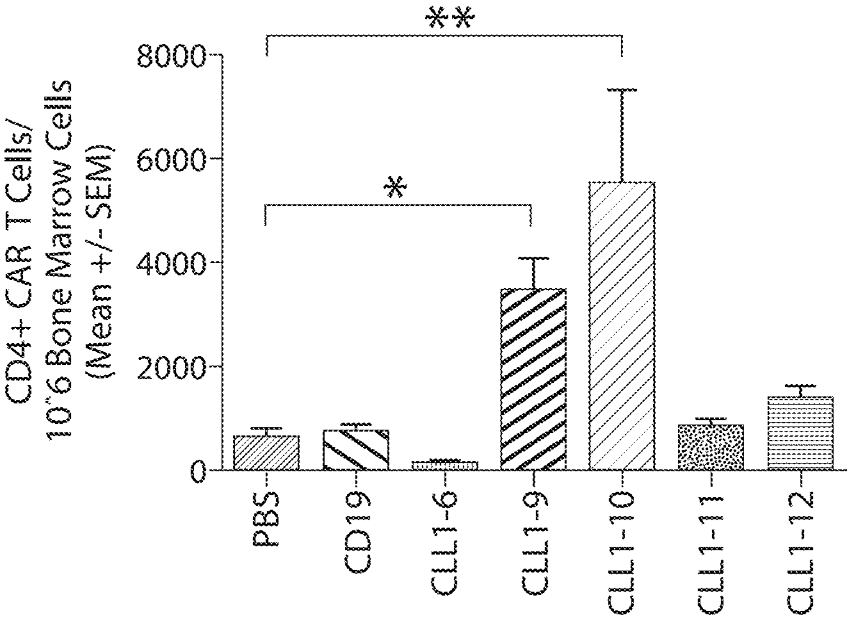
Figure 26C:
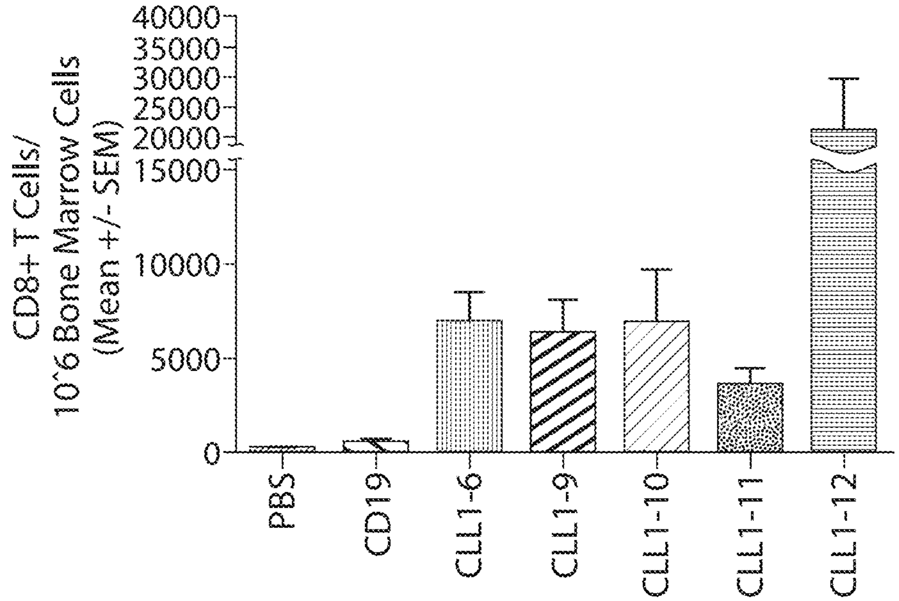
Figure 26D:
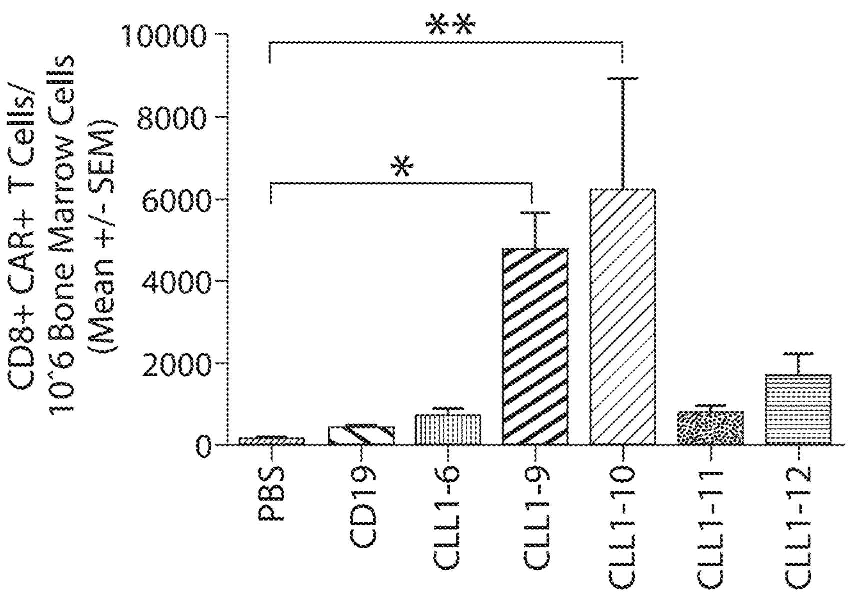
Figure 27A:
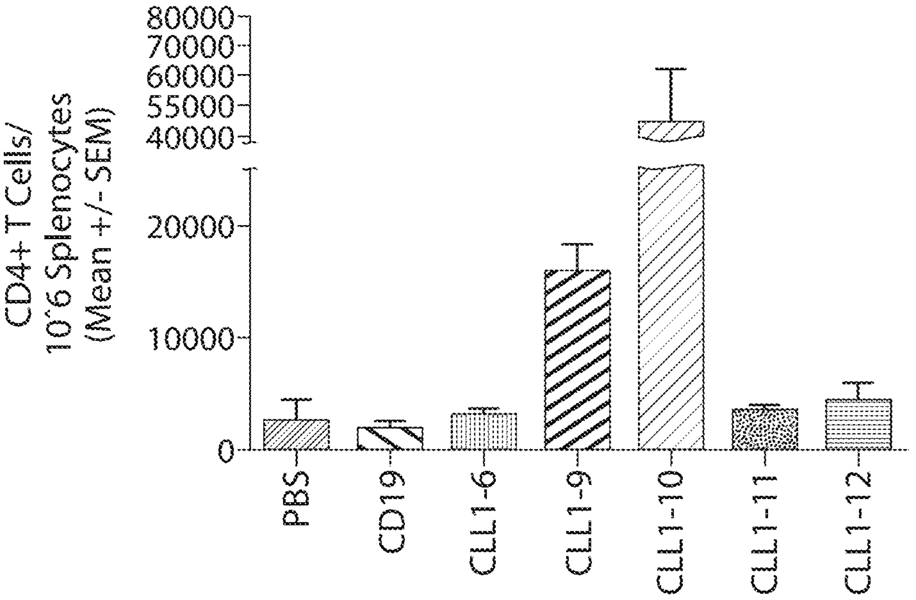
FIGS. 27A, 27B, 27C, and 27D, are bar graphs quantifying the $CD4^+$ T cells (FIG. 27A), $CD4^+$ CLL-1 CAR-expressing T cells (FIG. 27B), $CD8^+$ T cells (FIG. 27C), and the $CD8^+$ CLL-1 CAR-expressing T cells (FIG. 27D) in the spleen of the PL-21-luc tumor-bearing mice. Mean T cell number (+/−SEM) per million splenocytes is shown. Significance is calculated by one way ANOVA and is denoted as * $P<0.05$ and **$P<0.01$.
Figure 27B:
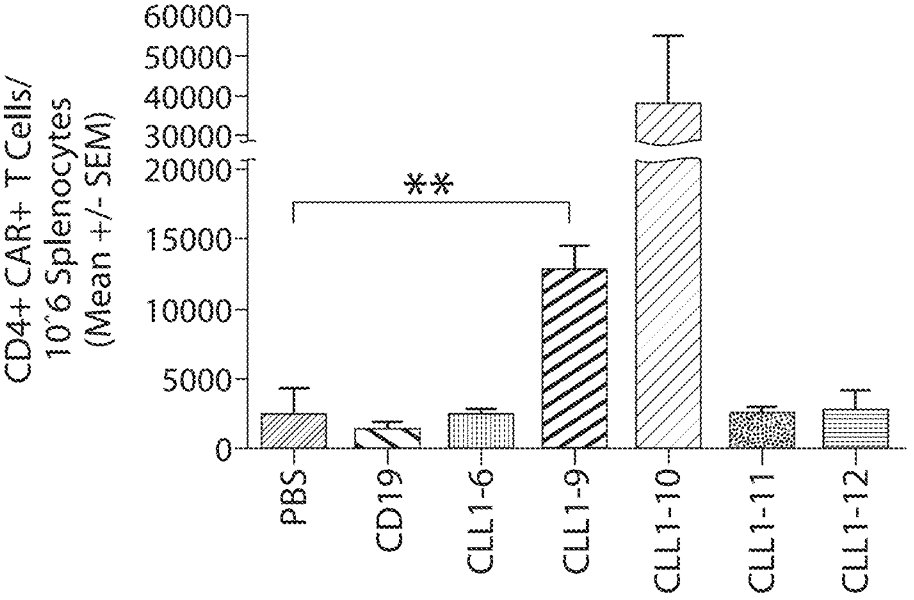
Figure 27C:
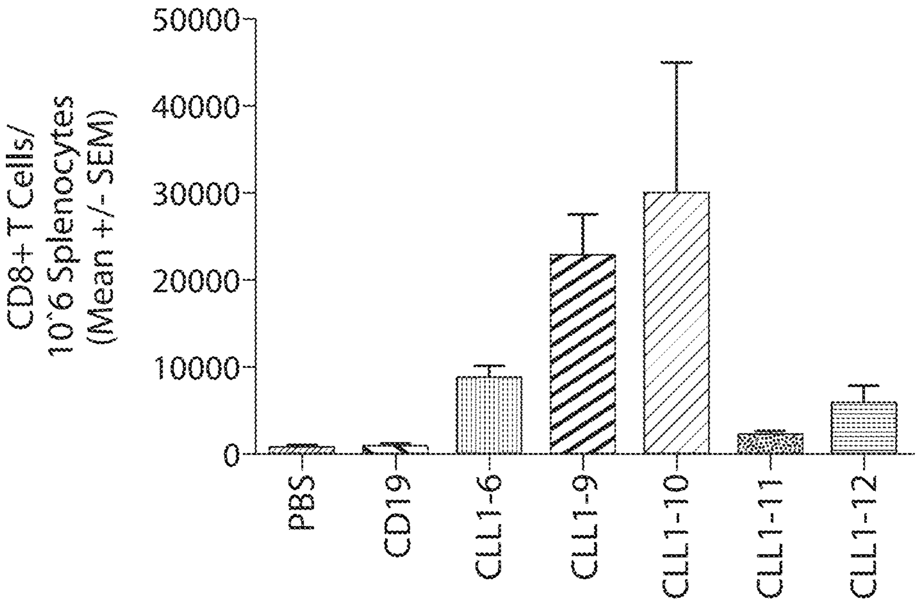
Figure 27D:
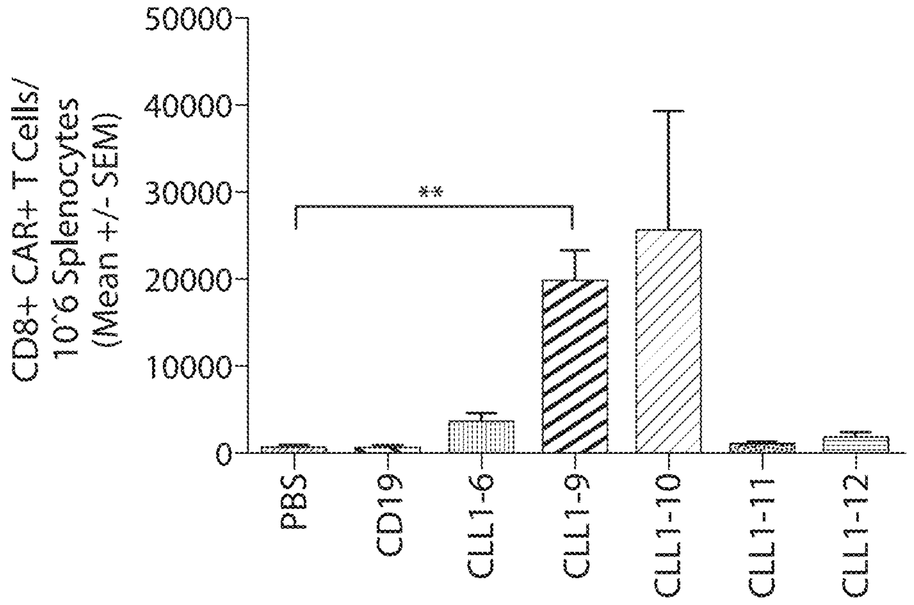
Figure 28A:
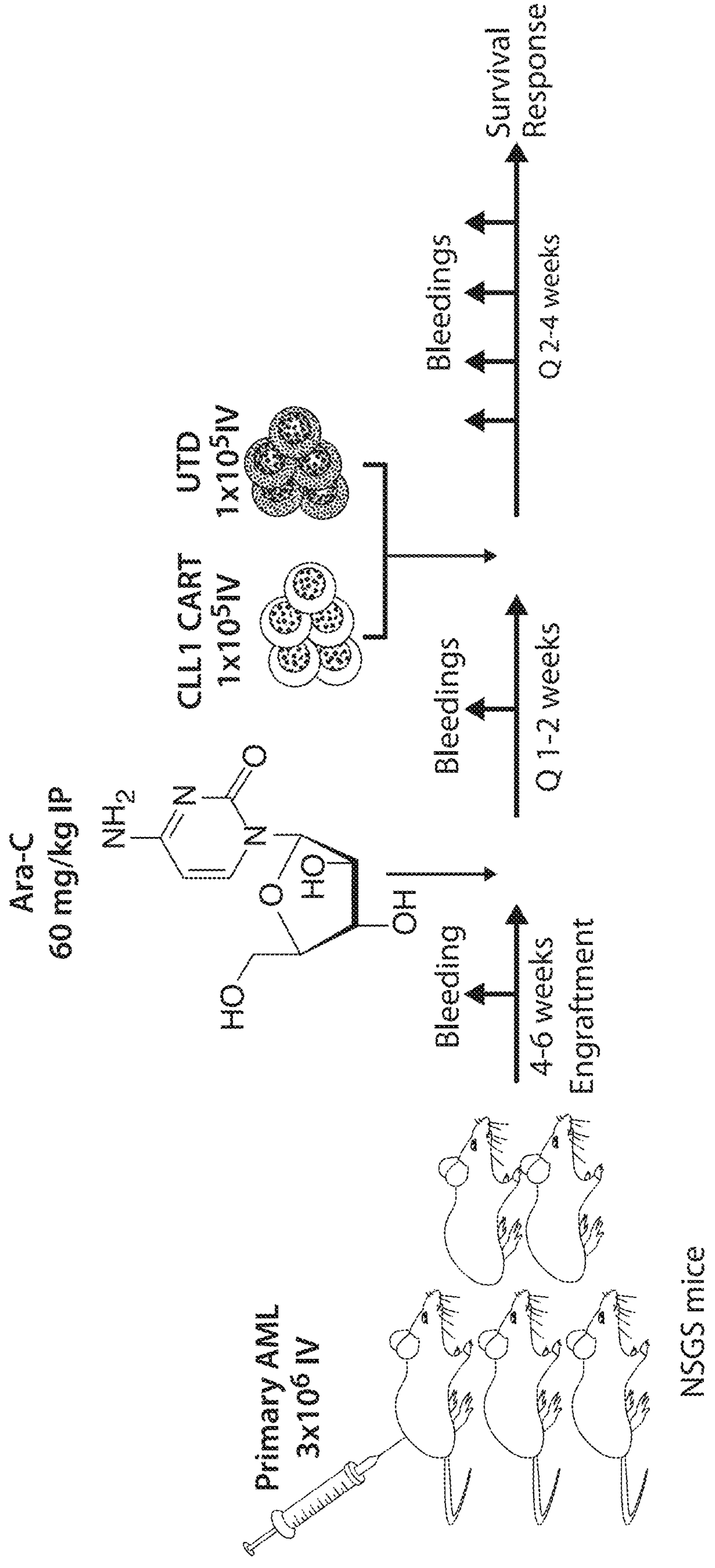
FIGS. 28A, 28B, 28C, and 28D, shows treatment with induction chemotherapy followed by CLL1-CART cells results in leukemic eradication in primary AML xenografts.
Figure 28B:
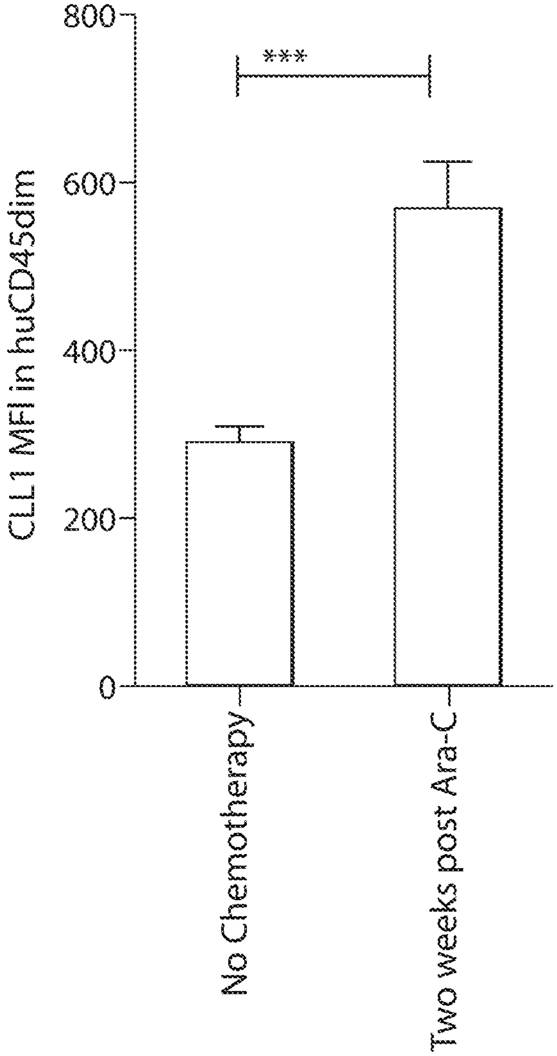
Figure 28C:
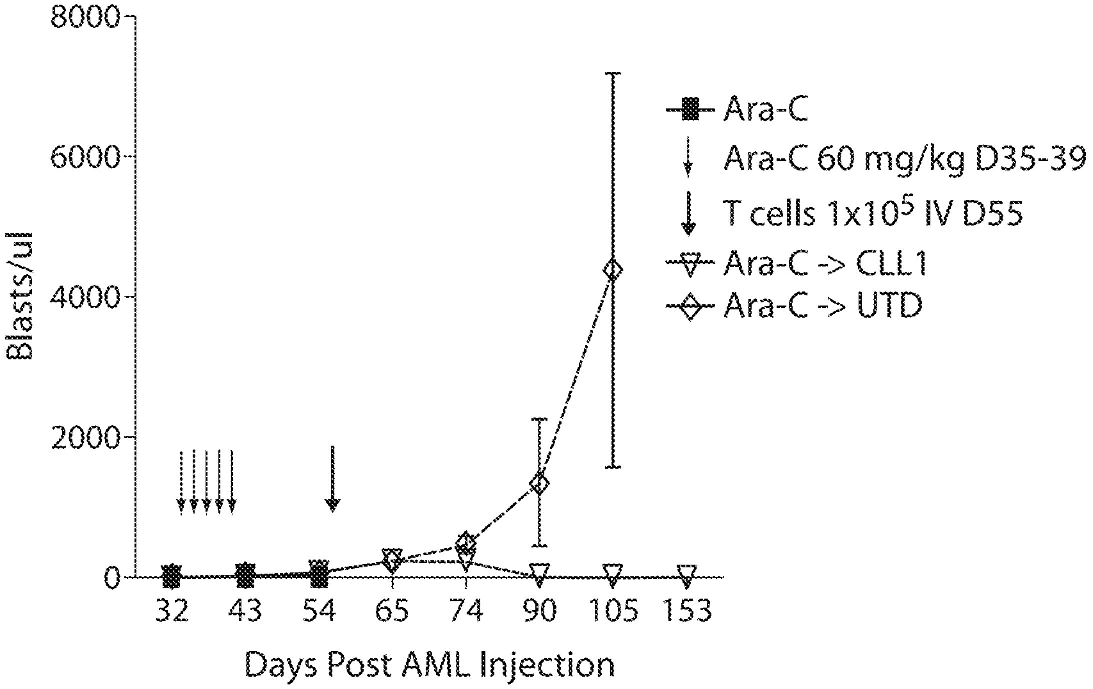
Figure 28D:
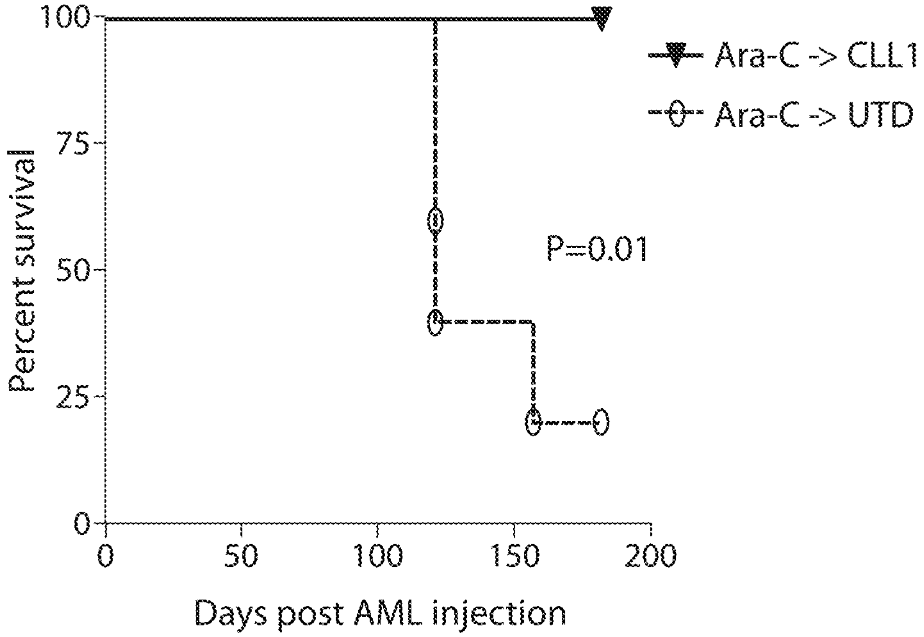
Figure 29A:
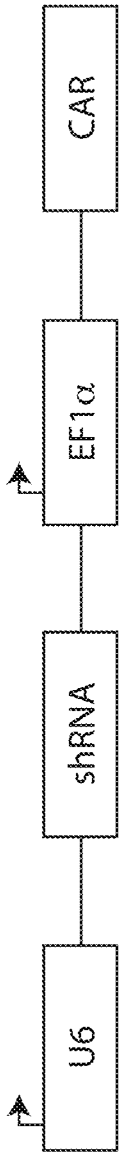
FIGS. 29A, 29B, 29C, 29D, and 29E, shows the various configurations on a single vector, e.g., where the U6 regulated shRNA is upstream or downstream of the EF1 alpha regulated CAR encoding elements. In the exemplary constructs depicted in FIGS. 29A and 29B, the transcription occurs through the U6 and EF1 alpha promoters in the same direction. In the exemplary constructs depicted in FIGS. 29C and 29D, the transcription occurs through the U6 and EF1 alpha promoters in different directions.
Figure 29B:
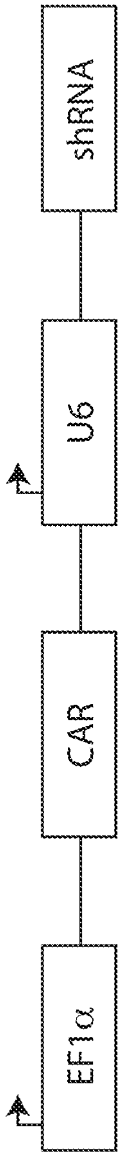
Figure 29C:
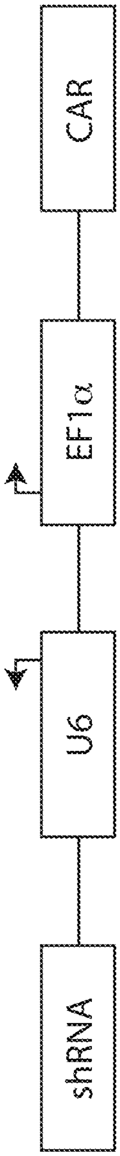
Figure 29D:
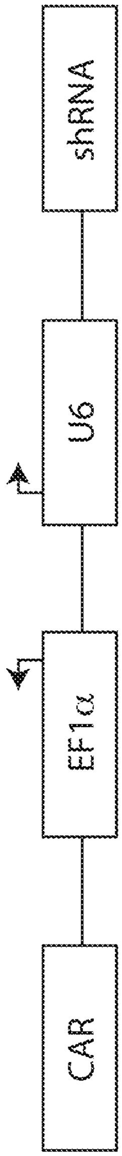
Figure 29E:
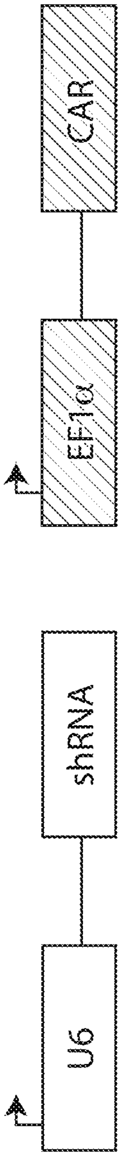
Figure 30:
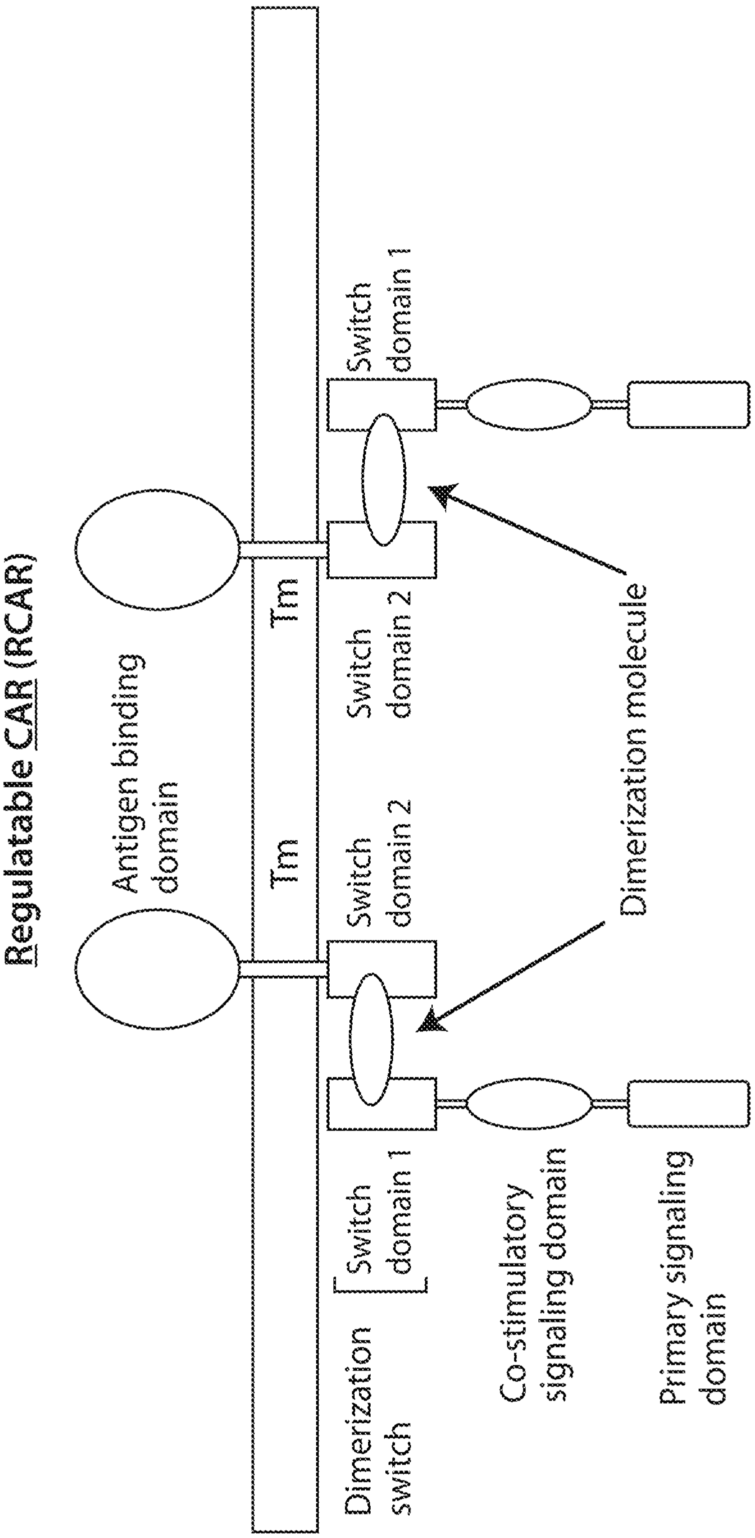
FIG. 30 depicts the structures of two exemplary RCAR configurations. The antigen binding members comprise an antigen binding domain, a transmembrane domain, and a switch domain. The intracellular binding members comprise a switch domain, a co-stimulatory signaling domain and a primary signaling domain. The two configurations demonstrate that the first and second switch domains described herein can be in different orientations with respect to the antigen binding member and the intracellular binding member. Other RCAR configurations are further described herein.

In addition to monitoring the disease burden via bioluminescence, the $CAR^+$ T cell numbers in each group was also monitored via peripheral blood FACS analysis. The FACS results of this study are shown in FIGS. 25A and 25B. The groups that showed the greatest anti-tumor activity and a delay in tumor growth after CAR T cell treatment showed an increase in both $CD4^+$ $CAR^+$ (FIG. 25A) and $CD8^+$ $CAR^+$ T cells (FIG. 25B) in the peripheral blood at late time points. Limited numbers of cells were observed in the peripheral blood at early time point. The AML was primarily in the bone marrow and the CAR T cells may also be in the bone marrow at these time points. However, this group showed no anti-tumor activity. At the final time point, there was an expanding population of CAR T cells in the peripheral blood for of the CLL-1-6, CLL-1-9, and CLL-1-10 groups.

At the end of the study, spleen and bone marrow cells were harvested from the mice and analyzed to determine if the CAR T cells persist. As seen in FIGS. 26A-26D, CD4 and CD8 CAR+ T cells were seen in appreciable numbers in the CLL-1-9 and CLL-1-10 treated groups. An expansion of T cells was also seen in some of the other groups, in particular the CLL-1-12 CART cell treated group. However, although large numbers of both CD4+ and CD8+ T cells were seen in the bone marrow of this group, the cells are not CAR+, indicating a non-specific expansion of T cells in these mice. CLL-1-6, CLL-1-9, and CLL-10, showed the greatest anti-tumor effect and delay in tumor growth and this corresponded to the terminal bone marrow CAR+ T cell numbers. Of note, the CLL-1-6 CAR was not well detected, so the CAR+ numbers in this group may be underestimated. A slight persistence of both CD4 and CD8 T cells in the CLL-1-11 group and larger numbers of these cells in the CLL-1-12 group may correlate to a non-specific late stage activity on the tumors resulting in the slight dip in tumor burden seen at the late time points in FIG. 24.

At the termination of the study, the phenotype of the cells in the spleen was also determined. Similar to what was observed in the bone marrow samples of these mice, the only groups with appreciable numbers of CD4 and CD8 $CAR^+$ T cells in the spleen were the CLL-1-9 and CLL-1-10 groups, as shown in FIGS. 27A-27D. These were also the only groups that had large numbers of $CD4^+$ and $CD8^+$ T cells in the spleen. The CLL-1-11 and CLL-12 groups did not show the non-CAR accumulation of T cells in the spleen that was observed in the bone marrow samples. Due to the large variation in CAR+ T cells detected in the spleen samples of the CLL-1-10 mice, this group did not correlate as significantly different when compared to the control groups.

Discussion:

The anti-tumor activity of novel CLL-1 CAR transduced T cells was assessed in an efficacy study in NSG mice bearing a xenograft model of human AML. These studies showed that the PL-21-luc model recapitulates human AML in the NSG mouse and is capable of being targeted by CLL-1 CAR T cells (FIG. 24). This study demonstrated that the three of the CLL-1 CARs (CLL-1-6, CLL-1-9, and CLL-1-10) were capable of mounting an anti-tumor response in a xenograft model of AML (FIG. 24). Minimal numbers of CAR T cells were detected in the blood for all of the groups, however at late time points, CAR T cells were seen in increasing numbers in the CLL-1-6, CLL-1-9, and CLL-1-10 groups (FIGS. 25A and 25B). The groups treated with these three CAR T cells showed a delay in tumor growth, and in particular, the CLL-1-9 and CLL-1-10 groups showed significant numbers of CAR T cells in the terminal bone marrow and spleen samples at the end of the study (FIGS. 26A-26D and 27A-27D). The CLL-1-6 group also showed an initial and prolonged delay in tumor growth, but the terminal CAR T cell numbers could not accurately be calculated due to difficulties in detecting the expression of the scFv on the surface of the T cells. Taken together, the CLL-1-9 and CLL-1-10 groups showed a delay in tumor growth, an increase in $CD4^+$ $CAR^+$ T cells and $CD8^+$ $CAR^+$ T cells in the peripheral blood, along with significant numbers of $CD4^+$ $CAR^+$ T cells and $CD8^+$ $CAR^+$ T cells in the terminal bone marrow and spleen samples. Only the CLL-1-9 group had significantly different amounts of $CD4^+$ $CAR^+$ and $CD8^+$ $CAR^+$ T cells as compared to the control groups in both the bone marrow and spleen.

Example 5: Chemotherapy and CLL1-CAR Combined Therapy

The effect of CLL-1 CAR therapy combined with chemotherapy was examined using an in vivo AML mouse model. Treatment with induction chemotherapy followed by CLL1-CART cells (clone 6) result in leukemic eradication in primary AML xenografts.

NSG mice that are additionally transgenic for stem cell factor, GM-CSF and IL-3 (NSG-S) were injected with primary AML blasts ($3\times10^6$ via tail vain injection, day 0). After 4-6 weeks, peripheral blood (PB) was collected to confirm engraftment, which was defined as the presence of >1% circulating leukemic cells (live human CD45dim cells). AML xenografts were then treated with cytarabine (Ara-C, 60 mg/kg by intra-peritoneal injection, daily between days 35-39). Peripheral blood counts were monitored and then these xenografts were randomized to receive CLL1 directed CART cells or control untransduced T cells ($1\times10^5$ I.V.) on day 55. Following that, serial retro-orbital bleedings were performed and absolute leukemic blast count was calculated as a measure of disease burden and the xenografts were followed up for survival.

Figure 33A:
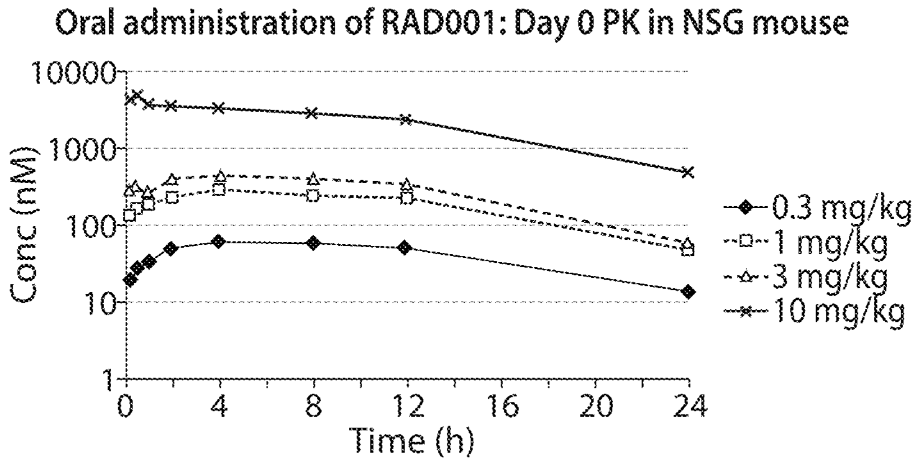
FIGS. 33A and 33B, shows pharmacokinetic curves showing the amount of RAD001 in the blood of NSG mice with NALM6 tumors.
Figure 33B:
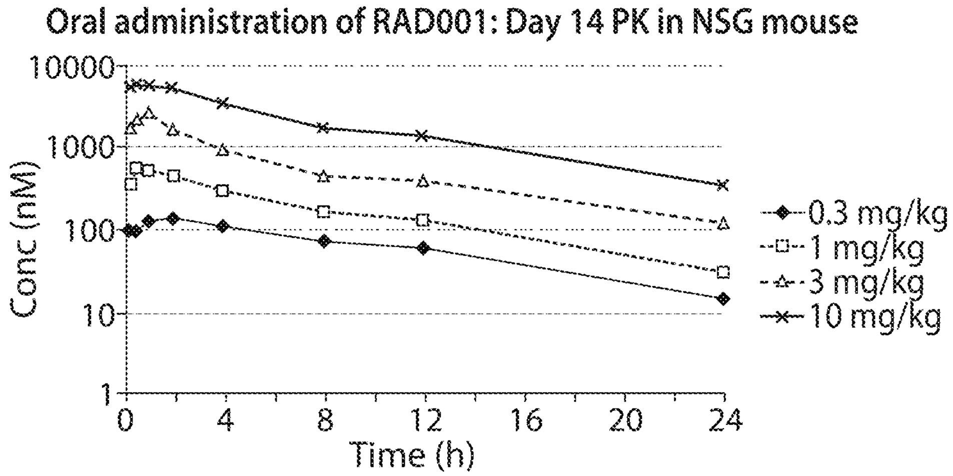

FIG. 33B comprises representative plots of the mean fluorescence intensity (MFI) of CLL1 in leukemic cells (live huCD45dim compartment), and demonstrates that treatment with chemotherapy results in upregulation of CLL-1 antigen in the residual AML. There was a significant increase in CLL1-MFI in AML xenografts two weeks after treatment with cytarabine chemotherapy.

Mice that were treated with induction chemotherapy followed by untransduced T cells did not show reduction of peripheral blood leukemic blast count. In contrast, mice treated with induction chemotherapy followed by CLL-1-CARTs resulted in significant reduction of the peripheral blood leukemic blast count and eradication of leukemia in AML xenografts, as shown in FIG. 33C. Plots are representative of the peripheral blood absolute leukemic blast count per 1 ul of peripheral blood (mean+/−SD) at different time points post AML injection as indicated. Analysis of overall survival also showed that induction chemotherapy followed by CLL1-CARTs, but not by untransduced T cells results in a significant advantage in overall survival in AML xenografts (FIG. 33D).

Example 6: Low Dose RAD001 Stimulates CART Proliferation in a Cell Culture Model The effect of low doses of RAD001 on CAR T cell proliferation in vitro was evaluated by co-culturing CART-expressing cells with target cells in the presence of different concentrations of RAD001.

Materials and Methods

Generation of CAR-Transduced T Cells

A humanized, anti-human CD19 CAR (huCART19) lentiviral transfer vector was used to produce the genomic material packaged into VSVg pseudotyped lentiviral particles. The amino acid and nucleotide sequence of the humanized anti-human CD19 CAR (huCART19) is CAR 1, ID 104875 described in PCT publication, WO2014/153270, filed Mar. 15, 2014, and is designated SEQ ID NOs. 85 and 31 therein.

Lentiviral transfer vector DNA is mixed with the three packaging components VSVg env, gag/pol and rev in combination with lipofectamine reagent to transfect Lenti-X 293T cells. Medium is changed after 24 h and 30 h thereafter, the virus-containing media is collected, filtered and stored at −80° C. CARTs are generated by transduction of fresh or frozen naïve T cells obtained by negative magnetic selection of healthy donor blood or leukopak. T cells are activated by incubation with anti-CD3/anti-CD28 beads for 24 h, after which viral supernatant or concentrated virus (MOI=2 or 10, respectively) is added to the cultures. The modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~350 fL determines the state for T cells to be cryopreserved for later analysis.

Evaluating Proliferation of CARTs

To evaluate the functionality of CARTs, the T cells are thawed and counted, and viability is assessed by Cellometer. The number of CAR-positive cells in each culture is normalized using non-transduced T cells (UTD). The impact of RAD001 on CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 31:
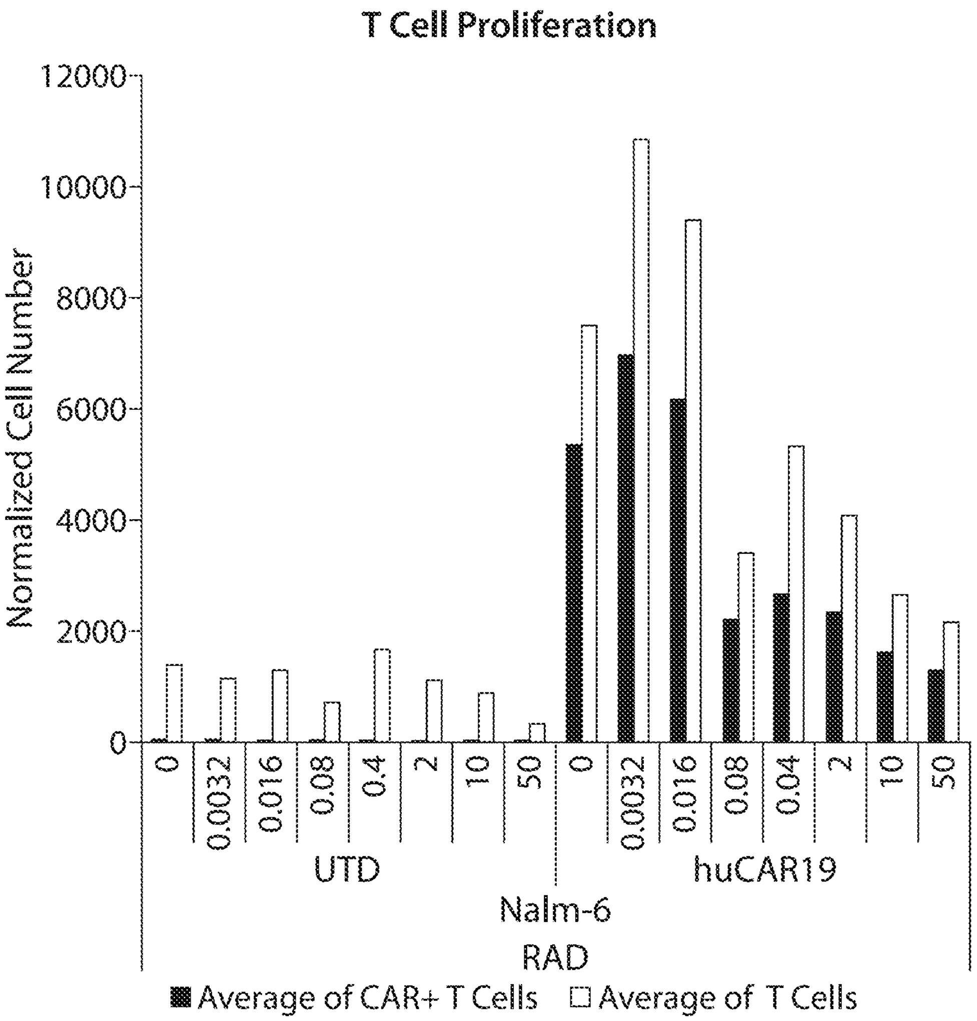
FIG. 31 shows that the proliferation of CAR-expressing, transduced T cells is enhanced by low doses of RAD001 in a cell culture system. CARTs were co-cultured with Nalm-6 cells in the presence of different concentrations of RAD001. The number of CAR-positive CD3-positive T cells (black) and total T cells (gray) was assessed after 4 days of co-culture.

The proliferative capacity of CART cells was tested in a 4 day co-culture assay. The number of CAR-positive CD3-positive T cells (dark bars) and total CD3-positive T cells (light bars) was assessed after culturing the CAR-transduced and non-transduced T cells with Nalm-6 (FIG. 31). huCART19 cells expanded when cultured in the presence of less than 0.016 nM of RAD001, and to a lesser extent at higher concentrations of the compound. Importantly, both at 0.0032 and 0.016 nM RAD001 the proliferation was higher than observed without the addition of RAD001. The non-transduced T cells (UTD) did not show detectable expansion.

Example 7: Low Dose RAD001 Stimulates CART Expansion In Vivo

This example evaluates the ability of huCAR19 cells to proliferate in vivo with different concentrations of RAD001.

Materials and Methods:

NALM6-Luc Cells:

The NALM6 human acute lymphoblastic leukemia (ALL) cell line was developed from the peripheral blood of a patient with relapsed ALL. The cells were then tagged with firefly luciferase. These suspension cells grow in RPMI supplemented with 10% heat inactivated fetal bovine serum.

Mice:

6 week old NSG (NOD.Cg-Prkdc$^{scid}$Il2rg$^{tm1Wjl}$/SzJ) mice were received from the Jackson Laboratory (stock number 005557).

Tumor Implantation:

NALM6-luc cells were grown and expanded in vitro in RPMI supplemented with 10% heat inactivated fetal bovine serum. The cells were then transferred to a 15 ml conical tube and washed twice with cold sterile PBS. NALM6-luc cells were then counted and resuspended at a concentration of $10\times10^6$ cells per milliliter of PBS. The cells were placed on ice and immediately (within one hour) implanted in the mice. NALM6-luc cells were injected intravenously via the tail vein in a 100 μl volume, for a total of $1\times10^6$ cells per mouse.

CAR T Cell Dosing:

Mice were administered $5\times10^6$ CAR T cells 7 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of $50\times10^6$ CAR T cells per ml of cold PBS and kept on ice until the mice were dosed. The mice were injected intravenously via the tail vein with 100 μl of the CAR T cells for a dose of $5\times10^6$ CAR T cells per mouse. Eight mice per group were treated either with 100 μl of PBS alone (PBS), or humanized CD19 CAR T cells.

RAD001 Dosing:

A concentrated micro-emulsion of 50 mg equal to 1 mg RAD001 was formulated and then resuspended in D5W (dextrose 5% in water) at the time of dosing. Mice were orally dosed daily (via oral gavage) with 200 μl of the desired doses of RAD001.

PK Analysis:

Mice were dosed daily with RAD001 starting 7 days post tumor implantation. Dosing groups were as follows: 0.3 mg/kg, 1 mg/kg, 3 mg/kg, and 10 mg/kg. Mice were bled on days 0 and 14 following the first and last dose of RAD001, at the following time points for PK analysis: 15 minutes, 30 minutes, 1 hour, 2 hours, 4 hours, 8 hours, 12 hours, and 24 hours.

Figure 32:
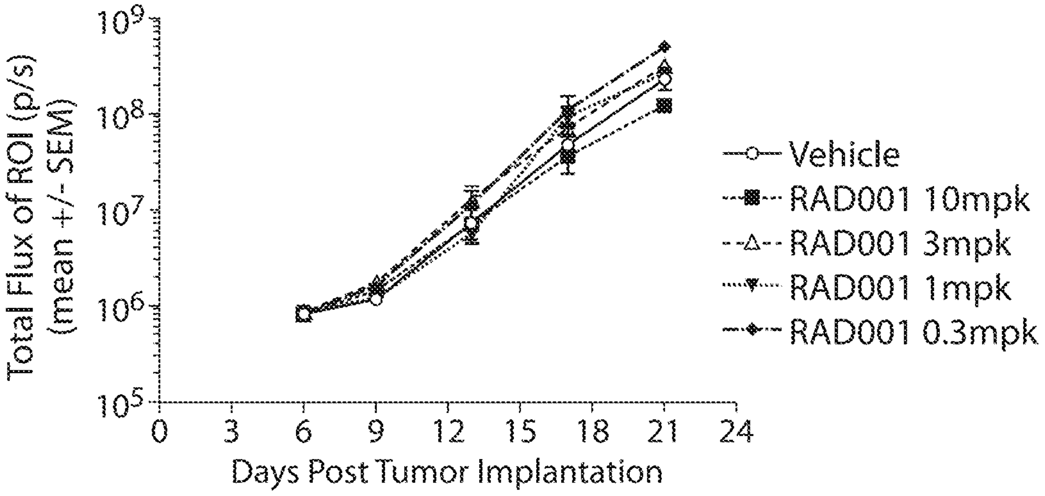
FIG. 32 depicts tumor growth measurements of NALM6-luc cells with daily RAD001 dosing at 0.3, 1, 3, and 10 mg/kg (mpk) or vehicle dosing. Circles denote the vehicle; squares denote the 10 mg/kg dose of RAD001; triangles denote the 3 mg/kg dose of RAD001, inverted triangles denote the 1 mg/kg dose of RAD001; and diamonds denote the 0.3 mg/kg dose of RAD001.

Results:

The expansion and pharmacokinetics of RAD001 was tested in NSG mice with NALM6-luc tumors. Daily oral dosing of RAD001 alone did not have an impact on the growth of NALM6-luc tumors (FIG. 32). The pharmacokinetic analysis of RAD001 shows that it is fairly stable in the blood of tumor bearing mice (FIGS. 33A and 33B). Both the day 0 and day 14 PK analyses show that the RAD001 concentrations in the blood is above 10 nm even 24 hours after dosing at the lowest dose tested (0.3 mg/kg).

Based on these doses, huCAR19 CAR T cells were dosed with and without RAD001 to determine the proliferative ability of these cells. The highest dose used was 3 mg/kg based on the levels of RAD001 in the blood 24 hours after dosing. As the concentration of RAD001 was above 10 nM 24 hours after the final dose of RAD001, several lower doses of RAD001 were used in the in vivo study with CAR T cells. The CAR T cells were dosed IV one day prior to the start of the daily oral RAD001 dosing. Mice were monitored via FACS for T cell expansion.

Figure 34A:
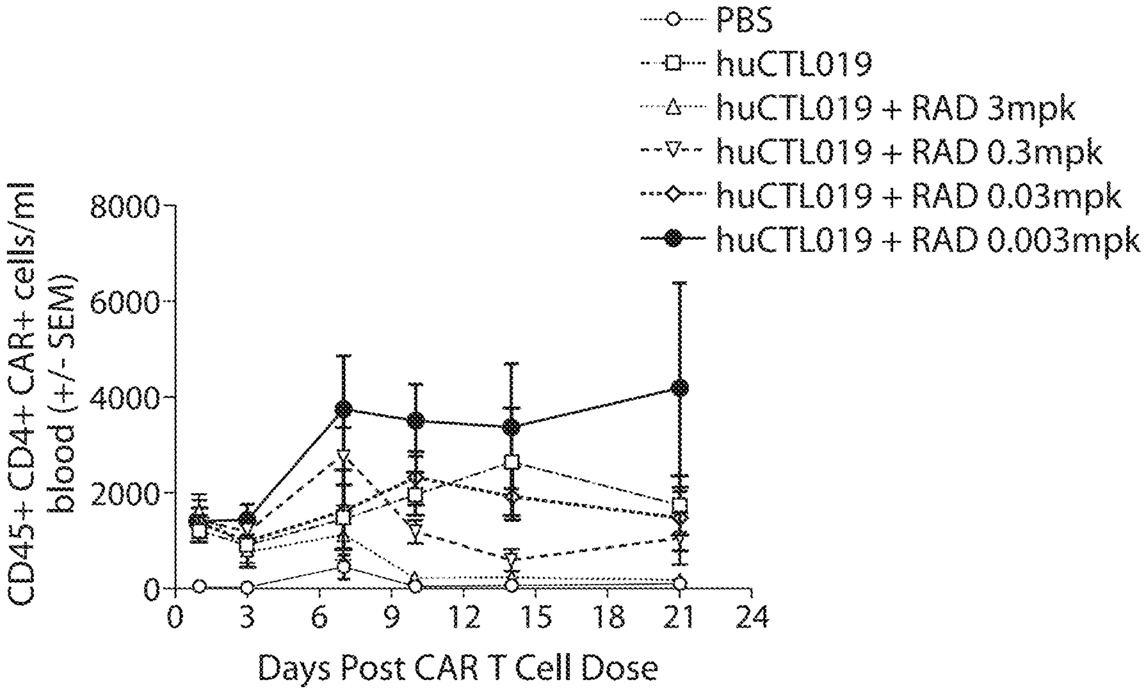
FIGS. 34A and 34B, shows in vivo proliferation of humanized CD19 CART cells with and without RAD001 dosing. Low doses of RAD001 (0.003 mg/kg) daily lead to an enhancement in CAR T cell proliferation, above the normal level of huCAR19 proliferation.
Figure 34B:
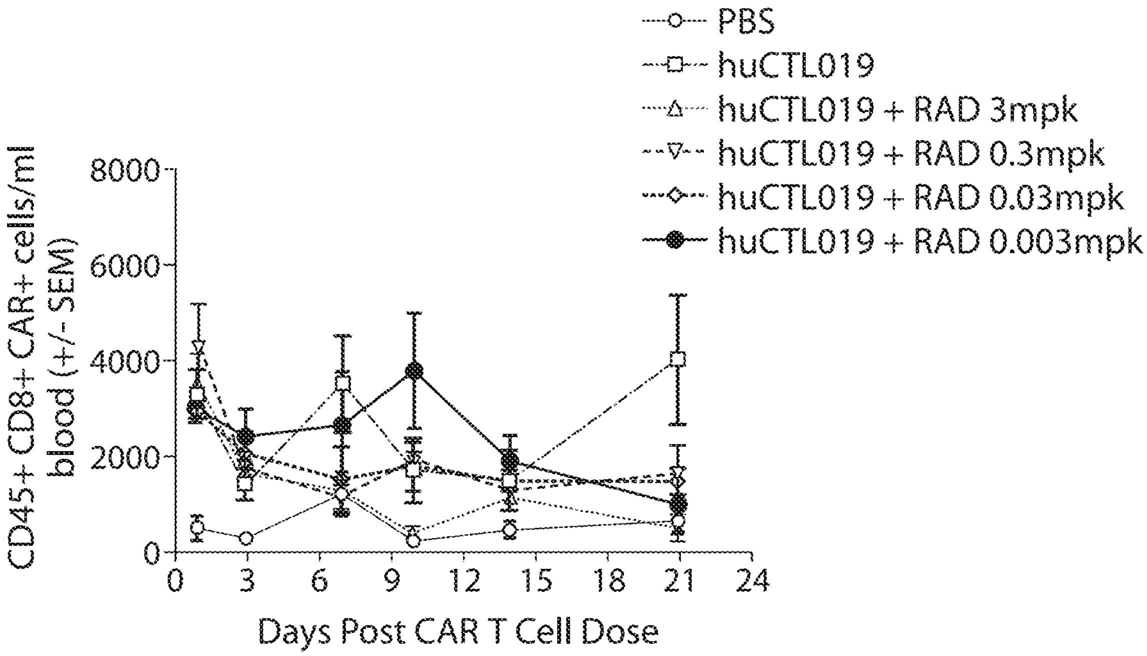

The lowest doses of RAD001 show an enhanced proliferation of the CAR T cells (FIG. 34). This enhanced proliferation is more evident and prolonged with the $CD4^+$ CAR T cells than the $CD8^+$ CAR T cells. However, with the $CD8^+$ CAR T cells, enhanced proliferation can be seen at early time points following the CAR T cell dose.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. An isolated nucleic acid molecule encoding a chimeric antigen receptor (CAR), wherein the CAR comprises from N-terminus to C-terminus an extracellular anti-CLL-1 binding domain, a transmembrane domain, and an intracellular signaling domain, and wherein said anti-CLL-1 binding domain comprises:

(i) a heavy chain variable region comprising a heavy chain complementary determining region 1 (HC CDR1) comprising the amino acid sequence of SEQ ID NO: 406, a heavy chain complementary determining region 2 (HC CDR2) comprising the amino acid sequence of SEQ ID NO: 420, and a heavy chain complementary determining region 3 (HC CDR3) comprising the amino acid sequence of SEQ ID NO: 434, and a light chain variable region comprising a light chain complementary determining region 1 (LC CDR1) comprising the amino acid sequence of SEQ ID NO: 448, a light chain complementary determining region 2 (LC CDR2) comprising the amino acid sequence of SEQ ID NO: 462, and a light chain complementary determining region 3 (LC CDR3) comprising the amino acid sequence of SEQ ID NO: 476;

(ii) a heavy chain variable region comprising a HC CDR1 comprising the amino acid sequence of SEQ ID NO: 125, a HC CDR2 comprising the amino acid sequence of SEQ ID NO: 138, and HC CDR3 comprising the amino acid sequence of SEQ ID NO: 151, and a light chain variable region comprising a LC CDR1 comprising the amino acid sequence of SEQ ID NO: 164, a LC CDR2 comprising the amino acid sequence of SEQ ID NO: 177, and a LC CDR3 comprising the amino acid sequence of SEQ ID NO: 190; or (iii) a heavy chain variable region comprising a HC CDR1 comprising the amino acid sequence of SEQ ID NO: 322, a HC CDR2 comprising the amino acid sequence of SEQ ID NO: 336, and a HC CDR3 comprising the amino acid sequence of SEQ ID NO: 350, and a light chain variable region comprising a LC CDR1 comprising the amino acid sequence of SEQ ID NO: 364, a LC CDR2 comprising the amino acid sequence of SEQ ID NO: 378, and a LC CDR3 comprising the amino acid sequence of SEQ ID NO: 392.

2. The isolated nucleic acid molecule of claim 1, wherein the encoded light chain variable region comprises:

(i) the amino acid sequence of SEQ ID NO: 86;

(ii) an amino acid sequence having at least one, two or three modifications but not more than 30, 20 or 10 modifications of the amino acid sequence of SEQ ID NO: 86; or (iii) an amino acid sequence with 95-99% identity to the amino acid sequence of SEQ ID NO: 86.

3. The isolated nucleic acid molecule of claim 1, wherein the encoded heavy chain variable region comprises:

(i) the amino acid sequence of SEQ ID NO: 73;

(ii) an amino acid sequence having at least one, two or three modifications but not more than 30, 20 or 10 modifications of the amino acid sequence of SEQ ID NO: 73: or (iii) an amino acid sequence with 95-99% identity to the amino acid sequence of SEQ ID NO: 73.

4. The isolated nucleic acid molecule of claim 1, wherein the encoded light chain variable region comprises the amino acid sequence of SEQ ID NO: 86, and the encoded heavy chain variable region comprises the amino acid sequence of SEQ ID NO: 73.

5. The isolated nucleic acid molecule of claim 1, wherein the encoded CAR comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

6. The isolated nucleic acid molecule of claim 1, wherein:

(i) the encoded transmembrane domain comprises the amino acid sequence of SEQ ID NO: 6, an amino acid sequence comprises one or two modifications of the amino acid sequence of SEQ ID NO:6, or a sequence with 95-99% identity to the amino acid sequence of SEQ ID NO:6; or (ii) the nucleic acid sequence encoding the transmembrane domain comprises the nucleotide sequence of nucleotides 937-1008 of SEQ ID NO: 112, or a nucleotide sequence with 95-99% identity thereof.

7. The isolated nucleic acid molecule of claim 1, wherein the encoded anti-CLL-1 binding domain is connected to the transmembrane domain by a hinge region, wherein (i) the encoded hinge region comprises the amino acid sequence of SEQ ID NO:2, or a sequence with 95-99% identity thereof; or (ii) the nucleic acid sequence encoding the hinge region comprises the nucleotide sequence of nucleotides 802-936 of SEQ ID NO: 112, or a nucleotide sequence with 95-99% identity thereof.

8. The isolated nucleic acid molecule of claim 1, wherein the encoded intracellular signaling domain comprises a costimulatory intracellular signaling domain, wherein the costimulatory intracellular signaling domain comprises a functional signaling domain derived from a costimulatory molecule selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

9. The isolated nucleic acid molecule of claim 8, wherein the encoded costimulatory intracellular signaling domain comprises the amino acid sequence of SEQ ID NO:7, or an amino acid sequence having one, two, three or four modifications of the amino acid sequence of SEQ ID NO:7, or a sequence with 95-99% identity to the amino acid sequence of SEQ ID NO:7.

10. The isolated nucleic acid molecule of claim 8, wherein the nucleic acid sequence encoding the costimulatory intracellular signaling domain comprises the nucleotide sequence of nucleotides 1009-1134 of SEQ ID NO: 112, or a sequence with 95-99% identity thereof.

11. The isolated nucleic acid molecule of claim 1, wherein the encoded intracellular signaling domain comprises a functional signaling domain of 4-1BB and a functional signaling domain of CD3 zeta.

12. The isolated nucleic acid molecule of claim 1, wherein the encoded intracellular signaling domain comprises:

the amino acid sequence of SEQ ID NO: 7 and the sequence of SEQ ID NO:9 or SEQ ID NO:10; or an amino acid sequence having one, two, three, or four modifications of the amino acid sequence of SEQ ID NO:7, or at least one, two or three modifications but not more than 10 modifications of the amino acid sequence of SEQ ID NO:9 or SEQ ID NO:10; or a sequence with 95-99% identity to the amino acid sequence of SEQ ID NO:7 and the amino acid sequence of SEQ ID NO:9 or SEQ ID NO:10.

13. The isolated nucleic acid molecule of claim 1, wherein the nucleic acid sequence encoding the intracellular signaling domain comprises the sequence of nucleotides 1009-1134 of SEQ ID NO: 112, or a sequence with 95-99% identity thereof, and the sequence of nucleotides 1135-1470 of SEQ ID NO: 112 or the sequence of SEQ ID NO:21, or a sequence with 95-99% identity thereof.

14. The isolated nucleic acid molecule of claim 1, further comprising a leader sequence which encodes the amino acid sequence of SEQ ID NO:1.

15. The isolated nucleic acid molecule of claim 1, which encodes a CAR comprising:

(i) the amino acid sequence of SEQ ID NO:99;

(ii) an amino acid sequence having at least one, two or three modifications but not more than 30, 20 or 10 modifications to SEQ ID NO: 99; or (iii) an amino acid sequence with 95-99% identity to SEQ ID NO: 99.

16. The isolated nucleic acid of claim 1, which encodes a CAR comprising the nucleotide sequence of SEQ ID NO: 112, or a nucleotide sequence with 95-99% identity to SEQ ID NO: 112.

17. A vector comprising the nucleic acid molecule encoding a CAR of claim 1, wherein the vector is a DNA vector, an RNA vector, a plasmid, a lentivirus vector, adenoviral vector, or a retrovirus vector.

18. A method of making an immune effector cell, comprising transducing the immune effector cell with the vector of claim 17.

19. An immune effector cell expressing the nucleic acid molecule of claim 1.

20. The cell of claim 19, further expressing a fusion protein comprising from N-terminus to C-terminus:

an extracellular domain of PD1;

a transmembrane domain; and an intracellular signaling domain, wherein the intracellular signaling domain comprises a costimulatory intracellular signaling domain derived from 4-IBB, CD27 or CD28, or a primary signaling domain derived from CD3 zeta, or both.

21. A method of generating a population of RNA-engineered cells, comprising introducing an in vitro transcribed RNA or synthetic RNA into a cell, where the RNA comprises the nucleic acid molecule of claim 1.

22. The isolated nucleic acid molecule of claim 1, wherein the encoded intracellular signaling domain comprises a primary cytoplasmic signaling domain comprising a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d.

23. The isolated nucleic acid molecule of claim 22, wherein the encoded primary cytoplasmic signaling domain comprises a functional signaling domain of CD3 zeta, wherein the CD3 zeta comprises the amino acid sequence of SEQ ID NO: 9 or SEQ ID NO: 10, or an amino acid sequence having at least one, two or three modifications but not more than 10 modifications of the amino acid sequence of SEQ ID NO: 9 or SEQ ID NO: 10, or a sequence with 95-99% identity to the amino acid sequence of SEQ ID NO: 9 or SEQ ID NO: 10.

24. The isolated nucleic acid molecule of claim 23, wherein the nucleic acid sequence encoding the primary signaling domain comprises the nucleotide sequence nucleotides 1135-1470 of SEQ ID NO: 112 or the sequence of SEQ ID NO: 21, or a sequence with 95-99% identity thereof.

25. An isolated chimeric antigen receptor (CAR) polypeptide, wherein the CAR comprises an extracellular anti- CLL-1 binding domain, a transmembrane domain, and an intracellular signaling domain, and wherein said anti-CLL-1 binding domain comprises:

(i) a heavy chain variable region comprising a heavy chain complementary determining region 1 (HC CDR1) comprising the amino acid sequence of SEQ ID NO: 406, a heavy chain complementary determining region 2 (HC CDR2) comprising the amino acid sequence of SEQ ID NO: 420, and a heavy chain complementary determining region 3 (HC CDR3) comprising the amino acid sequence of SEQ ID NO: 434, and a light chain variable region comprising a light chain complementary determining region 1 (LC CDR1) comprising the amino acid sequence of SEQ ID NO: 448, a light chain complementary determining region 2 (LC CDR2) comprising the amino acid sequence of SEQ ID NO: 462, and a light chain complementary determining region 3 (LC CDR3) comprising the amino acid sequence of SEQ ID NO: 476;

(ii) a heavy chain variable region comprising a HC CDR1 comprising the amino acid sequence of SEQ ID NO: 125, a HC CDR2 comprising the amino acid sequence of SEQ ID NO: 138, and HC CDR3 comprising the amino acid sequence of SEQ ID NO: 151, and a light chain variable region comprising a LC CDR1 comprising the amino acid sequence of SEQ ID NO: 164, a LC CDR2 comprising the amino acid sequence of SEQ ID NO: 177, and a LC CDR3 comprising the amino acid sequence of SEQ ID NO: 190; or (iii) a heavy chain variable region comprising a HC CDR1 comprising the amino acid sequence of SEQ ID NO: 322, a HC CDR2 comprising the amino acid sequence of SEQ ID NO: 336, and a HC CDR3 comprising the amino acid sequence of SEQ ID NO: 350, and a light chain variable region comprising a LC CDR1 comprising the amino acid sequence of SEQ ID NO: 364, a LC CDR2 comprising the amino acid sequence of SEQ ID NO: 378, and a LC CDR3 comprising the amino acid sequence of SEQ ID NO: 392.

26. The isolated CAR polypeptide of claim 25, wherein:

(a) the light chain variable region comprises:

(i) the amino acid sequence of SEQ ID NO: 86;

(ii) an amino acid sequence having at least one, two or three modifications but not more than 30, 20 or 10 modifications of the amino acid sequence of SEQ ID NO: 86; or (iii) an amino acid sequence with 95-99% identity to the amino acid sequence of SEQ ID NO: 86; and (b) the heavy chain variable region comprises:

(i) the amino acid sequence of SEQ ID NO: 73;

(ii) an amino acid sequence having at least one, two or three modifications but not more than 30, 20 or 10 modifications of the amino acid sequence of SEQ ID NO: 73; or (iii) an amino acid sequence with 95-99% identity to the amino acid sequence of SEQ ID NO: 73.

27. The isolated CAR polypeptide of claim 25, wherein the transmembrane domain comprises a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

28. The isolated CAR polypeptide of claim 25, wherein:

(i) the transmembrane domain comprises the amino acid sequence of SEQ ID NO: 6, (ii) an amino acid sequence comprises one or two modifications of the amino acid sequence of SEQ ID NO:6, or (iii) a sequence with 95-99% identity to the amino acid sequence of SEQ ID NO:6.

29. The isolated CAR polypeptide of claim 25, wherein the anti-CLL-1 binding domain is connected to the transmembrane domain by a hinge region, wherein the hinge region comprises SEQ ID NO:2, or a sequence with 95-99% identity thereof.

30. The isolated CAR polypeptide of claim 25, wherein the intracellular signaling domain comprises a costimulatory intracellular signaling domain, wherein the costimulatory intracellular signaling domain comprises a functional signaling domain derived from a costimulatory molecule selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

31. The isolated CAR polypeptide of claim 25, wherein the costimulatory intracellular signaling domain comprises the amino acid sequence of SEQ ID NO:7, or an amino acid sequence having one, two, three or four modifications of the amino acid sequence of SEQ ID NO:7, or a sequence with 95-99% identity to the amino acid sequence of SEQ ID NO:7.

32. The isolated CAR polypeptide of claim 25, wherein the intracellular signaling domain comprises a functional signaling domain of 4-1BB and a functional signaling domain of CD3 zeta.

33. The isolated CAR polypeptide of claim 25, wherein the intracellular signaling domain comprises:

the amino acid sequence of SEQ ID NO: 7 and the sequence of SEQ ID NO:9 or SEQ ID NO:10; or an amino acid sequence having at least one, two three of four modifications of the amino acid sequence of SEQ ID NO:7, or an amino acid sequence having at least one, two or three modifications but not more than 10 modifications of the amino acid sequence of SEQ ID NO:9 or SEQ ID NO:10; or a sequence with 95-99% identity to the amino acid sequence of SEQ ID NO:7 and the amino acid sequence of SEQ ID NO:9 or SEQ ID NO:10.

34. The isolated CAR polypeptide of claim 25, comprising:

(i) the amino acid sequence of SEQ ID NO: 99;

(ii) an amino acid sequence having at least one, two or three modifications but not more than 30, 20 or 10 modifications to SEQ ID NO: 99; or (iii) an amino acid sequence with 95-99% identity to SEQ ID NO: 99.

35. The isolated CAR polypeptide of claim 25, wherein the intracellular signaling domain comprises a primary cytoplasmic signaling domain comprising a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d.

36. The isolated CAR polypeptide of claim 35, wherein the primary cytoplasmic signaling domain comprises a functional signaling domain of CD3 zeta, wherein the CD3 zeta comprises the amino acid sequence of SEQ ID NO: 9 or SEQ ID NO: 10, or an amino acid sequence having at least one, two or three modifications but not more than 10 modifications of the amino acid sequence of SEQ ID NO: 9 or SEQ ID NO: 10, or a sequence with 95-99% identity to the amino acid sequence of SEQ ID NO: 9 or SEQ ID NO: 10.

37. An isolated nucleic acid molecule encoding a chimeric antigen receptor (CAR), wherein the encoded CAR comprises the amino acid sequence of SEQ ID NO: 99.

38. An isolated chimeric antigen receptor (CAR) polypeptide comprising the amino acid sequence of SEQ ID NO: 99.

* * * * *

UNITED STATES PATENT AND TRADEMARK OFFICE

CERTIFICATE OF CORRECTION

PATENT NO. : 10,568,947 B2
APPLICATION NO. : 14/805075
DATED : February 25, 2020
INVENTOR(S) : Brogden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this
Thirteenth Day of December, 2022

Katherine Kelly Vidal

Katherine Kelly Vidal
*Director of the United States Patent and Trademark Office*